United States Patent
Einav et al.

(10) Patent No.: US 9,101,628 B2
(45) Date of Patent: Aug. 11, 2015

(54) METHODS AND COMPOSITION OF TREATING A FLAVIVIRIDAE FAMILY VIRAL INFECTION

(75) Inventors: Shirit Einav, Stanford, CA (US); Jeffrey S. Glenn, Palo Alto, CA (US); Wenjin Yang, Foster City, CA (US); Hadas Dvory-Sobol, Mountain View, CA (US); Ingrid C. Choong, Palo Alto, CA (US); Robert McDowell, San Francisco, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 492 days.

(21) Appl. No.: 12/383,030

(22) Filed: Mar. 18, 2009

(65) Prior Publication Data
US 2010/0028299 A1 Feb. 4, 2010

Related U.S. Application Data

(63) Continuation-in-part of application No. PCT/US2008/076806, filed on Sep. 18, 2008, which is a continuation-in-part of application No. PCT/US2008/076804, filed on Sep. 18, 2008.

(60) Provisional application No. 61/092,537, filed on Aug. 28, 2008, provisional application No. 60/973,309, filed on Sep. 18, 2007, provisional application No. 61/088,759, filed on Aug. 14, 2008.

(51) Int. Cl.
| | | |
|---|---|---|
| *A01N 43/00* | (2006.01) |
| *A61K 31/33* | (2006.01) |
| *A61K 38/21* | (2006.01) |
| *A61K 31/497* | (2006.01) |
| *A61K 31/4184* | (2006.01) |
| *A61K 31/4439* | (2006.01) |
| *A61K 31/708* | (2006.01) |
| *A61K 45/06* | (2006.01) |
| *C07K 14/005* | (2006.01) |

(52) U.S. Cl.
CPC ............ *A61K 31/497* (2013.01); *A61K 31/4184* (2013.01); *A61K 31/4439* (2013.01); *A61K 31/708* (2013.01); *A61K 45/06* (2013.01); *C07K 14/005* (2013.01); *C12N 2770/24222* (2013.01); *G01N 2333/186* (2013.01); *G01N 2500/02* (2013.01)

(58) Field of Classification Search
None
See application file for complete search history.

(56) References Cited

U.S. PATENT DOCUMENTS

| | | | |
|---|---|---|---|
| 2,684,327 A | 7/1954 | Passal et al. | |
| 2,689,853 A | 9/1954 | Schenck et al. | |
| 3,265,691 A * | 8/1966 | Richter et al. | 544/139 |
| 3,423,413 A | 1/1969 | Priewe et al. | |
| 3,428,634 A | 2/1969 | Palazzo | |
| 4,011,322 A | 3/1977 | Rahtz et al. | |
| 4,269,835 A | 5/1981 | Whittle | |
| 5,552,426 A | 9/1996 | Lunn et al. | |
| 6,211,177 B1 | 4/2001 | Sperl et al. | |
| 6,369,235 B1 | 4/2002 | Michejda et al. | |
| 6,476,062 B2 | 11/2002 | Chu | |
| 7,495,015 B2 | 2/2009 | Arora et al. | |
| 2002/0128307 A1 | 9/2002 | Chu | |
| 2004/0092575 A1 | 5/2004 | Peuvot et al. | |
| 2004/0097438 A1 | 5/2004 | Hashimoto et al. | |
| 2004/0224876 A1 | 11/2004 | Jost-Price et al. | |
| 2005/0187261 A1 | 8/2005 | Verner et al. | |
| 2005/0192261 A1 | 9/2005 | Jost-Price et al. | |
| 2006/0052602 A1 | 3/2006 | Kim et al. | |
| 2008/0161324 A1 | 7/2008 | Johansen et al. | |
| 2010/0028299 A1 | 2/2010 | Einav et al. | |

FOREIGN PATENT DOCUMENTS

| | | |
|---|---|---|
| DE | 102007028521 A1 | 12/2008 |
| EP | 1400241 A1 | 3/2004 |
| KR | 10-1995-0031074 A | 12/1995 |
| WO | 200204425 A2 | 1/2002 |
| WO | 0207761 A1 | 3/2002 |
| WO | 03060475 A2 | 7/2003 |
| WO | 2005012288 A1 | 2/2005 |
| WO | WO 2005/032329 | 4/2005 |
| WO | 2006010446 A2 | 2/2006 |
| WO | 2006131737 | 12/2006 |
| WO | 2006131737 A2 | 12/2006 |
| WO | 2006135383 A2 | 12/2006 |
| WO | WO 2006/131737 A2 | 12/2006 |

(Continued)

OTHER PUBLICATIONS

Testa; "Prodrug research: futile or fertile?"; 2004; Biochemical Pharmacology; 68: 2097-2106.*

(Continued)

*Primary Examiner* — Craig Ricci
*Assistant Examiner* — Jared D Barsky
(74) *Attorney, Agent, or Firm* — Thomas Horstemeyer, LLP

(57) ABSTRACT

Briefly described, embodiments of this disclosure include compounds, pharmaceutical compositions, methods of treating a host infected with a virus from the Flaviviridae family of viruses, methods of inhibiting HCV replication in a host, methods of inhibiting the binding of NS4B polypeptide to the 3'UTR of HCV negative strand RNA in a host, methods of treating liver fibrosis in a host, and the like. In an embodiment, the compounds can include clemizole or a clemizole analog, or a pharmaceutically acceptable salt, an isomer, a tautomer, or a prodrug thereof.

3 Claims, 18 Drawing Sheets

(56) References Cited

FOREIGN PATENT DOCUMENTS

| WO | 2007103111 A2 | 9/2007 |
| WO | 2007115077 A2 | 10/2007 |
| WO | 2007117465 A2 | 10/2007 |
| WO | PCT/US2007/019932 | 3/2008 |
| WO | 2009039248 A2 | 3/2009 |

OTHER PUBLICATIONS

Greco et al., "The Search for Cytotoxic Synergy Between Anticancer Agents: a Case of Dorothy and the Ruby Slippers?" Journal of the National Cancer Institute, Vol., No. 11, Jun. 5, 1996.*

International Search Report and Written Opinion dated Dec. 24, 2010.

International Search Report and Written Opinion dated Dec. 27, 2010.

Selwood, D.L., et al., "Synthesis and Biological Evaluation of Novel Pyrazoles and Indazoles as Activators of the Nitric Oxide Receptor, Soluable Guanylate Cyclase," Journal of Medicinal Chemistry, 2001, vol. 44, pp. 78-93.

Patel, P.D., et al., "3D QSAR and Molecular Docking Studies of Benzimidazole Derivatives as Hepatitis C Virus NS5B Polymerase Inhibitors." Journal of Chemical Information and Modeling, 2008, vol. 48, pp. 42-55.

Beaulieu, C., et al., "Benzimidazoles as New Potent and Selective DP Antagonists for the Treatment of Allergic Rhinitis," Bioorganic & Medicinal Chemistry Letters, 2004, vol. 14, pp. 3195-3199.

Einav, S., et al., "Discovery of a Hepatitis C Target and its Pharmacological Inhibitors by Microfluidic Affinity Analysis," Nature Biotechnology, Sep. 2008, vol. 26, No. 9, pp. 1019-1027.

Einav, S., et al., "The Hepatitis C Virus (HCV) NS$B RNA Binding Inhibitor Clemizole is Highly Synergistic with HCV Protease Inhibitors," Anti-HCV Drug Synergy with Clemizole, JID 2010:202 (Jul. 1) pp. 65-74.

Cho, et al., "Identification of a Class of HCV Inhibitors Directed Against the Nonstructural Protein NS4B," www.scienceTranslationalMedicine.org, Jan. 20, 2010, vol. 2, Issue 15, pp. 1-8.

Cho, et al., Supplementary Materials for "Identification of a Class of HCV Inhibitors Directed Against the Nonstructural Protein NS4S," www.scienceTranslationalMedicine.org, Jan. 20, 2010, vol. 2, Issue 15, pp. 1-23.

International Search Report and Written Opinion dated Apr. 1, 2009.

Blight, K.J., er al., "allelic Variation in the Hepatitis C Virus NS4B Protein Dramatically Influences RNA Replication," J. Virology, Jun. 2007, vol. 81, No. 11, pp. 5724-5736.

Einav, S., et al., "A Nucleotide Binding Motif in Hepatitis C Virus (HCV) NS4B Mediates HCV RNA Replication, "J. Virology, Oct. 2004, vol. 78, No. 20, pp. 11288-11295.

Puerstinger, G., et al., "Antiviral 2,5-disubstituted Imidazo[4,5-c]pyridines: From Anti-Pestivirus to Anti-Hepatitis C Virus Activity, " Bioorganic Medicinal Chemistry Letters, Jan. 2007, vol. 17, No. 2, pp. 390-393.

Hirashima, S., et al. "Benzimidazole Derivatives Bearing Substituted Biphenyls as Hepatitis C Virus NS5B RNA-Dependent RNA Polymerase Inhibitors: Structure-Activity Relationship Studies and Identification of a Potent and Highly Selective Inhibitor JTK-109," J. Medicinal Chemistry, Jun. 2006, vol. 49, No. 15, pp. 4721-4736.

Korba, B.E., et al. "Nitazoxanide, Tizoaxanide and Other Thiazolides are Potent Inhibitors of Hepatitis B Virus and Hepatitis C Virus Replication," Antiviral Research, Sep. 4, 2007, vol. 77, No. 1, pp. 56-63.

International Search Report and Written Opinion dated Aug. 13, 2009.

Blight, et al.; Efficient Initiation of HCV RNA Replication in Cell Culture; Science; vol. 290; Dec. 8, 2009, 19721974.

Einav, et al.; A Nucleotide Binding Motif in Hepatitis C Virus (HCV) NS4B Mediates HCV RNA Replication; Journal of Virology; Oct. 2004; vol. 78, No. 20; pp. 1128-11295.

Hwang, et al.; Inhibition of Hepatitis C Virus Replication by Arsenic Trioxide; Antimicrobial Agents and Chemotheraphy; vol. 48, No. 8; Aug. 2004; p. 2876-2882.

Lohmann, et al.; Replication of Subgenomic Hepatitis C Virus RNAs in a Hepatoma Cell Line; Science; vol. 285; Jul. 2, 1999; pp. 110-113.

Maerkl, et al.; A Systems Approach to Measuing the Binding Energy Landscapes of Transcription Factors; Science; vol. 315; Jan. 12, 2007; pp. 233-237.

Takhampunya, et al.; Inhibition of Dengue Virus Replication by Mycophenolic Acid and Ribavirin; Journal of General Virology; vol. 87; 2006; 1947-1952.

Supplemental European Search Report dated Oct. 13, 2011.

Beaulieu, P.L., et al., "Non-nucleoside Inhibitors of the Hepatitis C Virus NS5B polymerase: Discovery and Preliminary SAR of Benzimidazolde Derivatives," Bioorganic & Medicinal Chemistry Letters, Pergamon, Elsevier Science, GB, vol. 14, No. 1, Jan. 1, 2004, pp. 119-124.

Beaulieu, P.L., et al., "Improved Replicon Cellular Activity of Non-Nucleoside Allosteric Inhibitors of HCV NS5B Polymerase: From Benzimidazole to Indole Scaffolds," Bioorganic & Medicinal Chemistry Letters, Pergamon, Elsevier Science, GB, vol. 16, No. 19, Oct. 1, 2006, pp. 4987-4993.

"Martindale, the Complete Drug Reference", 2000, Pharmaceutical Press, XP000002659125, Clemizole Hydrochoiroide, p. 406.

Einav, Shirit, et al., "Discovery of a Hepatitis C Target and its Pharmacological Inhibitors of Microfluidic Affinity Analysis," Nature Biotechnology, Nature Publishing Group, NY, vol. 26, No. 9, Sep. 1, 2008, pp. 1019-1027.

Patani et al. Bioisosterism: A Rational Approach in Drug Design. Chem. Rev. 1996. vol. 96, pp. 3147-3176.

Supplementary European Search Report dated Sep. 19, 2011.

Iacobellis et al. "External validation of biochemical indices for noninvasive evaluation of liver fibrosis in HCV chronic Hepatitis". American Journal of Gastroenterology, 2005, vol. 100, pp. 868-873.

Voronina et al. "Synthesis and pharmaceutical properties of amidine analogs of pyracetatam". Khimiko-Farmatsevticheskii Zhurnal, 1990, vol. 24, 11:26-29. CAPLUS Abstract, AN 1991:101601.

Office Action dated Sep. 9, 2013 for Chinese Application Serial No. 201080021845.9, 4 pages.

Office Action dated Sep. 11, 2013 for Chinese Appiication Serial No. 201080021850.X, 3 pages.

Schilders G. et al. MPP6 is an exosome-associated RNA-binding protein involved in 5.8S rRNA maturation. Nucleic Acids Research, 2005, vol. 33(21), pp. 6795-6804.

Blight KJ et al. Efficient Initiation of HCV RNA Replication in Cell Culture. Science, 2000, vol. 290, pp. 1972-1974.

Tong X et al. Identification and analysis of fitness of resistance mutations against the HCV protease inhibitor SCH 503034. Antiviral Research, 2006, vol. 70, pp. 28-38.

Lindenbach et al. Complete Replication of Hepatitis C Virus in Cell Culture. Science, 2005, vol. 309, pp. 623-626.

Echeverri, A.C. & Dasgupta, A. Amino Terminal Regions of Poliovirus 2C Protein Mediate Membrane Binding. Virology, 1995. vol. 208, pp. 540-553.

Rodriguez, P.L. & Carrasco L. Poliovirus Protein 2C Contains Two Regions Involved in RNA Binding Activity. J. Biol. Chem. 1995, vol. 270 (17), pp. 10105-10112.

Hadd, A.D. et al. Microchip Device for Performing Enzyme Assays. Anal. Chem. 1997, vol. 69, pp. 3407-3412.

El-Hage, N. & Luo, G. Replication of Hepatitis C Virus RNA Occurs in a Membrane-Bound Replication Complex Containing Nonstructural Viral Proteins and RNA. Journal of General Virology, 2003, vol. 84, pp. 2761-2769.

Park-Lee et al. Characterization of the Interaction between Neuronal RNA-binding Protein HuD and AU-rich RNA. Journal of Biological Chemistry, 2003, vol. 278(41) pp. 39801-39808.

Einav, S. et al. A Nucleotide Binding Motif in Hepatitis C Virus (HCV) NS4B Mediates HCV RNA Replication. Journal of Virology, 2004, vol. 78(20) pp. 11288-11295.

Lundin, M et al. Topology of the Membrane-Associated Hepatitis C Virus Protein NS4B. Journal of Virology, 2003, vol. 77(9), pp. 5428-5438.

(56) References Cited

OTHER PUBLICATIONS

Gosert, R. et al. Identification of the Hepatitis C Virus RNA Replication Complex in Huh-7 Cells Harboring Subgenomic Replicons. Journal of Virology, 2003, vol. 77(9), pp. 5487-5492.

Tscherne, D.M. Time- and Temperature-Dependent Activation of Hepatitis C Virus for Low-pH-Triggered Entry. Journal of Virology, 2006, vol. 80(4), pp. 1734-1741.

Elazar, M. et al. An N-Terminal Amphipathic Helix in Hepatitis C Virus (HCV) NS4B Mediates Membrane Association, Correct Localization of Replication Complex Proteins, and HCV RNA Replication. Journal of Virology, 2004, vol. 78(20), pp. 11393-11400.

Dimitrova M. et al. Protein-Protein Interactions between Hepatitis C Virus Nonstructural Proteins. Journal of Virology, 2003, vol. 77(9), pp. 5401-5414.

Glenn J.S. et al. In Vitro-Synthesized Hepatitis Delta Virus RNA Initiates Genome Replication in Cultured Cells. Journal of Virology, 1990, vol. 64(6), pp. 3104-3107.

Huang L. et al. Hepatitis C Virus Nonstructural Protein 5A (NS5A) is an RNA-binding Protein. Journal of Biological Chemistry, 2005, vol. 280(43) pp. 36414-36428.

Elazar, M. et al. Amphipathic Helix-Dependent Localization of NS5A Mediates Hepatitis C Virus RNA Replication. Journal of Virology, 2003, vol. 77(70), pp. 6055-6061.

Egger D. et al. Expression of Hepatitis C Virus Proteins Induces Distinct Membrane Alterations Including a Candidate Viral Replication Complex. Journal of Virology, 2002, vol. 76(12), pp. 5974-5984.

Kang L. et al. Microfluidics for drug discovery and development: From target selection to product lifecycle management. Drug Discovery Today, 2008, vol. 13 (1/2), pp. 1-13.

Kusov YY. et al. Membrane association and RNA binding of recombinant hepatitis a virus protein 2C. Arch Virol. 1998, vol. 143, pp. 931-944.

Liang, T.J. et al. Pathogenesis, Natural History, Treatment, and Prevention of Hepatitis C, Ann. Intern. Med., 2000, vol. 132, pp. 296-305.

Park, S. et al. HuD RNA Recognition Motifs Play Distinct Roles in the Formation of a Stable Complex with AU-Rich RNA. Mol. Cell. Biol. 2000, vol. 20(13), pp. 4765-4772.

Lee, N. L. et al. Solvent Compatibility of Poly(dimethylsiloxane)-Based Microfluidic Devices. Anal. Chem., 2003, vol. 75, pp. 6544-6554.

Roosild, T.P. et al. NMR Structure of Mistic, a Membrane-Integrating Protein for Membrane Protein Expression. Science, 2005, vol. 307, pp. 1317.

Reed K.E. & Rice C.M. Overview of Hepatitis C Virus Genome Structure, Polyprotein Processing, and Protein Properties. The Hepatitis C Viruses, Current Topics in Microbiology and Immunology, 2000, vol. 242, pp. 55-84.

Overington, J.P. et al. How many drug targets are there? Nat Rev Drug Discov. 2006, vol. 5, pp. 993-996.

Maerkl, SJ. et al. A Systems Approach to Measuring the Binding Energy Landscapes of Transcription Factors. Science, 2007, vol. 315, pp. 233-237.

Toepke, MW, et al. PDMS absorption of small molecules and consequences in microfluidic applications. Lab on a Chip, 2006, vol. 6, pp. 1484-1483.

Whitesides, GM. The origins and the future of microfluidics. Nature 2006, vol. 442, pp. 368-373.

Myer, VE et al. Identification of HuR as a protein implicated in AUUUA-mediated mRNA decay. The EMBO Journal, 1997, vol. 16, pp. 2130-2139.

Spangberg, K et al. HuR, a Protein Implicated in Oncogene and Growth Factor mRNA Decay, Binds to the 39 Ends of Hepatitis C Virus RNA of Both Polarities. Virology, 2000, vol. 274, pp. 378-390.

Glenn, JS et al. Identification of a Prenylation Site in Delta Virus Large Antigen. Science, 1992, vol. 256, pp. 1331-1333.

Burd, CG & Dreyfuss G. Conserved Structures and Diversity of Functions of RNA-Binding Proteins. Science, 1994, vol. 265, pp. 615-621.

Wung, CH et al. Identification of the RNA-binding sites of the triple gene block protein 1 of bamboo mosaic potexvirus. J. Gen. Virol. 1999, vol. 80, pp. 1119-1126.

Gupta AK et al. Antifungal Agents: An overview. Part I. Journal of the American Academy of Dermatology, 1994, vol. 30(5) Part 1, pp. 677-698.

Supplemental European Search Report dated Jul. 2, 2012.

Supplemental European Search Report dated Aug. 8, 2012.

Einav, et al., Discovery of a Hepatitis C Target and its Pharmacological Inhibitors by Microfluidic Affinity Analysis, Nature Biotechnology, Nature Publishing Group, New York, NY, vol. 26, No. 9, Sep. 1, 2008, pp. 1019-1027.

Caroti, et al., "Synthesis, Antilipidemic and Platelet Antiaggregatory Activity of 2-Aminobenzimidazole Amide Derivatives," II Farmaco, Elsevier France, Scientifiques Et Medicals, IT, vol. 44, No. 3, Jan. 1, 1989, pp. 227-255.

Tuncbilek, et al., "Synthesis and Antimicrobial Activity of Some New Anilino Benzimidazoles," Archiv Der Pharmazie, Wiley, VH Verlag GmBH & Co. KGAA, Dec. 1, 1997, pp. 372-376.

Manganaro, et al., "Activity of Antiinflammatory Steroidal and Nonsteroidal Compounds in Some Experimental Functions, II, Activity of Certain Nonsteroidal Antiinflammatory Agents as Compared with that of Prednisone in Murine Hepatitis Due to MHV3," Inflammation, Plenum Press, New York, NY, Vol. Proc. Int. Symp. No. 1968, Jan. 1, 1968, pp. 67-71.

Anonymous, Registry, Dec. 8, 2008, XP007920913.

Anonymous, Registry, Dec. 18, 1984-Dec. 22, 2009, XP007920912.

Anonymous, Registry, Nov. 8, 2004, XP007920909.

* cited by examiner

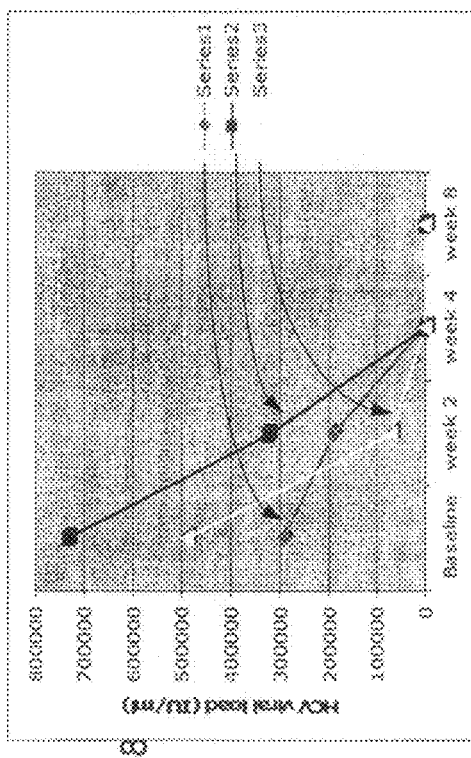
3 male, HCV genotype 4 patients:
| | Baseline | week 2 | week 4 | week 8 |
|---|---|---|---|---|
| #1 24 y.o., ALT 59 | 290,000 | 190,000 | 2,400 | <10 |
| #2 27 y.o., ALT 124 | 730,000 | 320,000 | <10 | <10 |
| #3 32 y.o., ALT 99 | 489,000 | 70,000 | <10 | <10 |
Normal ALT = <45
100 BID clemizole X 8 weeks
180 ug/wk pegasys on weeks 4-8
Continued on NTZ + pegasys
Fig. 2

Upper: HCV 5'-UTR positive strand (SEQ ID NO. 1); GenBank NC_004102; nt 1-341 5'UTR
Lower: HCV 3'UTR negative strand (SEQ ID NO. 2)
For genotype 1a

```
  5'   1  gccagccccc  tgatggggc   gacactccac  catgaatcac  tcccctgtga  ggaactactg
          cggucggggg  acuaccccg   cugugaggug  guacuuagug  aggggacacu  ccuugaugac 61  tcttcacgca  gaaagcgtct  agccatggcg  ttagtatgag  tgtcgtgcag  cctccaggac
          agaagugcgu  cuuucgcaga  ucgguaccgc  aaucauacuc  acagcacguc  ggagguccug 121  ccccctccc   gggagagcca  tagtggtctg  cggaaccggt  gagtacaccg  gaattgccag
          ggggggaggg  cccucucggu  aucaccagac  gccuuggcca  cucaugugge  cuuaacgguc 181  gacgaccggg  tcctttcttg  gataaacccg  ctcaatgcct  ggagatttgg  gcgtgccccc
          cugcuggccc  aggaaagaac  cuauuuggge  gaguuacgga  ccucuaaacc  cgcacggggg 241  gcaagactgc  tagccgagta  gtgttgggtc  gcgaaaggcc  ttgtggtact  gcctgatagg
          cguucugacg  aucggcucau  cacaacccag  cgcuuuccgg  aacaccauga  cggacuaucc 301  gtgcttgcga  gtgccccggg  aggtctcgta  gaccgtgcac  c
          cacgaacgcu  cacggggccc  uccagagcau  cuggcacgug  g 5'
```

(SEQ ID NO. 3)
5' UTR pos (For genotype 1b)
agacccaagctggctagcgtttaaacttaagcttggtaccgagctcggatccactagtccagtgtggtggaattctgca
gatatcataatacgactcactatagccagccccgattgggggcgacactccaccatagatcactcccctgtgaggaac
tactgtcttcacgcagaaagcgtctagccatggcgttagtatgagtgtcgtgcagcctccaggaccccccctcccggga
gagccatagtggtctgcggaaccggtgagtacaccggaattgccaggacgaccgggtcctttcttggatcaacccgctc
aatgcctggagatttgggcgtgccccgcgagactgctagccgagtagtgttgggtcgcgaaaggccttgtggtactgc
ctgatagggtgcttgcgagtgccccgggaggtctcgtagaccgtgcaccatgagcacgaatcctaaacctcaaagaaaa
accaaagggcgcgccatggatcgatatccagcacagtggcggccgctcgagt (SEQ ID NO. 4)
3' UTR neg (For genotype 1b)
acucgagcggccgccacugugcuggauaucgauccauggcgcgcccuuugguuuuucuuugaggguuuaggauucgugcu
cauggugcacggucuacgagaccucccggggcacucgcaagcacccuaucaggcaguaccacaaggccuuucgcgaccc
aacacuacucggcuagcagucucgcggggcacgcccaaaucuccaggcauugagcgggungauccaagaaaggacccg
gucguccuggcaauuccgguguacucaccgguuccgcagaccacuauggcucucccggggaggggggguccuggaggcug
cacgacacucauacuaacgccauggcuagacgcuuucgcgugaagacaguaguuccucacaggggagugaucuauggu
ggaguugcccccaaucgggggcuggcuauagugagucguauuaugauaucugcagaauuccaccacacuggacuagu
ggauccgagcucgguaccaagcuuaaguuuaaacgcuagccagcuugggucu
```

Fig. 3

Preparation of 5, 6-Disubstituted Chemizoles Compounds

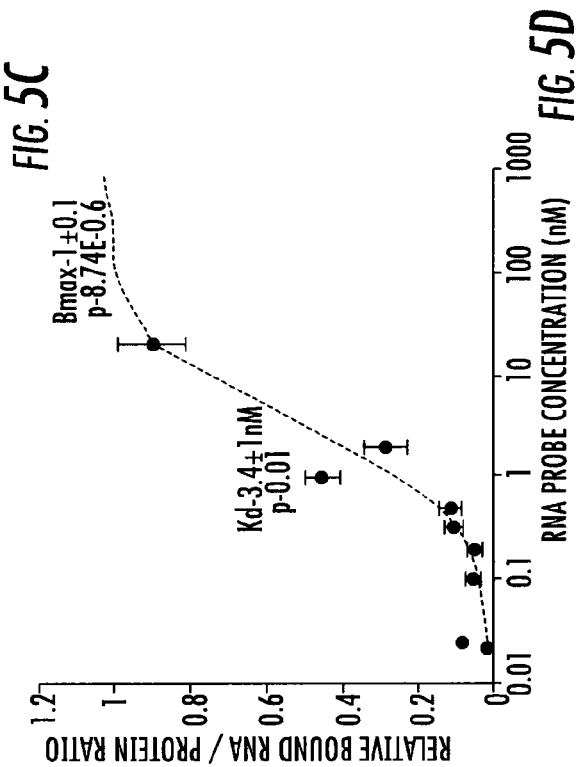
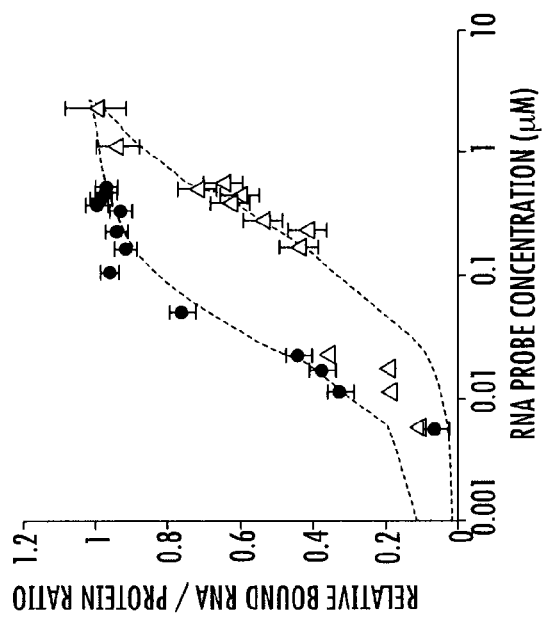

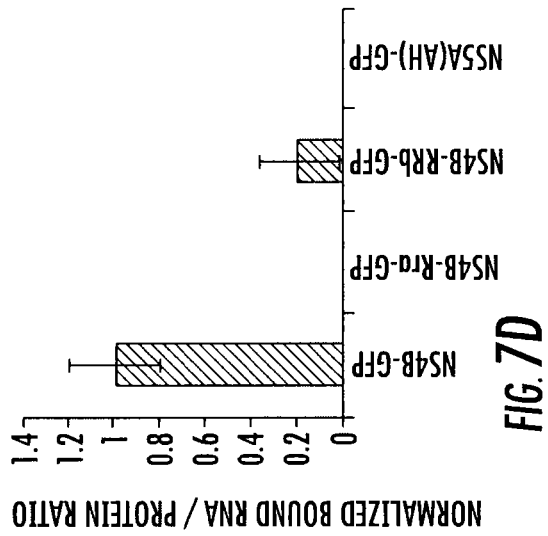

FIG. 7B

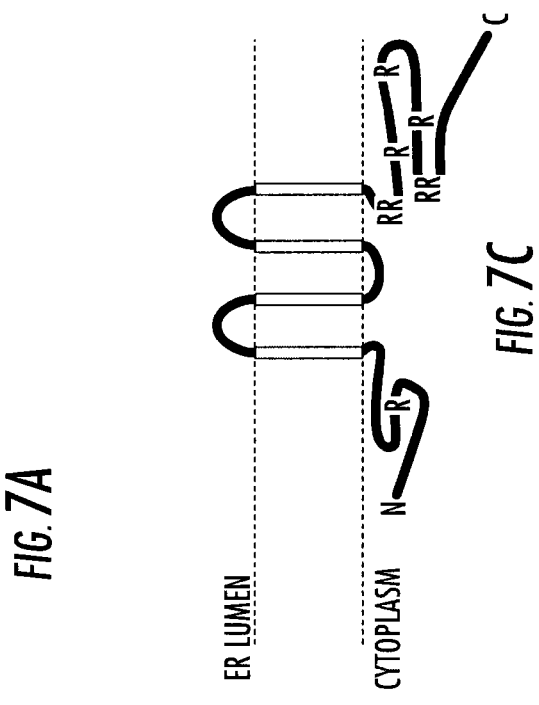

FIG. 7D

| | PROTEIN | RNA BINDING DOMAIN |
|---|---|---|
| SEQ. ID NO: 5 | HIV REV | TRQARRNRRRRWRERQ |
| SEQ. ID NO: 6 | HIV TAT | ALGIBYGRKKRRQRRRP |
| SEQ. ID NO: 7 | λN | MDAQTRRRERRAEKQAQW |
| SEQ. ID NO: 8 | φ21 N | GTAKBRYKARRAELIAER |
| SEQ. ID NO: 9 | P22 N | GNAKTRRHERRRKLAIER |
| SEQ. ID NO: 10 | BaMV TGBp1 | MDNRITDLLTRBGYLRTBEPRGAGQQLWHAVAGAGKT |
| SEQ. ID NO: 11 | POLLOVIRUS 2C | NERNRRBN |
| SEQ. ID NO: 12 | HCV NS4B | RRHVGPEGAVQWMNRLIAFASR GNHVSPTHYVPESDAAARVTAILSSLTVTQLRR |

| SEQ. ID NO: | | RNA PROBE SEQUENCE | PHENOTYPE (BY MOBILITY SHIFT ASSAY / UV CROSS LINKING) |
|---|---|---|---|
| 14 | 4A (AUUU)$_4$A | AUUUAUUUAUUU AUUUA | BINDING |
|  | 2A (AUUU)$_2$A | AUUUAUUUA | NO BINDING |
| 15 | 4C (CUUU)$_4$C | CUUUCUUUCUUU CUUUC | NO BINDING |

Table 7. Antiviral activity and cytotoxicity of the drugs used.

| Compound | EC50[a] | | | CC50[b] | | |
|---|---|---|---|---|---|---|
| | 2a genotype | 1b genotype | Measured by others (1b genotype) | 2a genotype | 1b genotype | Measured by others (1b genotype) |
| clemizole | 8μM | 23±7μM | NA | 35±0.5μM | 40±5μM | NA |
| SCH-503034 | 0.8μM | 0.2135-0.574μM | 0.2μM | >100μM | >100μM | >100μM |
| VX-950 | 0.3μM | ND | 0.354-0.56μM | ND | ND | 26.7-82μM |
| Interferon | 2.8±0.4 (u/ml) | ND | 1.8 (u/ml)* | ND | ND | >10,000 (u/ml) |
| NM-283 | 1.16±0.2μM | ND | 1.23±0.52μM | ND | ND | >100μM |
| HCV-796 | 0.068±0.008μM | ND | 0.017±0.005μM | ND | ND | >100μM |

Fig. 15

Table 8

SPECIFICATION DATA SHEET SDS INTERMEDIATE / PRODUCT

| Trivial Name | Name AXAPTA / LIMS | C-Number | Article Number |
|---|---|---|---|
| Clemizol hydrochlorid | Clemizol hydrochlorid | C-023018 | M014525 |

| API Component | Method | Specification | Comment |
|---|---|---|---|
| Appearance | AVG-01 | White to off-white solid | --- |
| Identiy by H-NMR | AVG-02 | Concordant with reference C-023018-PRS-NE-01 | In d6-DMSO |
| Identity by FT-IR | AVG-03 | Concordant with reference C-023018-PRS-NE-01 | ATR |
| Residual solvents by GC-HS | AVG-04 | Ethanol $\leq$ 0.500 % w/w<br>Methanol $\leq$ 0.300 % w/w<br>N,N-Dimethylformamide $\leq$ 0.089% w/w<br>tert-Butylmethylether $\leq$ 0.500% w/w | n=2 |
| Assay by HPLC | HPLC-C-023018-QM1 | $\geq$ 98 % w/w on dry base | n=2<br>% w/w dry = % w/w HPLC/(100-Residual solvents-water) |
| Purity by HPLC | HPLC-C-023018-QM1 | $\geq$ 98 % a/a<br>unknown impurities <=0.15% a/a<br>Sum of impurities <=2.0% a/a | n=2<br>Impurities $\geq$ 0.05 % a/a are reported with RRT |
| Assay Chloride by Titration (AgNO$_3$) | ANV-09 | Report result | n=3 |
| Melting Point (DSC) | AVG-06 | 230-250°C | n=1 |
| Elemental Analysis | External at Solvias AG, Basel, Switzerland | Report Result for C, H, N, Cl (Theory: C: 63.0 %; H: 5.8%; Cl: 19.6 %; N: 11.6%) | n=2 |
| Water content by Karl-Fischer | ANV-08 | Report result | Oven 160°C |
| Microbiological Quality | USP <61> | Total yeasts and moulds: report<br>Total microbial count: report | External at Confarma AG, Hombourg, France |
| Bacterial Endotoxins | USP <85> | Report | External at Confarma AG, Hombourg, France | n: number of measurements

FIG. 16

METHODS AND COMPOSITION OF TREATING A FLAVIVIRIDAE FAMILY VIRAL INFECTION

CROSS-REFERENCE TO RELATED APPLICATION

This application is a continuation in-part application of PCT patent applications US/2008/076804 (entitled "Methods of Treating a Flaviviridae Family Viral Infection, Compositions For Treating A Flaviviridae Family Viral Infection, and Screening Assays for Identifying Compositions For Treating A Flaviviridae Family Viral Infection") and US/2008/076806 (entitled "Methods of Treating A Flaviviridae Family Viral Infection and Compositions For Treating A Flaviviridae Family Viral Infection"), both filed Sep. 18, 2008, which in turn claim priority to U.S. provisional application having Ser. No. 60/973,309 (entitled "Methods for Treating Hepatitis C Virus Infection"), filed on Sep. 18, 2007, U.S. provisional application having Ser. No. 61/088,759 (entitled "Methods and Compositions for Treating Hepatitis C Virus Infection"), filed on Aug. 14, 2008, as well as U.S. provisional application having Ser. No. 61/092,537 (entitled "Methods of Treating a Flaviviridae family viral Infection, Compositions for treating a Flaviviridae family viral Infection, and screening assays for identifying compositions for treating a Flaviviridae family viral Infection") filed on Aug. 28, 2008; all of the foregoing PCT and U.S. provisional applications are entirely incorporated herein by reference.

This application is related to U.S. patent application entitled "Methods and compositions of Treating a Flaviviridae family viral Infection" filed on Mar. 18, 2009, to Einav et al., (Express Mail number EM129179365) which is incorporated herein by reference.

STATEMENT REGARDING FEDERALLY SPONSORED RESEARCH OR DEVELOPMENT

This invention was made with Government support under contract DK066793 awarded by the National Institutes of Health. The Government has certain rights in this invention.

BACKGROUND

Over 150 million people are infected with Hepatitis C Virus (HCV) worldwide. Unfortunately, the current standard care, consisting of administration of a combination of interferon and ribavirin, is often unable to clear HCV infection in many infected individuals. Moreover, this treatment is associated with significant side effects, precluding its use by many individuals. Thus, current therapies are inadequate for the majority of the patients, and there is a pressing need for new drugs to treat HCV infection (See, *Annals Internal Med.* 132:296-305 (2000)).

The 9.6-kb positive single-stranded RNA HCV genome encodes a 3,000-amino-acid polyprotein that is proteolytically processed into structural proteins, which are components of the mature virus, and nonstructural proteins (NS), which are involved in replicating the viral genome (*Curr Top Microbiol Immunol* 242, 55-84 (2000)). Like other positive strand RNA viruses (B. N. Fields, D. M. Knipe, and P. M. Howley (ed.), *Fields Virology*. (Lippincott-Raven Publications, Philadelphia, Pa., 1996, in "The viruses and their replication")), HCV appears to replicate in association with intracellular membrane structures. In the case of HCV, the structures are referred to as the membranous web (*J Virol* 76, 5974-5984 (2002)), the formation of which is believed to be induced by the NS4B protein. NS4B is also used to assemble the other viral NS proteins within the apparent sites of RNA replication (*J Virol* 78, 11393-11400 (2004)). It is not known how viral RNA, especially the negative strand template used in production of progeny genomes, might be incorporated or maintained at these replication sites.

There is an ongoing need in the art for agents that treat HCV infection and for methods of identifying candidate agents that are suitable for treating HCV infection.

SUMMARY

Briefly described, embodiments of this disclosure include compounds, compositions, pharmaceutical compositions, methods of treating a host infected with a virus from the Flaviviridae family of viruses, methods of treating HCV replication in a host, methods of inhibiting the binding of NS4B polypeptide to the 3'UTR of HCV negative strand RNA in a host, methods of treating liver fibrosis in a host, and the like.

In one embodiment, the present invention provides a method of treating a subject infected with a virus from the Flaviviridae family. The method comprises administering to the subject clemizole or clemizole analog, or a pharmaceutically acceptable salt, isomer, tautomer or prodrug thereof, in an amount that is effective in reducing viral load of said virus in said subject.

In another embodiment, the present invention provides a method of inhibiting formation of a complex between NS4B polypeptide and hepatitis C viral (HCV) RNA in a cell. The method comprises administering to the cell clemizole or clemizole analog, or a pharmaceutically acceptable salt, isomer, tautomer or prodrug thereof, in an amount that is effective in reducing binding of NS4B polypeptide to HCV RNA.

In yet another embodiment, the present invention provides a method of treating liver fibrosis in a subject. The method comprises administering to the subject a therapeutically effective amount of clemizole or clemizole analog, or a pharmaceutically acceptable salt, isomer, tautomer or prodrug thereof.

In some aspects, any of the methods of the present invention involves administration of clemizole or clemizole analog having a structure of Formula I:

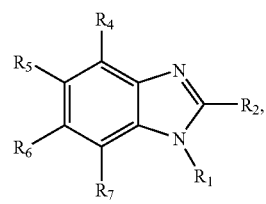

Formula (I)

wherein $R_1$ is selected from the group consisting of: —H,

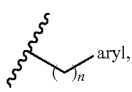

$n = 0, 1, 2$ and

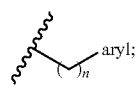

n = 0, 1, 2 wherein $R_2$ is selected from the group consisting of: —H and

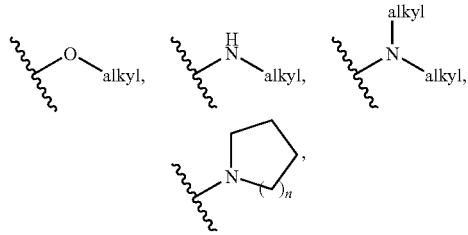

n = 1, 2, or 3

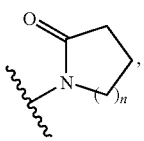

n = 1 or 2

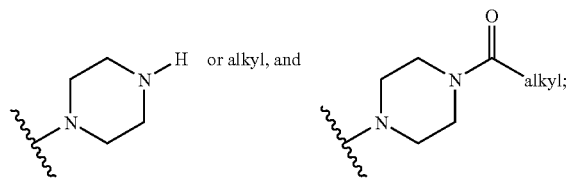

wherein X is selected from the group consisting of: -alkyl, —CH$_2$OH —CF$_3$, —OH, -aryl,

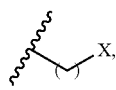

n = 0, 1, 2 each of $R_4$-$R_7$ is independently selected from the group consisting of: —H, —Cl, —F, —I, —Br, —CH$_3$, —OCH$_3$, —NH$_2$,

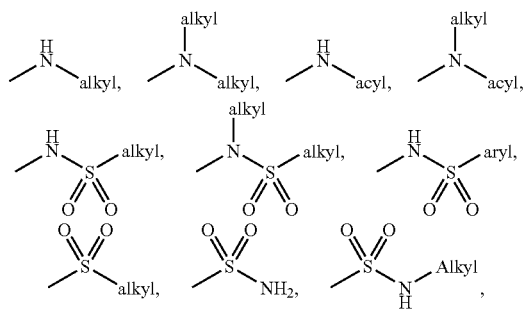

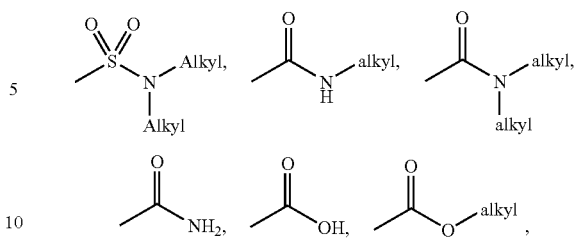

—NHC(O)aryl, —NHC(O)alkyl, —NHSO$_2$NH$_2$, —NHSO$_2$NH-alkyl, —NHC(O)NH$_2$, —NHC(O)NH-alkyl, —N(alkyl)C(O)aryl, —N(alkyl)C(O)alkyl, —N(alkyl)SO$_2$NH$_2$, —N(alkyl)SO$_2$NH-alkyl, —N(alkyl)C(O)NH$_2$, and —N(alkyl)C(O)NH-alkyl; or, optionally, $R_4$ and $R_5$, $R_5$ and $R_6$, or $R_6$ and $R_7$ are joined together with a bond to form a 5, 6, or 7-membered ring; or, optionally, $R_4$ and $R_5$, $R_5$ and $R_6$, or $R_6$ and $R_7$ are joined together to form a 1,2-(methylenedioxy)benzene ring system; wherein the alkyl group is independently selected from the group consisting of —CH$_3$, —CH$_2$CH$_3$, —CH(CH$_3$)$_2$, —CF$_3$, cyclopropyl, cyclopentyl, and cyclohexyl; wherein the aryl group is independently selected from the group consisting of Group A to Group F:

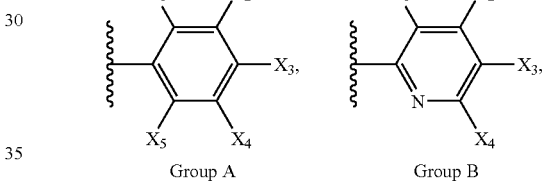

Group A                Group B

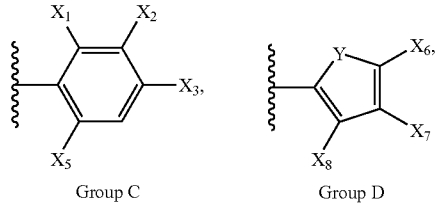

Group C                Group D

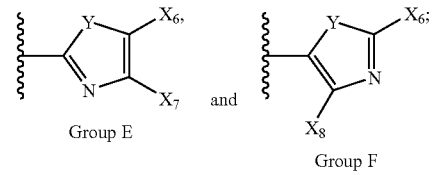

Group E        and        Group F wherein $X_1$-$X_5$ are each independently selected from the group consisting of —H, -alkyl, —I, —Br, —Cl, —F, —O-alkyl,

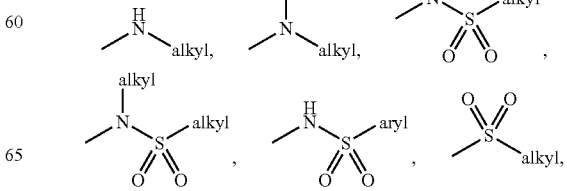

-continued

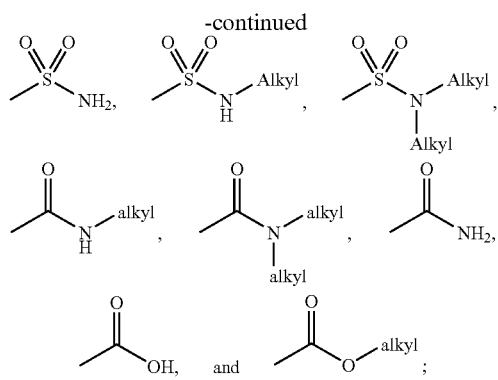

and wherein Y is selected from the group consisting of O, S, NH, N-alkyl, and N-acyl; $X_6$ is selected from the group consisting of —H, —$CH_3$, —I, —Br, —Cl, —F, —$CF_3$ and —$OCH_3$; and $X_7$ and $X_8$ are independently selected from H or $CH_3$.

In some other aspects, any of the methods of the present invention involves administration of clemizole or clemizole analog having a structure of Formula I:

Formula I

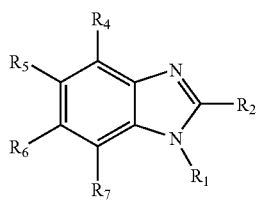

wherein $R_1$ is selected from the group consisting of: —H and

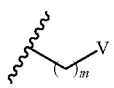

m=0, 1, 2 wherein V is selected from alkyl, cycloalkyl, heterocyclo, aryl or heteroaryl, and m is 0, 1 or 2; $R_2$ is selected from the group consisting of: —H,

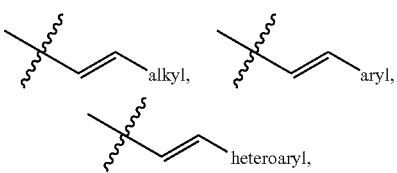

and

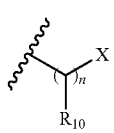

n=0, 1, 2, 3, 4; wherein X is selected from the group consisting of: —$NH_2$, —NH(alkyl), —N(alkyl)$_2$, CONH(alkyl), COHC(aryl), —OH, -alkyl, cycloalkyl, alkenyl, —$CF_3$, —O(alkyl), —O-cycloalkyl, —O-heterocyclo, -aryl, heteroaryl, N-attached heterocyclo, C-attached heterocyclo, —SH, —$SO_2$(alkyl), —S(alkyl), and —S(aralkyl); each of $R_4$-$R_7$ is independently selected from the group consisting of: —H, —I, —Br, —Cl, —F, —$CH_3$, —CN, —OH, —$OCH_3$, —$NO_2$, —$NH_2$,

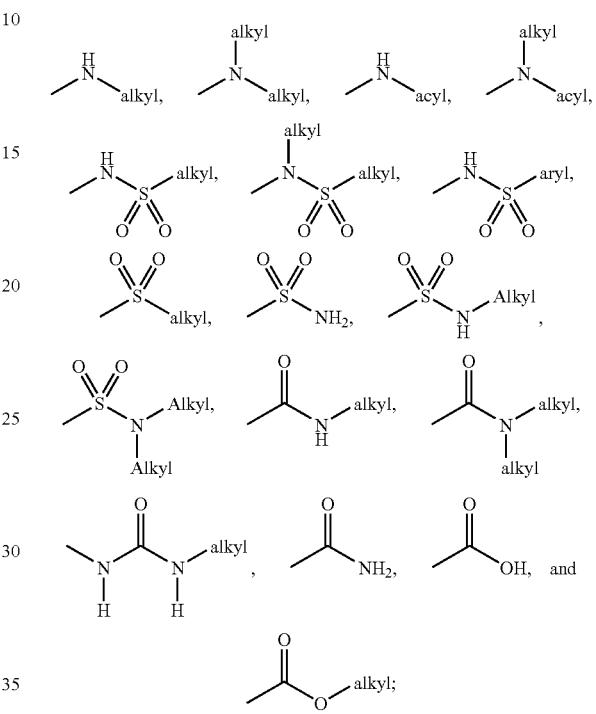

or, optionally, $R_4$ and $R_5$, $R_5$ and $R_6$, or $R_6$ and $R_7$ are joined together with a bond to form a 5, 6, or 7-membered ring; or, optionally, $R_4$ and $R_5$, $R_5$ and $R_6$, or $R_6$ and $R_7$ are joined together to form a 1,2-(methylenedioxy)benzene ring system; and $R_{10}$ is hydrogen or alkyl. In some other embodiments of the methods of the invention, X is selected from the group consisting of: —$CF_3$, —OH, —CH($CH_3$)OH, -alkyl, cycloalkyl, alkenyl, —O-alkyl, —O-cycloalkyl, —O-heterocyclo, -aryl,

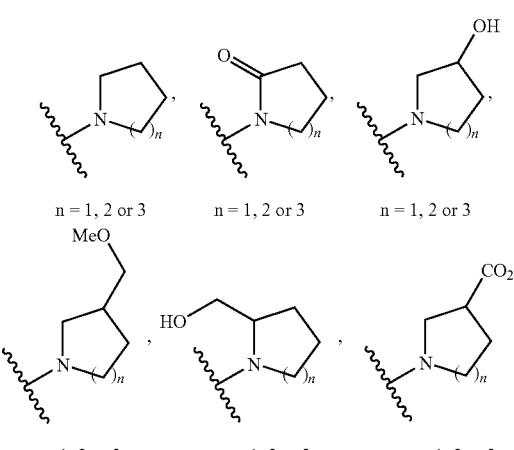

n = 1, 2 or 3    n = 1, 2 or 3    n = 1, 2 or 3 n = 1, 2 or 3    n = 1, 2 or 3    n = 1, 2 or 3

In further embodiments of the methods of the invention, the compound of Formula (I) has the structure:

and, optionally, $R_4$ and $R_7$ are hydrogen.

In other embodiments of the methods of the invention, the compound is clemizole:

or the HCl salt thereof.

In some embodiments of the methods of the invention, clemizole hydrochloride is administered in an amount of from about 15 mg to 200 mg per dose. In other embodiments, the clemizole hydrochloride is administered in an amount of about 200 mg per day. In other embodiments, the clemizole hydrochloride is administered in an amount of about 100 mg per day.

In other embodiments of the methods of the invention, the compound has one of the following formulae:

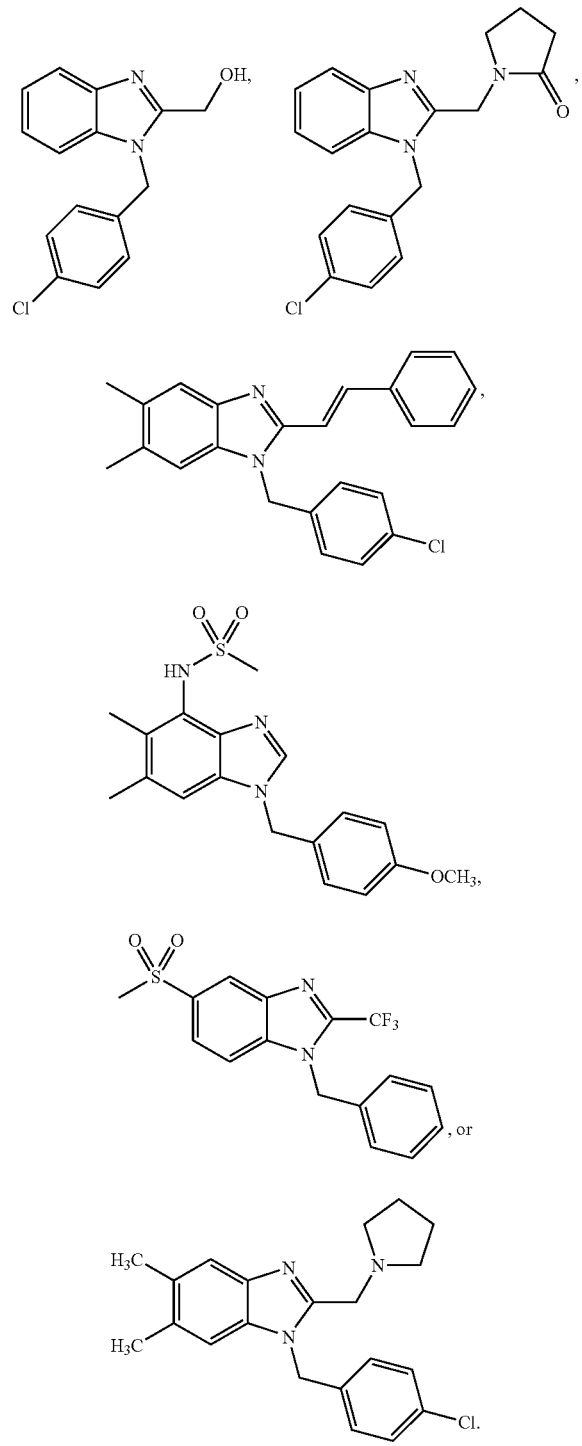

In yet other of the methods of the invention, the compound has a structure of one of the following formulae:

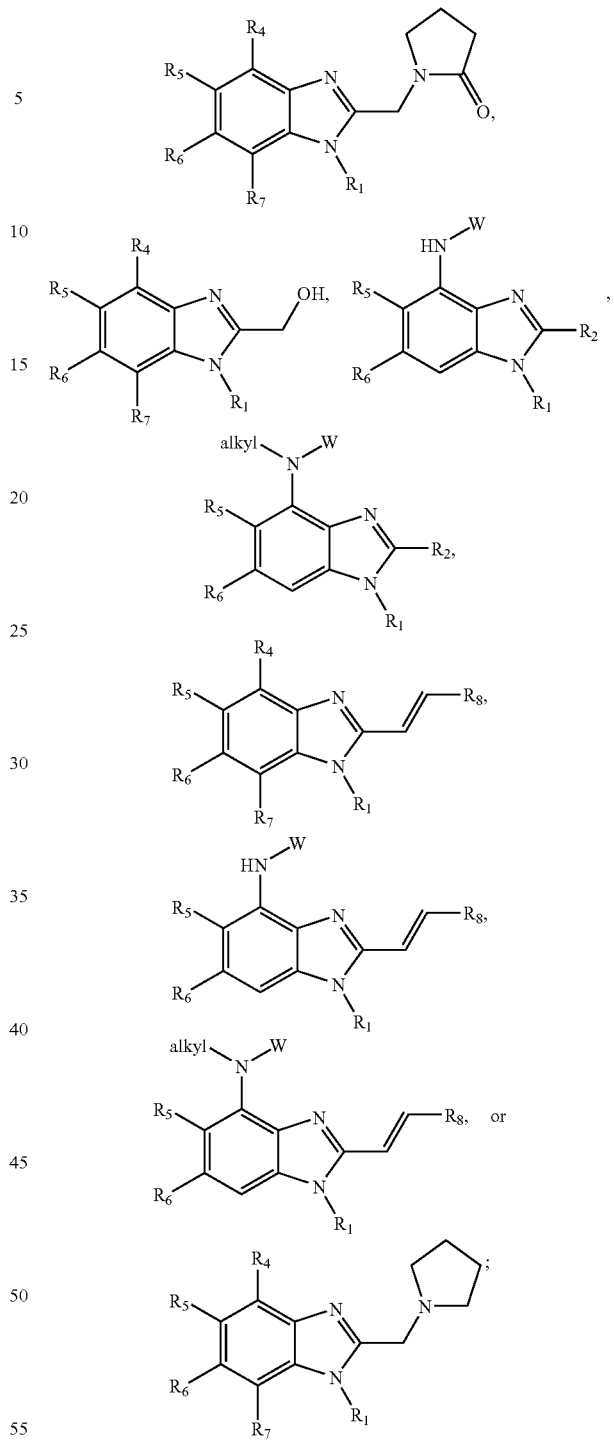

wherein $R_1$-$R_7$ are as described above; $R_8$ is alkyl, aryl or heteroaryl, and W is alkyl, —C(O)aryl, —C(O)alkyl, —SO$_2$aryl, —SO$_2$alkyl, —SO$_2$NH$_2$, —SO$_2$NH-alkyl, —C(O)NH$_2$ or —C(O)NH-alkyl.

Also included are methods of treating or prophylactically treating a subject who has been or is likely to be infected with a virus of the Flaviviridae family, comprising administering a clemizole, clemizole analog, or an isostere thereof, or their respective pharmaceutically acceptable salts, isomers, tautomers or prodrugs, in combination with one or more additional therapeutic agent(s), including, without limitation, an HCV NS3 protease inhibitor, an HCV NS5B RNA-dependent RNA polymerase inhibitor, a thiazolide, including but not limited to a sustained release thiazolide, a nucleoside analog, an interferon-alpha, a pegylated interferon, ribavirin, levovirin, viramidine, a TLR7 agonist, a TLR9 agonist, a cyclophilin inhibitor, an alpha-glucosidase inhibitor, an NS5A inhibitor, and an NS3 helicase inhibitor.

In another aspect of the invention, a compound of Formula I-a, or a pharmaceutically acceptable salt, isomer, tautomer or prodrug thereof, is provided wherein:

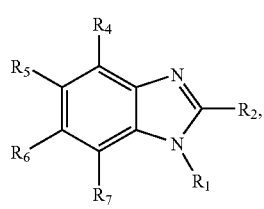

Formula I-a wherein $R_1$ is selected from the group consisting of:

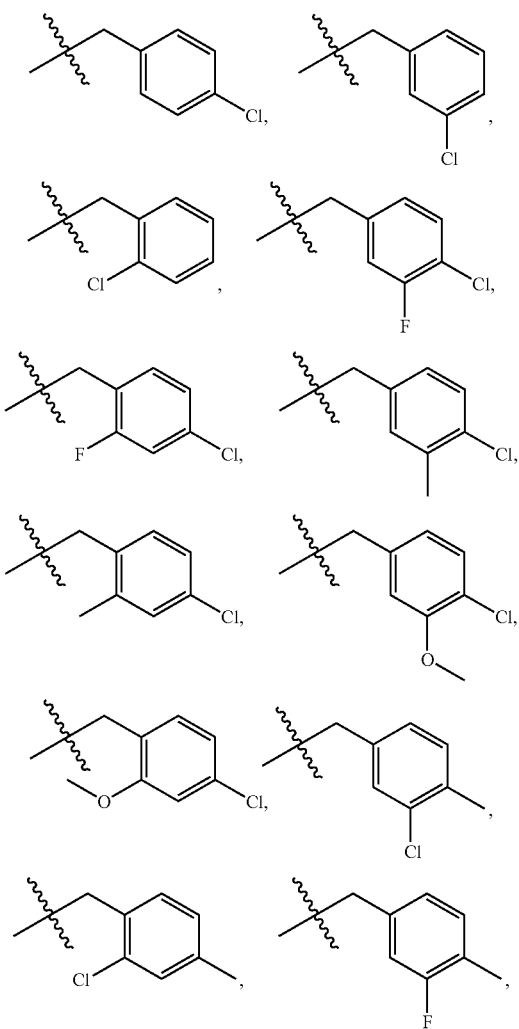

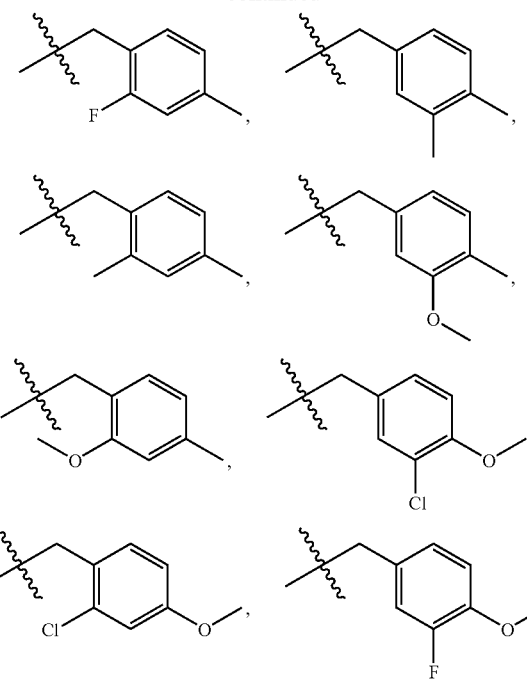

wherein $R_2$ is selected from the group consisting of: —$(CH_2)_n$—X, wherein n is 1 or 2, and X is selected from the group consisting of: —OH, aryl,

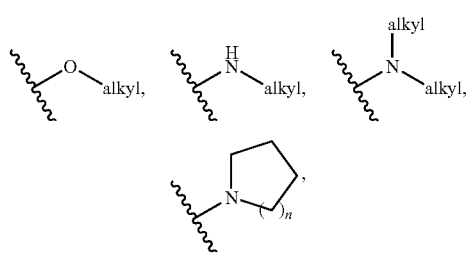

n = 2 or 3

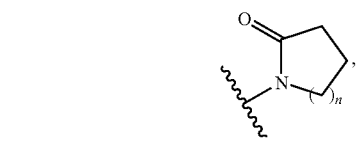

n = 1 or 2

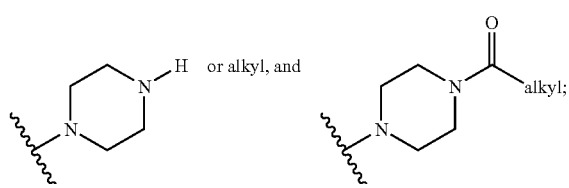

each of $R_4$-$R_7$ is independently selected from the group consisting of: —H, —Cl, —F, —CH$_3$, —OCH$_3$, —NH$_2$,

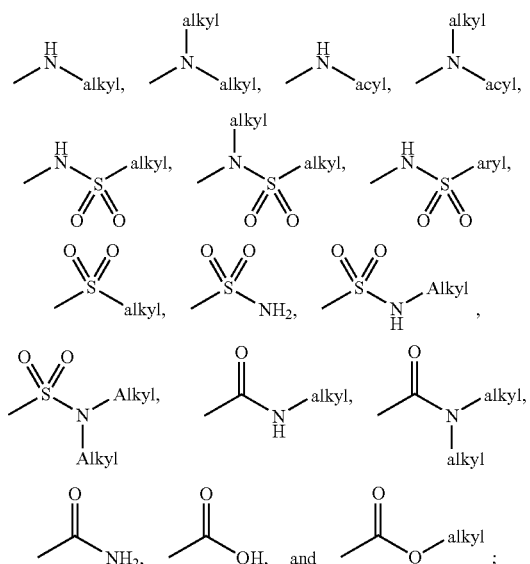

or, optionally, $R_5$ and $R_6$ are joined together with a bond to form a ring.

In a second aspect of the invention, a compound of Formula I-b, or a pharmaceutically acceptable salt, isomer, tautomer or prodrug thereof, is provided:

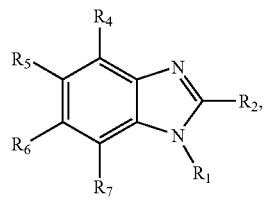

Formula I-b wherein $R_1$ is selected from the group consisting of:

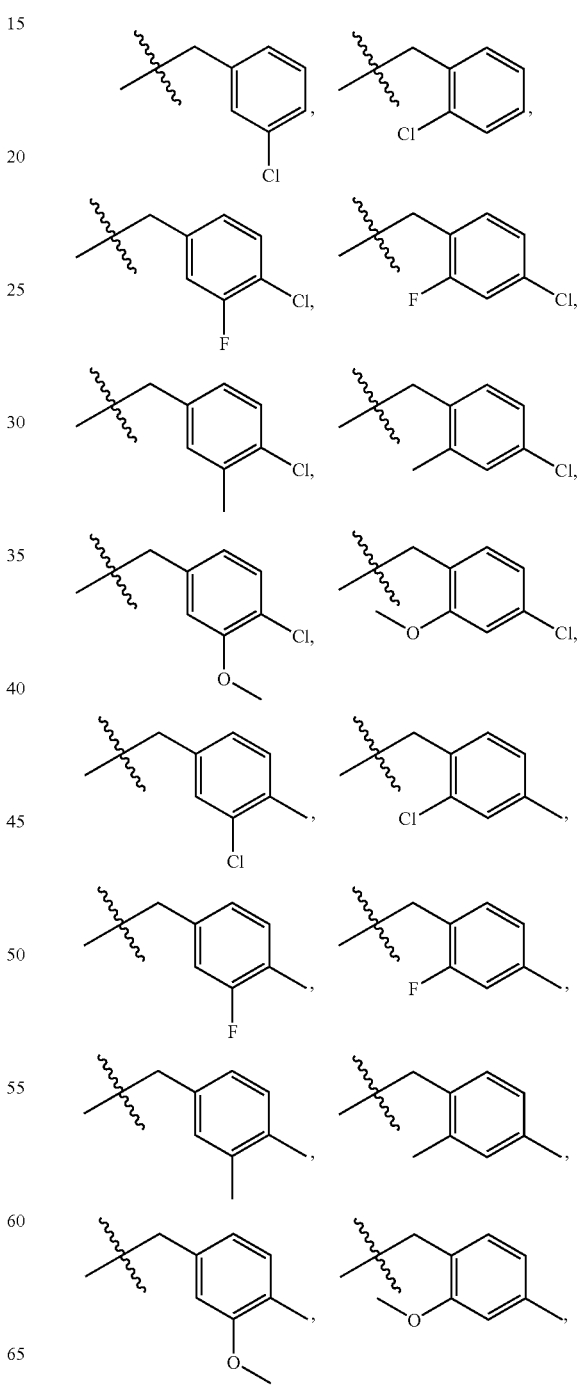

-continued

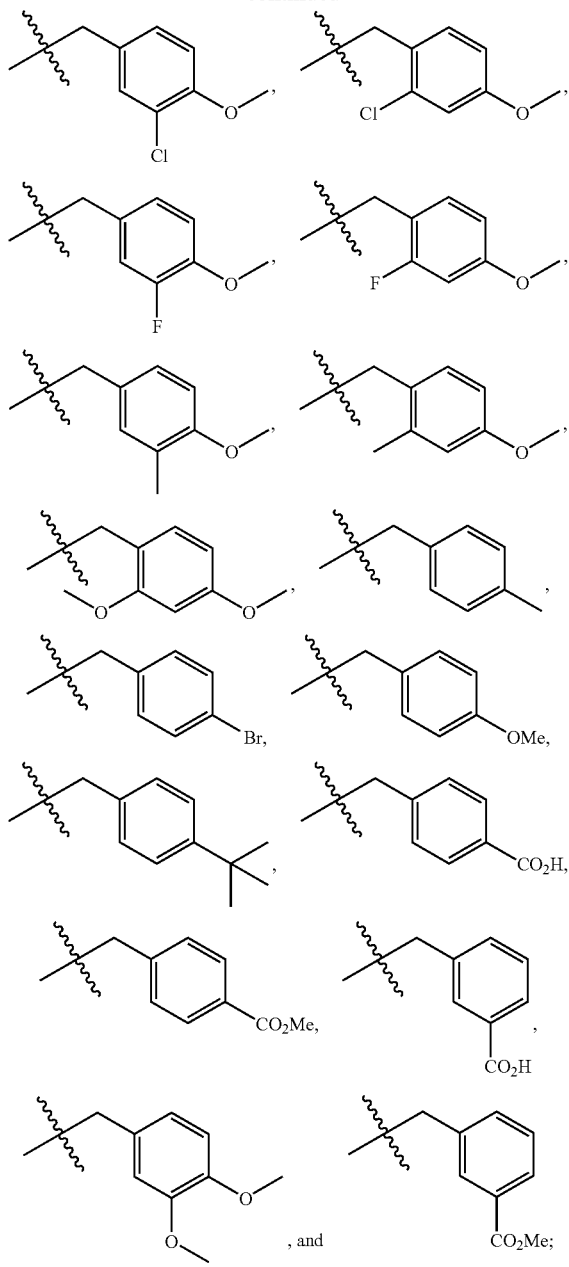

wherein $R_2$ is selected from the group consisting of —$(CH_2)_n$—X, wherein n is 1 or 2, and X is selected from the group consisting of: aryl,

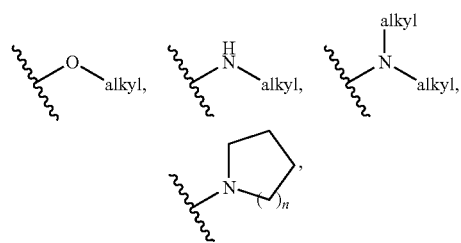

n = 1, 2, or 3

-continued

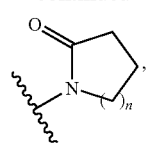

n = 1, or 2

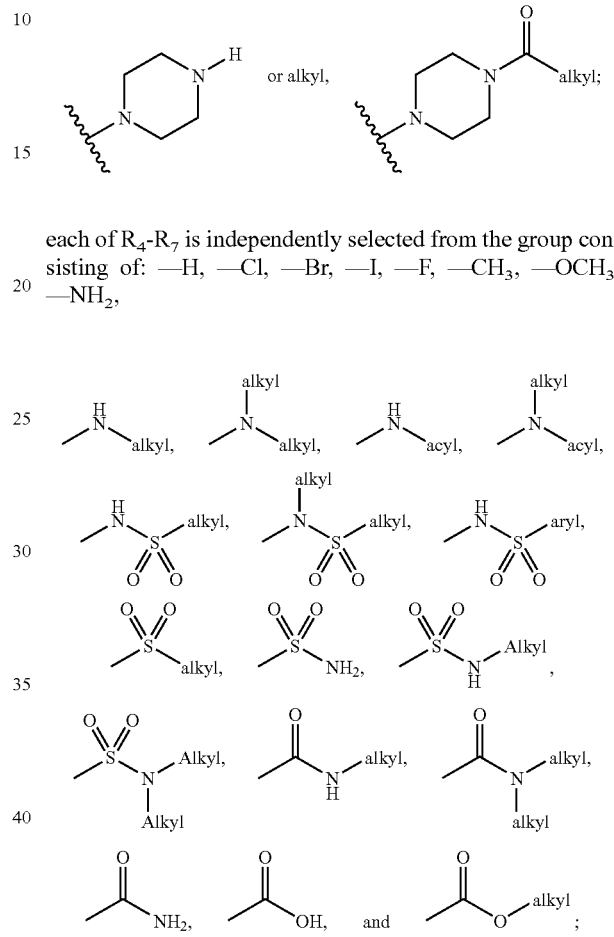

each of $R_4$-$R_7$ is independently selected from the group consisting of: —H, —Cl, —Br, —I, —F, —CH$_3$, —OCH$_3$, —NH$_2$, or, optionally, $R_5$ and $R_6$ are joined together with a bond to form a ring. In some embodiments, $R_1$ is 4-chlorobenzyl and $R_4$ and $R_7$ are hydrogen. In other embodiments, $R_2$ is CH$_2$OH.

In a third aspect of the invention, a compound of Formula I-c, or a pharmaceutically acceptable salt, isomer, tautomer or prodrug thereof, is provided:

Formula I-c

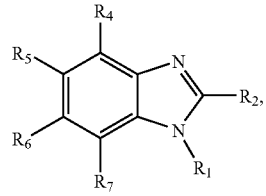

wherein $R_1$ is selected from the group consisting of:
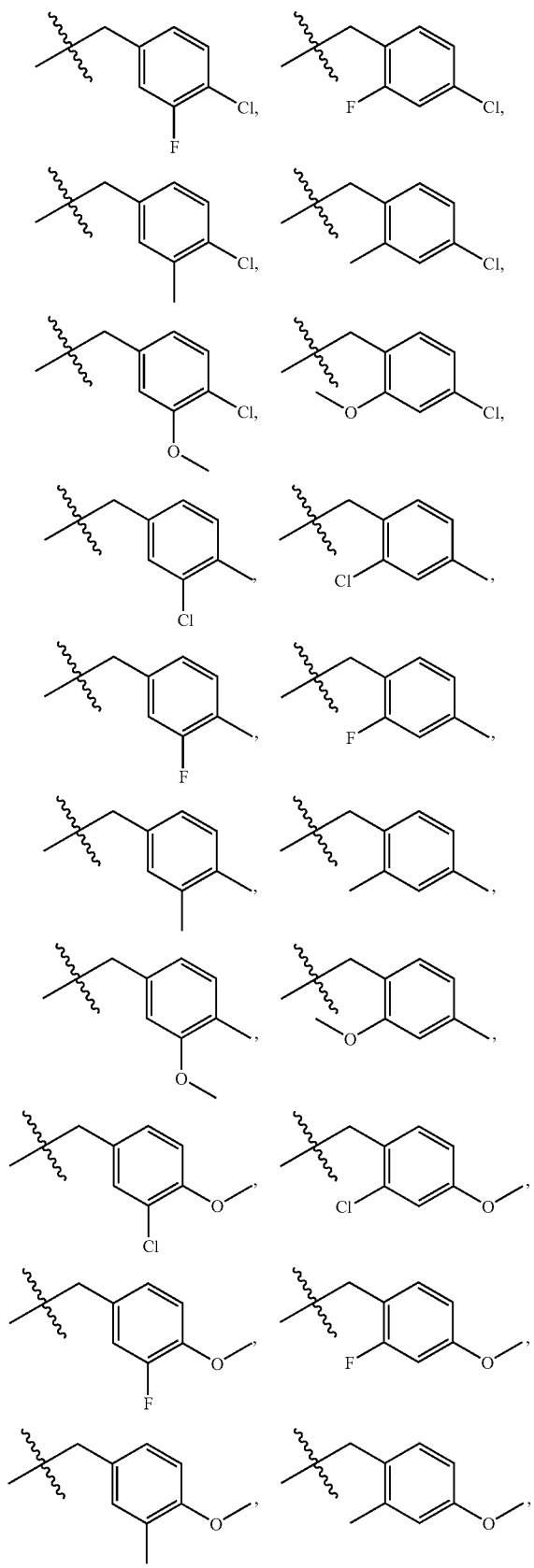
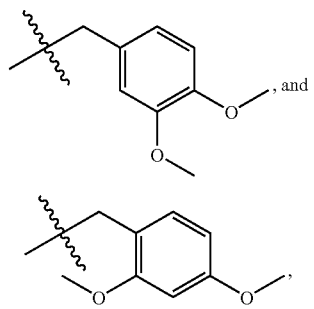
$R_2$ is $CF_3$; and each of $R_4$-$R_7$ is hydrogen.
In a fourth aspect of the invention, a compound of Formula I-d, or a pharmaceutically acceptable salt, isomer, tautomer or prodrug thereof:
Formula I-d
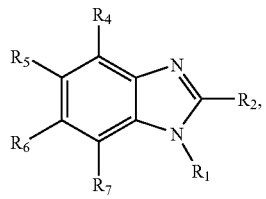
wherein $R_1$ is selected from the group consisting of:
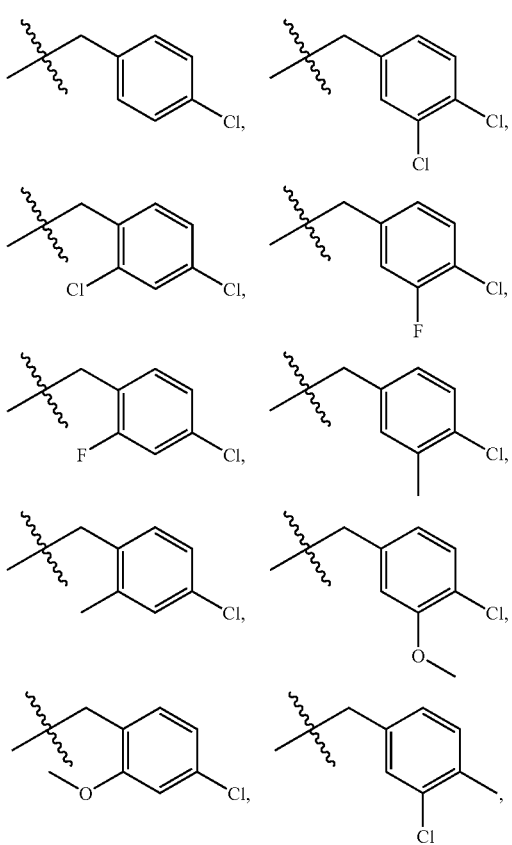

-continued
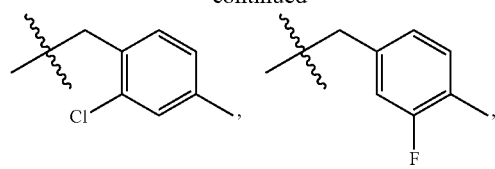
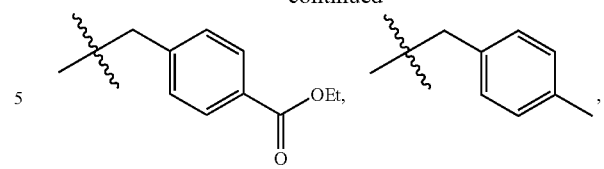
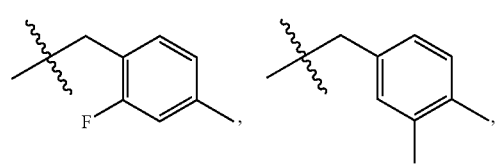
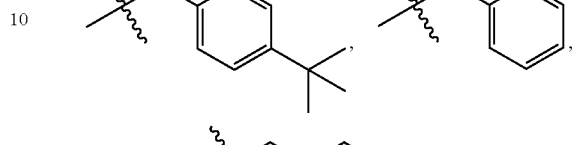
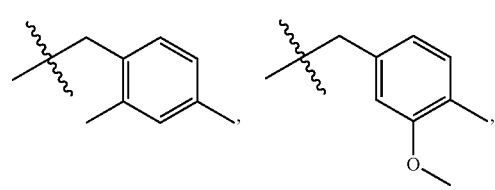
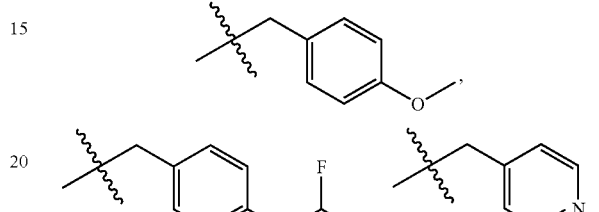
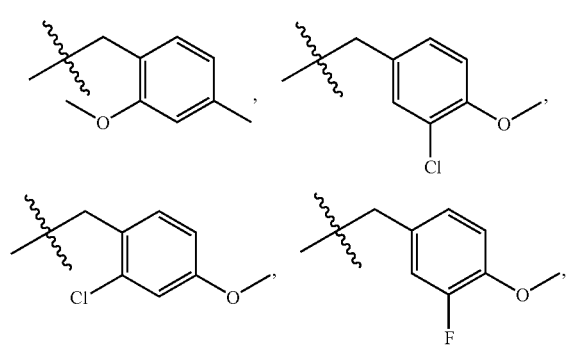
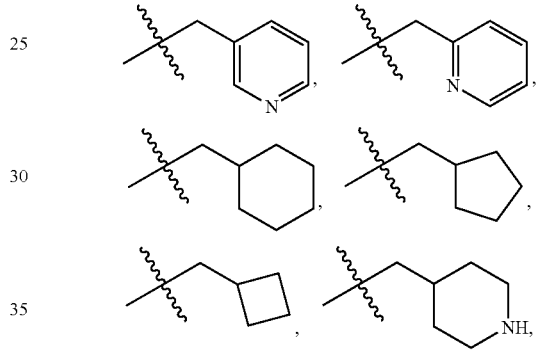
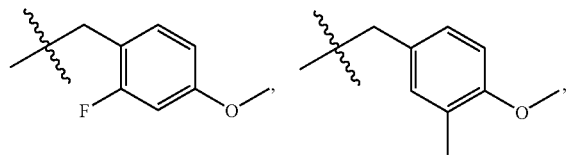
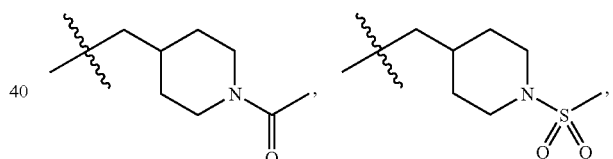
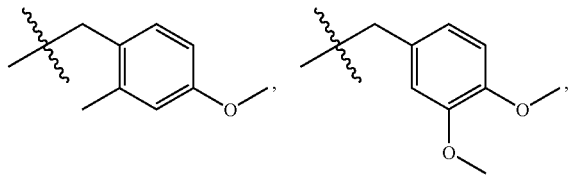
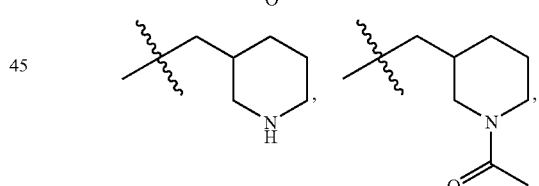
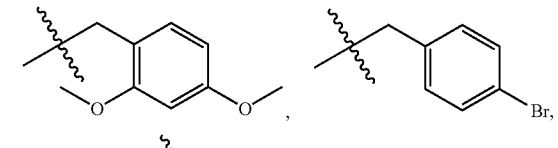
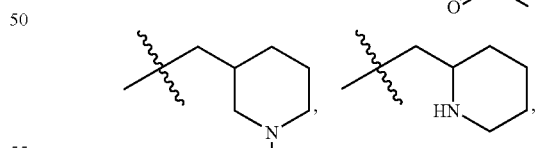
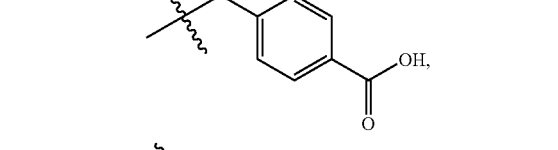
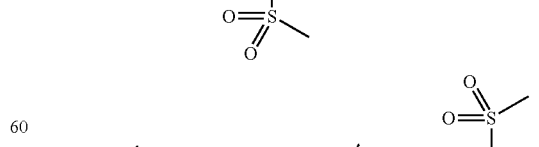
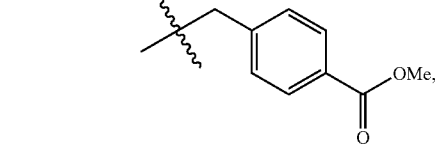
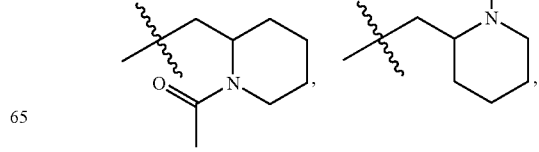

-continued
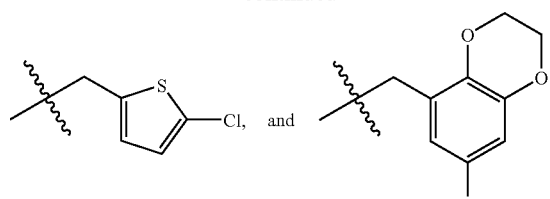 and 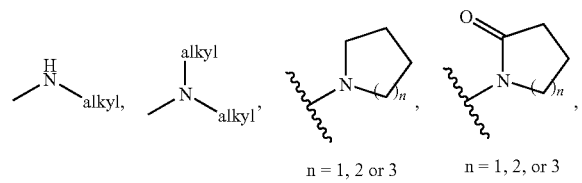;
R₂ is 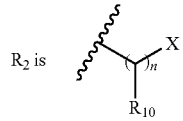
n = 0, 1, 2, 3, 4,
n is 1 or 2, and wherein X is selected from the group consisting of: —CF₃, —OH, -aryl, —CH(CH₃)OH,
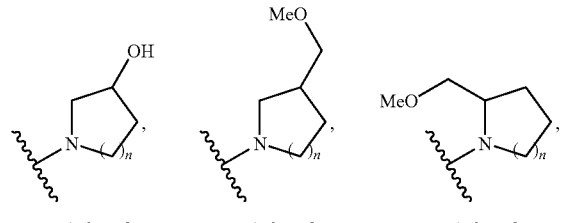
-continued
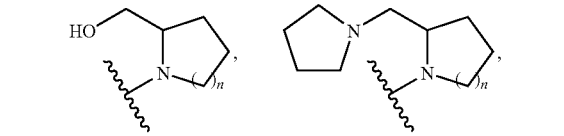
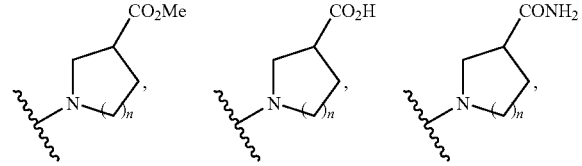
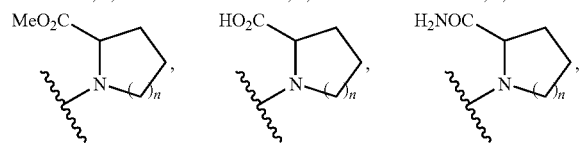
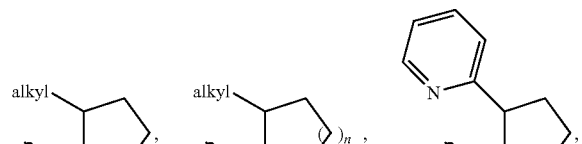
each of R₄-R₇ is independently selected from the group consisting of: —H, —Cl, —F, —CH₃, —OCH₃,

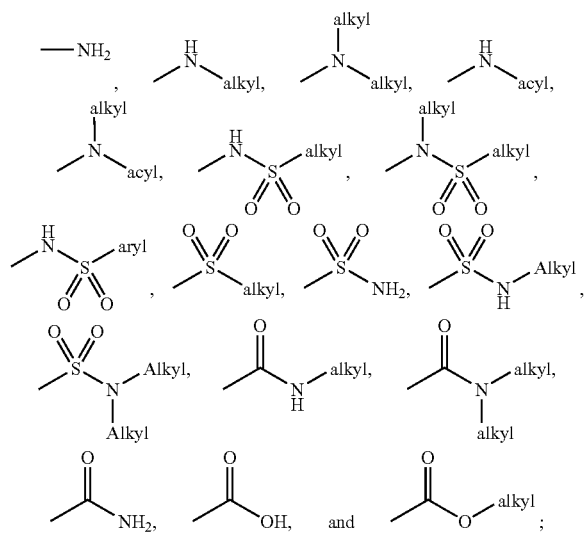

or, optionally, $R_5$ and $R_6$ are joined together with a bond to form a ring; and provided that the compound of Formula I-d is not clemizole, and is not the compound having the following structure:

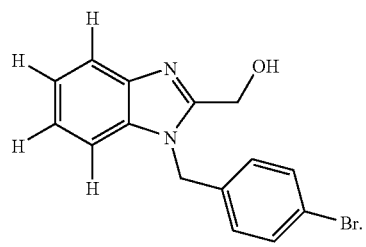 [SMILES: OCc1nc2ccccc2n1Cc1ccc(Br)cc1]

In some embodiments of the compound of Formula I-d, $R_1$ is 4-chlorobenzyl and $R_4$ and $R_7$ are hydrogen.

In other embodiments, the compound has a structure of Formula XXXX:

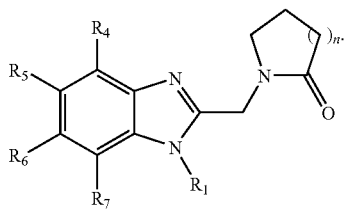

Additionally, the compound of Formula I-d may have a structure of the following formula:

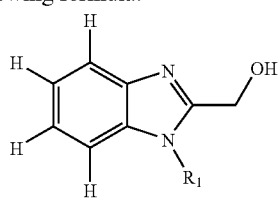

wherein $R_1$ is not para-bromobenzyl.

In a fifth aspect of the invention, a compound of Formula I having a structure of Formula XXXXI, or a pharmaceutically acceptable salt, isomer, tautomer or prodrug thereof, is provided:

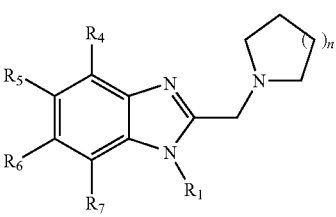

wherein $R_1$ is selected from the group consisting of: —H or

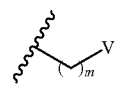

m=0, 1, 2 wherein V is selected from alkyl, cycloalkyl, heterocyclo, aryl or heteroaryl, and n is 0, 1 or 2;

each of $R_4$-$R_7$ is independently selected from the group consisting of: —H, —Br, —I, —Cl, —F, —$CH_3$, —CN, —OH, —$OCH_3$, —$NO_2$, —$NH_2$,

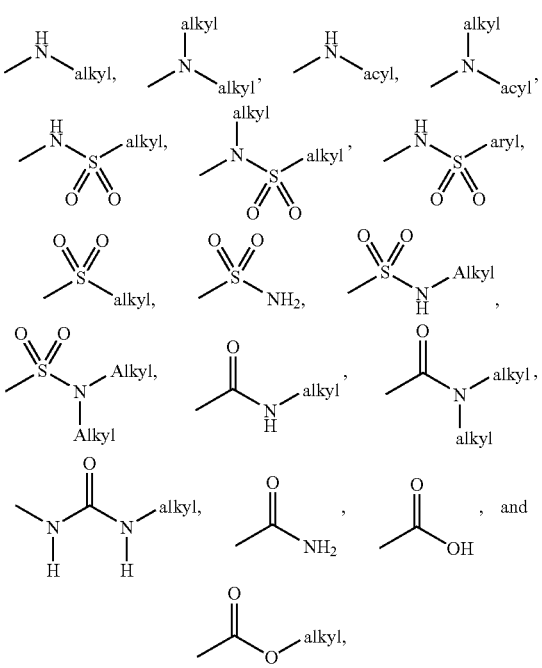

or, optionally, $R_4$ and $R_5$, $R_5$ and $R_6$, or $R_6$ and $R_7$ are joined together with a bond to form a 5, 6, or 7-membered ring; or, optionally, $R_4$ and $R_5$, $R_5$ and $R_6$, or $R_6$ and $R_7$ are joined together to form a 1,2-(methylenedioxy)benzene ring system; at least one of $R_4$-$R_7$ is not hydrogen; and wherein when n is 1, and $R_4$ and $R_7$ are hydrogen, then $R_5$ and $R_6$ are not both methoxy. In some embodiments, n is 1 and $R_5$ is —$S(O)_2$ alkyl, —$S(O)_2NH_2$, or —$S(O)_2NH(alkyl)$.

In a sixth aspect of the invention, a compound of Formula I having a structure of Formula XXXV, or a pharmaceutically acceptable salt, isomer, tautomer or prodrug thereof, is provided:

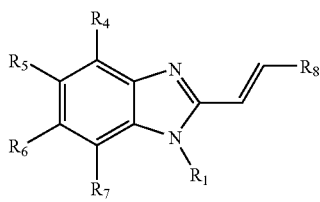

Formula XXXV wherein R₁ is selected from the group consisting of: —H and

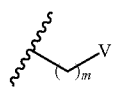

m=0, 1, 2, wherein V is selected from alkyl, cycloalkyl, heterocyclo, aryl or heteroaryl, and m is 0, 1 or 2;

each of R₄-R₇ is independently selected from the group consisting of: —H, —I, —Br, —Cl, —F, —CH₃, —CN, —OH, —OCH₃, —NO₂, —NH₂,

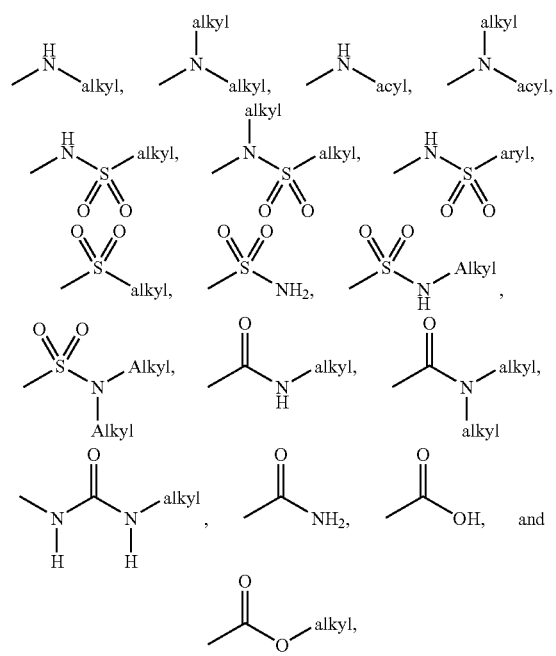

or, optionally, R₄ and R₅, R₅ and R₆, or R₆ and R₇ are joined together with a bond to form a 5, 6, or 7-membered ring; or, optionally, R₄ and R₅, R₅ and R₆, or R₆ and R₇ are joined together to form a 1,2-(methylenedioxy)benzene ring system; R₈ is alkyl, aryl or heteroaryl, and wherein when R₅ and R₆ are both methyl, and R₄ and R₇ are hydrogen, then R₈ is not phenyl. In some of the embodiments of the compound of Formula XXXV, heteroaryl is 2-pyridyl, 3-pyridyl or 4-pyridyl. In other embodiments of the compound of Formula XXXV, R₄ is selected from the group consisting of:

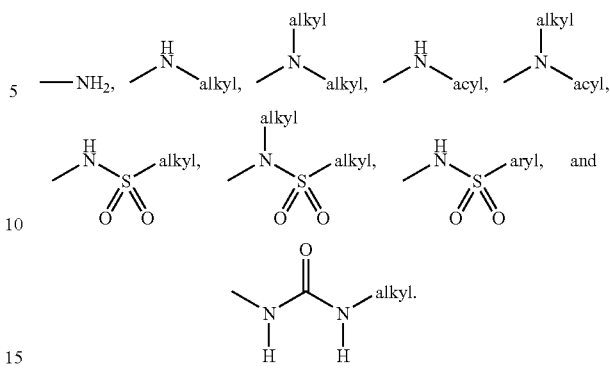

In a seventh aspect of the invention, a compound of Formula I having a structure of Formula I-e, or a pharmaceutically acceptable salt, isomer, tautomer or prodrug thereof, is provided:

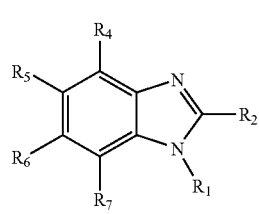

Formula I-e wherein R₁ is selected from the group consisting of: —H and

m=0, 1, 2 wherein V is selected from alkyl, cycloalkyl, heterocyclo, aryl or heteroaryl, and m is 0, 1 or 2; R₂ is selected from the group consisting of: —H,

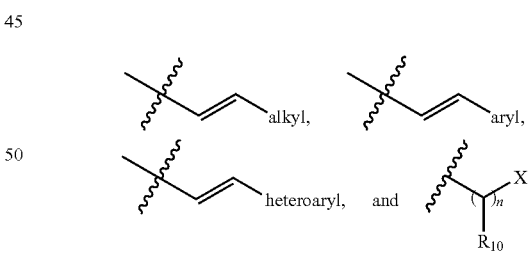

n = 0, 1, 2, 3, 4;

wherein X is selected from the group consisting of: —NH₂, —NH(alkyl), —N(alkyl)₂, CONH(alkyl), COHC(aryl), —OH, -alkyl, cycloalkyl, alkenyl, —CF₃, —O-alkyl, —O-cycloalkyl, —O-heterocyclo, -aryl, heteroaryl, N-attached heterocyclo, C-attached heterocyclo, —SH, —SO₂(alkyl), —S(alkyl), and —S(aralkyl); R₄ is selected from the group consisting of:

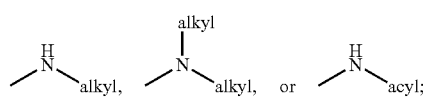

each of $R_5$-$R_7$ is independently selected from the group consisting of: —H, —I, —Br, —Cl, —F, —CH, —CN, —OH, —OCH$_3$, —NO$_2$, —NH$_2$,

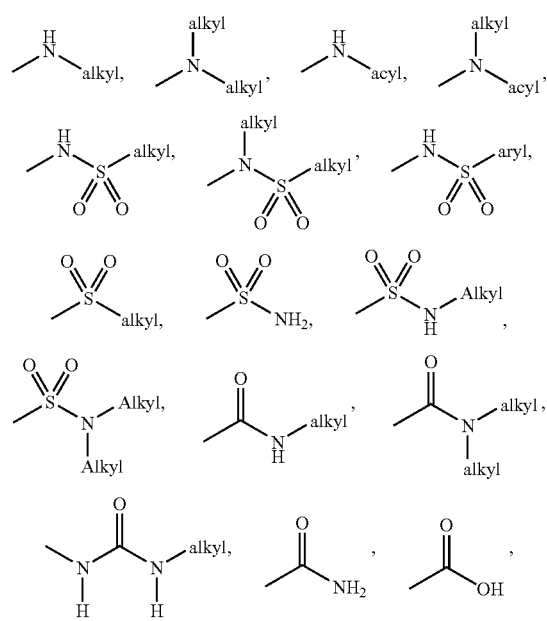

and

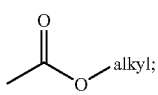

or, optionally, $R_4$ and $R_5$, $R_5$ and $R_6$, or $R_6$ and $R_7$ are joined together with a bond to form a 5, 6, or 7-membered ring; or, optionally, $R_4$ and $R_5$, $R_5$ and $R_6$, or $R_6$ and $R_7$ are joined together to form a 1,2-(methylenedioxy)benzene ring system; $R_{10}$ is hydrogen or alkyl; and wherein when $R_4$ is

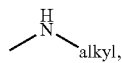

at least one of $R_5$-$R_7$ is not hydrogen.

In an eighth aspect of the invention, a compound of Formula I having a structure of Formula I-f, or a pharmaceutically acceptable salt, isomer, tautomer or prodrug thereof, is provided:

Formula I-f

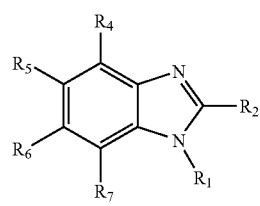

wherein $R_1$ is selected from the group consisting of: —H and

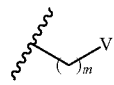

m=0, 1, 2 wherein V is selected from cycloalkyl or heterocyclo, and m is 0, 1 or 2; $R_2$ is selected from the group consisting of:

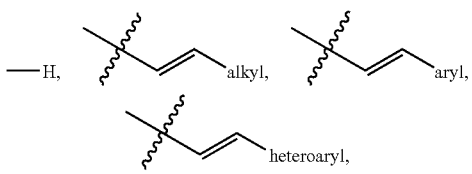

and

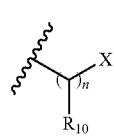

n=0, 1, 2, 3, 4; wherein X is selected from the group consisting of: —NH$_2$, —NH(alkyl), —N(alkyl)$_2$, CONH(alkyl), COHC(aryl), —OH, -alkyl, cycloalkyl, alkenyl, —CF$_3$, —O(alkyl), -aryl, heteroaryl, N-attached heterocyclo, C-attached heterocyclo, —SH, —SO$_2$(alkyl), —S(alkyl), and —S(aralkyl); each of $R_4$-$R_7$ is independently selected from the group consisting of: —H, —I, —Br, —Cl, —F, —CH$_3$, —CN, —OH, —OCH$_3$, —NO$_2$, —NH$_2$,

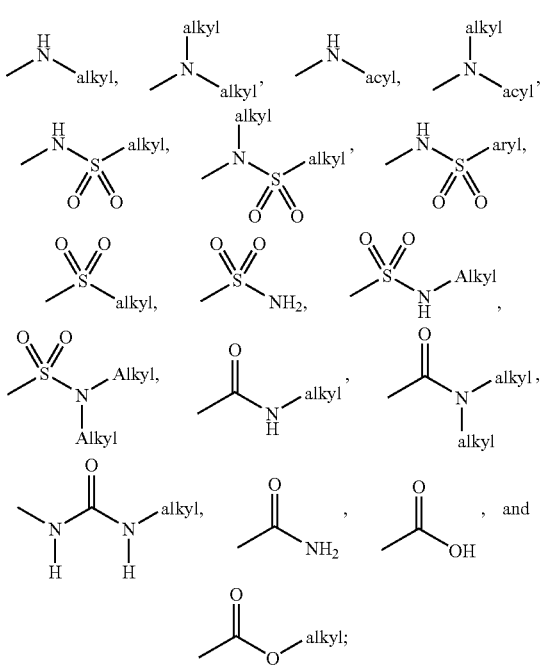

or, optionally, $R_4$ and $R_5$, $R_5$ and $R_6$, or $R_6$ and $R_7$ are joined together with a bond to form a 5, 6, or 7-membered ring; or, optionally, $R_4$ and $R_5$, $R_5$ and $R_6$, or $R_6$ and $R_7$ are joined together to form a 1,2-(methylenedioxy)benzene ring system; and $R_{10}$ is hydrogen or alkyl.

In a ninth aspect of the invention, a compound of Formula I having a structure of Formula XXXXI, or a pharmaceutically acceptable salt, isomer, tautomer or prodrug thereof, is provided:

Formula XXXXI

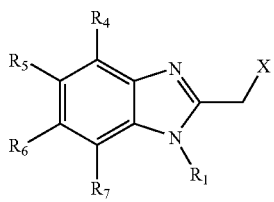

wherein X is selected from the group consisting of: —OH, alkyl, cycloalkyl, heteroaryl, —O(CH$_2$)$_d$CH$_3$, —O-cycloalkyl, or —O-heterocyclo; d is 1, 2, or 3; $R_1$ is selected from the group consisting of: —H and

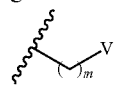

m=0, 1, 2 wherein V is selected from alkyl, cycloalkyl, heterocyclo, aryl or heteroaryl, and m is 0, 1 or 2; each of $R_4$-$R_7$ is independently selected from the group consisting of: —H, —Br, —Cl, —F, —CH$_3$, —CN, —OH, —OCH$_3$, —NO$_2$, —NH$_2$,

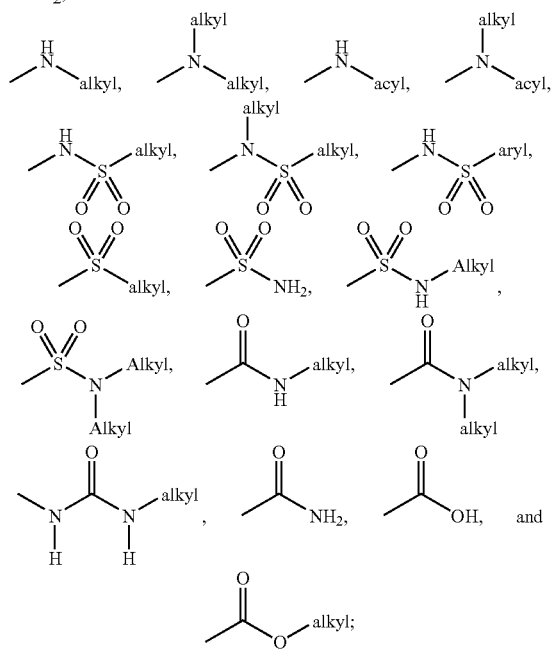

or, optionally, $R_4$ and $R_5$, $R_5$ and $R_6$, or $R_6$ and $R_7$ are joined together with a bond to form a 5, 6, or 7-membered ring; or, optionally, $R_4$ and $R_5$, $R_5$ and $R_6$, or $R_6$ and $R_7$ are joined together to form a 1,2-(methylenedioxy)benzene ring system; and wherein at least one of $R_4$-$R_7$ is other than hydrogen.

In a tenth aspect of the invention, a pharmaceutical composition is provided comprising a compound of any one of Formulae I-XXXXI, or a pharmaceutically acceptable salt, isomer, tautomer or prodrug thereof.

In an eleventh aspect of the invention, a pharmaceutical composition is provided, comprising a compound of any one of Formulae I-XXXXI, or a pharmaceutically acceptable salt, isomer, tautomer or prodrug thereof, and further comprising one or more additional anti-HCV therapeutic agents selected from the group consisting of: an HCV NS3 protease inhibitor, an HCV NS5B RNA-dependent RNA polymerase inhibitor, a thiazolide, a sustained release thiazolide, a nucleoside analog, an interferon-alpha, a pegylated interferon, ribavirin, levovirin, viramidine, a TLR7 agonist, a TLR9 agonist, a cyclophilin inhibitor, an alpha-glucosidase inhibitor, an NS5A inhibitor, and an NS3 helicase inhibitor.

In a twelfth aspect of the invention, a pharmaceutical composition is provided, comprising a compound of any one of Formulae I-XXXXI, or a pharmaceutically acceptable salt, isomer, tautomer or prodrug thereof, and at least one additional anti-HCV therapeutic agent selected from the group consisting of: an HCV NS3 protease inhibitor, an HCV NS5B RNA-dependent RNA polymerase inhibitor, a thiazolide, a sustained release thiazolide, a nucleoside analog, an interferon-alpha, a pegylated interferon, ribavirin, levovirin, viramidine, a TLR7 agonist, a TLR9 agonist, a cyclophilin inhibitor, an alpha-glucosidase inhibitor, an NS5A inhibitor, and an NS3 helicase inhibitor; wherein the compound of Formula I has the structure:

Formula I

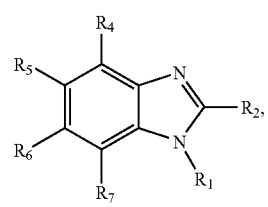

wherein $R_1$ is selected from the group consisting of: —H and

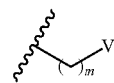

m=0, 1, 2; wherein V is selected from alkyl, cycloalkyl, heterocyclo, aryl or heteroaryl, and n is 0, 1 or 2; $R_2$ is selected from the group consisting of: —H and

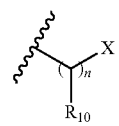

n=0, 1, 2, 3, 4; wherein X is selected from the group consisting of: —NH$_2$, —NH(alkyl), —N(alkyl)$_2$, —OH, -alkyl, cycloalkyl, alkenyl, —CF$_3$, —O-alkyl, -aryl, heteroaryl, N-attached heterocyclo, C-attached heterocyclo, —SH, —SO$_2$(alkyl), —S(alkyl), and —S(aralkyl); each of $R_4$-$R_7$ is independently selected from the group consisting of: —H, —Br, —Cl, —F, —CH$_3$, —CN, —OH, —OCH$_3$, —NO$_2$, —NH$_2$,

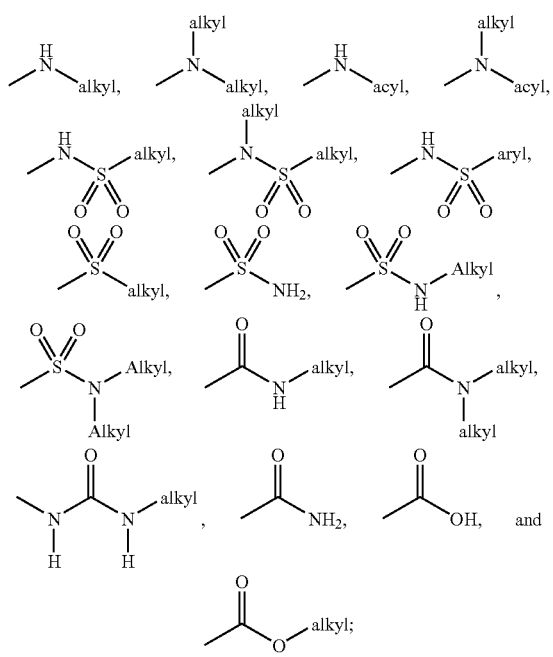

or, optionally, $R_4$ and $R_5$, $R_5$ and $R_6$, or $R_6$ and $R_7$ are joined together with a bond to form a 5, 6, or 7-membered ring; or, optionally, $R_4$ and $R_5$, $R_5$ and $R_6$, or $R_6$ and $R_7$ are joined together to form a 1,2-(methylenedioxy)benzene ring system; and $R_{10}$ is hydrogen or alkyl.

In some embodiments of the pharmaceutical compositions of the invention, the compound of formula (I) is clemizole hydrochloride and the at least one additional therapeutic agent is ribavirin. In some embodiments of the pharmaceutical compositions of the invention, the compound of formula (I) is clemizole hydrochloride and the at least one additional therapeutic agent is interferon-alpha.

BRIEF DESCRIPTION OF THE DRAWINGS

FIG. 2 illustrates baseline characteristics and serial HCV viral loads in the serum of patients.

FIG. 3 illustrates RNA strands for 5' untranslated region of the HCV positive strand RNA genome and the 3' untranslated region of the HCV negative strand RNA.

FIGS. 4B and 4C illustrate embodiments of synthesizing two 5,6-disubstituted clemizole compounds.

FIGS. 5a-5d illustrates that a small molecule screen reveals that clemizole hydrochloride inhibits RNA binding by NS4B and in vivo HCV RNA replication. FIG. 5a is a digital image of the first screen which represented a low stringency measurement of inhibition of 1280 compounds, where the latter were categorized as having high (light gray), ambiguous (black), or no (gray) inhibition. Based on the initial screen 214 compounds were then measured again with higher stringency and with greater number of replicates and the best 18 inhibitors were tested for their ability to inhibit HCV replication via an in vivo cellular assay. FIG. 5b illustrates a graph showing in vitro inhibition of NS4B-RNA binding by the top 18 small molecules. FIG. 5c is a graph showing in vivo HCV luciferase-linked reporter cellular assay showing that clemizole inhibits HCV replication (left axis, bottom line ♦) with no measurable toxicity to the cell as measured by Alamar Blue (right axis, top line □). FIG. 5d is a graph showing in vitro NS4B-RNA binding: inhibition curve of clemizole.

FIGS. 6a-6e illustrate results relating to clemizole-resistant mutants. Replicon cells were passaged in the presence of clemizole and individual colonies were isolated, propagated and the HCV genomes harbored within were subjected to sequence analysis. FIG. 6a is a schematic diagram indicating predicted transmembrane and intracellular segments of NS4B. Conserved positively-charged amino acids are shown as R or RR. The clemizole resistant mutation, WS5R, shown as W R. FIG. 6b is a graph that illustrates HCV replication in Huh7.5 cells electroporated with 50 μg of whole cell RNA extracted from cells harboring either wild-type or the W55R mutant clone, followed by growth in the absence (white bars) or presence (grey bars) of 10 μM clemizole. Results represent relative numbers of colonies obtained compared to each corresponding untreated control. FIG. 6c illustrates the HCV replication assays initiated by electroporation of in vitro transcribed luciferase reporter-linked wild-type or W55R mutant HCV RNA genomes performed in the absence (white bars) or presence (grey bars) of 10 μM clemizole. Results represent replication level of each genome relative to its untreated level. FIG. 6d illustrates HCV RNA binding of wild type NS4B and the W55R NS4B mutant as measured in vitro by microfluidics in the presence of 10 nM clemizole (grey bars) and its absence (white bars). FIG. 6e illustrates in vitro binding curves of W55R NS4B mutant (solid line, o) and wild type NS4B (broken line, ▲) to serial dilutions of the RNA probe.

FIGS. 7a-7c illustrate results from the microfluidics-based analysis of RNA binding by another human protein from the ELAV-like family, HuR (ELAV L1). FIG. 7a illustrates the target RNA sequences used to study binding of HuR to RNA and the phenotype demonstrated by conventional RNA binding methods (EMBO J 16, 2130-2139 (1997), which is incorporated herein by reference).

FIG. 7b illustrates that HuR binds RNA by microfluidics. A microarray of Cy3-labeled target RNA sequences was used to program a microfluidic device and binding of bodily-labeled proteins expressed on the device to the RNA sequences was assayed. Results represent the ratio of bound RNA (median Cy3 signal) to expressed protein (median bodipy signal). Normalized mean values for 10-20 replicates measured in two independent experiments are shown. Error bars represent standard deviation. The grey bars represent binding of HuR-his and the clear bars that of Gus-his, used as a negative control.

FIG. 7c illustrates that HUR binding is not affected by the 5 most active compounds, but is affected by ATA. We tested binding of HUR to its 4A RNA target in the presence and absence of NS4B RNA binding inhibitors. Data represent mean value of 10-20 replicates and bars represent standard deviation

FIG. 10A illustrates the effect of increasing doses of clemizole on HCV replication in the presence of increasing doses of SCH503034. FIG. 10B is an isobolgram of clemizole and SCH503034 induced inhibition of HCV replication which illustrates that the EC50, EC70, and EC90 values all exhibit synergistic activity of SCH50304 in combination with clemizole. FIG. 10C illustrates the combination indices for combination inhibition of HCV replication with clemizole and SCH503034 at the EC50, EC70, and EC90 levels as calculated using Calcusyn Software™. FIG. 10D illustrates an analysis of HCV replication data using Bliss Independence Theory as implemented in MacSynergy II. The graph is a three dimensional differential surface plot, wherein synergy is demonstrated by peaks above a theoretical additive plane and antagonism is represented by depressions below the plane.

FIG. 11A illustrates an analysis of a luciferase reporter gene assay of HCV genotype 1b replication using Bliss Independence Theory as implemented in MacSynergy II.

FIG. 13A illustrates MacSynergy analysis of clemizole and interferon combination treatment for inhibiting HCV replication using data from a luciferase reporter gene assay. The results suggest that the combination treatment of clemizole and interferon exhibit additive effects. FIG. 13B illustrates the additive effect of combination treatment with clemizole and the HCV nucleoside analog polymerase inhibitor NM 283. FIG. 13C illustrates the additive effect of combination treatment with clemizole and the HCV non-nucleoside analog polymerase inhibitor HCV 796.

FIG. 15 illustrates Table 7.

FIG. 16 illustrates Table 8, which is a specification data sheet.

DETAILED DESCRIPTION

Figure 1A:
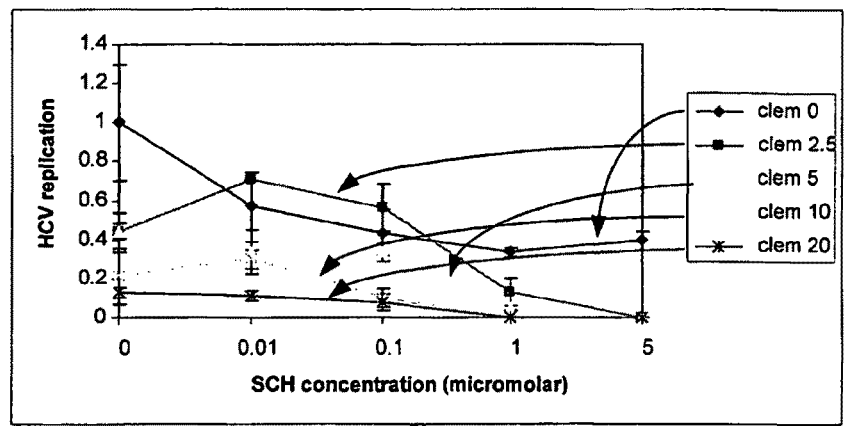
FIGS. 1A and 1B HCV show graphs illustrating data from replication assays employing a luciferase reporter-linked HCV genome in the presence of various combinations of clemizole and an NS3 protease inhibitor (SCH503034).

Before the present invention is described in greater detail, it is to be understood that this invention is not limited to particular embodiments described, and the embodiment of the invention as such may, of course, vary. It is also to be understood that the terminology used herein is for the purpose of describing particular embodiments only, and is not intended to be limiting, because the scope of the present disclosure will be limited only by the appended claims.

Unless defined otherwise, all technical and scientific terms used herein have the same meaning as commonly understood by one of ordinary skill in the art to which this invention belongs.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of synthetic organic chemistry, biochemistry, biology, molecular biology, recombinant DNA techniques, pharmacology, and the like, which are within the skill of the art. Such techniques are explained fully in the literature.

The examples herein are put forth so as to provide those of ordinary skill in the art with an illustrative disclosure and description of how to perform the methods and use the compounds disclosed and claimed herein. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also contemplated that, where multi-step processes are described in the present disclosure that steps can be executed in different sequence where this is logically possible.

As used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

A. DEFINITIONS

In describing and claiming the disclosed subject matter, the following terminology will be used in accordance with the definitions set forth below.

By "Flaviviridae virus" is meant any virus of the Flaviviridae family, including those viruses that infect humans and non-human animals. The polynucleotide and polypeptides sequences encoding these viruses are well known in the art, and may be found at NCBI's GenBank database, e.g., as Genbank Accession numbers NC_004102, AB031663, D11355, D11168, AJ238800, NC_001809, NC_001437, NC_004355 NC_004119, NC_003996, NC_003690, NC_003687, NC_003675, NC_003676, NC_003218, NC_001563, NC_000943, NC_003679, NC_003678, NC_003677, NC_002657, NC_002032, and NC_001461, the contents of which database entries are incorporated by references herein in their entirety.

As used herein, the terms "treatment", "treating", and "treat" are defined as acting upon a disease, disorder, or condition with an agent to reduce or ameliorate the pharmacologic and/or physiologic effects of the disease, disorder, or condition and/or its symptoms. "Treatment," as used herein, covers any treatment of a disease in a host (e.g., a mammal, typically a human or non-human animal of veterinary interest), and includes: (a) reducing the risk of occurrence of the disease in a subject determined to be predisposed to the disease but not yet diagnosed as infected with the disease (b) impeding the development of the disease, and (c) relieving the disease, i.e., causing regression of the disease and/or relieving one or more disease symptoms. "Treatment" is also meant to encompass delivery of an inhibiting agent to provide a pharmacologic effect, even in the absence of a disease or condition. For example, "treatment" encompasses delivery of a disease or pathogen inhibiting agent that provides for enhanced or desirable effects in the subject (e.g., reduction of pathogen load, reduction of disease symptoms, and the like.).

As used herein, the terms "prophylactically treat" and "prophylactically treating" refer completely or partially preventing a disease or symptom thereof and/or may be therapeutic in terms of a partial or complete cure for a disease and/or adverse effect attributable to the disease.

As used herein, the term "host," "subject," "patient," or "organism" includes humans and mammals (e.g., mice, rats, pigs, cats, dogs, and horses). Typical hosts to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living host" refers to a host noted above or another organism that is alive. The term "living host" refers to the entire host or organism and not just a part excised (e.g., a liver or other organ) from the living host.

The terms "isolated compound" and "purified compound" mean a compound which has been substantially separated from, or enriched relative to, other compounds with which it occurs in nature. Isolated compounds are usually at least about 80%, at least 90% pure, at least 98% pure, or at least about 99% pure, by weight. The present disclosure is meant to include diastereomers as well as their racemic and resolved, enantiomerically pure forms and pharmaceutically acceptable salts thereof.

The term "unit dosage form," as used herein, refers to physically discrete units suitable as unitary dosages for human and/or animal subjects, each unit containing a predetermined quantity of a compound (e.g., an anti-viral compound, as described herein) calculated in an amount sufficient to produce the desired effect in association with a pharmaceutically acceptable diluent, carrier or vehicle. The specifications for unit dosage forms depend on the particular compound employed, the route and frequency of administration, and the effect to be achieved, and the pharmacodynamics associated with each compound in the host.

A "pharmaceutically acceptable excipient," "pharmaceutically acceptable diluent," "pharmaceutically acceptable carrier," and "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one or more such excipients, diluents, carriers, and adjuvants.

As used herein, a "pharmaceutical composition" and a "pharmaceutical formulation" are meant to encompass a composition suitable for administration to a subject, such as a mammal, especially a human. In general a "pharmaceutical composition" or "pharmaceutical formulation" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intracheal, intramuscular, subcutaneous, inhalational and the like.

The terms "therapeutically effective amount" and "an effective amount" are used interchangeably herein and refer to that amount of an agent (which may be referred to as a compound, an inhibitory agent, and/or a drug) being administered that is sufficient to effect the intended application including but not limited to disease treatment. For example, an effective amount of an inhibiting agent will relieve to some extent one or more of the symptoms of the disease, i.e., infection, being treated, and/or that amount that will prevent, to some extent, one or more of the symptoms of the disease, i.e., infection, that the host being treated has or is at risk of developing. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. inhibiting viral replication in a target cell, and inhibiting NS4B binding to viral RNA. The specific dose will vary depending on the particular compounds chosen, the dosing regimen to be followed, whether it is administered in combination with other compounds, timing of administration, the tissue to which it is administered, and the physical delivery system in which it is carried.

"Pharmaceutically acceptable salt" refers to those salts (organic or inorganic) that retain the biological effectiveness and optionally other properties of the free bases. Pharmaceutically acceptable salts can be obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

In the event that embodiments of the disclosed agents form salts, these salts are within the scope of the present disclosure. Reference to an agent of any of the formulas herein is understood to include reference to salts thereof, unless otherwise indicated. The term "salt(s)", as employed herein, denotes acidic and/or basic salts formed with inorganic and/or organic acids and bases. In addition, when an agent contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds of an agent may be formed, for example, by reacting the agent with an amount of acid or base, such as an equivalent amount, in a medium such as one in which the salt precipitates or in an aqueous medium followed by lyophilization.

Embodiments of the agents that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, malates (salts formed with malic acid), maleates (formed with maleic acid), ethanesulfonates (formed with ethanesulfonic acid), methanesulfonates (formed with methanesulfonic acid), 2-naphthalenesulfonates, nicotinates, nitrates, oxalates, pectinates, persulfates, 3-phenylpropionates, phosphates (formed with phosphoric acid), picrates, pivalates, propionates, salicylates, succinates, sulfates (such as those formed with sulfuric acid), sulfonates (such as those mentioned herein including those formed with p-toluenesulfonic acid), tartrates, thiocyanates, toluenesulfonates such as tosylates, undecanoates, and the like.

Embodiments of the agents that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Solvates of the agents of the disclosure are also contemplated herein.

To the extent that the disclosed active compounds, and salts thereof, may exist in their tautomeric form, all such tautomeric forms are contemplated herein as part of the present disclosure.

All stereoisomers of the agents, such as those that may exist due to asymmetric carbons on the various substituents, including enantiomeric forms (which may exist even in the absence of asymmetric carbons) and diastereomeric forms, are contemplated within the scope of this disclosure. Individual stereoisomers of the compounds of the disclosure may, for example, be substantially free of other isomers, or may be admixed, for example, as racemates or with all other, or other selected, stereoisomers. The stereogenic centers of the compounds of the present disclosure can have the S or R configuration as defined by the IUPAC 1974 Recommendations.

The term "prodrug" refers to an inactive precursor of an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N.J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27:235-256; Mizen et al. (1998). The Use of Esters as Prodrugs for Oral Delivery of P-Lactam antibiotics, Pharm. Biotech. 11:345-365; Gaignault et al. (1996). Designing Prodrugs and Bioprecursors I. Carrier Prodrugs, Pract. Med. Chem. 671-696; M. Asghamejad (2000). Improving Oral Drug Transport Via Prodrugs, in G. L. Amidon, P. 1. Lee and E. M. Topp, Eds., Transport Processes in Pharmaceutical Systems, Marcell Dekker, p. 185-218; Balant et al. (1990) Prodrugs for the improvement of drug absorption via different routes of administration, Eur. J. Drug Metab. Pharmacokinet, 15(2): 143-53; Balimane and Sinko (1999). Involvement of multiple transporters in the oral absorption of nucleoside analogues, Adv. Drug Delivery Rev., 39(1-3):183-209; Browne (1997). Fosphenyloin (Cerebyx), Clin. Neuropharmacol. 20(1): 1-12; Bundgaard (1979). Bioreversible derivatization of drugs—principle and applicability to improve the therapeutic effects of drugs, Arch. Pharm. Chemi. 86(1): 1-39; H. Bundgaard, ed. (1985) Design of Prodrugs, New York: Elsevier; Fleisher et al. (1996). Improved oral drug delivery: solubility limitations overcome by the use of prodrugs, Adv. Drug Delivery Rev. 19(2): 115-130; Fleisher et al. (1985). Design of prodrugs for improved gastrointestinal absorption by intestinal enzyme targeting, Methods Enzymol. 112: 360-81; Farquhar D, et al. (1983). Biologically Reversible Phosphate-Protective Groups, J. Pharm. Sci., 72(3): 324-325; Han, H. K. et al. (2000). Targeted prodrug design to optimize drug delivery, AAPS PharmSci., 2(1): E6; Sadzuka Y. (2000). Effective prodrug liposome and conversion to active metabolite, Curr. Drug Metab, 1(1):31-48; D. M. Lambert (2000) Rationale and applications of lipids as prodrug carriers, Eur. J. Pharm. Sci., 11 Suppl 2:S15-27; Wang, W. et al. (1999) Prodrug approaches to the improved delivery of peptide drugs. Curr. Pharm. Des., 5(4):265-87.

The term "administration" refers to introducing an agent of the present disclosure into a host. One preferred route of administration of the agents is oral administration. Another preferred route is intravenous administration. However, any route of administration, such as topical, subcutaneous, peritoneal, intraarterial, inhalation, vaginal, rectal, nasal, introduction into the cerebrospinal fluid, or instillation into body compartments can be used.

The term "aliphatic group" refers to a saturated or unsaturated linear or branched hydrocarbon group and encompasses alkyl, alkenyl, and alkynyl groups, for example.

The terms "alk" or "alkyl" refers to straight or branched chain hydrocarbon groups having 1 to 12 carbon atoms, preferably 1 to 8 carbon atoms, such as methyl, ethyl, n-propyl, i-propyl, n-butyl, i-butyl, t-butyl, pentyl, hexyl, heptyl, n-octyl, dodecyl, octadecyl, amyl, 2-ethylhexyl, and the like. An alkyl group is optionally substituted, unless stated otherwise, with one or more groups, selected from aryl (optionally substituted), heterocyclo (optionally substituted), carbocyclo (optionally substituted), halo, hydroxy, protected hydroxy, alkoxy (e.g., $C_1$ to $C_7$) (optionally substituted), acyl (e.g., $C_1$ to $C_7$), aryloxy (e.g., $C_1$ to $C_7$) (optionally substituted), alkylester (optionally substituted), arylester (optionally substituted), alkanoyl (optionally substituted), aroyl (optionally substituted), carboxy, protected carboxy, cyano, nitro, amino, substituted amino, (monosubstituted)amino, (disubstituted) amino, protected amino, amido, lactam, urea, urethane, sulfonyl, and the like.

The term "alkenyl" refers to straight or branched chain hydrocarbon groups having 2 to 12 carbon atoms, preferably 2 to 4 carbon atoms, and at least one double carbon to carbon bond (either cis or trans), such as ethenyl. An alkenyl group is optionally substituted, unless stated otherwise, with one or more groups, selected from aryl (including substituted aryl), heterocyclo (including substituted heterocyclo), carbocyclo (including substituted carbocyclo), halo, hydroxy, alkoxy (optionally substituted), aryloxy (optionally substituted), alkylester (optionally substituted), arylester (optionally substituted), alkanoyl (optionally substituted), aroyl (optionally substituted), cyano, nitro, amino, substituted amino, amido, lactam, urea, urethane, sulfonyl, and the like.

The term "alkynyl" refers to straight or branched chain hydrocarbon groups having 2 to 12 carbon atoms, preferably 2 to 4 carbon atoms, and at least one triple carbon to carbon bond, such as ethynyl. An alkynyl group is optionally substituted, unless stated otherwise, with one or more groups, selected from aryl (including substituted aryl), heterocyclo (including substituted heterocyclo), carbocyclo (including substituted carbocyclo), halo, hydroxy, alkoxy (optionally substituted), aryloxy (optionally substituted), alkylester (optionally substituted), arylester (optionally substituted), alkanoyl (optionally substituted), aroyl (optionally substituted), cyano, nitro, amino, substituted amino, amido, lactam, urea, urethane, sulfonyl, and the like.

The term "alkoxy" refers to an alkyl group linked to oxygen thus: R—O—. In this function, R represents the alkyl group. An example is the methoxy group $CH_3O$—.

"Organic groups" may be functionalized or otherwise comprise additional functionalities associated with the organic group, such as carboxyl, amino, hydroxyl, and the like, which may be protected or unprotected. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, and the like. Thus, "alkyl group" includes ethers, esters, haloalkyls, nitroalkyls, carboxyalkyls, hydroxyalkyls, sulfoalkyls, and the like.

"Cyano" refers to a —CN radical.

The terms "halo" and "halogen" refer to the fluoro, chloro, bromo or iodo groups. There can be one or more halogen groups, which can be the same or different. In an embodiment, each halogen can be substituted by one of the other halogens.

The term "haloalkyl" refers to an alkyl group as defined above that is substituted by one or more halogen atoms. The halogen atoms may be the same or different. The term "dihaloalkyl" refers to an alkyl group as described above that is substituted by two halo groups, which may be the same or different. The term "trihaloalkyl" refers to an alkyl group as describe above that is substituted by three halo groups, which may be the same or different. The term "perhaloalkyl" refers to a haloalkyl group as defined above wherein each hydrogen atom in the alkyl group has been replaced by a halogen atom. The term "perfluoroalkyl" refers to a haloalkyl group as defined above wherein each hydrogen atom in the alkyl group has been replaced by a fluoro group.

The term "cycloalkyl" refers to a mono-, bi-, or tricyclic saturated ring that is fully saturated or partially unsaturated. Examples of such a group includes cyclopropyl, cyclobutyl, cyclopentyl, cyclohexyl, cycloheptyl, adamantyl, cyclooctyl, cis- or trans decalin, bicyclo[2.2.1]hept-2-ene, cyclohex-1-enyl, cyclopent-1-enyl, 1,4-cyclooctadienyl, and the like. A cycloalkyl group is optionally substituted, unless stated otherwise, with one or more groups, selected from aryl (including substituted aryl), heterocyclo (including substituted heterocyclo), carbocyclo (including substituted carbocyclo), halo, hydroxy, protected hydroxy, alkoxy (e.g., $C_1$ to $C_7$) (optionally substituted), acyl (e.g., $C_1$ to $C_7$), aryloxy (e.g., $C_1$ to $C_7$) (optionally substituted), alkylester (optionally substituted), arylester (optionally substituted), alkanoyl (optionally substituted), aroyl (optionally substituted), carboxy, protected carboxy, cyano, nitro, amino, substituted amino, (monosubstituted)amino, (disubstituted)amino, protected amino, amido, lactam, urea, urethane, sulfonyl, and the like.

The term "(cycloalkyl)alkyl" refers to the above-defined cycloalkyl group substituted by an above defined alkyl group. Examples of such a group include (cyclohexyl)methyl, 3-(cyclopropyl)-n-propyl, 5-(cyclopentyl)hexyl, 6-(adamantyl) hexyl, and the like. A (cycloalkyl)alkyl group is optionally substituted, unless stated otherwise, with one or more groups, selected from alkyl (including substituted alkyl), aryl (including substituted aryl), heterocyclo (including substituted heterocyclo), carbocyclo (including substituted carbocyclo), halo, hydroxy, protected hydroxy, alkoxy (e.g., $C_1$ to $C_7$) (optionally substituted), acyl (e.g., $C_1$ to $C_7$), aryloxy (e.g., $C_1$ to $C_7$) (optionally substituted), alkylester (optionally substituted), arylester (optionally substituted), alkanoyl (optionally substituted), aroyl (optionally substituted), carboxy, protected carboxy, cyano, nitro, amino, substituted amino, (monosubstituted)amino, (disubstituted)amino, protected amino, amido, lactam, urea, urethane, sulfonyl, and the like.

The term "substituted phenyl" refers to a phenyl group substituted with one or more moieties, and in some instances one, two, or three moieties, chosen from the groups consisting of halogen, hydroxy, protected hydroxy, cyano, nitro, trifluoromethyl, $C_1$ to $C_7$ alkyl, $C_1$ to $C_7$ alkoxy, $C_1$ to $C_7$ acyl, $C_1$ to $C_7$ acyloxy, carboxy, oxycarboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl)carboxamide, protected N—($C_1$ to $C_6$ alkyl)carboxamide, N,N-di($C_1$ to $C_6$ alkyl)carboxamide, trifluoromethyl, N—(($C_1$ to $C_6$ alkyl)sulfonyl)amino, N-(phenylsulfonyl)amino or phenyl, substituted or unsubstituted, such that, for example, a biphenyl or naphthyl group results.

Examples of the term "substituted phenyl" include a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3, or 4-hydroxyphenyl, 2,4-dihydroxyphenyl, the protected-hydroxy derivatives thereof and the like; a nitrophenyl group such as 2, 3, or 4-nitrophenyl; a cyanophenyl group, for example, 2, 3 or 4-cyanophenyl; a mono- or di(alkyl)phenyl group such as 2, 3, or 4-methylphenyl, 2,4-dimethylphenyl, 2, 3 or 4-(isopropyl)phenyl, 2, 3, or 4-ethylphenyl, 2, 3 or 4-(n-propyl) phenyl and the like; a mono or di(alkoxy)phenyl group, for example, 2,6-dimethoxyphenyl, 2, 3 or 4-(isopropoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-di(protected carboxy)phenyl; a mono- or di(hydroxymethyl)phenyl or (protected hydroxymethyl)phenyl such as 2, 3 or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl)phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like.

The term "(substituted phenyl)alkyl" refers to one of the above substituted phenyl groups attached to one of the above-described alkyl groups. The (substituted phenyl)alkyl is connected to another moiety, i.e a compound having a clemizole scaffold, through the alkyl portion of the (substituted phenyl) alkyl. Examples of (substituted phenyl)alkyl include such groups as 2-phenyl-1-chloroethyl, 2-(4'-methoxyphenyl) ethyl, 4-(2',6'-dihydroxy phenyl)n-hexyl, 2-(5'-cyano-3'-methoxyphenyl)n-pentyl, 3-(2',6'-dimethylphenyl)n-propyl, 4-chloro-3-aminobenzyl, 6-(4'-methoxyphenyl)-3-carboxy (n-hexyl), 5-(4'-aminomethylphenyl)-3-(aminomethyl)n-pentyl, 5-phenyl-3-oxo-n-pent-1-yl, (4-hydroxynapth-2-yl) methyl and the like.

The terms "ar" or "aryl" refer to aromatic homocyclic (i.e., hydrocarbon) mono-, bi- or tricyclic ring-containing groups preferably having 6 to 12 members such as phenyl, naphthyl and biphenyl. An aryl group is optionally substituted, unless stated otherwise, with one or more groups, selected from alkyl (optionally substituted alkyl), alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, and the like. Optionally, adjacent substituents, together with the atoms to which they are bonded, form a 3- to 7-member ring.

The term "heteroaryl" refers to optionally substituted five-membered or six-membered rings that have 1 to 4 heteroatoms, such as oxygen, sulfur and/or nitrogen atoms, either alone or in conjunction with, additional nitrogen, sulfur or oxygen ring atoms. Furthermore, the above optionally substituted five-membered or six-membered rings can optionally be fused to an aromatic 5-membered or 6-membered ring system. For example, the rings can be optionally fused to an aromatic 5-membered or 6-membered ring system such as a benzene, pyridine or a triazole system.

The following ring systems are non-limiting examples of the heterocyclic (whether substituted or unsubstituted) radicals denoted by the term "heteroaryl": thienyl, furyl, pyrrolyl, imidazolyl, pyrazolyl, oxazolyl, isoxazolyl, thiazolyl, isothiazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b] pyridazinyl and purinyl, as well as benzo-fused derivatives, for example, benzoxazolyl, benzthiazolyl, benzimidazolyl and indolyl.

A heteroaryl group is optionally substituted, unless stated otherwise, with one or more groups, selected from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, alkyl (optionally, substituted), cycloalkyl (optionally substituted), (cycloalkyl)alkyl (optionally substituted), phenyl (optionally substituted), phenylalkyl (optionally substituted phenylalkyl). Substituents for the heteroaryl group are as heretofore defined, or in the case of trihalomethyl, can be trifluoromethyl, trichloromethyl, tribromomethyl, or triiodomethyl. As used in conjunction with the above substituents for heteroaryl rings, "lower alkoxy" means a $C_1$ to $C_4$ alkoxy group, similarly, "lower alkylthio" means a $C_1$ to $C_4$ alkylthio group.

The terms "heterocycle", "heterocyclic", "heterocyclic group" or "heterocyclo" refer to fully saturated or partially unsaturated or completely unsaturated, including aromatic ("heteroaryl") or nonaromatic cyclic groups (for example, 3- to 13-member monocyclic, 7- to 17-member bicyclic, or 10- to 20-member tricyclic ring systems, preferably containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. An N-attached heterocyclo is a heterocyclo moiety where the heterocyclo moiety is attached to a compound, e.g., a compound of Formula I through a nitrogen that forms part of the heterocyclo ring. Non-limiting examples of N-attached heterocyclo include but are not limited to

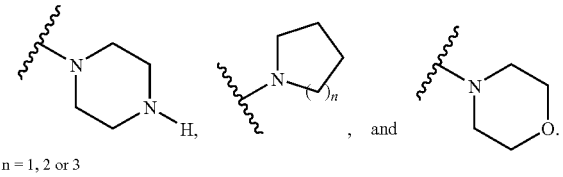

n = 1, 2 or 3

A C-attached heterocyclo is a heterocyclo moiety wherein the heterocyclo moiety is attached to a compound, e.g., a compound of formula II-a, b, or c through a carbon that forms part of the heterocyclo ring. Non-limiting examples include

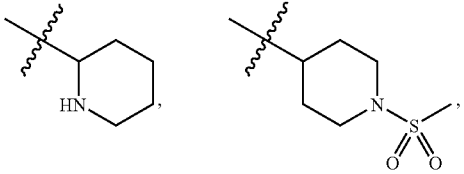 [SMILES: *C1CCCCN1 ; *C1CCN(S(C)(=O)=O)CC1]

and

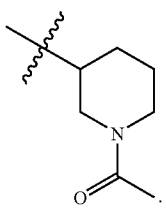 [SMILES: *C1CCCN(C(C)=O)C1]

The rings of multi-ring heterocycles may be fused, bridged and/or joined through one or more spiro unions.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxoazepinyl, azepinyl, 4-piperidonyl, pyridyl, pyrazinyl, pyrimidinyl, pyridazinyl, triazinyl, tetrahydropyranyl, tetrazoyl, triazolyl, morpholinyl, thiamorpholinyl, thiamorpholinyl sulfoxide, thiamorpholinyl sulfone, 1,3-dioxolane and tetrahydro-1,1-dioxothienyl, and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, benzofuranyl, dihydrobenzofuranyl, chromonyl, coumarinyl, benzodioxolyl, dihydrobenzodioxolyl, benzodioxinyl, cinnolinyl, quinoxalinyl, indazolyl, pyrrolopyridyl, furopyridinyl (such as furo[2,3-c]pyridinyl, furo[3,2-b]pyridinyl, or furo[2,3-b]pyridinyl), dihydroisoindolyl, dihydroquinazolinyl (such as 3,4-dihydro-4-oxo-quinazolinyl), tetrahydroquinolinyl, azabicycloalkyls (such as 6-azabicyclo[3.2.1]octane), azaspiroalkyls (such as 1,4dioxa-8-azaspiro[4.5]decane), imidazopyridinyl (such as imidazo[1,5-a]pyridin-3-yl), triazolopyridinyl (such as 1,2,4-triazolo[4,3-a]pyridin-3-yl), and hexahydroimidazopyridinyl (such as 1,5,6,7,8,8a-hexahydroimidazo[1,5-a]pyridin-3-yl), and the like.

Exemplary tricyclic heterocyclic groups include carbazolyl, benzidolyl, phenanthrolinyl, acridinyl, phenanthridinyl, xanthenyl and the like.

A heterocyclo group is optionally substituted, unless stated otherwise, with one or more groups, selected from alkyl (including substituted alkyl), alkenyl, oxo, aryl (including substituted aryl), heterocyclo (including substituted heterocyclo), carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, and the like, where optionally one or more pair of substituents together with the atoms to which they are bonded form a 3- to 7-member ring.

The term "alkanoyl" refers to an alkyl group (which may be optionally substituted as described above) linked to a carbonyl group (i.e. —C(O)-alkyl). Similarly, the term "aroyl" refers to an aryl group (which may be optionally substituted as described above) linked to a carbonyl group (i.e., —C(O)-aryl).

The term "(monosubstituted)amino" refers to an amino group with one substituent chosen from the group consisting of phenyl, substituted phenyl, alkyl (including substituted alkyl), $C_1$ to $C_4$ acyl, $C_2$ to $C_7$ alkenyl (including $C_2$ to $C_7$ substituted alkenyl), $C_2$ to $C_7$ alkynyl, $C_7$ to $C_{16}$ alkylaryl (including $C_7$ to $C_{16}$ substituted alkylaryl), and heteroaryl group. The (monosubstituted) amino can additionally have an amino-protecting group as encompassed by the term "protected (monosubstituted)amino." The term "(disubstituted) amino" refers to amino groups with two substituents chosen from the group consisting of phenyl, substituted phenyl, alkyl, substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_{16}$ substituted alkylaryl and heteroaryl. The two substituents can be the same or different.

The term "heteroaryl(alkyl)" refers to an alkyl group as defined above, substituted at any position by a heteroaryl group, as above defined.

"Isosteres" are different atoms, molecules, or ions that have different molecular formulae but have similar or identical outer shell electron arrangements and also have similar properties (e.g., pharmacological properties (e.g., pharmacokinetic and pharmacodynamic)).

"Moiety" refers to a specific segment or functional group of a molecule. Chemical moieties are often recognized chemical entities embedded in or appended to a molecule.

"Nitro" refers to the —$NO_2$ radical.

"Oxa" refers to the —O— radical.

"Oxo" refers to the =O radical.

"Sulfonyl" refers to the groups: —$S(O_2)$—H, —$S(O_2)$-(alkyl), —$S(O_2)$-(cycloalkyl), —$S(O_2)$-(amino), —$S(O_2)$-(aryl), —$S(O_2)$-(heteroaryl), and —$S(O_2)$-(heterocycloalkyl). "Sulfonamidyl" or "sulfonamido" refers to a —$S(O)_2$—NRR radical, where each R is selected independently from the group consisting of hydrogen, alkyl, cycloalkyl, aryl, heteroaryl (bonded through a ring carbon) and heteroalicyclic (bonded through a ring carbon). The R groups in —NRR of the —$S(O)_2$—NRR radical may be taken together with the nitrogen to which it is attached to form a 4-, 5-, 6-, or 7-membered ring (—$S(O_2)$-heterocycloalkyl). In some embodiments, it is a $C_1$-$C_{10}$ sulfonamido, wherein each R in sulfonamido contains 1 carbon, 2 carbons, 3 carbons, or 4 carbons total. A sulfonamido group is optionally substituted by one or more of the substituents described herein for alkyl, cycloalkyl, aryl, heteroaryl respectively. A "sulfone" refers to a —$S(O_2)$-(alkyl), —$S(O_2)$-(aryl), —$S(O_2)$-(heteroaryl), or —$S(O_2)$-(heterocycloalkyl) (when the sulfone group is attached to a carbon atom in the heterocycloalkyl). A sulfonamido group is optionally substituted by one or more of the substituents described herein for alkyl, cycloalkyl, aryl, and heteroaryl.

The terms "solvent," "organic solvent," and "inert solvent" each mean a solvent inert under the conditions of the reaction being described. Non-limiting examples include benzene, toluene, acetonitrile, tetrahydrofuran ("THF"), dimethylformamide ("DMF"), chloroform, methylene chloride (or dichloromethane), diethyl ether, methanol, N-methylpyrrolidone ("NMP"), pyridine and the like.

The term "protecting group" refers to chemical moieties that block some or all reactive moieties of a compound and prevent such moieties from participating in certain chemical reactions until the protective group is removed, for example, those moieties listed and described in T. W. Greene, P. G. M. Wuts, Protective Groups in Organic Synthesis, 3rd ed. John Wiley & Sons (1999). Where different protecting groups are employed, that each (different) protective group may be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid moieties may be blocked with base labile groups such as, without limitation, methyl, or ethyl, and hydroxy reactive moieties may be blocked with base labile groups such as acetyl in the presence of amines blocked with acid labile groups such as tert-butyl carbamate or with carbamates that are both acid and base stable but hydrolytically removable.

In an embodiment, the term "ring" can refer to a chemical moiety having a ring structure comprising 3 to 10 carbon atoms in which one or more carbon atoms may be optionally substituted with a heteroatom, such as N, O, or S. A ring may or may not be aromatic and thus may be completely unsaturated, completely saturated, or partially unsaturated; and a ring may refer to a ring within a fused system or an unfused ring. Unless state otherwise, the definition of "ring" does not modify other definitions of rings provided herein.

B

Embodiments of the present invention provides methods and compositions for treatment (including prophylactic treatment) of infection by a virus that encodes NS4B. Such a virus includes any virus—of the Flaviviridae family encompassing e.g., flaviviruses, pestiviruses and hepatitis C viruses. Other NS4B encoding viruses include yellow fever virus (YFV); Dengue virus, including Dengue types 1-4; Japanese Encephalitis virus; Murray Valley Encephalitis virus; St. Louis Encephalitis virus; West Nile virus; tick-borne encephalitis virus; Kunjin virus; Central European encephalitis virus; Russian spring-summer encephalitis virus; Powassan virus; Kyasanur Forest disease virus; Omsk hemorrhagic fever virus; and their respective genotypes as well as sub-genotypes. The subject methods and compositions are particularly useful for treating or prophylactically treating HCV, including genotype 1, 2, 3, 4, 5, 6, and the like, as well as subtypes of an HCV genotype (e.g., 1a, 1b, 2a, 2b, 3a, and the like.).

In one embodiment, the method of treating such viral infection comprises administering to a subject infected with a virus from the Flaviviridae family, an effective amount of clemizole or clemizole analog, or a pharmaceutically acceptable salt, an isomer, a tautomer or a prodrug thereof.

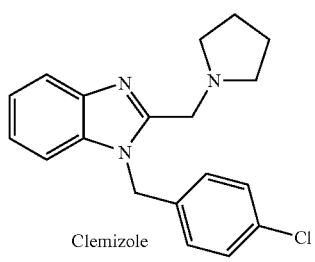 [SMILES: Clc1ccc(Cn2c(CN3CCCC3)nc3ccccc32)cc1]

Clemizole

In one aspect, the subject method is effective in reducing viral load in the infected subject by e.g., at least about 5%, 10%, 15%, 20%, 25%, 30%, 35%, 40%, 45%, 50%, 60%, 70%, 80%, 90%, 95% or even higher as compared to the level of viral load present in the subject prior to such treatment. Without being bound by any particular theory, the reduction in viral load can be effected, in whole or in part, by reducing binding of NS4B polypeptide to the viral genome. In the case of HCV, a decrease in viral load upon administering clemizole or clemizole analog can be attributable to, at least in part, a decrease in binding of NS4B polypeptide to HCV negative strand RNA, e.g., at a site on the 3'UTR.

A large number of clemizole or clemizole analog, or a pharmaceutically acceptable salt, an isomer, a tautomer or a prodrug thereof can be used in the treatment methods of the present invention. The subject methods can also utilize one or more isosteres, including but not limited to H1 receptor antagonists that share structural similarity with clemizole and exhibit anti-viral activity. Illustrative H1 receptor antagonists that share structural similarity with clemizole include, but are not limited to, the compounds in the classes known as alcoholamines (e.g., diphenhydramine, carbinoxamine, and clemastine), ethylenediamines (e.g., mepyramine and tripelennamine (clemizole is in this class)), alkylamines (e.g., triprolidine and chlorpheniramine), piperazines (e.g., meclizine and homchlorcyclizine), and phenothiazines (e.g., promethazine).

The subject treatment methods can also employ prodrugs of clemizole, clemizole analogs or isosteres thereof. Exemplary prodrugs can be activated by liver enzymes (e.g., cyclic-1,3-propanyl esters substituted with groups that promote an oxidative cleavage reaction by CYP3A, and the like.). These modifications can render clemizole inactive or less active until it reaches the liver (see, Current Opinion in Investigational Drugs 2006 Vol 7 No 2, 109-117; *J. Med. Chem.* 2008, 51, 2328-2345; and Nucleosides, Nucleotides, and Nucleic Acids, 24 (5-7):375-381, (2005) each of which is incorporated herein by reference for the corresponding discussion).

In one embodiment, a clemizole analog provided by the present invention is a compound of Formula I shown below. The structure of clemizole is shown beside Formula I-A.

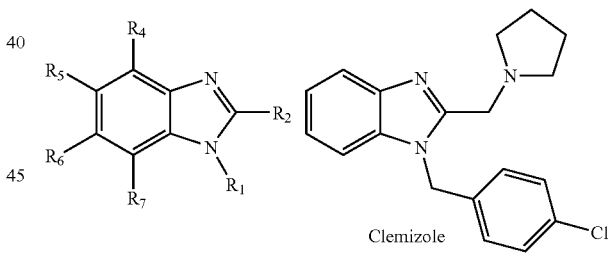

Formula I

Clemizole

Additional inhibiting agents of the invention include isosteres of a clemizole scaffold. Non-limiting exemplary isosteres are compounds of the following formulae (structures). In each of the structures $R_1$-$R_2$ and $R_3$-$R_7$ are as defined herein.

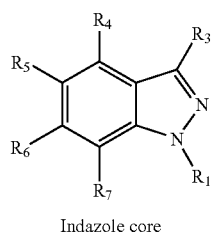

Formula II

Indazole core

Formula III

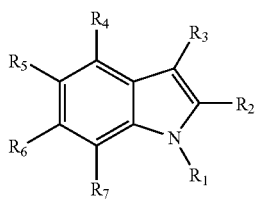

Indole

Formula IV

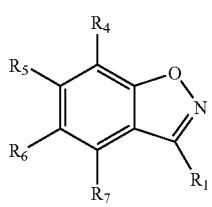

Benzoisoxazole

Formula V

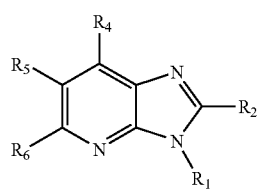

Imidazopyridine

Formula VI

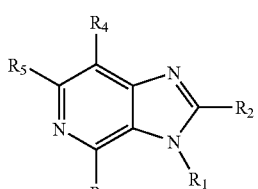

Imidazopyridine

Formula VII

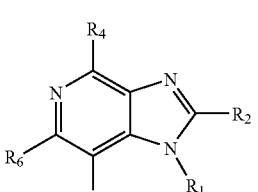

Imidazopyridine

Formula VIII

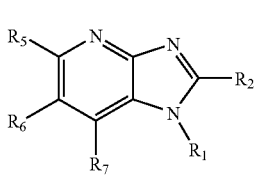

Imidazopyridine

Formula IX

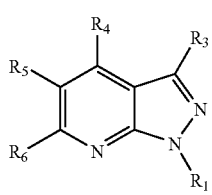

Pyrazolopyridine

Formula X

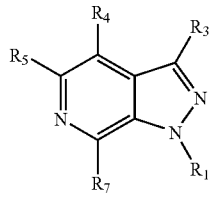

Pyrazolopyridine

Formula XI

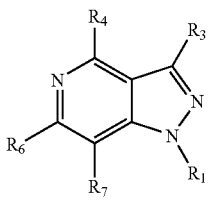

Pyrazolopyridine

Formula XII

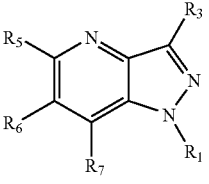

Pyrazolopyridine

Formula XIII

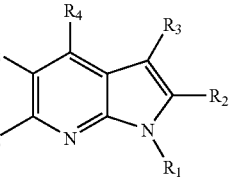

Pyrrolopyridine

Formula XIV

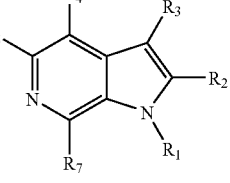

Pyrrolopyridine

Formula XV

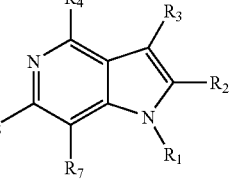

Pyrrolopyridine

Formula XVI

Pyrrolopyridine

Formula XVII

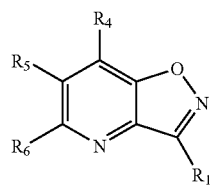

Isoxazolopyridine

Formula XVIII

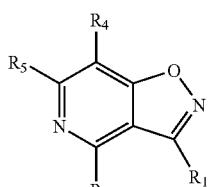

Isoxazolopyridine

Formula XIX

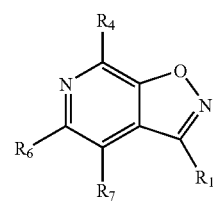

Isoxazolopyridine

Formula XX

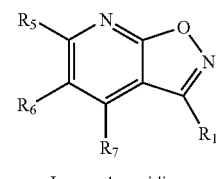

Isoxazolopyridine

Formula XXI

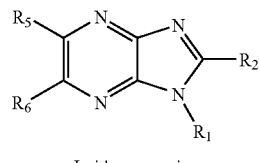

Imidazopyrazine

Formula XXII

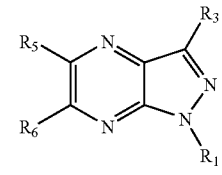

Pyrazolopyrazine

Formula XXIII

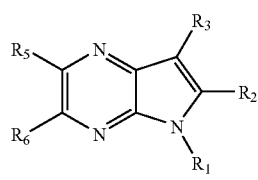

Pyrrolopyrazine

Formula XXIV

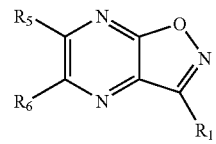

Isoxazolopyrazine

Formula XXV

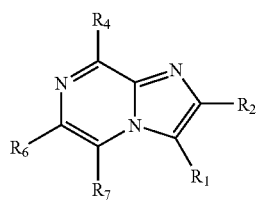

Imidazopyrazine

Formula XXVI

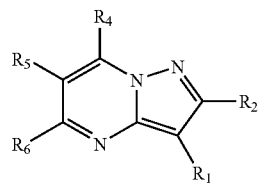

Pyrazolopyrimidine

Formula XXVII

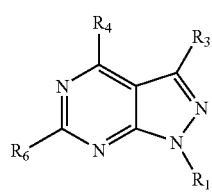

Pyrazolopyrimidine

Formula XXVIII

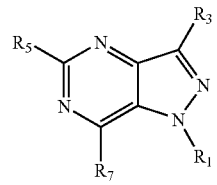

Pyrazolopyrimidine

Formula XXIX

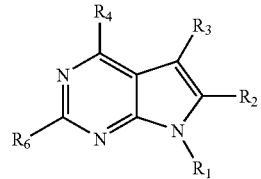

Pyrrolopyrimidine

Formula XXX

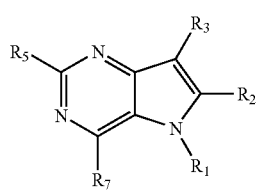

Pyrrolopyrimidine

-continued

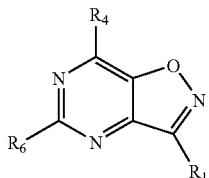

Isoxazolopyrimidine
Formula XXXI

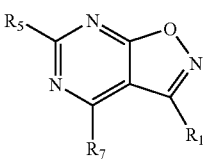

Isoxazolopyrimidine
Formula XXXII

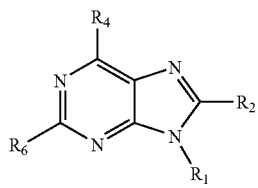

Purine
Formula XXXIII

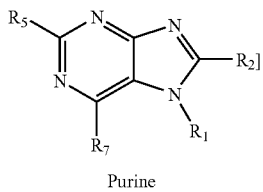

Purine
Formula XXXIV

In one embodiment, for compounds having a clemizole scaffold or an isostere scaffold as described above, $R_1$ is —H or

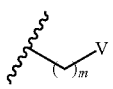

m=0, 1, 2 wherein V is selected from alkyl, cycloalkyl, heterocyclo, aryl or heteroaryl.

In another embodiment, $R_1$ is

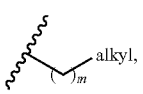

m = 0, 1, 2 wherein the alkyl moiety is unsubstituted or substituted. The alkyl moiety forming part (m=1 or 2) or all (m=0) of $R_1$, can be branched or unbranched. The alkyl moiety of $R_1$ includes but is not limited to methyl, ethyl, n-propyl, iso-propyl, n-butyl, iso-butyl, tert-butyl, n-pentyl, iso-pentyl, n-hexyl, septyl, heptyl, nonyl, and decyl.

In yet another embodiment, $R_1$ is

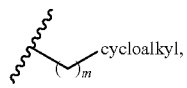

n = 0, 1, 2 wherein the cycloalkyl moiety is unsubstituted or substituted. The cycloalkyl moiety forming part (m=1 or 2) or all (m=0) of $R_1$, includes but is not limited to cyclopropyl, cyclobutyl, cyclopentyl and cyclohexyl. Non-limiting exemplary $R_1$ include the following formulae:

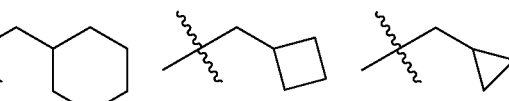

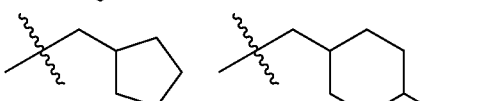 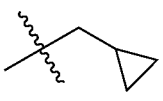

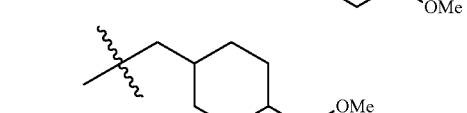

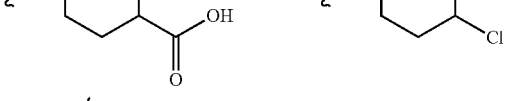

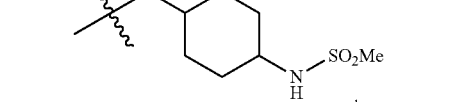

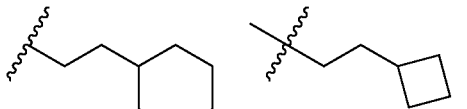

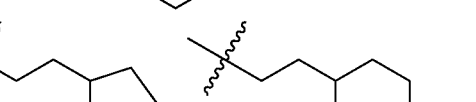

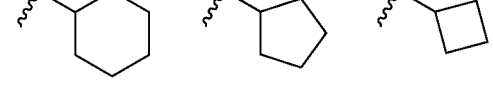

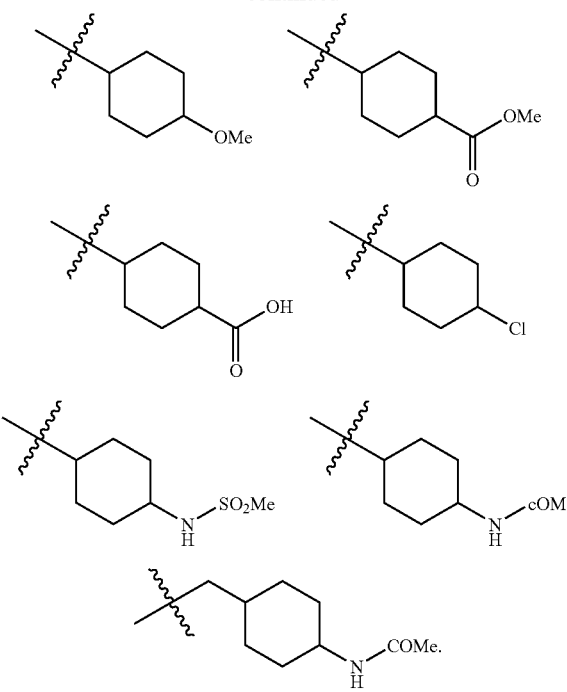
The invention further provides $R_1$ having the formula:
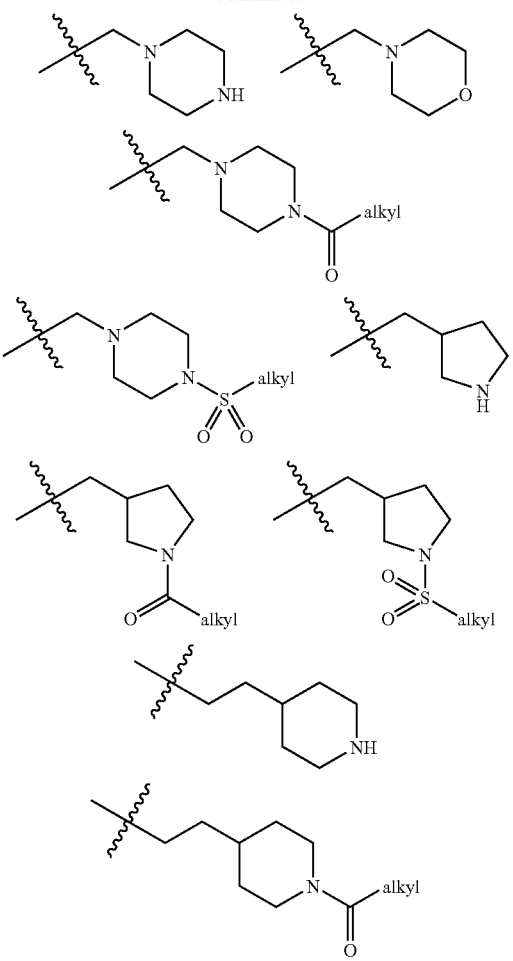
m = 0, 1, 2
wherein the heterocyclo moiety is unsubstituted or substituted. The heterocyclo moiety forming part (m=1 or 2) or all (m=0) of $R_1$, includes but is not limited to azetidinyl, pyrrolidinyl, morpholinyl, piperidinyl, or piperazinyl. Non-limiting exemplary $R_1$ include the following formulae:
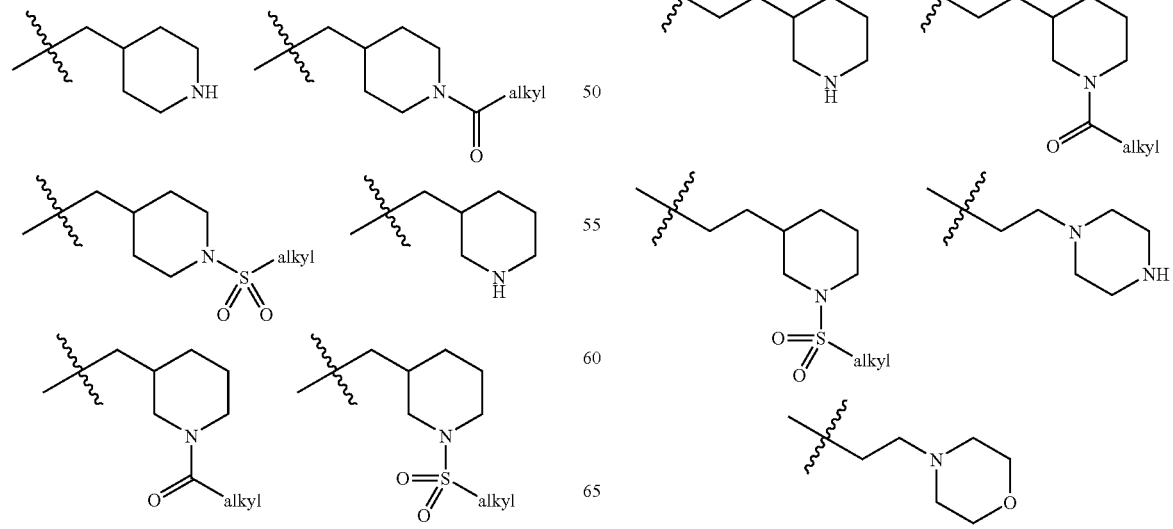

-continued

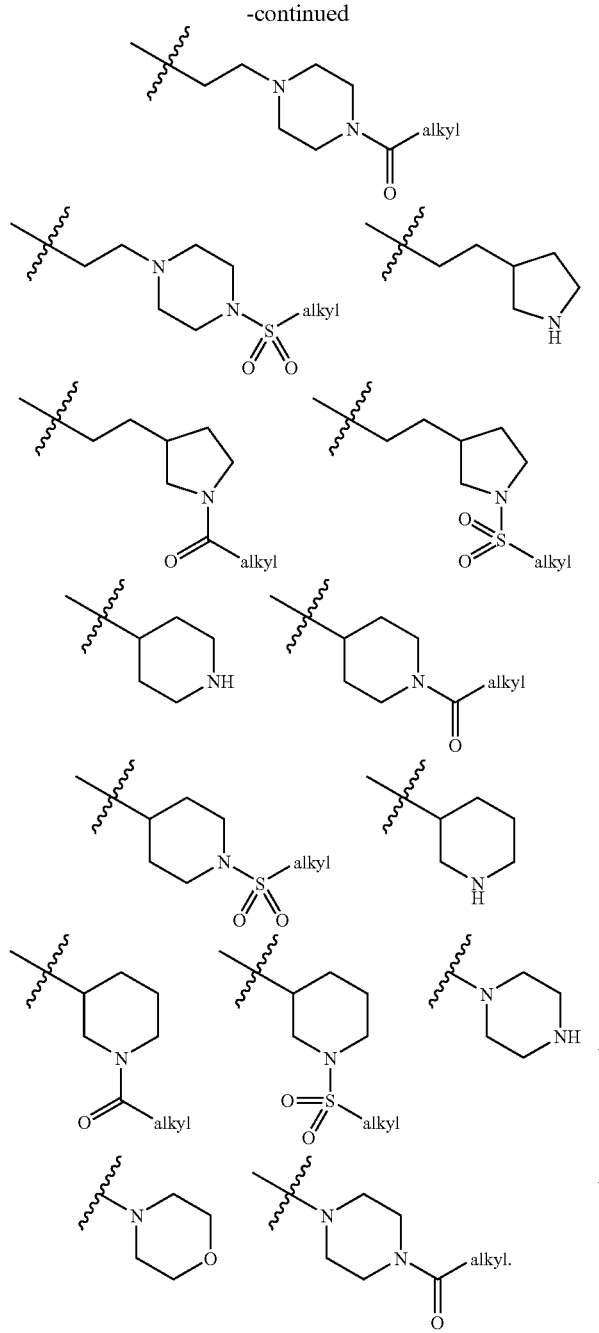

In the above formulae, alkyl includes but is not limited to methyl, ethyl, n-propyl, iso-propyl, n-butyl, iso-butyl, tert-butyl, n-pentyl, iso-pentyl, n-hexyl, septyl, heptyl, nonyl, and decyl.

In yet other embodiments, $R_1$ is

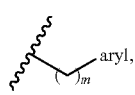

m = 0, 1, 2 wherein the aryl moiety is unsubstituted or substituted. The aryl moiety forming part (m=1 or 2) or all (m=0) of $R_1$, includes but is not limited to phenyl, naphthyl and fluorenyl. Non-limiting exemplary $R_1$ include the following formulae:

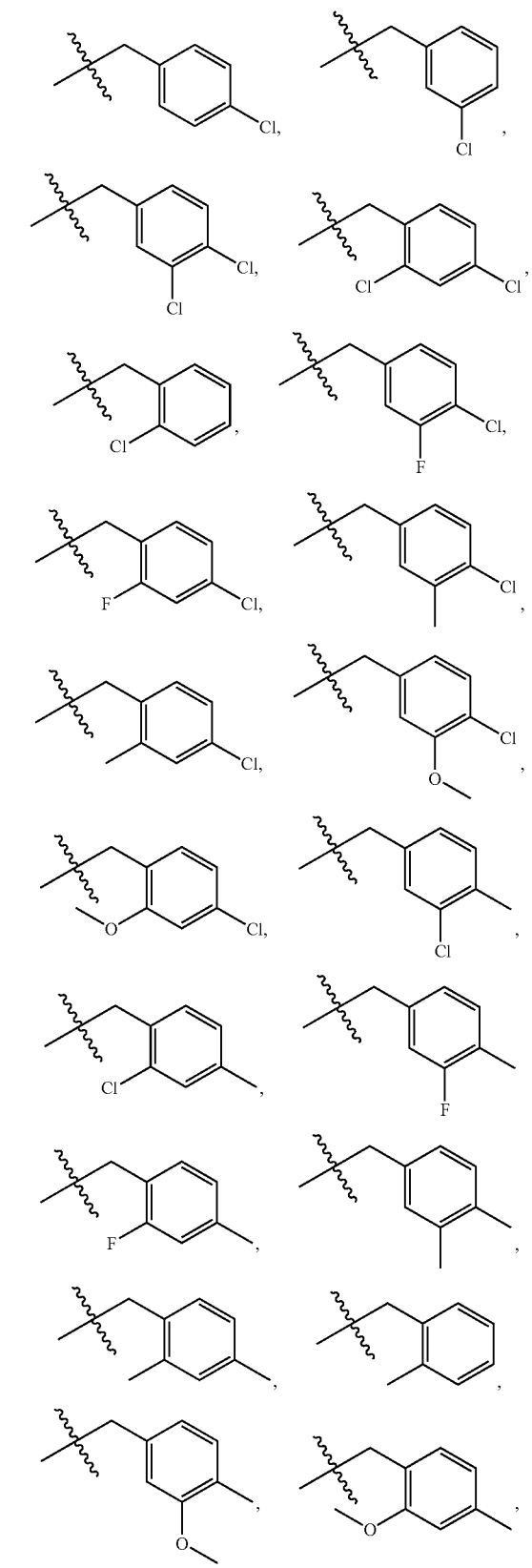

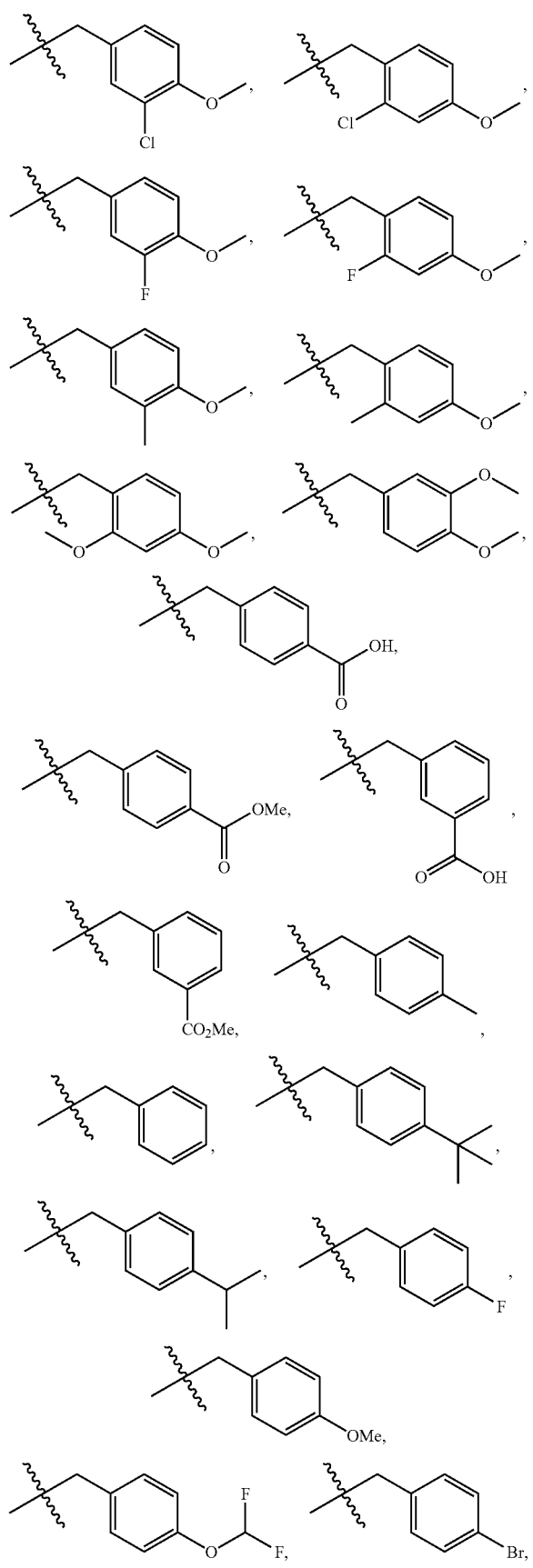

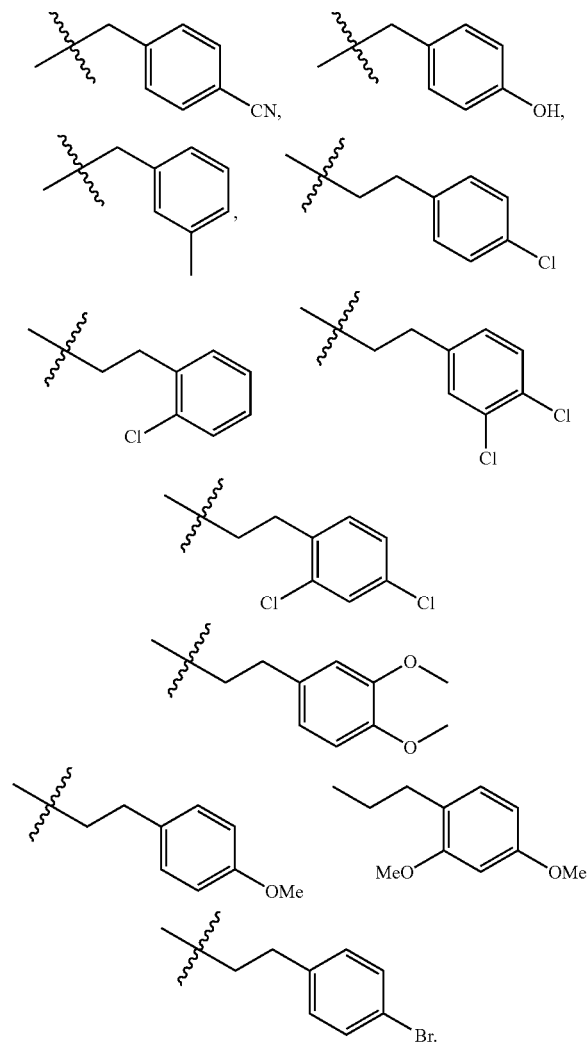

Additionally, $R_1$ can be

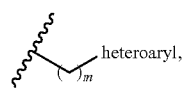

$m = 0, 1, 2$ wherein the heteroaryl moiety is unsubstituted or substituted. In some embodiments, the heteroaryl moiety is a monocyclic 5 membered heteroaryl. Monocyclic heteroaryl includes but is not limited to pyrrolyl, imidazolyl, thiazolyl, and pyrazolyl. Additional non-limiting monocyclic 5-membered heteroaryl moieties include the following formulae:

Group E

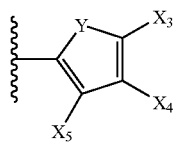

-continued

Group D

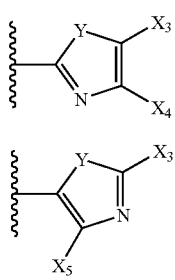

For compounds of Group D, E, and F, Y is selected from the group consisting of: —O, —S, —NH, —N-alkyl, and —N-acyl; $X_3$ is selected from the group consisting of: —H, —$CH_3$, —Cl, —F, $CF_3$ and —$OCH_3$; and $X_4$ and $X_5$ are, when present, independently selected from the group consisting of: H and $CH_3$.

Alternatively, when $R_1$ is heteroaryl, m = 0, 1, 2 heteroaryl may be a six membered heteroaryl moiety. The six membered heteroaryl moiety includes but is not limited to 2-pyridyl, 3-pyridyl, 4-pyridyl, pyrimidinyl, pyridizinyl, pyrazinyl, or triazinyl.

Non limiting examples of $R_1$ include the following formulae:

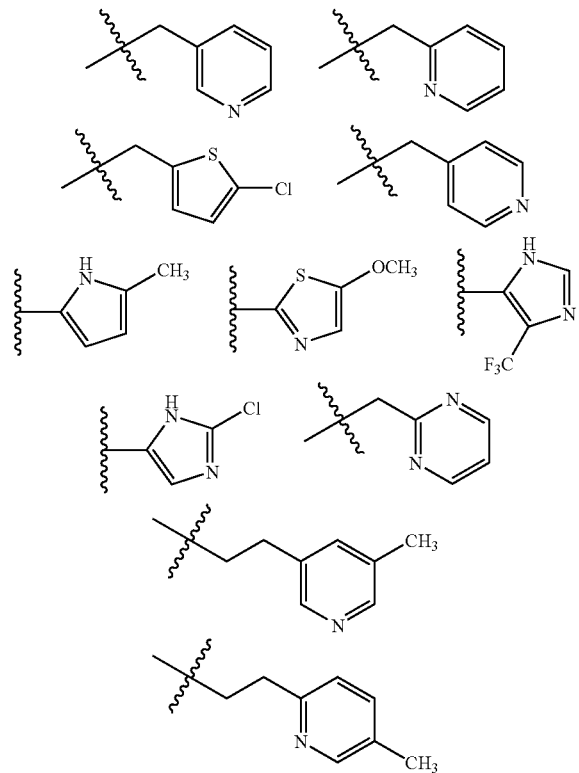

Group F

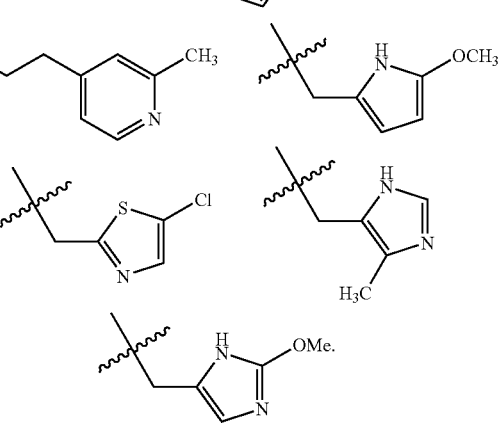

The alkyl, cycloalkyl, heterocyclo, aryl or heteroaryl moiety of $R_1$ may be substituted by one or more substituents selected from the group consisting of alkyl, aryl, heterocyclo, carbocyclo, halo, hydroxy, protected hydroxy, alkoxy, acyl, aryloxy, alkylester, arylester, alkanoyl, aroyl, carboxy, protected carboxy, cyano, nitro, amino, substituted amino, (monosubstituted)amino, (disubstituted)amino, protected amino, amido, lactam, urea, urethane, and sulfonyl.

$R_2$ is —H,

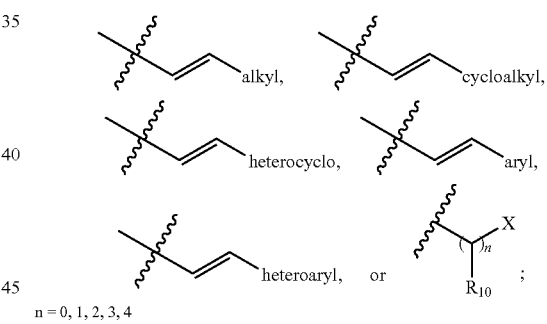

n = 0, 1, 2, 3, 4 wherein X is selected from the group consisting of: —$NH_2$, —NH(alkyl), —N(alkyl)$_2$, CONH(alkyl), COHC(aryl), —OH, -alkyl, cycloalkyl, alkenyl, —$CF_3$, —O(alkyl), —O-cycloalkyl, —O-heterocyclo, -aryl, heteroaryl, N-attached heterocyclo, C-attached heterocyclo, —SH, —$SO_2$(alkyl), —S(alkyl), and —S(aralkyl), $R_{10}$ is hydrogen or alkyl (including but not limited to methyl, ethyl, n-propyl, iso-propyl, n-butyl, iso-butyl, tert-butyl, n-pentyl, iso-pentyl, n-hexyl, septyl, heptyl, nonyl, and decyl).

In some embodiments, $R_2$ is —H, —$NH_2$, —SH, —S-alkyl or alkyl, where alkyl includes but is not limited to methyl, ethyl, n-propyl, iso-propyl, n-butyl, iso-butyl, tert-butyl, n-pentyl, iso-pentyl, n-hexyl, septyl, heptyl, nonyl, and decyl. In other embodiments, $R_2$ is -alkenyl (including but not limited to vinyl, allyl, 3-buten-1yl, 2-buten-1yl, methallyl, 3-methyl-2-penten-1-yl, 4-penten-1-yl, 3-penten-1-yl, 5-hexen-1-yl, and 4-methyl-3-penten-1-yl) or perfluoroalkyl (including but not limited to —$CF_3$ and —$CF_2CF_3$). When $R_2$ is —S-alkyl, alkyl, or alkenyl, the alkyl or alkenyl moiety is substituted by one or more substituents selected from the group consisting of alkyl, aryl, heterocyclo, carbocyclo, halo, hydroxy, protected hydroxy, alkoxy, acyl, aryloxy, alkylester, arylester, alkanoyl, aroyl, carboxy, protected carboxy, cyano, nitro, amino, substituted amino, (monosubstituted)amino, (disubstituted)amino, protected amino, amido, lactam, urea, urethane, and sulfonyl.

Some exemplary S-alkyl $R_2$ include but are not limited to:

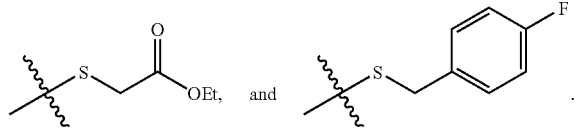

Alternatively, $R_2$ is heteroaryl, —CH$_2$CH$_2$CH$_2$NHCO (aryl), —CH$_2$CH$_2$CH$_2$NHCO(heteroaryl),

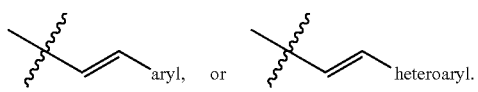

The aryl moiety forming part of $R_2$ is unsubstituted or substituted. The aryl moiety includes but is not limited to phenyl, naphthyl and fluorenyl. The heteroaryl moiety forming part or all of $R_2$ is unsubstituted or substituted. In some embodiments, heteroaryl moiety forming part or all of $R_2$ is a monocyclic 5 membered heteroaryl. Monocyclic heteroaryl includes but is not limited to pyrrolyl, imidazolyl, thiazolyl, and pyrazolyl. Additional non-limiting monocyclic 5 membered heteroaryl moieties include the following formulae:

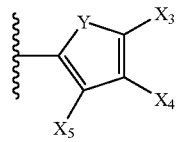
Group E

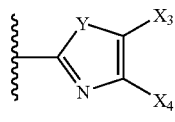
Group D

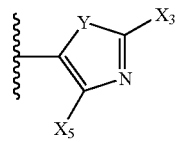
Group F

For compounds of Group D, E, and F, Y is selected from the group consisting of:

—O, —S, —NH, —N-alkyl, and —N-acyl; $X_3$ is selected from the group consisting of: —H, —CH$_3$, —Cl, —F, —Br, —I, CF$_3$ and —OCH$_3$; and $X_4$ and $X_5$ are, when present, independently selected from the group consisting of: H and CH$_3$.

Additionally the invention provides compounds wherein when $R_2$ is heteroaryl, —CH$_2$CH$_2$CH$_2$NHCO(heteroaryl), or

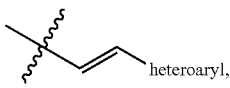

the heteroaryl moiety may be a six membered heteroaryl moiety. The six membered heteroaryl moiety includes but is not limited to 2-pyridyl, 3-pyridyl, 4-pyridyl, pyridazinyl, pyrimidinyl, pyrazinyl, or triazinyl.

When $R_2$ is heteroaryl, —CH$_2$CH$_2$CH$_2$NHCO(aryl), —CH$_2$CH$_2$CH$_2$NHCO(heteroaryl)

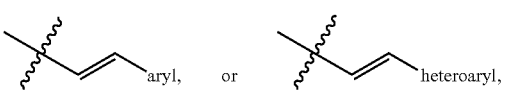

the aryl or heteroaryl moiety may be substituted with one or more substituents selected from the group consisting of alkyl, aryl, heterocyclo, carbocyclo, halo, hydroxy, protected hydroxy, alkoxy, acyl, aryloxy, alkylester, arylester, alkanoyl, aroyl, carboxy, protected carboxy, cyano, nitro, amino, substituted amino, (monosubstituted)amino, (disubstituted) amino, protected amino, amido, lactam, urea, urethane, and sulfonyl.

Some non-limiting exemplary $R_2$ include the following:

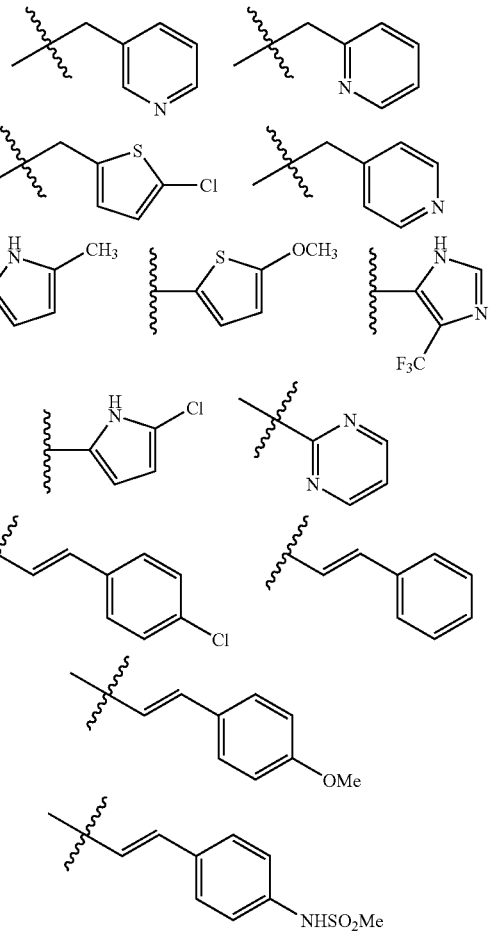

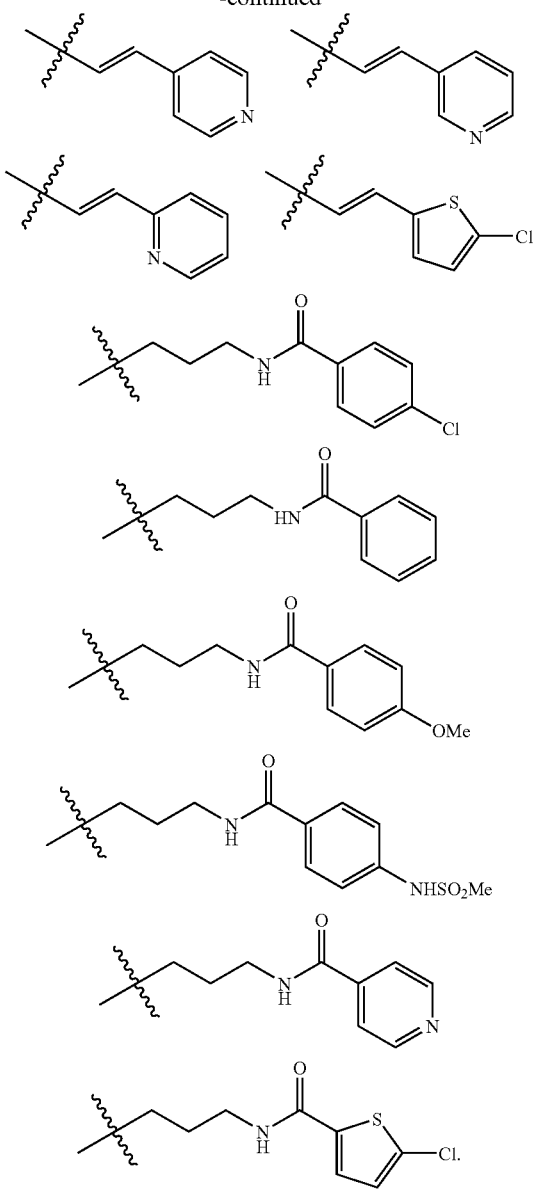

The invention also provides for compounds wherein $R_2$ is

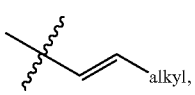alkyl, wherein alkyl is unsubstituted or substituted. Alkyl is branched or unbranched and includes but is not limited to methyl, ethyl, n-propyl, iso-propyl, n-butyl, iso-butyl, tert-butyl, n-pentyl, iso-pentyl, n-hexyl, septyl, heptyl, nonyl, and decyl). Non limiting examples of $R_2$ include

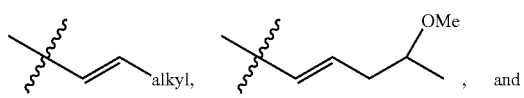

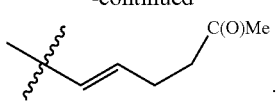

In other embodiments of the invention, $R_2$ may also be

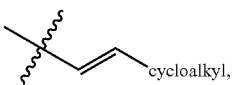cycloalkyl, wherein cycloalkyl is unsubstituted or substituted. The cycloalkyl is a 3, 4, 5, 6, 7, or 8 membered ring and includes but is not limited to cyclopropyl, cyclobutyl, cyclopentyl and cyclohexyl. Exemplary examples include but are not limited to

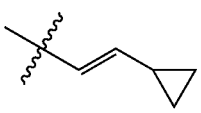 [SMILES: */C=C/C1CC1]

and

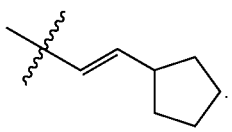 [SMILES: */C=C/C1CCCC1]

Additionally, $R_2$ may be

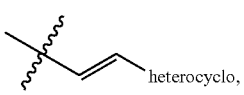heterocyclo, wherein heterocyclo is unsubstituted or substituted. The heterocyclo includes but is not limited to azetidinyl, pyrrolidinyl, morpholinyl, piperidinyl, or piperazinyl.

In yet other embodiments, $R_2$ is

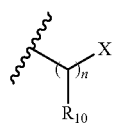

n=0, 1, 2, 3, 4 where X is selected from alkyl, aryl, —$CF_3$, —$NH_2$, —OH, —O(alkyl), —O-cycloalkyl, —O-heterocyclo, —NH-acyl, —$NHSO_2$-aryl, —$CO_2Et$, —NH(alkyl), —N(alkyl)$_2$, and heterocyclo. $R_{10}$ is hydrogen or alkyl (including but not limited to methyl, ethyl, n-propyl, iso-propyl, n-butyl, iso-butyl, tert-butyl, n-pentyl, iso-pentyl, n-hexyl, septyl, heptyl, nonyl, and decyl). For example, $R_{10}$ is hydrogen, methyl, or ethyl. In some embodiments when $R_2$ is

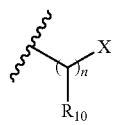

n=0, 1, 2, 3, 4 and X is alkyl, —O(alkyl), —NH-acyl (wherein acyl is C(O)alkyl), NH(alkyl), or —N(alkyl)$_2$, the alkyl moiety is unsubstituted or substituted. The alkyl moiety forming part of X includes but is not limited to methyl, ethyl, n-propyl, iso-propyl, n-butyl, iso-butyl, tert-butyl, n-pentyl, iso-pentyl, n-hexyl, septyl, heptyl, nonyl, and decyl.

In other embodiments when R$_2$ is

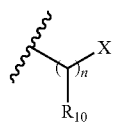

n=0, 1, 2, 3, 4 and X is cycloalkyl or —O-cycloalkyl, the cycloalkyl moiety is unsubstituted or substituted. The cycloalkyl is a 3, 4, 5, 6, 7, or 8 membered ring and includes but is not limited to cyclopropyl, cyclobutyl, cyclopentyl and cyclohexyl. Exemplary R$_2$ includes but is not limited to —CH$_2$-cyclopentyl, —CH$_2$—O-cyclohexyl, and —O-cyclobutyl.

Additionally, R$_2$ is

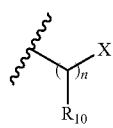

n=0, 1, 2, 3, 4, and X is aryl, —NH-acyl (where acyl is C(O)aryl), or —NHSO$_2$-aryl. R$_{10}$ is hydrogen or alkyl (including but not limited to methyl, ethyl, n-propyl, iso-propyl, n-butyl, iso-butyl, tert-butyl, n-pentyl, iso-pentyl, n-hexyl, septyl, heptyl, nonyl, and decyl). In some embodiments, R$_{10}$ is hydrogen, methyl, or ethyl. The aryl moiety forming part of X is phenyl, naphthyl or fluorenyl, any of which phenyl, naphthyl or fluorenyl are unsubstituted or substituted. In further embodiments, R$_2$ is

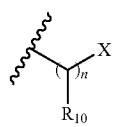

n=0, 1, 2, 3, 4, and X is heterocyclo or —O-heterocyclo, wherein the heterocyclo moiety is unsubstituted or substituted. The heterocyclo moiety forming X, includes but is not limited to azetidinyl, pyrrolidinyl, morpholinyl, piperidinyl, or piperazinyl. R$_{10}$ is hydrogen or alkyl (including but not limited to methyl, ethyl, n-propyl, iso-propyl, n-butyl, iso-butyl, tert-butyl, n-pentyl, iso-pentyl, n-hexyl, septyl, heptyl, nonyl, and decyl). For example, R$_{10}$ is hydrogen, methyl, or ethyl). Non-limiting embodiments include —CH(CH$_3$) piperidinyl, —CH$_2$pyrrolidinyl, and

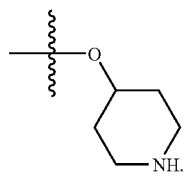

The alkyl, aryl, heteroaryl and heterocyclo moiety forming all or part of X may be substituted by one or more substituents which is selected from the group consisting of: alkyl, aryl, heterocyclo, carbocyclo, halo, hydroxy, protected hydroxy, alkoxy, acyl, aryloxy, alkylester, arylester, alkanoyl, aroyl, carboxy, protected carboxy, cyano, nitro, amino, substituted amino, (monosubstituted)amino, (disubstituted)amino, protected amino, amido, lactam, urea, urethane, and sulfonyl. Additionally, the alkyl and heterocyclo moiety forming all or part of X may be substituted by an oxo group.

In some embodiments, R$_2$ is —X, —CH$_2$—X or —CH$_2$CH$_2$—X, wherein X is selected from the group consisting of:

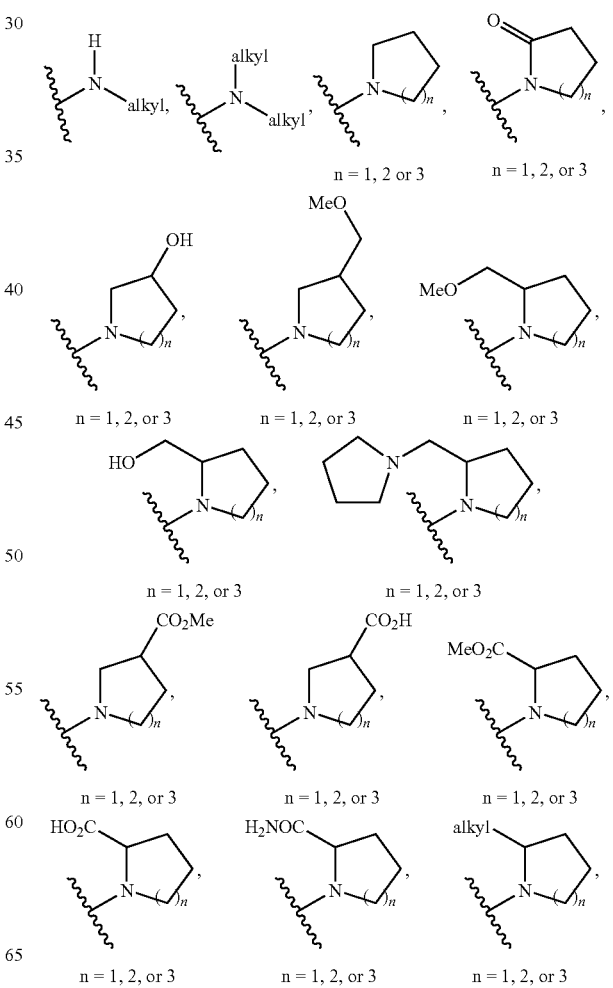

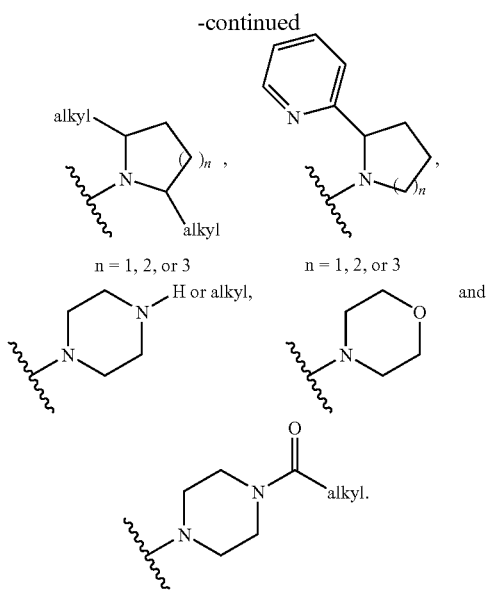

Other examples of R$_2$ moieties are listed in Table 3b.

In various embodiments of compounds having a clemizole scaffold or an isostere scaffold as described above, each of R$_4$-R$_7$, and R$_3$, if present, is independently selected from the group consisting of: —H, —Cl, —F, —CH$_3$, —OCH$_3$, —OH, —NH$_2$, —NO$_2$,

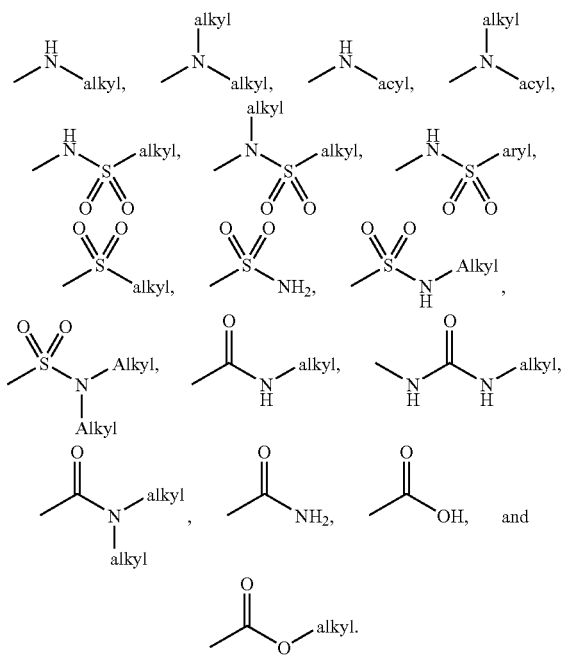

In the moieties that form part of R$_3$-R$_7$, the alkyl and aryl moieties are unsubstituted or substituted. The alkyl moieties that form part of R$_3$-R$_7$ include but are not limited to methyl, ethyl, n-propyl, iso-propyl, n-butyl, iso-butyl, tert-butyl, n-pentyl, iso-pentyl, n-hexyl, septyl, heptyl, nonyl, and decyl. The aryl moieties that form part of R$_3$-R$_7$ include but are not limited to phenyl, naphthyl and fluorenyl. The alkyl and aryl moieties that form part of R$_3$-R$_7$ may be substituted by one or more substituents which is selected from the group consisting of alkyl, aryl, heterocyclo, carbocyclo, halo, hydroxy, protected hydroxy, alkoxy, acyl, aryloxy, alkylester, arylester, alkanoyl, aroyl, carboxy, protected carboxy, cyano, nitro, amino, substituted amino, (monosubstituted)amino, (disubstituted)amino, protected amino, amido, lactam, urea, urethane, and sulfonyl.

In one embodiment, at least one of R$_4$-R$_7$ is a hydrogen. In other embodiments, R$_3$ is hydrogen. In further embodiments, at least two of R$_4$-R$_7$ is a hydrogen. Alternatively, at least two of R$_4$-R$_7$ are hydrogen, and the remaining R$_4$-R$_7$ groups (and R$_3$, if present) are independently selected from the group consisting of: —I, —Br, —Cl, —F, —CH$_3$, and —OCH$_3$. In yet other embodiments, R$_5$ and R$_6$ are substituted, and the substituted moiety is, for each substituted position, independently selected from the group consisting of: —I, —Br, —Cl, —F, —CH$_3$, and —OCH$_3$, while R$_4$ and R$_7$ (and R$_3$ if present) are hydrogen.

In some other embodiments, R$_4$ and R$_5$, R$_5$ and R$_6$, or R$_6$ and R$_7$ are joined together with a bond to form a ring; or, optionally, R$_4$ and R$_5$, R$_5$ and R$_6$, or R$_6$ and R$_7$ are joined together to form a 1,2-(methylenedioxy)benzene ring system, such as

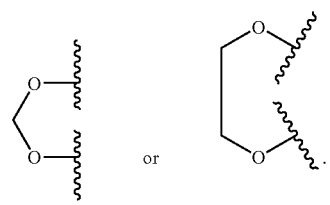 [SMILES: *OCO* ; "or" ; *OCCO* ; "."]

In one embodiment, the ring is composed of a structure selected from the group consisting of:

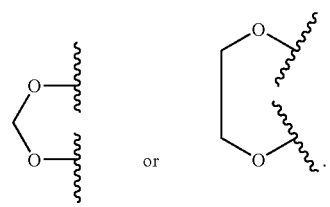 [SMILES: *OCO* ; "or" ; *OCCO* ; "."]

In a further embodiment, R$_5$ and R$_6$ are connected by one of the rings having a structure selected from the group consisting of:

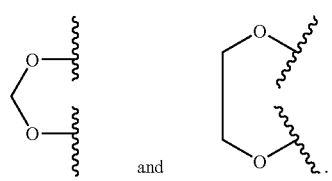 [SMILES: *OCO* ; *OCCO*]

In some of the embodiments of the invention, a compound of Formula I having a structure of Formula I-I is provided:

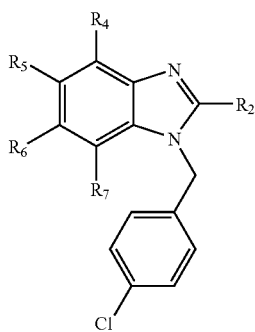

Formula I-I

In various embodiments of the invention, a compound of Formula I having a structure of Formula XXXV is provided:

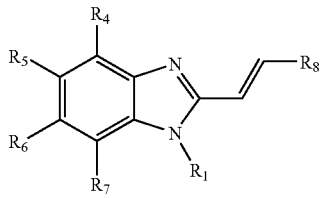

Formula XXXV wherein $R_8$ is aryl, cycloalkyl, heterocyclo, heteroaryl or alkyl. The $R_8$ aryl, cycloalkyl, heterocyclo, heteroaryl or alkyl are as described for $R_2$ aryl, cycloalkyl, heterocyclo, heteroaryl or alkyl above. In some embodiments when $R_5$ and $R_6$ are both methyl, and $R_4$ and $R_7$ are hydrogen, then $R_8$ is not phenyl. In other embodiments, $R_2$ heteroaryl is 2-pyridyl, 3-pyridyl or 4-pyridyl. Additionally, the invention provides compounds of Formula XXXV, wherein $R_4$ is selected from the group consisting of: —NH$_2$,

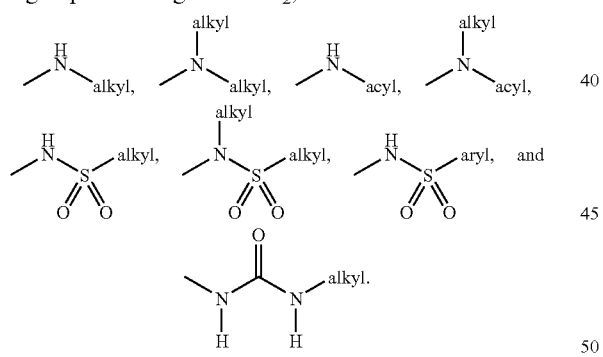

Other compounds of Formula XXXV are provided wherein the compounds have a structure of one of the following formulae:

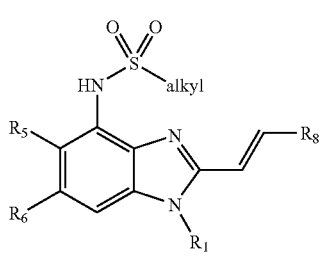

Formula XXXV-A

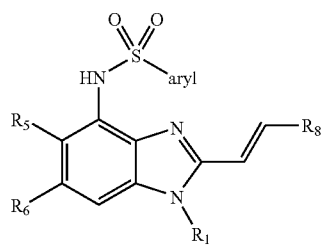

Formula XXXV-B

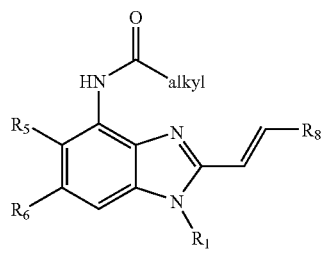

Formula XXXV-C

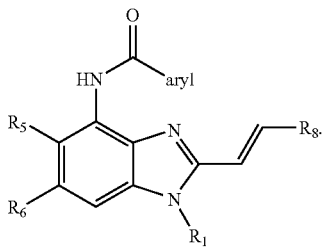

Formula XXXV-D

The invention also provides compounds of Formula I having a structure of Formula XXXVI-A or Formula XXXVI-B:

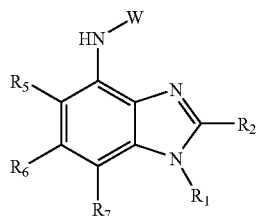

Formula XXXVI-A

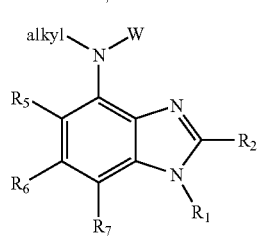

Formula XXXVI-B wherein W is H, alkyl, —C(O)aryl, —C(O)alkyl, —SO$_2$aryl, —SO$_2$alkyl, or —C(O)NHR wherein alkyl and aryl are as defined above for

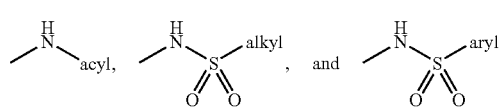

of $R_3$-$R_7$. In some embodiments, the compound of Formula XXXVI is a compound wherein when W is —SO$_2$alkyl, alkyl is ethyl, propyl, butyl, pentyl, hexyl, septyl, nonyl, or decyl. In other embodiments of compounds of Formula XXXVI-A and Formula XXXVI-B, when R$_4$— is,

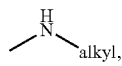

at least one of R$_5$-R$_7$ is other than hydrogen.

The invention provides additional compounds of Formula XXXVII:

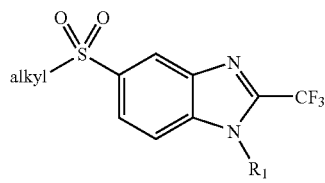

Formula XXXVII wherein alkyl is defined as above for

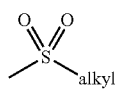

of R$_4$-R$_7$. In some embodiments, the compound of Formula XXXVIII is not: a compound wherein alkyl is methyl and R$_1$ is unsubstituted benzyl.

The invention provides additional compounds of Formula XXXVIII:

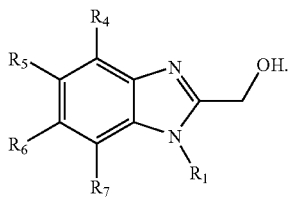

Formula XXXVIII

In some embodiments, the compounds of Formula XXXVIII is a compound of Formula XXXVIII-A:

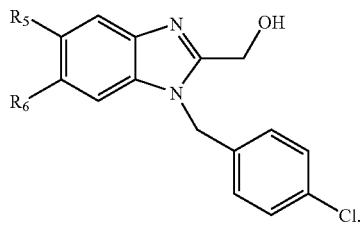

Formula XXXVIII-A

In some embodiments of the invention, the compound of Formula XXXIX is a compound where when R$_4$, R$_5$, R$_6$, and R$_7$ are all hydrogen, then R$_1$ is not para-bromo benzyl. In some embodiments of the compound of Formula XXXVIII, R$_4$ and R$_7$ are hydrogen. In other embodiments, R$_4$ is —I, —Br, —Cl, —F, —CH$_3$, —OCH$_3$, —OH, —NH$_2$, —NO$_2$,

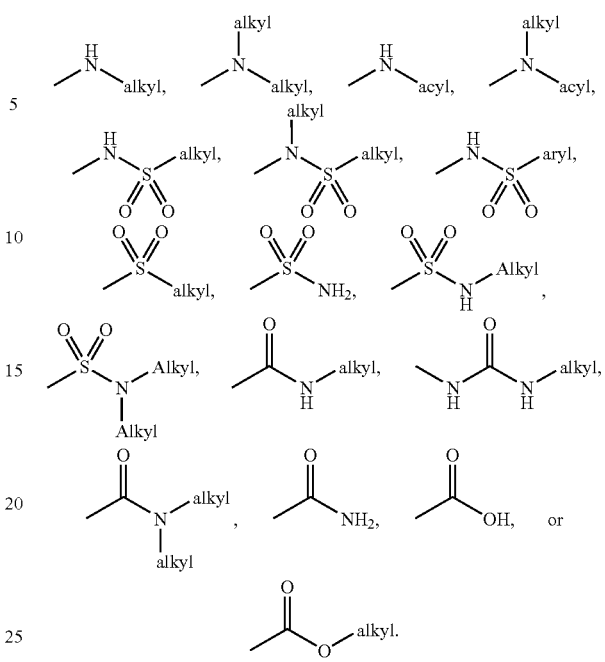

The invention provides yet other compounds of Formula I having a structure of Formula XXXIX:

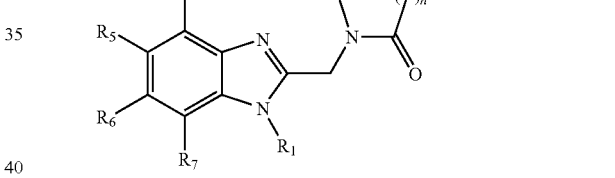

Formula XXXIX wherein n is 1 or 2.

Alternatively, the invention provides compounds of Formula I having a structure of Formula XXXX:

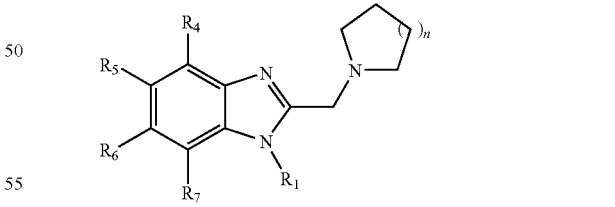

Formula XXXX wherein n is 1 or 2. In some embodiments of the invention, at least one of R$_4$-R$_7$ is not hydrogen. In other embodiments of the invention, when n is 1 and R$_4$ and R$_7$ are hydrogen, then R$_5$ and R$_6$ are not both ethoxy. In yet other embodiments of the invention, a compound of Formula XXXX is the compound wherein n is 1 and R$_5$ is —S(O)$_2$alkyl, —S(O)$_2$NH$_2$, or —S(O)$_2$NH(alkyl).

The invention provides yet other compounds of Formula I having a structure of Formula XXXXI:

Formula XXXXI

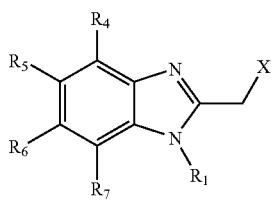

wherein X is selected from the group consisting of: —OH, alkyl, cycloalkyl, heteroaryl, —O(CH$_2$)$_d$CH$_3$, —O-cycloalkyl, or —O-heterocyclo;

d is 1, 2, or 3;

R$_1$ is selected from the group consisting of: —H and

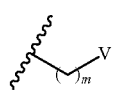

m=0, 1, 2 wherein V is selected from alkyl, cycloalkyl, heterocyclo, aryl or heteroaryl, and m is 0, 1 or 2;

each of R$_4$-R$_7$ is independently selected from the group consisting of: —H, —I, —Br, —Cl, —F, —CH$_3$, —CN, —OH, —OCH$_3$, —NO$_2$, —NH$_2$,

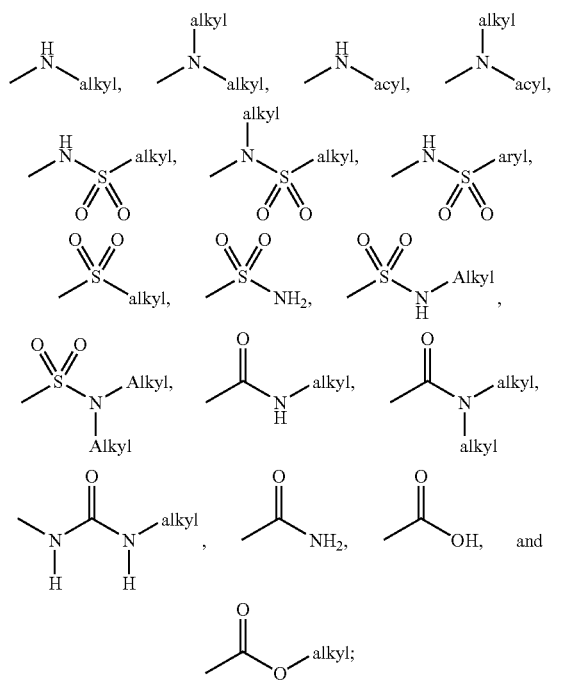

or, optionally, R$_4$ and R$_5$, R$_5$ and R$_6$, or R$_6$ and R$_7$ are joined together with a bond to form a 5, 6, or 7-membered ring; or, optionally, R$_4$ and R$_5$, R$_5$ and R$_6$, or R$_6$ and R$_7$ are joined together to form a 1,2-(methylenedioxy)benzene ring system; and wherein at least one of R$_4$-R$_7$ is other than hydrogen.

Other inhibiting agents of the present invention include a compound having one of the following structures:

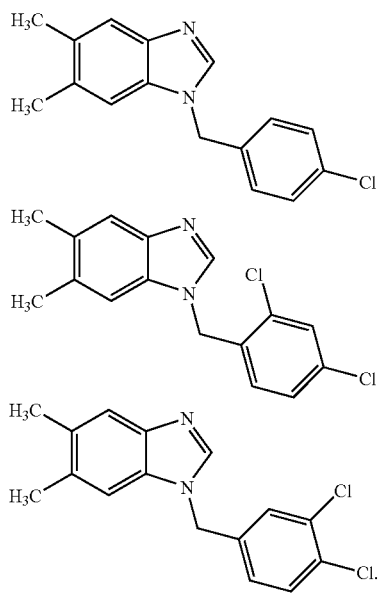

In some other embodiments, the inhibiting agent provided by the present invention is a compound having one of the following structures:

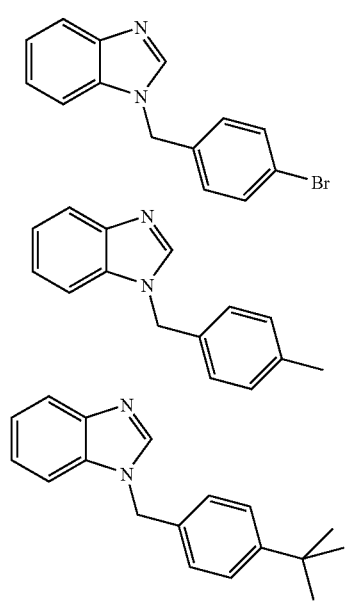

In yet other embodiments, the inhibiting agent includes compounds having a 5,6-disubstituted clemizole scaffold. In some embodiments, the inhibiting agent includes 5,6-disubstituted clemizole compounds, where the substitution does not include diethoxy substitutions. In another embodiment, the inhibiting agent can include 5,6-disubstituted clemizole compounds of the following structure:

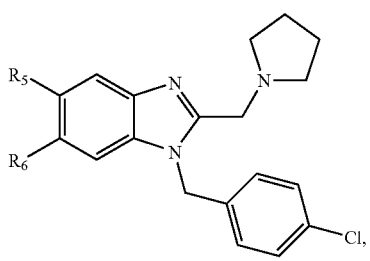

where R₅ and R₆ are as defined above. In another embodiment, $R_5$ is selected from the group consisting of: —H, —CH₃, —I, —Br, —Cl, —F, —OCH₃, —NH₂,

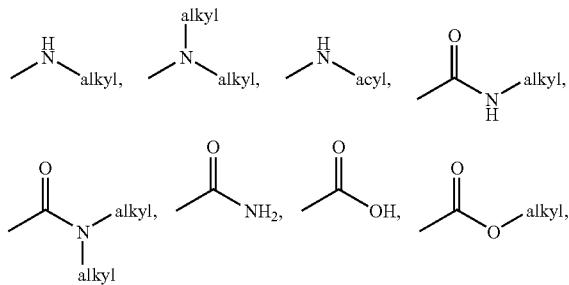

and —SO₂CH₃; and $R_6$ is selected from the group consisting of —H, —CH₃, —I, —Br, —Cl, F, —OCH₃,

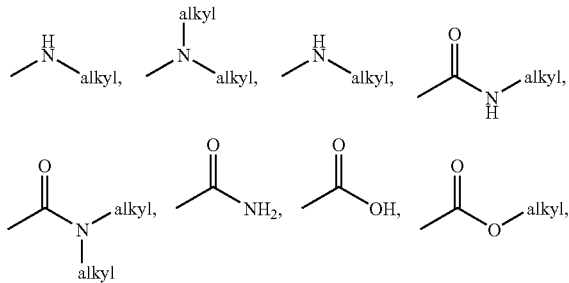

and —NH₂.

In still other embodiments of the invention, for compounds of Formula I and Formulae II-XXXIV, $R_1$ is —H or

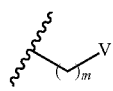

m=0, 1, 2 wherein V is selected from alkyl, cycloalkyl, heterocyclo, aryl or heteroaryl; $R_2$ is —H,

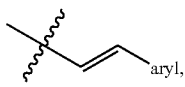 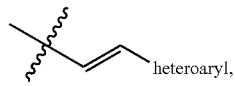

or

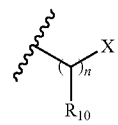

n=0, 1, 2, 3, 4; X is selected from the group consisting of: —NH₂, —NH(alkyl), —N(alkyl)₂, CONH(alkyl), COHC(aryl), —OH, -alkyl, cycloalkyl, alkenyl, —CF₃, —O(alkyl), -aryl, heteroaryl, N-attached heterocyclo, C-attached heterocyclo, —SH, —SO₂(alkyl), —S(alkyl), and —S(aralkyl); $R_{10}$ is hydrogen or alkyl, and each of $R_3$-$R_7$ is independently selected from the group consisting of: —H, —I, —Br, —Cl, —F, —CH₃, —OCH₃, —OH, —NH₂, —NO₂,

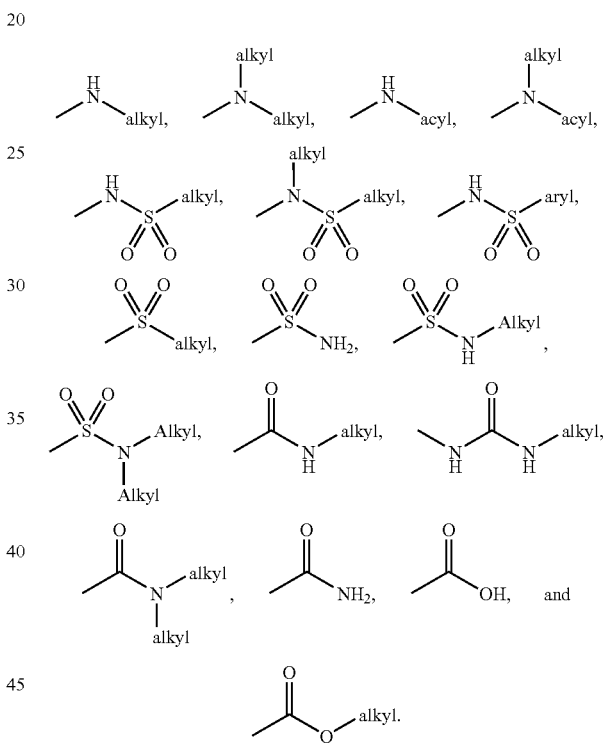

In other embodiments of the invention, for compounds of Formula I and Formulae II-XXXIV, $R_1$ is —H or

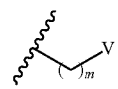

m=0, 1, 2 wherein V is selected from alkyl, cycloalkyl, heterocyclo, aryl or heteroaryl; $R_2$ is —H,

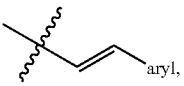 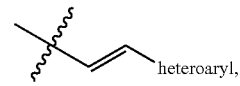

or

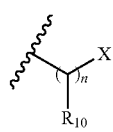

n=0, 1, 2, 3, 4; X is selected from the group consisting of: —NH$_2$, —NH(alkyl), —N(alkyl)$_2$, CONH(alkyl), COHC(aryl), —OH, -alkyl, cycloalkyl, alkenyl, —CF$_3$, —O(alkyl), -aryl, heteroaryl, N-attached heterocyclo, C-attached heterocyclo, —SH, —SO$_2$(alkyl), —S(alkyl), and —S(aralkyl); R$_{10}$ is hydrogen or alkyl, and n is 0, 1, 2, 3, or 4; R$_7$ is H; and R$_4$, R$_5$, R$_6$, and R$_3$ (if present) are each independently selected from the group consisting of: —H, —I, —Br, —Cl, —F, —CH$_3$, —OCH$_3$, —OH, —NH$_2$, —NO$_2$,

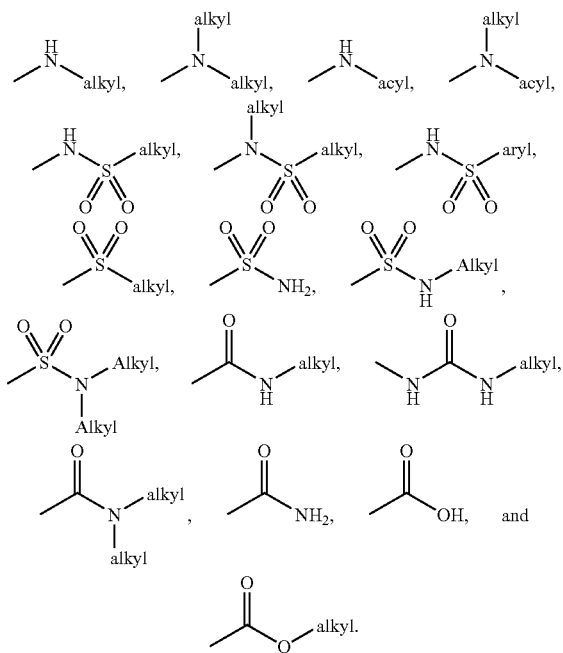

For compounds of Formula I and Formulae II-XXXIV, R$_1$ can be —H or

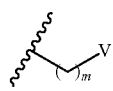

m=0, 1, 2 wherein V is selected from alkyl, cycloalkyl, heterocyclo, aryl or heteroaryl, and m is 0, 1 or 2; R$_2$ can be —H,

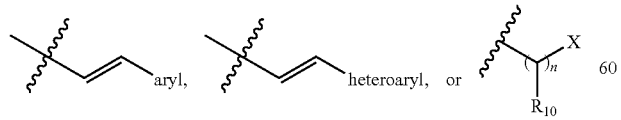

n=0, 1, 2, 3, 4; X is selected from the group consisting of: —NH$_2$, —NH(alkyl), —N(alkyl)$_2$, CONH(alkyl), COHC(aryl), —OH, -alkyl, cycloalkyl, alkenyl, —CF$_3$, —O(alkyl), -aryl, heteroaryl, N-attached heterocyclo, C-attached heterocyclo, and —SO$_2$(alkyl); R$_{10}$ is hydrogen or alkyl, and n is 0, 1, 2, 3, or 4, R$_7$ is H; R$_4$ is selected from the group consisting of:

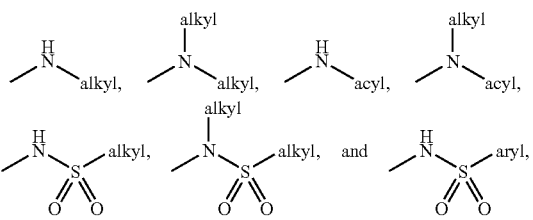

and R$_4$, R$_6$, and R$_3$ (if present) can each independently be selected from the group consisting of: —H, —I, —Br, —Cl, —F, —CH$_3$, —OCH$_3$, and —OH.

In addition, compounds of Formula I and Formulae II-XXXIV can have the following substitution pattern: R$_1$ is —H or

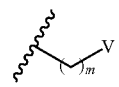

m=0, 1, 2 wherein V is selected from alkyl, cycloalkyl, heterocyclo, aryl or heteroaryl; R$_2$ is —H,

or

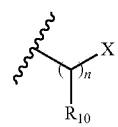

n=0, 1, 2, 3, 4; X is selected from the group consisting of: —NH$_2$, —NH(alkyl), —N(alkyl)$_2$, CONH(alkyl), COHC(aryl), —OH, -alkyl, cycloalkyl, alkenyl, —CF$_3$, —O(alkyl), -aryl, heteroaryl, N-attached heterocyclo, C-attached heterocyclo, and —SO$_2$(alkyl); R$_{10}$ is hydrogen or alkyl; R$_7$ is H; R$_5$ is selected from the group consisting of:

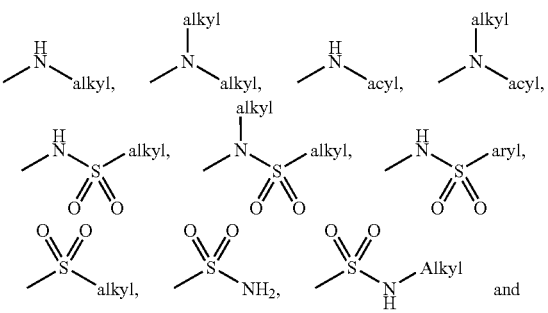

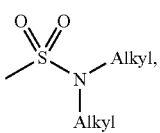
and $R_4$, $R_6$, and $R_3$ (if present) are each independently selected from the group consisting of: —H, —I, —Br, —Cl, —F, —CH$_3$, —OCH$_3$, and —OH.
Moreover, the compounds of Formula I and Formulae II-XXXIV can include the following combinations of substitutents: $R_1$ is selected from the group consisting of
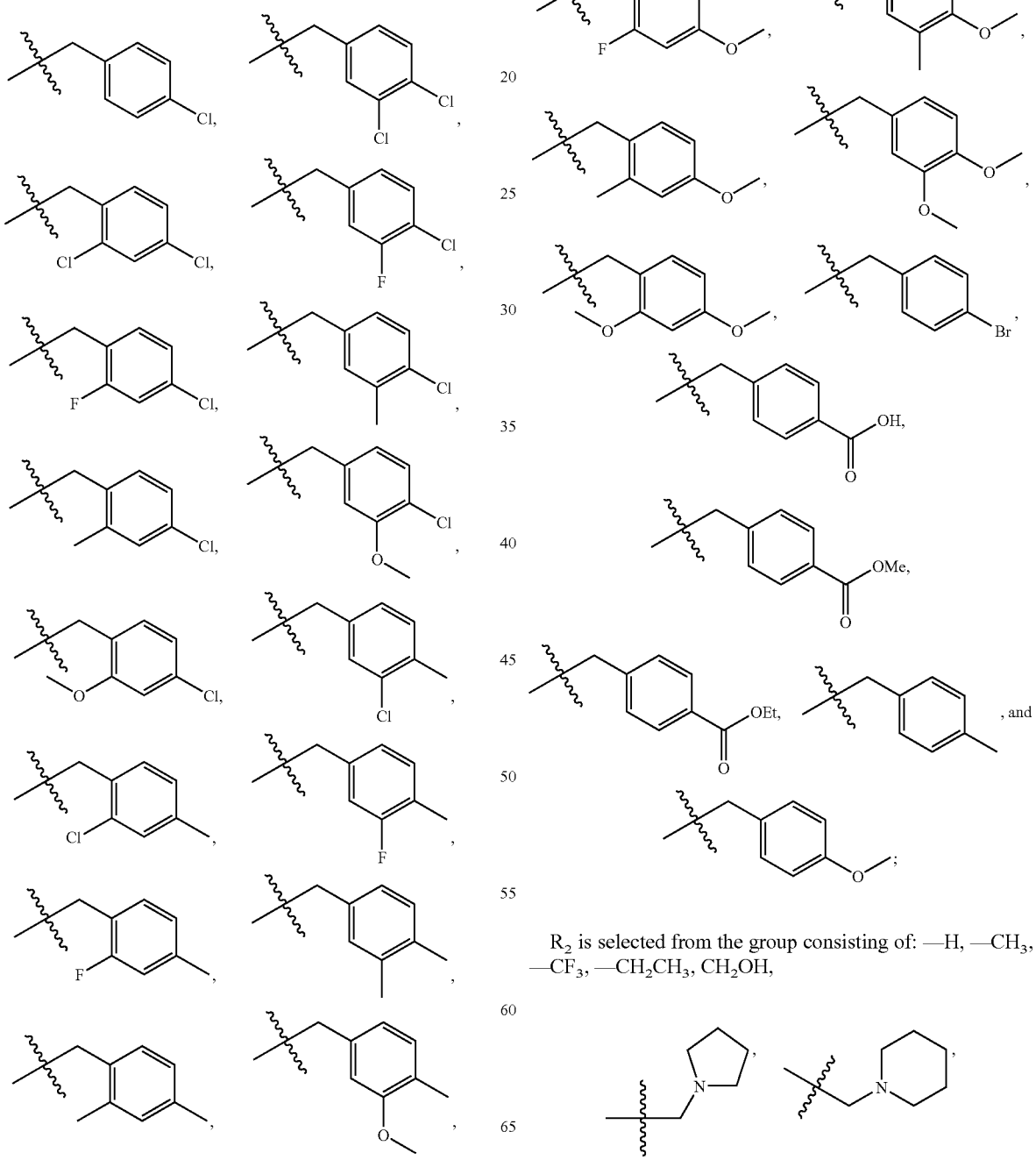
$R_2$ is selected from the group consisting of: —H, —CH$_3$, —CF$_3$, —CH$_2$CH$_3$, CH$_2$OH,

81

-continued

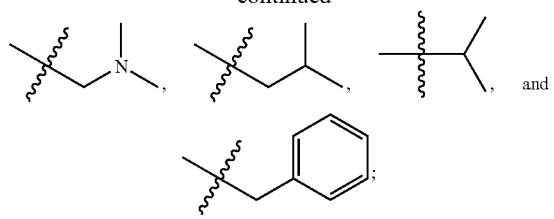

R₃, if present, is hydrogen; R₄ is selected from the group consisting of: —H and —NH₂; R₅ and R₆ are independently selected from the group consisting of: —H, —CH₃, —I, —Br, —Cl, —F, —OCH₃, —NH₂,

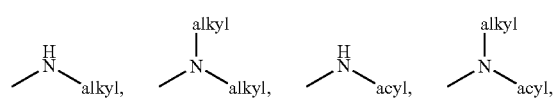

82

-continued

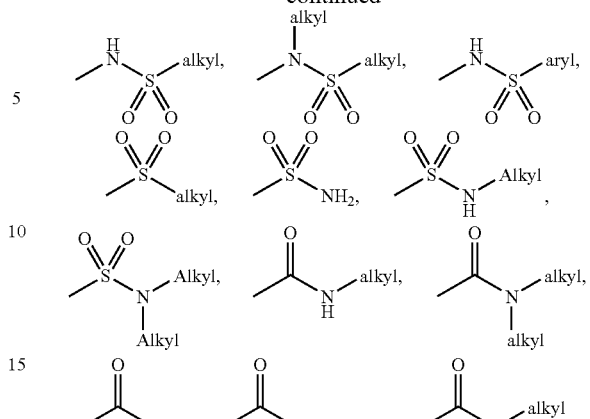

and R₇ is —H. Table 1 shows structures of additional inhibiting agents of the invention and illustrative starting materials to prepare them.

TABLE 1

| | Structure | Illustrative Starting Material |
|---|---|---|
| 1 | 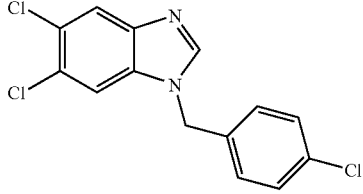 [SMILES: Clc1ccc(Cn2cnc3cc(Cl)c(Cl)cc32)cc1] | 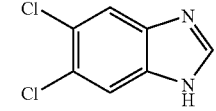 |
| 2 | 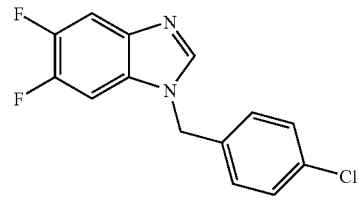 [SMILES: Fc1cc2ncn(Cc3ccc(Cl)cc3)c2cc1F] | 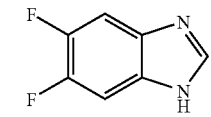 |
| 3 | 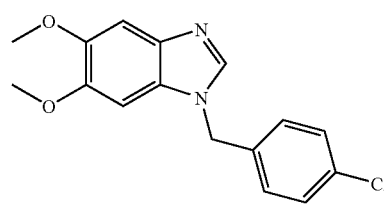 | 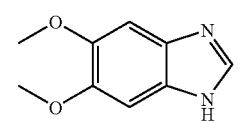 |
| 4 | 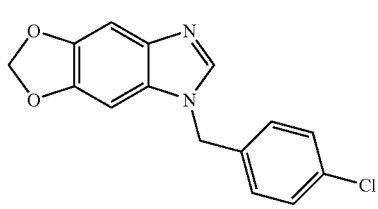 [SMILES: Clc1ccc(Cn2cnc3cc4c(cc32)OCO4)cc1] | 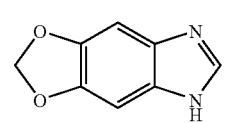 |

TABLE 1-continued

| | Structure | Illustrative Starting Material |
|---|---|---|
| 5 | 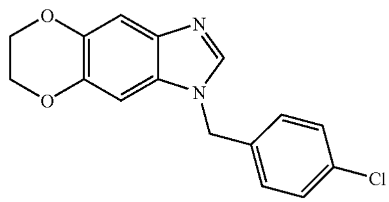 [SMILES: Clc1ccc(Cn2cnc3cc4c(cc32)OCCO4)cc1] | |
| 6 | 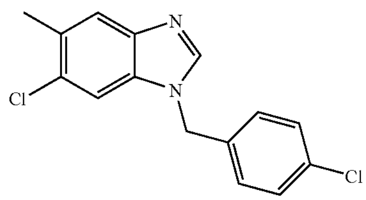 [SMILES: Cc1cc2ncn(Cc3ccc(Cl)cc3)c2cc1Cl] | |
| 7 | 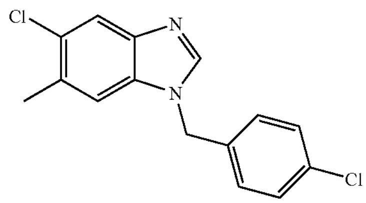 [SMILES: Cc1cc2c(cc1Cl)ncn2Cc1ccc(Cl)cc1] | |
| 8 | 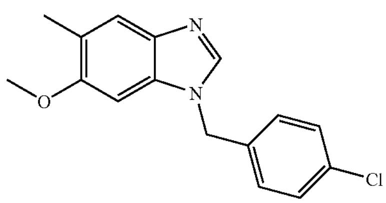 [SMILES: COc1cc2c(cc1C)ncn2Cc1ccc(Cl)cc1] | |
| 9 | 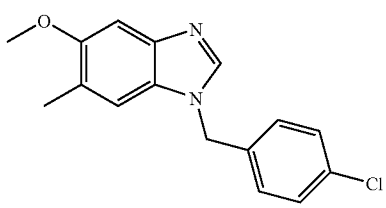 [SMILES: COc1cc2ncn(Cc3ccc(Cl)cc3)c2cc1C] | |
| 10 | 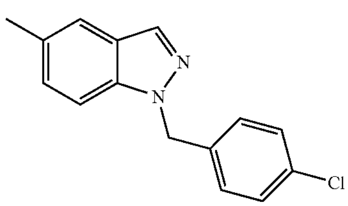 [SMILES: Cc1ccc2c(cnn2Cc2ccc(Cl)cc2)c1] | |
| 11 | 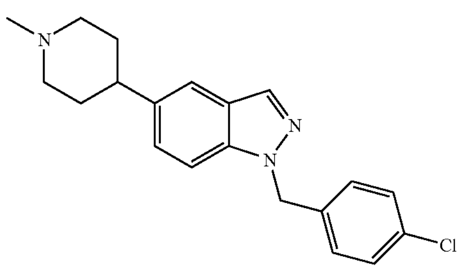 [SMILES: CN1CCC(c2ccc3c(cnn3Cc3ccc(Cl)cc3)c2)CC1] | |

TABLE 1-continued

| | Structure | Illustrative Starting Material |
|---|---|---|
| 12 | 5-(trifluoromethyl)-1-(4-chlorobenzyl)-1H-indazole | 5-(trifluoromethyl)-1H-indazole |
| 13 | 5-cyano-6-fluoro-1-(4-chlorobenzyl)-1H-indazole | 5-cyano-6-fluoro-1H-indazole |
| 14 | 5-chloro-1-(4-chlorobenzyl)-1H-indazole | 5-chloro-1H-indazole |
| 15 | 5,6-dichloro-1-(4-chlorobenzyl)-1H-indazole | 5,6-dichloro-1H-indazole |
| 16 | 5,6-dimethyl-1-(4-chlorobenzyl)-1H-indazole | 5,6-dimethyl-1H-indazole |
| 17 | 6-methyl-1-(4-chlorobenzyl)-1H-indazole | 6-methyl-1H-indazole |
| 18 | 5-chloro-6-methyl-1-(4-chlorobenzyl)-1H-indazole | 5-chloro-6-methyl-1H-indazole |

TABLE 1-continued

| | Structure | Illustrative Starting Material |
|---|---|---|
| 19 | (5-methoxy-6-methyl-1-(4-chlorobenzyl)-1H-indazole) | (5-methoxy-6-methyl-1H-indazole) |
| 20 | (5,6-dimethyl-1-(4-chlorobenzyl)-1H-indole) | (5,6-dimethyl-1H-indole) |
| 21 | (5,6-dimethyl-3-(4-chlorobenzyl)-3H-imidazo[4,5-b]pyridine) | (5,6-dimethyl-3H-imidazo[4,5-b]pyridine) |
| 22 | (3-(4-chlorobenzyl)-3H-imidazo[4,5-c]pyridine) | (3H-imidazo[4,5-c]pyridine) |

Table 2 shows structures of additional inhibiting agents of the invention based on the structure below.

TABLE 2

(benzimidazole core with $R_1$, $R_2$, $R_4$, $R_5$, $R_6$, $R_7$ substituents)

| $R_1$ | $R_2$ | $R_4$ | $R_5$ | $R_6$ | $R_7$ |
|---|---|---|---|---|---|
| 3,4-dichlorobenzyl | piperidinylmethyl | H | H | H | H |
| 3-fluoro-4-chlorobenzyl | piperidinylmethyl | H | H | H | H |

TABLE 2-continued
| R₁ | R₂ | R₄ | R₅ | R₆ | R₇ |
|---|---|---|---|---|---|
| 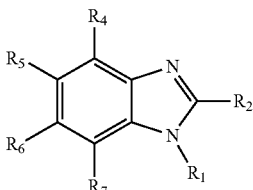 | 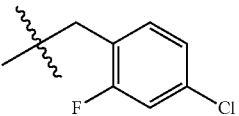 [SMILES: *Cc1ccc(Cl)cc1F] | H | H | H | H |
| 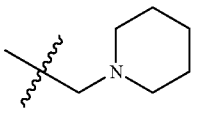 | 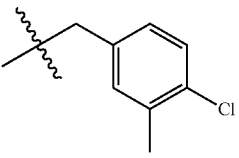 [SMILES: *Cc1ccc(Cl)c(C)c1] | H | H | H | H |
| 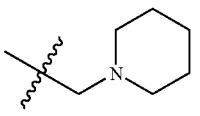 [SMILES: *CN1CCCCC1] | 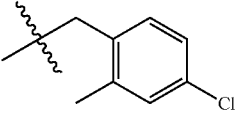 [SMILES: *Cc1ccc(Cl)cc1C] | H | H | H | H |
| 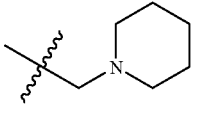 | 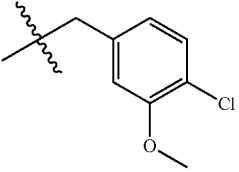 [SMILES: *Cc1ccc(Cl)c(OC)c1] | H | H | H | H |
| 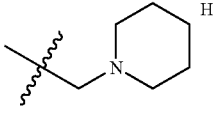 | 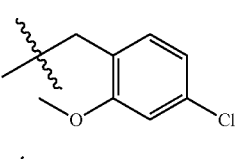 | H | H | H | H |
| 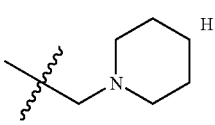 | 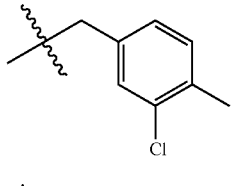 | H | H | H | H |
| 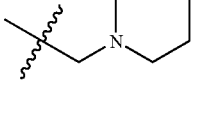 | 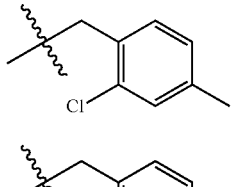 | H | H | H | H |
| 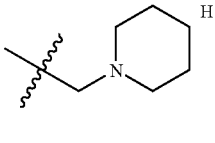 | 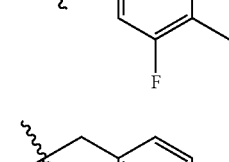 | H | H | H | H |
| 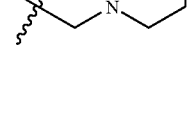 | 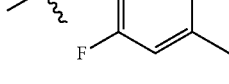 | H | H | H | H |

TABLE 2-continued
| R₁ | R₂ | R₄ | R₅ | R₆ | R₇ |
|---|---|---|---|---|---|
| 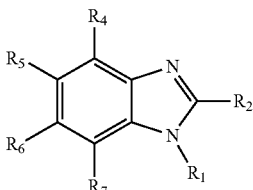 | 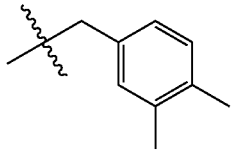 [SMILES: *Cc1ccc(C)c(C)c1] | H | H | H | H |
| 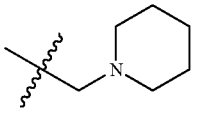 [SMILES: *CN1CCCCC1] | 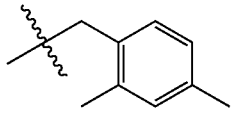 [SMILES: *Cc1ccc(C)cc1C] | H | H | H | H |
| 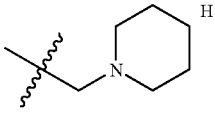 | 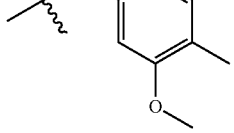 | H | H | H | H |
| 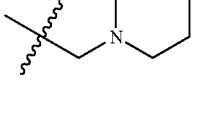 | 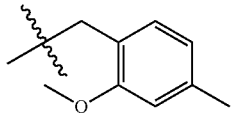 [SMILES: *Cc1ccc(C)cc1OC] | H | H | H | H |
| 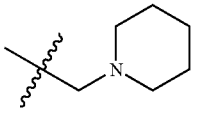 [SMILES: *CN1CCCCC1] | 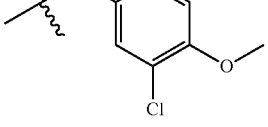 | H | H | H | H |
| 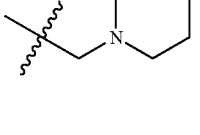 | 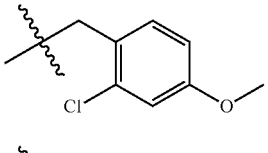 | H | H | H | H |
| 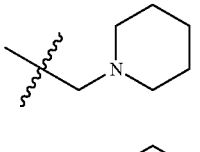 | 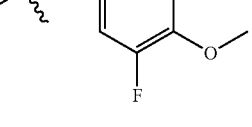 | H | H | H | H |
| 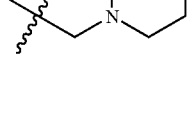 | 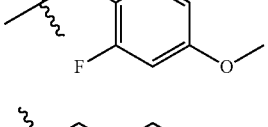 | H | H | H | H |
| 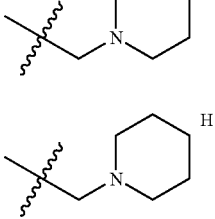 | 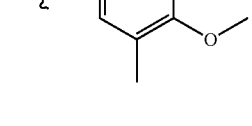 | H | H | H | H |

TABLE 2-continued

[Benzimidazole core structure with substituents R1, R2, R4, R5, R6, R7]

| R1 | R2 | R4 | R5 | R6 | R7 |
|---|---|---|---|---|---|
| 4-methoxy-2-methylbenzyl | piperidin-1-ylmethyl | H | H | H | H |
| 3,4-dimethoxybenzyl | piperidin-1-ylmethyl | H | H | H | H |
| 2,4-dimethoxybenzyl | piperidin-1-ylmethyl | H | H | H | H |
| 3,4-dichlorobenzyl | (dimethylamino)methyl | H | H | H | H |
| 2,4-dichlorobenzyl | (dimethylamino)methyl | H | H | H | H |
| 4-chloro-3-fluorobenzyl | (dimethylamino)methyl | H | H | H | H |
| 4-chloro-2-fluorobenzyl | (dimethylamino)methyl | H | H | H | H |
| 4-chloro-3-methylbenzyl | (dimethylamino)methyl | H | H | H | H |
| 4-chloro-2-methylbenzyl | (dimethylamino)methyl | H | H | H | H |

TABLE 2-continued

| R₁ | R₂ | R₄ | R₅ | R₆ | R₇ |
|---|---|---|---|---|---|
| | | H | H | H | H |
| | | H | H | H | H |
| | | H | H | H | H |
| | | H | H | H | H |
| | | H | H | H | H |
| | | H | H | H | H |
| | | H | H | H | H |
| | | H | H | H | H |

TABLE 2-continued
| R₁ | R₂ | R₄ | R₅ | R₆ | R₇ |
|---|---|---|---|---|---|
| 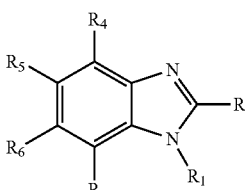 | 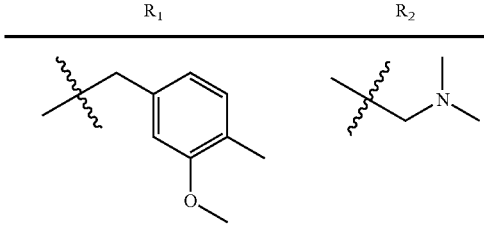 | H | H | H | H |
| 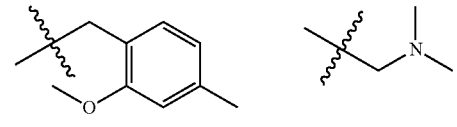 | 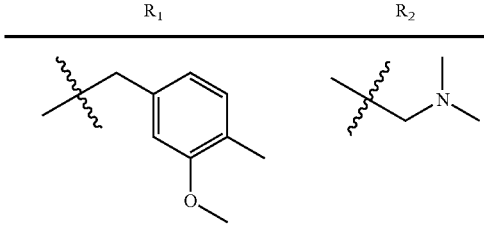 | H | H | H | H |
| 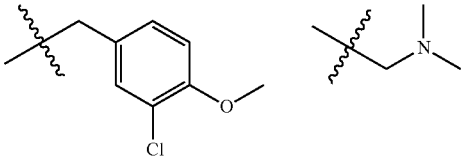 | 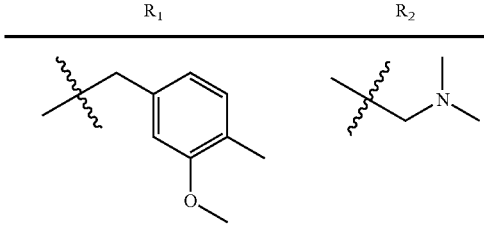 | H | H | H | H |
| 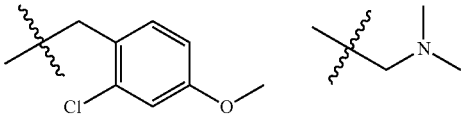 | 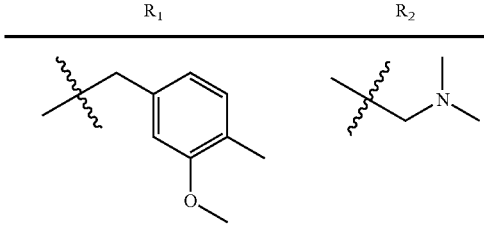 | H | H | H | H |
| 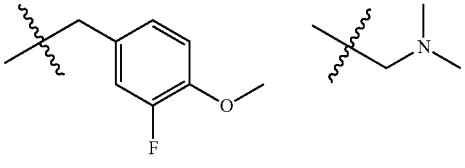 | 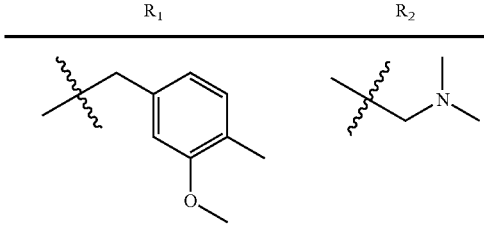 | H | H | H | H |
| 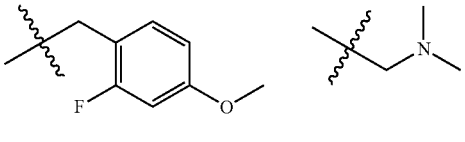 | 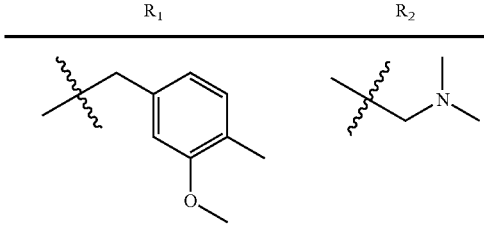 | H | H | H | H |
| 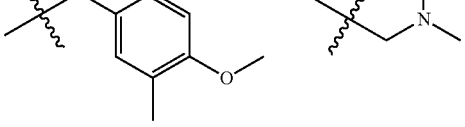 | 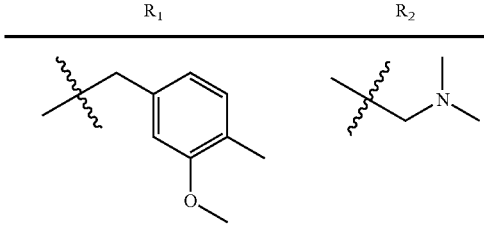 | H | H | H | H |
| 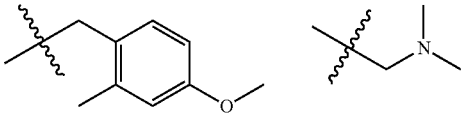 | 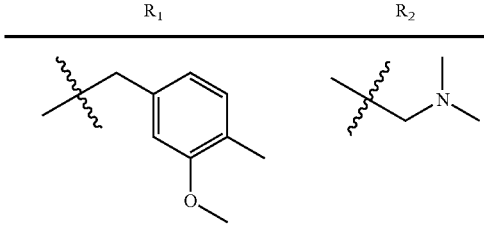 | H | H | H | H |

TABLE 2-continued
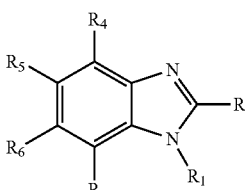
| R₁ | R₂ | R₄ | R₅ | R₆ | R₇ |
|---|---|---|---|---|---|
| 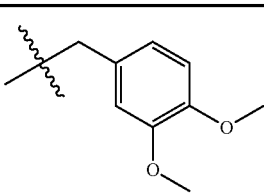 | 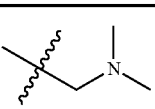 | H | H | H | H |
| 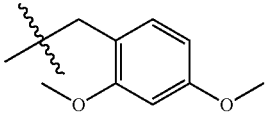 [SMILES: *Cc1ccc(OC)cc1OC] | 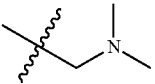 | H | H | H | H |
| 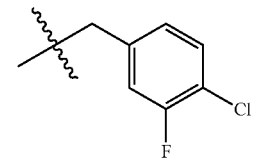 [SMILES: *Cc1ccc(Cl)c(F)c1] | 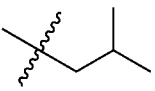 [SMILES: *CC(C)C] | H | H | H | H |
| 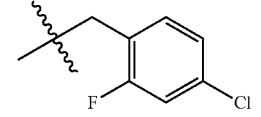 | 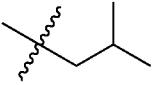 | H | H | H | H |
| 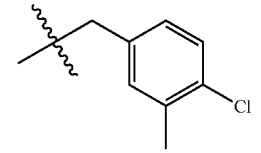 [SMILES: *Cc1ccc(Cl)c(C)c1] | 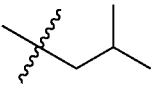 | H | H | H | H |
| 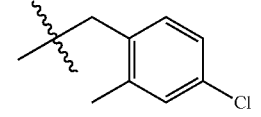 [SMILES: *Cc1ccc(Cl)cc1C] | 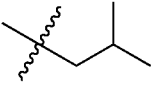 | H | H | H | H |
| 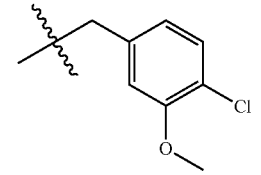 [SMILES: *Cc1ccc(Cl)c(OC)c1] | 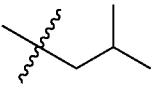 | H | H | H | H |
| 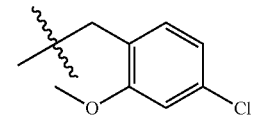 [SMILES: *Cc1ccc(Cl)cc1OC] | 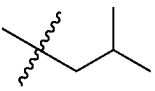 [SMILES: *CC(C)C] | H | H | H | H |

TABLE 2-continued
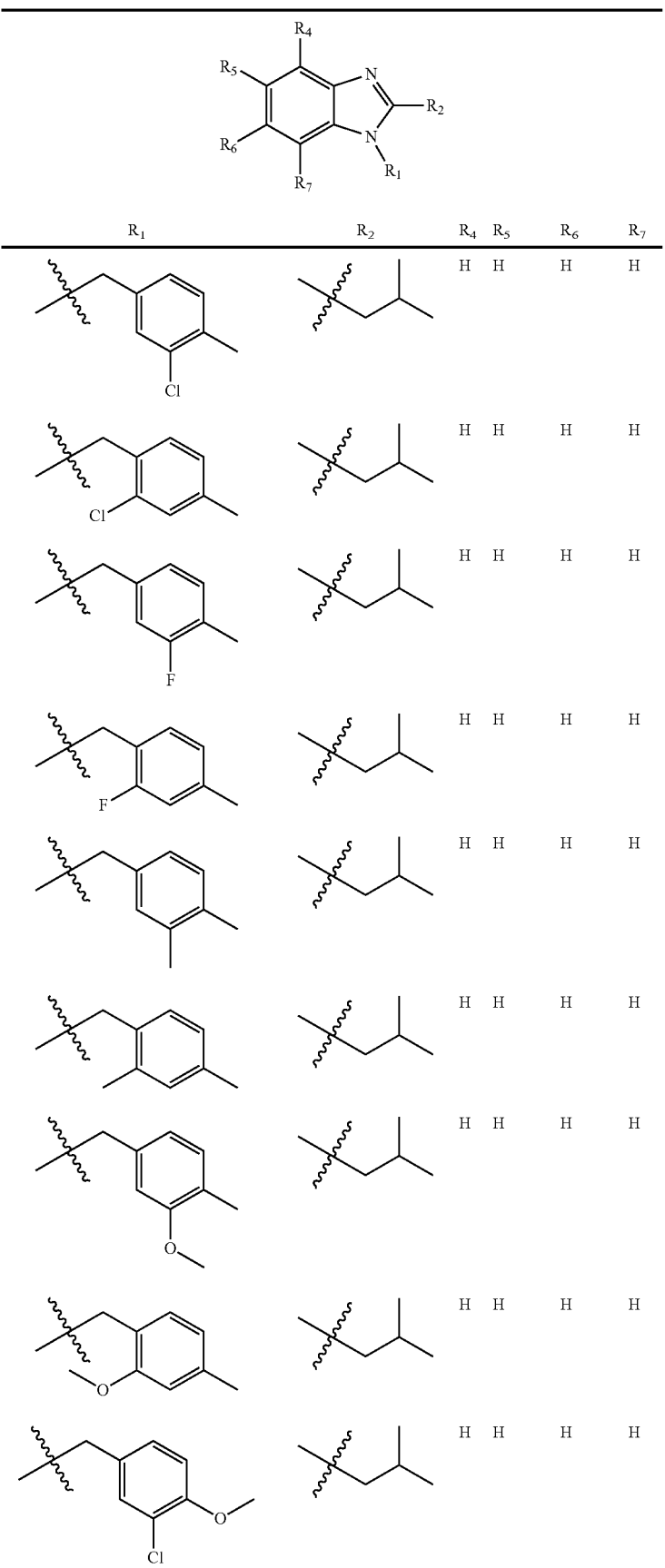

TABLE 2-continued

| R₁ | R₂ | R₄ | R₅ | R₆ | R₇ |
|---|---|---|---|---|---|
| 4-methoxy-2-chlorobenzyl | isobutyl | H | H | H | H |
| 4-methoxy-3-fluorobenzyl | isobutyl | H | H | H | H |
| 4-methoxy-3-fluorobenzyl (alt) | isobutyl | H | H | H | H |
| 4-methoxy-3-methylbenzyl | isobutyl | H | H | H | H |
| 4-methoxy-3-methylbenzyl (alt) | isobutyl | H | H | H | H |
| 2,4-dimethoxybenzyl | isobutyl | H | H | H | H |
| 4-chloro-3-fluorobenzyl | isopropyl | H | H | H | H |
| 4-chloro-2-fluorobenzyl | isopropyl | H | H | H | H |
| 4-chloro-3-methylbenzyl | isopropyl | H | H | H | H |

TABLE 2-continued

| R₁ | R₂ | R₄ | R₅ | R₆ | R₇ |
|---|---|---|---|---|---|
| 4-Cl, 2-methyl benzyl | isopropyl | H | H | H | H |
| 3-Cl, 4-methoxy... | isopropyl | H | H | H | H |
| 3-chloro-4-methoxybenzyl | isopropyl | H | H | H | H |
| 4-chloro-2-methoxybenzyl | isopropyl | H | H | H | H |
| 3-chloro-4-methylbenzyl | isopropyl | H | H | H | H |
| 2-chloro-4-methylbenzyl | isopropyl | H | H | H | H |
| 3-fluoro-4-methylbenzyl | isopropyl | H | H | H | H |
| 2-fluoro-4-methylbenzyl | isopropyl | H | H | H | H |
| 3,4-dimethylbenzyl | isopropyl | H | H | H | H |
| 2,4-dimethylbenzyl | isopropyl | H | H | H | H |

TABLE 2-continued
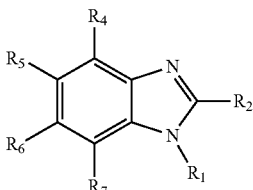

TABLE 2-continued
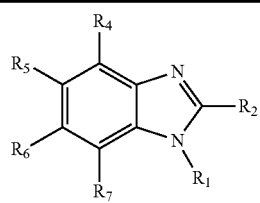
| R₁ | R₂ | R₄ | R₅ | R₆ | R₇ |
|---|---|---|---|---|---|
| 4-Cl-2-F-benzyl | H | H | CH₃ | CH₃ | H |
| 4-Cl-3-methyl-benzyl | H | H | CH₃ | CH₃ | H |
| 4-Cl-2-methyl-benzyl | H | H | CH₃ | CH₃ | H |
| 4-Cl-3-methoxy-benzyl | H | H | CH₃ | CH₃ | H |
| 4-Cl-2-methoxy-benzyl | H | H | CH₃ | CH₃ | H |
| 3-Cl-4-methyl-benzyl | H | H | CH₃ | CH₃ | H |
| 2-Cl-4-methyl-benzyl | H | H | CH₃ | CH₃ | H |
| 3-F-4-methyl-benzyl | H | H | CH₃ | CH₃ | H |
| 2-F-4-methyl-benzyl | H | H | CH₃ | CH₃ | H |

TABLE 2-continued
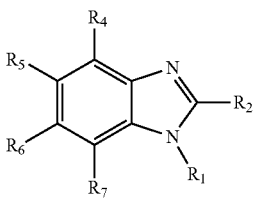
| R₁ | R₂ | R₄ | R₅ | R₆ | R₇ |
|---|---|---|---|---|---|
| 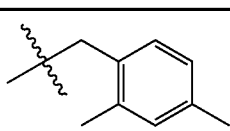 | H | H | CH₃ | CH₃ | H |
| 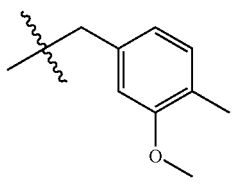 [SMILES: *Cc1ccc(C)c(OC)c1] | H | H | CH₃ | CH₃ | H |
| 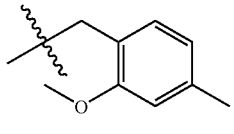 [SMILES: *Cc1ccc(C)cc1OC] | H | H | CH₃ | CH₃ | H |
| 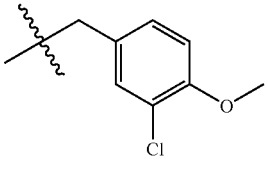 [SMILES: *Cc1ccc(OC)c(Cl)c1] | H | H | CH₃ | CH₃ | H |
| 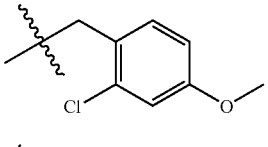 | H | H | CH₃ | CH₃ | H |
| 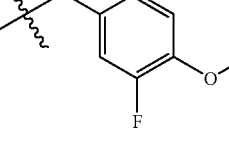 | H | H | CH₃ | CH₃ | H |
| 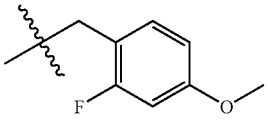 | H | H | CH₃ | CH₃ | H |
| 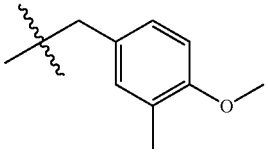 [SMILES: *Cc1ccc(OC)c(C)c1] | H | H | CH₃ | CH₃ | H |
| 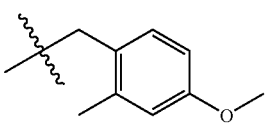 [SMILES: *Cc1ccc(OC)cc1C] | H | H | CH₃ | CH₃ | H |

TABLE 2-continued
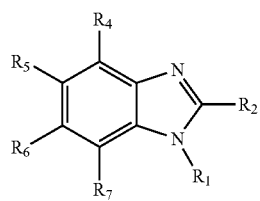
| R₁ | R₂ | R₄ | R₅ | R₆ | R₇ |
|---|---|---|---|---|---|
| 3,4-dimethoxybenzyl | H | H | CH₃ | CH₃ | H |
| 2,4-dimethoxybenzyl | H | H | CH₃ | CH₃ | H |
| 4-chloro-3-fluorobenzyl | CF₃ | H | H | H | H |
| 4-chloro-2-fluorobenzyl | CF₃ | H | H | H | H |
| 4-chloro-3-methylbenzyl | CF₃ | H | H | H | H |
| 4-chloro-2-methylbenzyl | CF₃ | H | H | H | H |
| 4-chloro-3-methoxybenzyl | CF₃ | H | H | H | H |
| 4-chloro-2-methoxybenzyl | CF₃ | H | H | H | H |

TABLE 2-continued
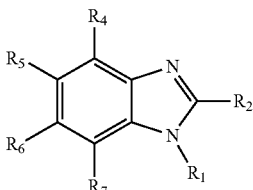
| R₁ | R₂ | R₄ | R₅ | R₆ | R₇ |
|---|---|---|---|---|---|
| 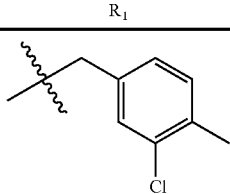 | CF₃ | H | H | H | H |
| 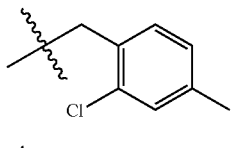 | CF₃ | H | H | H | H |
| 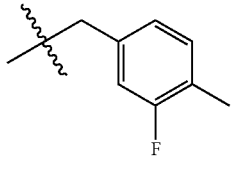 [SMILES: *Cc1ccc(C)c(F)c1] | CF₃ | H | H | H | H |
| 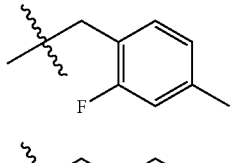 | CF₃ | H | H | H | H |
| 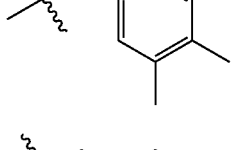 | CF₃ | H | H | H | H |
| 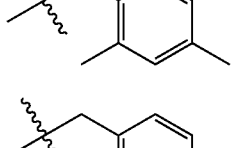 | CF₃ | H | H | H | H |
| 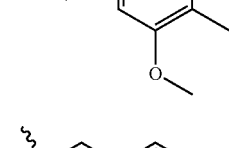 | CF₃ | H | H | H | H |
| 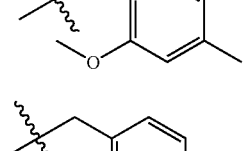 | CF₃ | H | H | H | H |
| 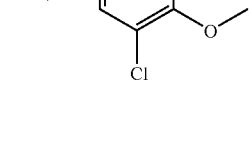 | CF₃ | H | H | H | H |

TABLE 2-continued
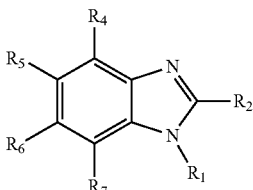
| R₁ | R₂ | R₄ | R₅ | R₆ | R₇ |
|---|---|---|---|---|---|
| 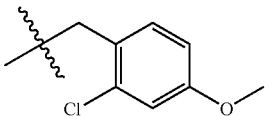 [SMILES: *Cc1ccc(OC)cc1Cl] | CF₃ | H | H | H | H |
| 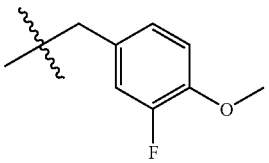 | CF₃ | H | H | H | H |
| 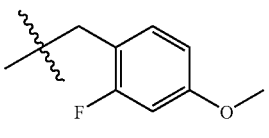 | CF₃ | H | H | H | H |
| 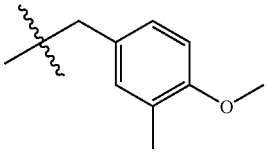 [SMILES: *Cc1ccc(OC)c(C)c1] | CF₃ | H | H | H | H |
| 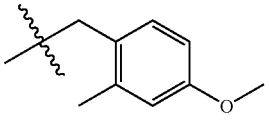 [SMILES: *Cc1ccc(OC)cc1C] | CF₃ | H | H | H | H |
| 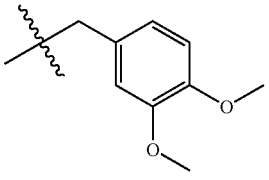 [SMILES: *Cc1ccc(OC)c(OC)c1] | CF₃ | H | H | H | H |
| 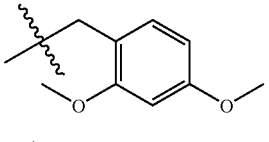 | CF₃ | H | H | H | H |
| 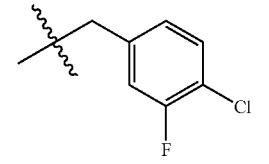 [SMILES: *Cc1ccc(Cl)c(F)c1] | 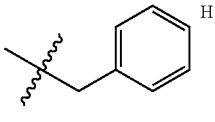 | H | H | H | H |
| 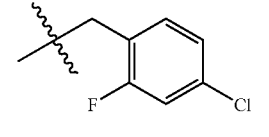 | 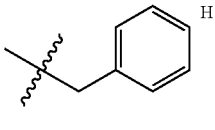 | H | H | H | H |

TABLE 2-continued
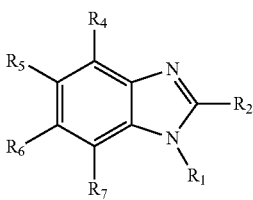

TABLE 2-continued
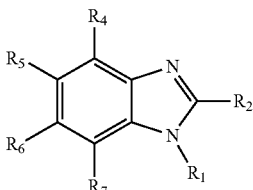
| R₁ | R₂ | R₄ | R₅ | R₆ | R₇ |
|---|---|---|---|---|---|
| 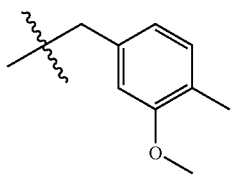 [SMILES: *Cc1ccc(C)c(OC)c1] | 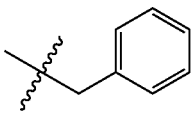 [SMILES: *Cc1ccccc1] | H | H | H | H |
| 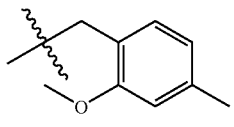 [SMILES: *Cc1ccc(C)cc1OC] | 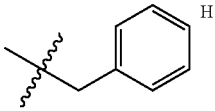 | H | H | H | H |
| 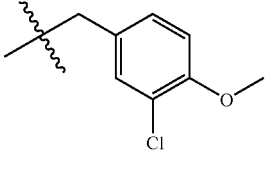 [SMILES: *Cc1ccc(OC)c(Cl)c1] | 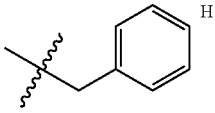 | H | H | H | H |
| 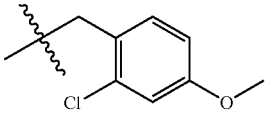 [SMILES: *Cc1ccc(OC)cc1Cl] | 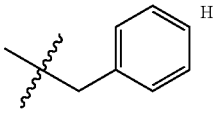 | H | H | H | H |
| 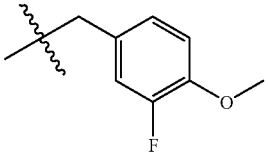 [SMILES: *Cc1ccc(OC)c(F)c1] | 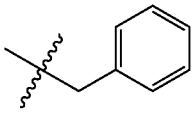 [SMILES: *Cc1ccccc1] | H | H | H | H |
| 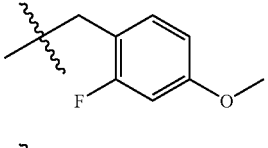 | 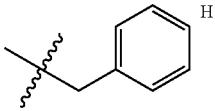 | H | H | H | H |
| 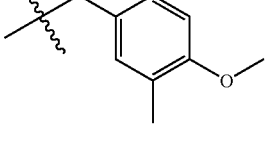 | 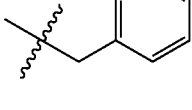 | H | H | H | H |
| 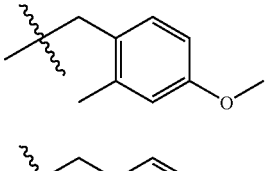 | 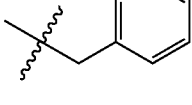 | H | H | H | H |
| 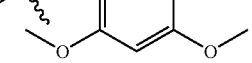 | 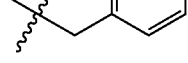 | H | H | H | H |

TABLE 2-continued
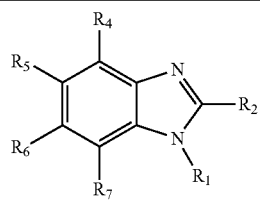
| R₁ | R₂ | R₄ | R₅ | R₆ | R₇ |
|---|---|---|---|---|---|
| 4-(CO₂H)benzyl | CH₃ | H | CH₃ | CH₃ | H |
| 4-(CO₂Me)benzyl | H | H | CH₃ | CH₃ | H |
| 4-(CO₂Me)benzyl | CH₃ | H | CH₃ | CH₃ | H |
| 4-(CO₂Et)benzyl | H | H | CH₃ | CH₃ | H |
| 4-(CO₂Et)benzyl | CH₃ | H | CH₃ | CH₃ | H |
| 4-(OMe)benzyl | CH₃ | H | CH₃ | CH₃ | H |
| 3,4-(OMe)₂benzyl | H | H | CH₃ | CH₃ | H |
| 3,4-(OMe)₂benzyl | CH₃ | H | CH₃ | CH₃ | H |

TABLE 2-continued
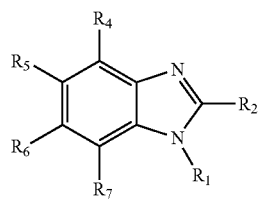
| R₁ | R₂ | R₄ | R₅ | R₆ | R₇ |
|---|---|---|---|---|---|
| 4-bromobenzyl | H | H | Cl | Cl | H |
| 4-bromobenzyl | CH₃ | H | Cl | Cl | H |
| 4-carboxybenzyl | H | H | Cl | Cl | H |
| 4-carboxybenzyl | CH₃ | H | Cl | Cl | H |
| 4-(methoxycarbonyl)benzyl | H | H | Cl | Cl | H |
| 4-(methoxycarbonyl)benzyl | CH₃ | H | Cl | Cl | H |
| 4-(ethoxycarbonyl)benzyl | H | H | Cl | Cl | H |
| 4-(ethoxycarbonyl)benzyl | CH₃ | H | Cl | Cl | H |

TABLE 2-continued

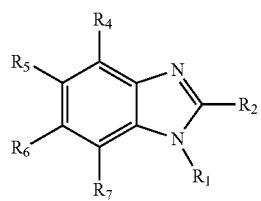

| R₁ | R₂ | R₄ | R₅ | R₆ | R₇ |
|---|---|---|---|---|---|
| ⁓⁓CH₂-C₆H₄-OCH₃ (4-methoxybenzyl) | H | H | Cl | Cl | H |
| ⁓⁓CH₂-C₆H₄-OCH₃ (4-methoxybenzyl) | CH₃ | H | Cl | Cl | H |
| ⁓⁓CH₂-C₆H₃(OCH₃)₂ (3,4-dimethoxybenzyl) | H | H | Cl | Cl | H |
| ⁓⁓CH₂-C₆H₃(OCH₃)₂ (3,4-dimethoxybenzyl) | CH₃ | H | Cl | Cl | H |
| ⁓⁓CH₂-C₆H₄-Br (4-bromobenzyl) | H | H | OCH₃ | OCH₃ | H |
| ⁓⁓CH₂-C₆H₄-Br (4-bromobenzyl) | CH₃ | H | OCH₃ | OCH₃ | H |
| ⁓⁓CH₂-C₆H₄-COOH (4-carboxybenzyl) | H | H | OCH₃ | OCH₃ | H |
| ⁓⁓CH₂-C₆H₄-COOH (4-carboxybenzyl) | CH₃ | H | OCH₃ | OCH₃ | H |

TABLE 2-continued
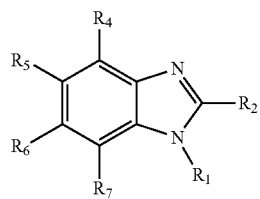
| R₁ | R₂ | R₄ | R₅ | R₆ | R₇ |
|---|---|---|---|---|---|
| 4-(methoxycarbonyl)benzyl | H | H | OCH₃ | OCH₃ | H |
| 4-(methoxycarbonyl)benzyl | CH₃ | H | OCH₃ | OCH₃ | H |
| 4-(ethoxycarbonyl)benzyl | H | H | OCH₃ | OCH₃ | H |
| 4-(ethoxycarbonyl)benzyl | CH₃ | H | OCH₃ | OCH₃ | H |
| 4-methoxybenzyl | H | H | OCH₃ | OCH₃ | H |
| 4-methoxybenzyl | CH₃ | H | OCH₃ | OCH₃ | H |
| 3,4-dimethoxybenzyl | CH₃ | H | OCH₃ | OCH₃ | H |

Formula I

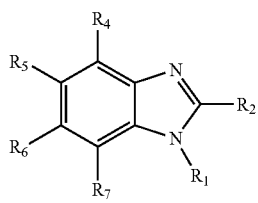

Some non-limiting illustrative compounds of the present invention having a structure of Formula I include those in which $R_1$ is any $R_1$ moiety described in Table 3a, in combination with any $R_2$ moiety described in Table 3b, and any $R_4$, $R_5$, $R_6$, and $R_7$ as described in Table 3c. A compound of Formula I includes any combination of $R_1$, $R_2$, $R_4$, $R_5$, $R_6$, and $R_7$. Additional exemplary compounds of Formula I are illustrated in Table 4.

TABLE 3a $R_1$ moieties of the compounds of Formula I include, but are not limited to, the following:
Illustrative $R_1$ moieties

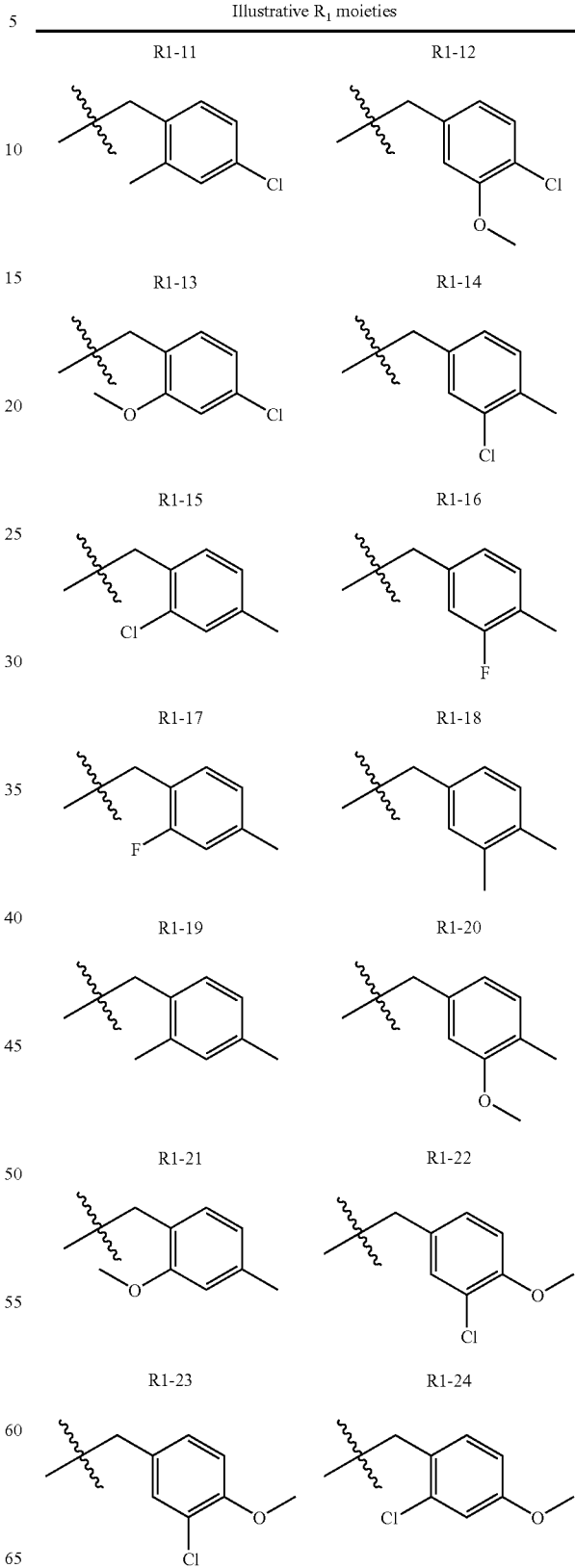

TABLE 3a-continued
R₁ moieties of the compounds of Formula I include, but are not limited to, the following:
Illustrative R₁ moieties
| R1-25 | R1-26 |
|---|---|
| 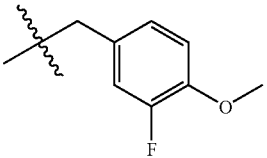 | 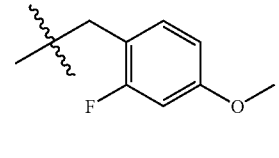 |
| R1-27 | R1-28 |
|---|---|
| 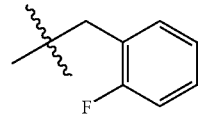 | 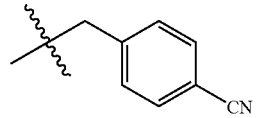 |
| R1-29 | R1-30 |
|---|---|
| 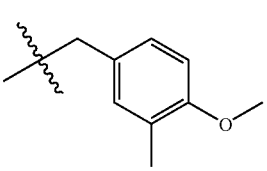 | 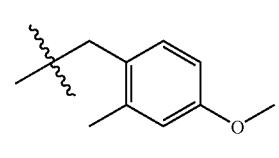 |
| R1-31 | R1-32 |
|---|---|
| 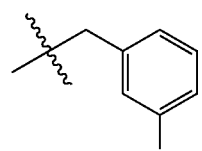 | 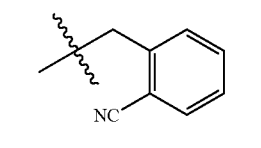 |
| R1-33 | R1-34 |
|---|---|
| 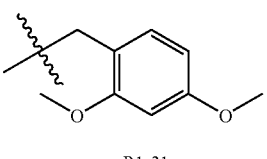 | 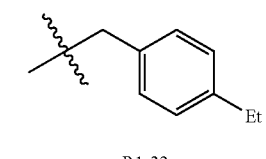 |
| R1-35 | R1-36 |
|---|---|
| 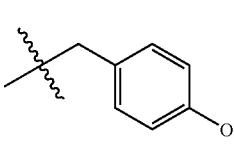 | 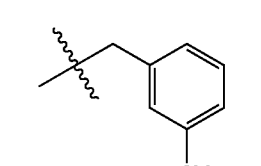 |
| R1-37 | R1-38 |
|---|---|
| 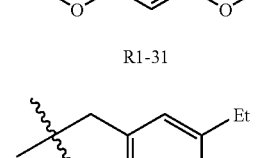 | 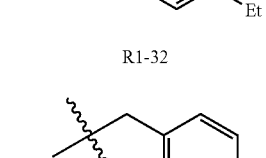 |
| R1-39 | R1-40 |
|---|---|
| 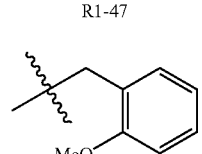 [SMILES: *Cc1ccccc1C] | 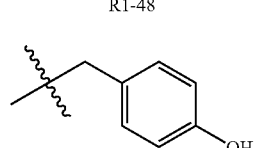 |
TABLE 3a-continued
R₁ moieties of the compounds of Formula I include, but are not limited to, the following:
Illustrative R₁ moieties
| R1-41 | R1-42 |
|---|---|
| 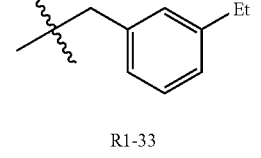 | 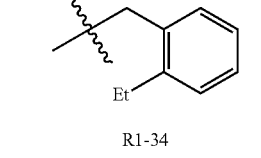 |
| R1-43 | R1-44 |
|---|---|
| 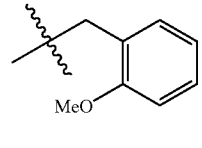 | 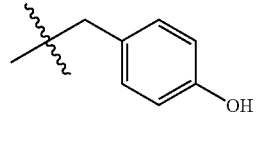 |
| R1-45 | R1-46 |
|---|---|
| 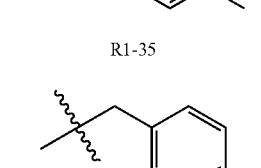 | 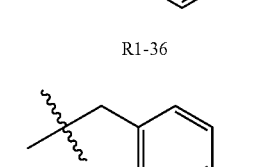 |
| R1-47 | R1-48 |
|---|---|
| 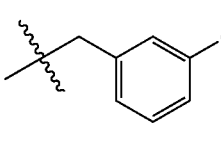 | 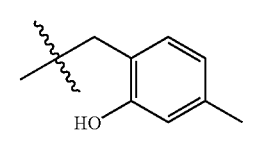 |
| R1-49 | R1-50 |
|---|---|
| 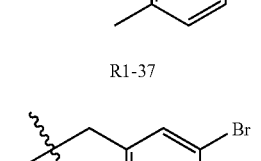 | 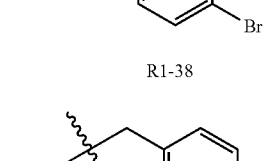 |
| R1-51 | R1-52 |
|---|---|
| 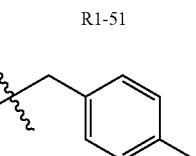 | 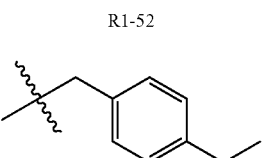 |
| R1-53 | R1-54 |
|---|---|
| 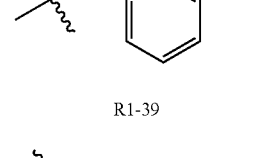 | 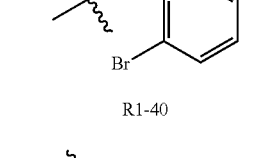 |

TABLE 3a-continued
R₁ moieties of the compounds of Formula I include, but are not limited to, the following:
Illustrative R₁ moieties
| R1-55 | R1-56 |
|---|---|
| 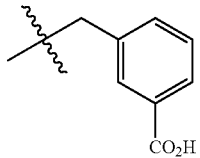 | 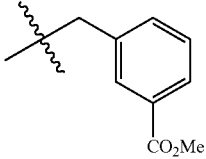 |
| R1-57 |
|---|
| 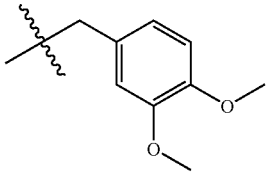 |
| R1-58 |
|---|
| 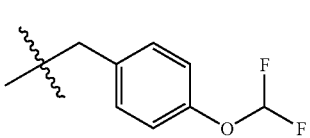 |
| R1-59 | R1-60 |
|---|---|
| 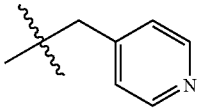 | 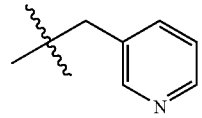 |
| R1-61 | R1-62 |
|---|---|
| 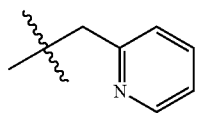 | 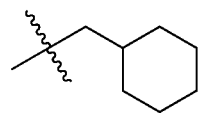 |
| R1-63 | R1-64 |
|---|---|
| 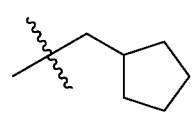 | 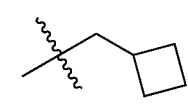 |
| R1-65 | R1-66 |
|---|---|
| 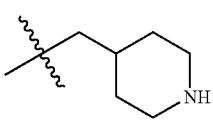 | 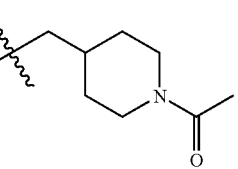 |
| R1-67 | R1-68 |
|---|---|
| 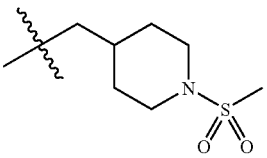 | 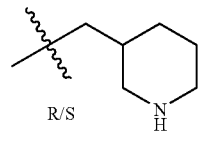 |
TABLE 3a-continued
R₁ moieties of the compounds of Formula I include, but are not limited to, the following:
Illustrative R₁ moieties
| R1-69 | R1-70 |
|---|---|
| 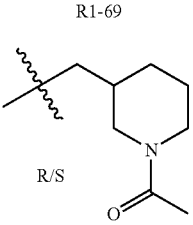 [SMILES: *CC1CCCN(C(C)=O)C1] R/S | 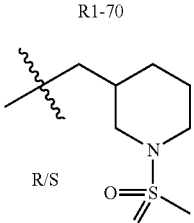 R/S |
| R1-71 | R1-72 |
|---|---|
| 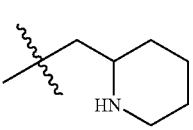 RS | 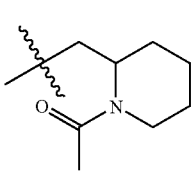 R/S |
| R1-73 | R1-74 |
|---|---|
| 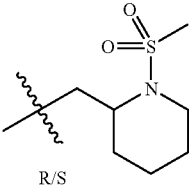 R/S | 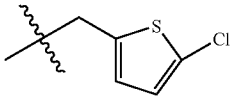 |
| R1-75 | R1-76 |
|---|---|
| 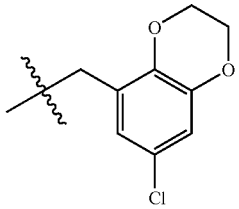 | 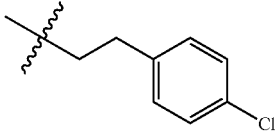 |
| R1-77 | R1-78 |
|---|---|
| 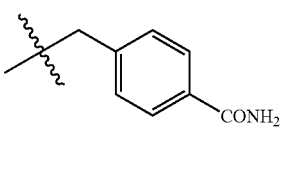 | 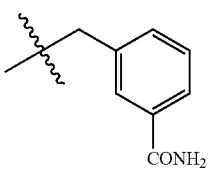 |
| R1-79 | R1-80 |
|---|---|
| 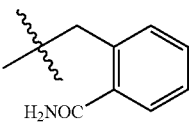 | 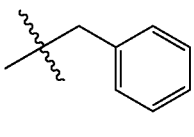 |

TABLE 3a-continued

R₁ moieties of the compounds of Formula I include, but are not limited to, the following:
Illustrative R₁ moieties

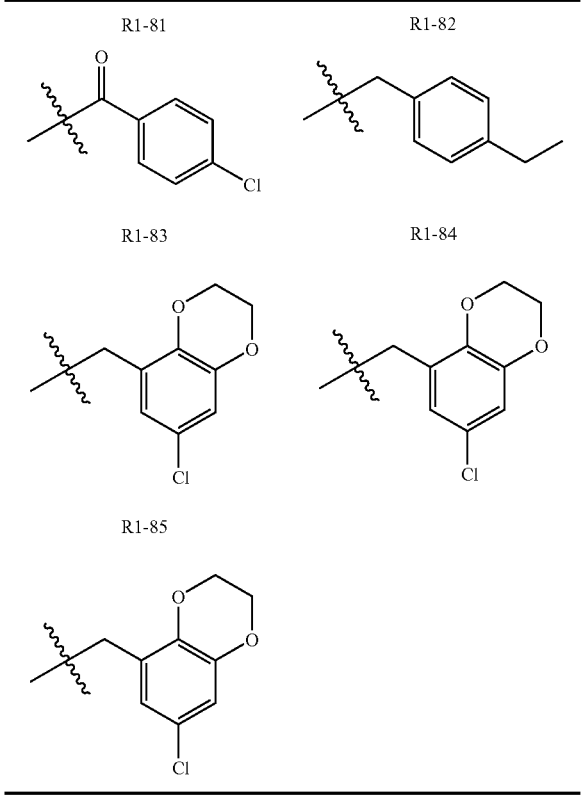

TABLE 3b

R₂ moieties of the compounds of Formula I include, but are not limited to, the following:
Exemplary R₂

| R2-1 | R2-2 |
| --- | --- |
| —CH₂NH₂ | —CH₂NMe₂ |
| R2-3 | R2-4 |
| —CH₂NEt₂ | —CH₂N(nPr)₂ |
| R2-5 | |
| —CH₂N(iPr)₂ | |

TABLE 3b-continued

R₂ moieties of the compounds of Formula I include, but are not limited to, the following:
Exemplary R₂

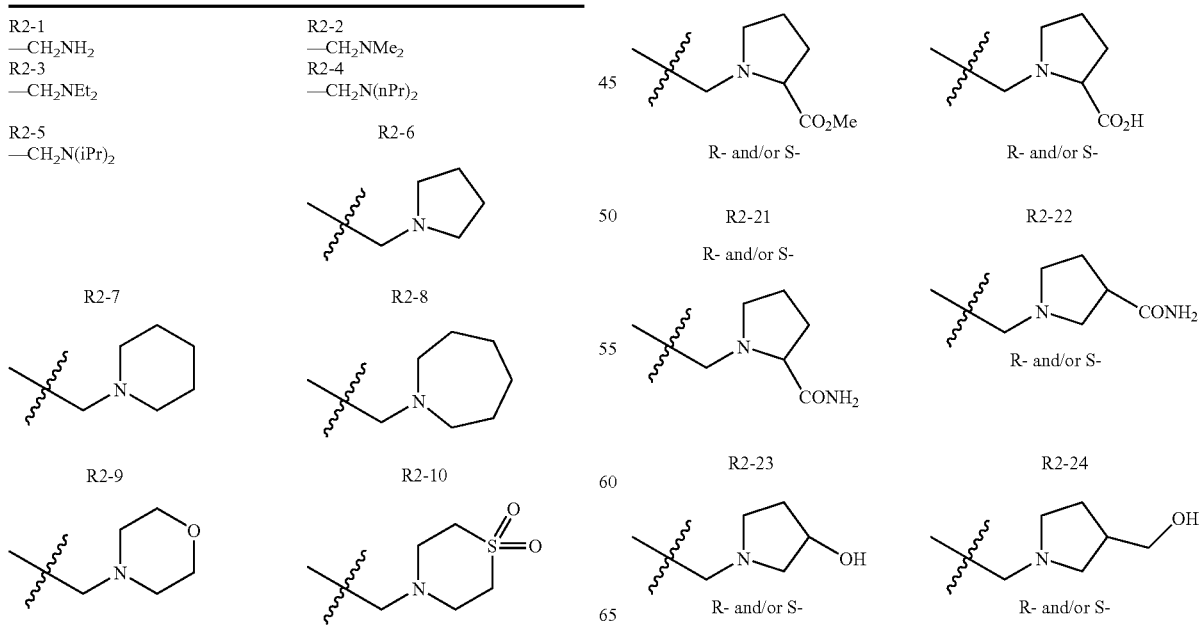

TABLE 3b-continued

R₂ moieties of the compounds of Formula I include, but are not limited to, the following:
Exemplary R₂

| R2-25 | R2-26 |
|---|---|
| 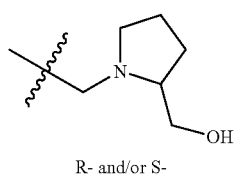 | 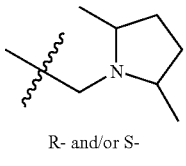 |
| R- and/or S- | R- and/or S- |
| R2-27 | R2-28 |
| 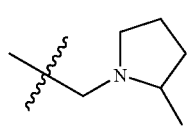 | 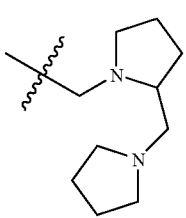 |
| R- and/or S- | R- and/or S- |
| R2-29 | R2-30<br>—CH₂OH |
| 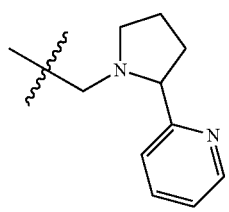 | |
| R- and/or S- | |
| R2-31<br>—CH(CH₃)OH | R2-32<br>H |
| R2-33 | R2-34 |
| 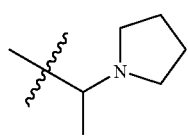 | 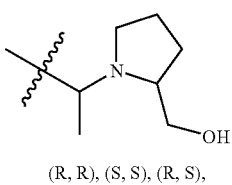 |
| R- and/or S- | (R, R), (S, S), (R, S), (S, R) |
| R2-35<br>—CF₃ | R2-36<br>—CH₃ |
| R2-37<br>—CH₂CH₃ | R2-38<br>—CH(CH₃)₂ |
| R2-39<br>—CH₂CH(CH₃)₂ | R2-40<br>—C₄H₉ |
| R2-41<br>—C₅H₁₁ | R2-42<br>—CH₂Ph |
| R2-43 | R2-44 |
| 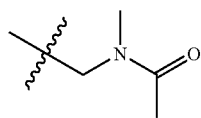 | 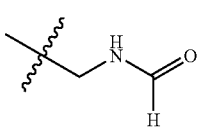 |

TABLE 3b-continued

R₂ moieties of the compounds of Formula I include, but are not limited to, the following:
Exemplary R₂

| R2-45 | R2-46 |
|---|---|
| 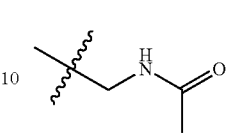 | 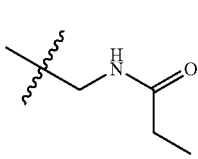 |

R2-47

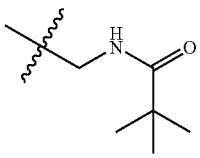

R2-48

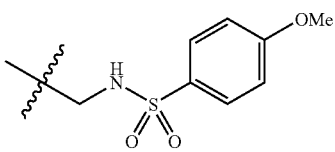

R2-49

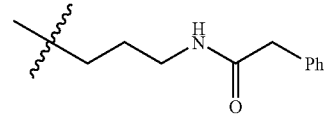

| R2-50<br>—SH | R2-51 |
|---|---|
| | 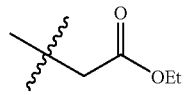 |
| R2-52 | R2-53 |
| 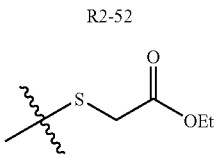 [SMILES: *SCC(=O)OCC] | 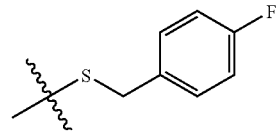 |
| R2-54<br>—NH₂ | R2-55 |
| | 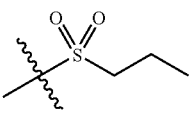 |
| R2-56 | R2-57 |
| 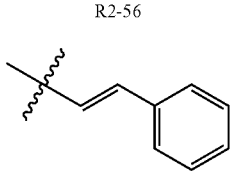 [SMILES: */C=C/c1ccccc1] | 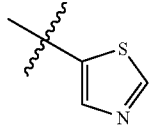 |

TABLE 3b-continued

R₂ moieties of the compounds of Formula I include, but are not limited to, the following:
Exemplary R₂

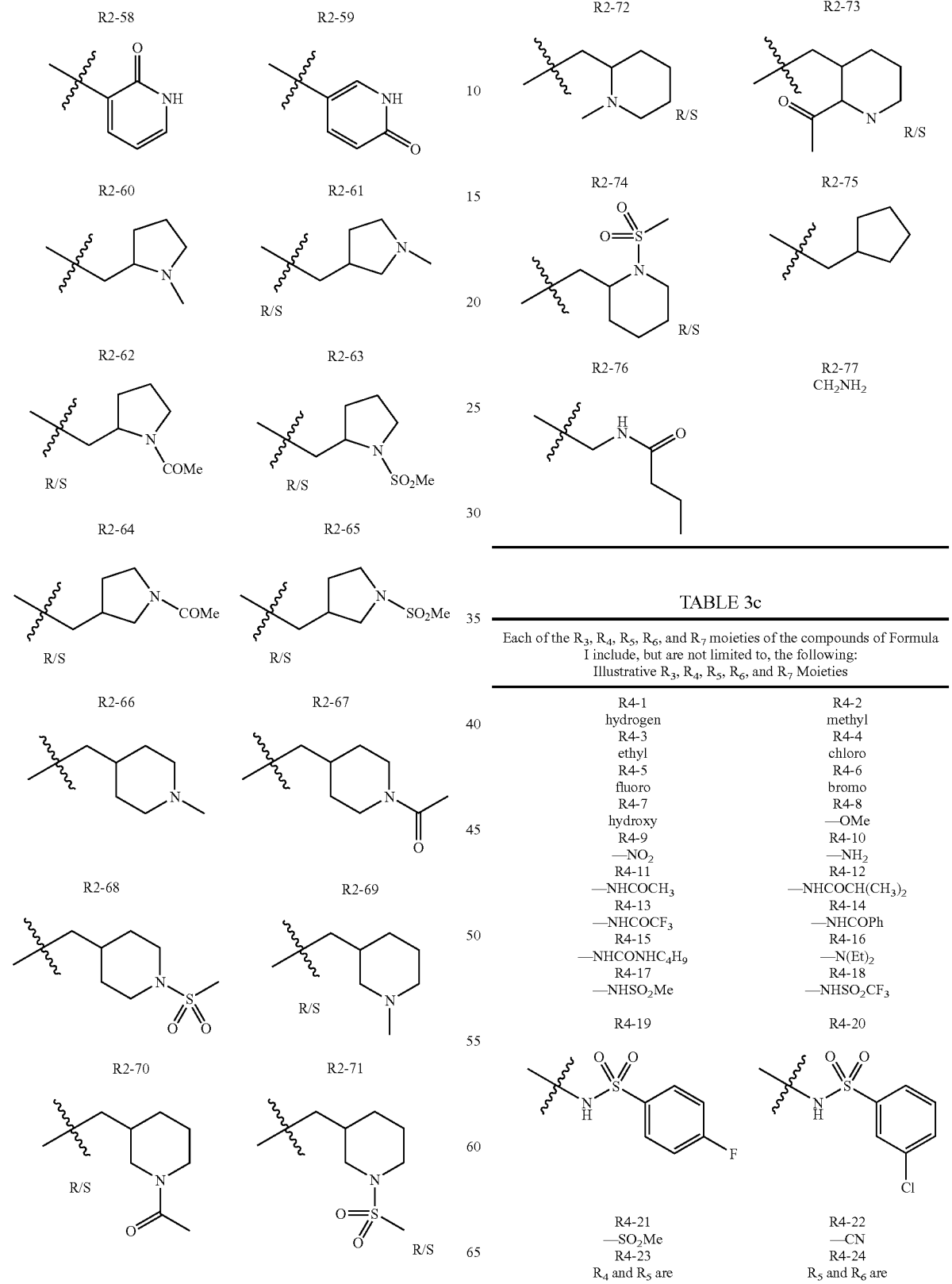

TABLE 3c

Each of the R₃, R₄, R₅, R₆, and R₇ moieties of the compounds of Formula I include, but are not limited to, the following:
Illustrative R₃, R₄, R₅, R₆, and R₇ Moieties

| | |
|---|---|
| R4-1 | R4-2 |
| hydrogen | methyl |
| R4-3 | R4-4 |
| ethyl | chloro |
| R4-5 | R4-6 |
| fluoro | bromo |
| R4-7 | R4-8 |
| hydroxy | —OMe |
| R4-9 | R4-10 |
| —NO₂ | —NH₂ |
| R4-11 | R4-12 |
| —NHCOCH₃ | —NHCOCH(CH₃)₂ |
| R4-13 | R4-14 |
| —NHCOCF₃ | —NHCOPh |
| R4-15 | R4-16 |
| —NHCONHC₄H₉ | —N(Et)₂ |
| R4-17 | R4-18 |
| —NHSO₂Me | —NHSO₂CF₃ |
| R4-19 | R4-20 |
| 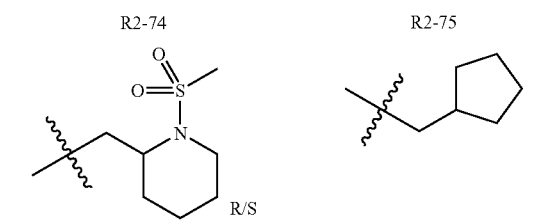 | 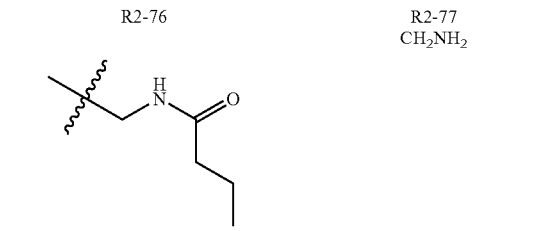 |
| R4-21 | R4-22 |
| —SO₂Me | —CN |
| R4-23 | R4-24 |
| R₄ and R₅ are | R₅ and R₆ are |

TABLE 3c-continued

Each of the $R_3$, $R_4$, $R_5$, $R_6$, and $R_7$ moieties of the compounds of Formula I include, but are not limited to, the following:
Illustrative $R_3$, $R_4$, $R_5$, $R_6$, and $R_7$ Moieties

| | |
|---|---|
| —OCH$_2$O— | —OCH$_2$O— |
| R4-25 | R4-26 |
| $R_6 R_7$ are | $R_4$ and $R_5$ are |
| —OCH$_2$O— | —OCH$_2$CH$_2$O— |
| R4-27 | R4-28 |
| $R_5$ and $R_6$ are | $R_6$ and $R_7$ are |
| —OCH$_2$CH$_2$O— | —OCH$_2$CH$_2$O— |
| R4-29 | R4-30 |
| —CO$_2$H | —CF$_3$ |
| R4-31 | R4-32 |
| —OEt | —SO$_2$NH$_2$ |
| R4-33 | R4-34 |
| —SO$_2$NHMe | SO$_2$NMe$_2$ |
| R4-35 | R4-36 |
| NHC(O)Me | —NHC(O)Ph |
| R4-37 | R4-38 |
| —NMeC(O)Et | —NMeC(O)Ph |
| R4-39 | R4-40 |
| —C(O)NHMe | —C(O)NEt$_2$ |
| R4-41 | R4-42 |
| —C(O)NH$_2$ | —NHC(O)NHMe |
| R4-43 | R4-41 |
| —CO$_2$Me | —C(O)NH$_2$ |
| R4-42 | |
| —NHC(O)NHMe | |

Additional non-limiting illustrative compounds of the present invention have a structure of any of Formulae II-XXXIX include those in which $R_1$ is any $R_1$ moiety described in Table 3a in combination with any $R_2$ moiety described in Table 3b, and any $R_3$, $R_4$, $R_5$, $R_6$, and $R_7$ as described in Table 3c. Thus, a compound of any of Formulae II-XXXIX can include any combination of $R_1$, $R_2$, $R_3$, $R_4$, $R_5$, $R_6$, and $R_7$.

Embodiments of the present invention include prodrugs of clemizole, clemizole analogs, and compounds having a clemizole scaffold, and their isosteres. The compounds provided herein as viral inhibiting agents are generally capable of inhibiting viral replication in vitro and/or in vivo. For example a compound of the present invention when contacted with an HCV-infected cell (e.g., an HCV-infected liver cell), reduces the amount of infectious HCV viral particles produced by the HCV-infected cell by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or at least about 95% or even higher, compared to the number of infectious HCV viral particles produced by the cell not contacted with the inhibiting agent. A wide variety of methods are available to assess whether a compound can reduce viral load in vitro and/or in vivo. In vitro assay typically determines the number of viral particles present in the culture medium, wherein an in vivo assay typically measures the viral titer present in a bodily fluid of an infected subject. Bodily fluids suitable for viral titer measurement include but are not limited to blood, serum, plasma, saliva, semen, spinal fluid, urine, sweat, and cerebral spinal fluid. Commonly employed methods for detecting viral load in vitro or in vivo include quantitative polymerase chain reaction (PCR) and branched DNA (bDNA) test. Numerous quantitative assays for measuring the viral load (titer) of HCV RNA have been developed. Many such assays are available commercially, including a quantitative reverse transcription PCR(RT-PCR) (Amplicor HCV Monitor™, Roche Molecular Systems, New Jersey); and a branched DNA (deoxyribonucleic acid) signal amplification assay (Quantiplex™ HCV RNA Assay (bDNA), Chiron Corp., Emeryville, Calif.). See, e.g., Gretch et al. (1995) *Ann. Intern. Med.* 123:321-329. Also of interest is a nucleic acid test (NAT) sold by Chiron Corporation under the trade name Procleix®, which NAT simultaneously tests for the presence of HIV-1 and HCV. See, e.g., Vargo et al. (2002) *Transfusion* 42:876-885.

The compounds provided herein can also be characterized by their ability to inhibit binding of NS4B polypeptide to the 3'UTR of HCV negative strand RNA by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or at least about 95% or higher, compared to the binding of NS4B polypeptide to the 3'UTR of HCV negative strand RNA in the absence of the compound.

In some embodiments, the inhibiting agents of the present invention inhibit binding of NS4B polypeptide to the 3'UTR of HCV negative strand RNA (SEQ ID NO: 2) with a 50% inhibitory concentration (IC$_{50}$) of about 100 µM to 50 µM, about 50 µM to 25 µM, about µM to 10 µM, about 10 µM to 5 µM, about 5 µM to 1 µM, about 1 µM to 500 nM, about 500 nM to 400 nM, about 400 nM to 300 nM, about 300 nM to 250 nM, about 250 nM to 200 nM, about 200 nM to 150 nM, about 150 nM to 100 nM, about 100 nM to 50 nM, about 50 nM to 30 nM, about 30 nM to 25 nM, about 25 nM to 20 nM, about 20 nM to 15 nM, about 15 nM to 10 nM, about 10 nM to 5 nM, less than about 5 nM, less than about 1 nM, less than about 0.1 nM, or less than about 0.01 nM.

In other embodiments, the inhibiting agents of the present invention lack substantial cross-reactivity with HERG K$^+$ channel. Drug-induced cardiac arrhythmia, such as QT prolongation, is a serious safety concern in the discovery, development and use of new medications. Drug-induced QT interval prolongation is an active field of research and has been reviewed (Pearlstein et al. *J. Med. Chem.* (2003), 46(11): 2017-2022; Fermini et al., *Annual Reports in Medicinal Chemistry* (2004), 39:323; http://www.qtdrugs.org). A common cause of QT prolongation is the inhibition of the cardiac HERG K$^+$ channel by a drug. Drugs from widely different chemical classes and therapeutic utility have been shown to block HERG activity. Many medications known to be HERG channel inhibitors interact with the channel at concentrations similar to the desired therapeutic concentration. One strategy to prevent the occurrence of drug-induced QT interval prolongation is to select drug candidates that show a reduced affinity for the HERG K$^+$ channel. This property can be characterized by an in vitro assay utilizing HEK293 or CHO cells stably transfected with the hERG gene and utilizing a patch-clamp technique to determine Ikr current. Accordingly, some preferred inhibiting agents of the present invention exhibit reduced affinity for or lack substantial cross-reactivity with the HERG K$^+$ channel. In one aspect, an exemplary inhibiting agent of the present invention has a HERG IC$_{50}$ of greater than about 100 nM. In another aspect, the inhibiting agent described herein has a HERG IC$_{50}$ of greater than about 500 nM, 1,000 nM, 5,000 nM, 1 µM, 5 µM, 10 µM, 50 µM, 100 µM or even higher. For instance, to mitigate hERG channel inhibition, the following compounds can be synthesized where the basicity of the tertiary amine of clemizole-like compounds is attenuated by steric or electronic modifications.

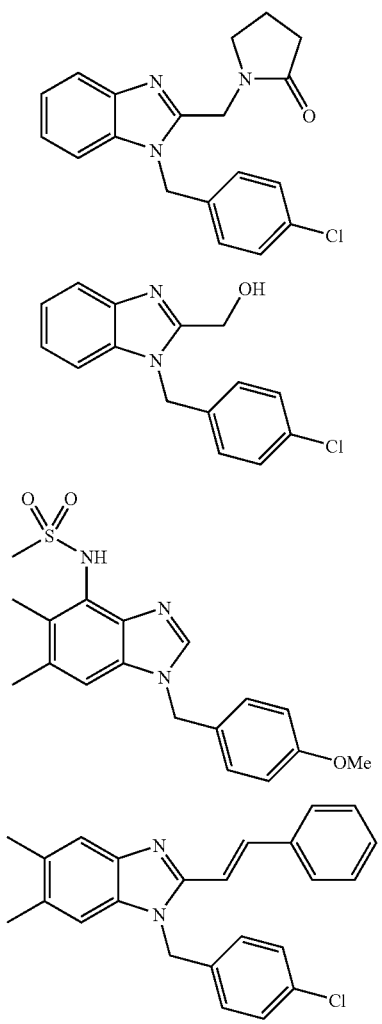

Methods of Synthesis

In general, the inhibiting agents provided herein including clemizole, clemizole analogs, isosteres thereof can be made according to organic synthesis techniques known to those skilled in this art and/or according to the synthesis schemes provided herein. Where desired, synthesis of the subject compound begins with commercially available chemicals and/or from compounds described in the chemical literature. "Commercially available chemicals" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hanover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.). In addition, Methods known to one of ordinary skill in the art may be identified through various reference books and databases. Suitable reference books and treatise that detail the synthesis of reactants useful in the preparation of the inhibiting agents described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes. Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

Unless specified to the contrary, the solvents used in the reactions described herein are inert organic solvents. Unless specified to the contrary, for each gram of the limiting reagent, one cc (or mL) of solvent constitutes a volume equivalent.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples herein below. However, other equivalent separation or isolation procedures can also be used.

When desired, the (R)- and (S)-isomers of the compounds of the present invention, if present, may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

The compounds described herein can be optionally contacted with a pharmaceutically acceptable acid to form the corresponding acid addition salts.

Many of the optionally substituted starting compounds and other reactants are commercially available, e.g., from Aldrich Chemical Company (Milwaukee, Wis.) or can be readily prepared by those skilled in the art using commonly employed synthetic methodology.

The compounds of the invention can be synthesized by an appropriate combination of known synthetic methods in the art and the instant disclosure. The discussion below is offered to illustrate certain of the diverse methods available for use in making the compounds of the invention and is not intended to limit the scope of reactions or reaction sequences that can be used in preparing the compounds of the present invention.

Scheme 1: A general method is illustrated for introducing amine side chains at the 2-position of benzimidazole.
Scheme 1

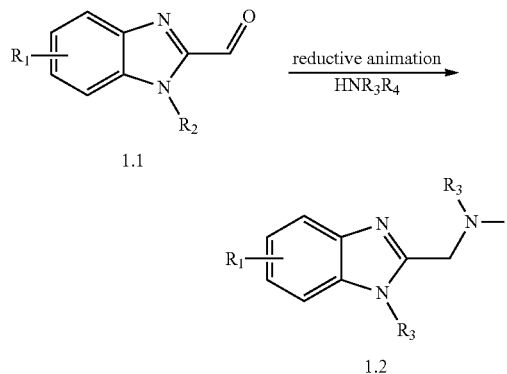

Compounds of structure 1.2 can be synthesized by treating an appropriately substituted benzimidazole-carbaldehyde 1.1 with a primary or secondary amine and NaBH(OAc)$_3$.

Scheme 2: A general method is illustrated for cyclization to a benzimidazole ring system.
Scheme 2

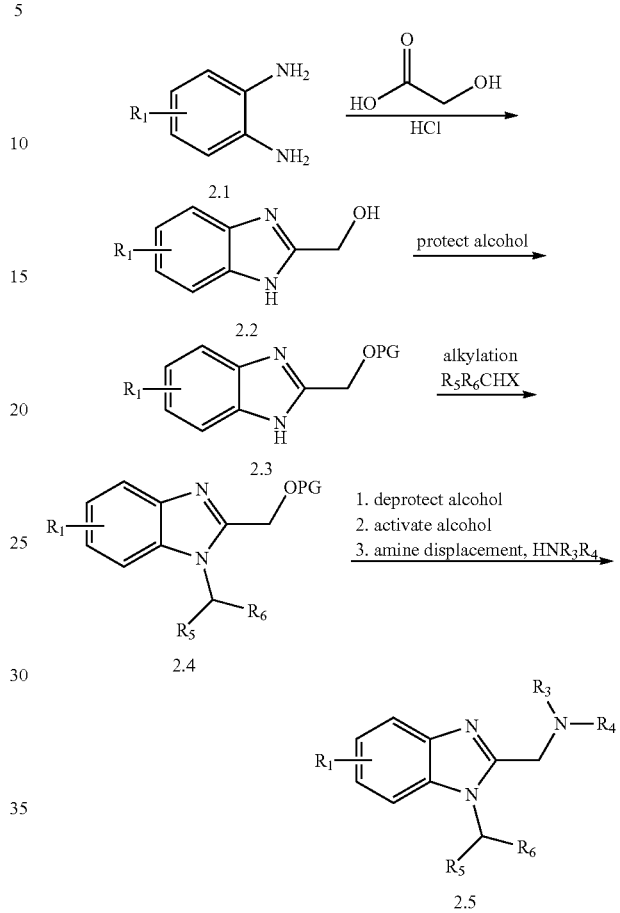

Compounds of general structure 2.5 can be synthesized by treating substituted 1,2-phenylenediamine 2.1 with 4 N HCl and glycolic acid at 110° C. (Roth, T. et al. *J. Med Chem.* 1997, 40 (26), 4199) to provide 2.2. Alcohol 2.2 is then protected with an appropriate protecting group followed by alkylation of the benzimidazole to provide 2.4. The alcohol is then deprotected, activated, and displaced with an appropriate primary or secondary amine to provide final compound 2.5.

Scheme 3: A general method is illustrated for benzimidazole nitration.
Scheme 3

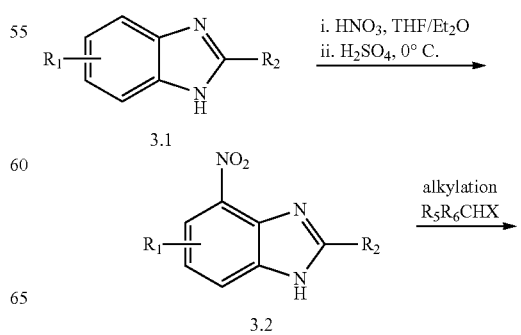

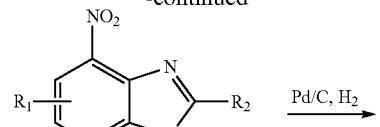
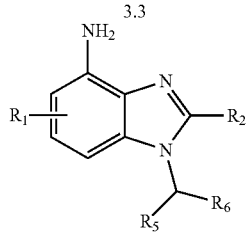
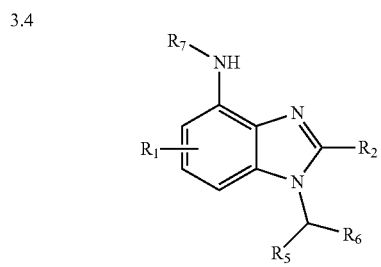

Compounds of general structure 3.5 can be obtained by treating substituted benzimidazole 3.1 with 70% nitric acid to provide the nitric acid salt of 3.1. Addition of concentrated sulfuric acid then provides 3.2 (Zhang, P. et al, *Tet. Lett.* 2007, 48, 8659). Alkylation with an alkyl halide, followed by hydrogenation over palladium-on-carbon provides 3.4. The resulting aromatic amine can then be acylated or alkylated to provide compound 3.5.

Scheme 4: A general method is illustrated for the synthesis of 2-styryl-benzimidazoles.
Scheme 4

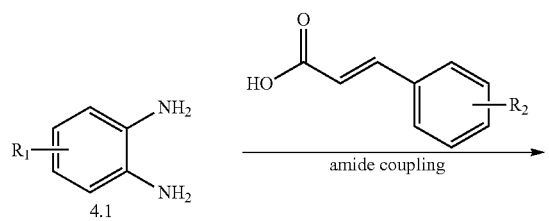
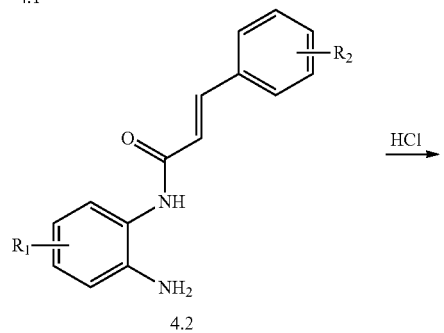

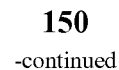
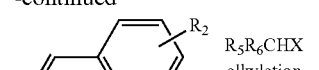
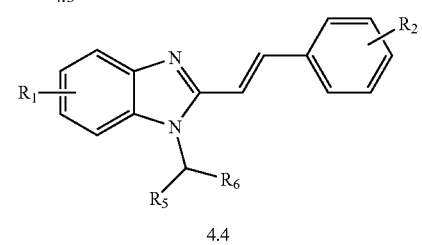

Compounds of general structure 4.4 can be obtained by treating substituted 1,2-phenylenediamines with substituted cinnamic acids to obtain monoacylated intermediate 4.2. Treatment with HCl provides the cyclized benzimidazole 4.3 (van den Berg et al., *Bioorg. Med. Chem.* 2007, 15, 3692). Alkylation with an alkyl halide provides 4.4.

Scheme 5: A general method is illustrated for the synthesis of unsymmetrically substituted benzimidazoles analogs.
Scheme 5

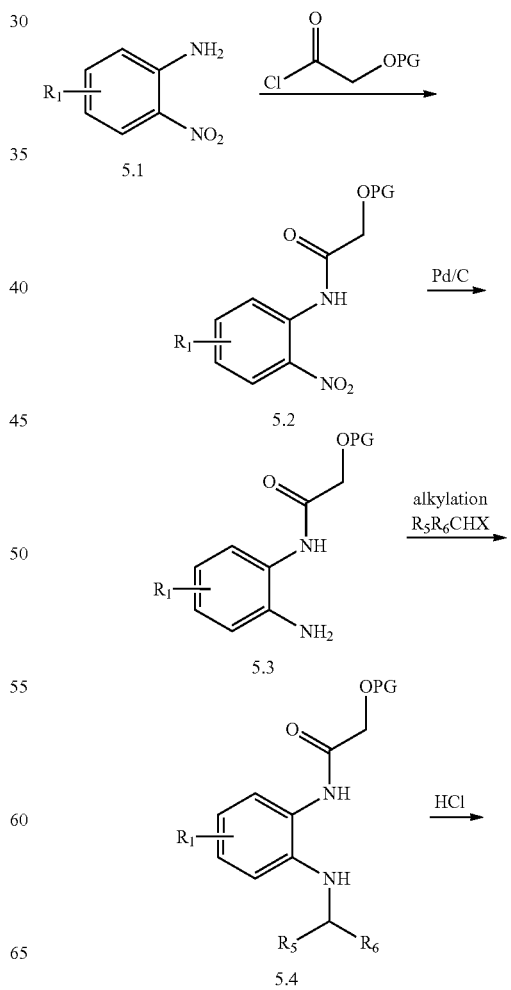

-continued

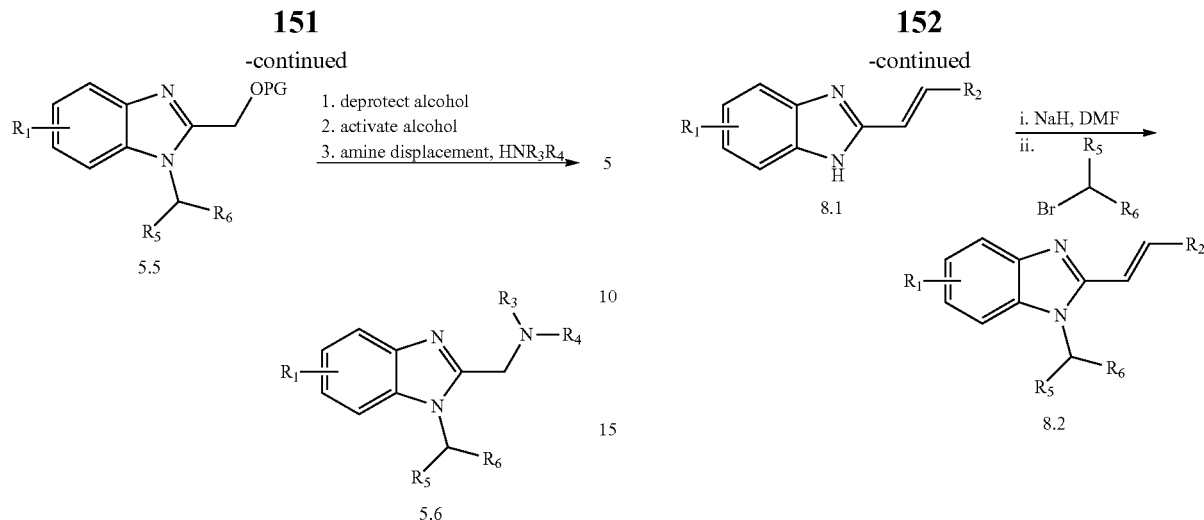

Compounds of structure 5.6 can be obtained by acylating substituted 2-nitroaniline 5.1 with an appropriate acyl chloride to obtain 5.2. Hydrogenation followed by alkylation provides intermediate 5.4 which is cyclized with HCl to provide benzimidazole 5.5. As illustrated for compound 5.5, further functionalization at the 2-position of the benzimidazole is performed to provide 5.6.

Scheme 6: A general method is illustrated for the synthesis of benzimidazole analogs with ether linkages:

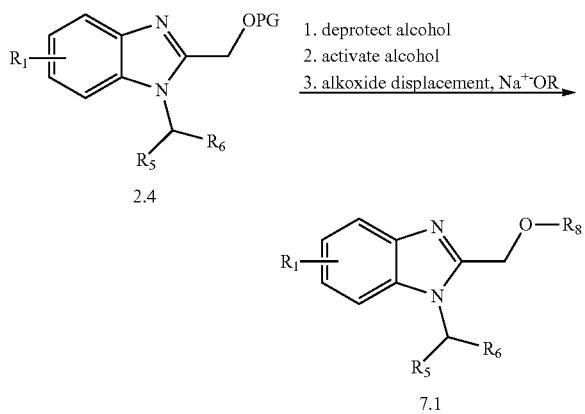

Compounds of general structure 7.1 are synthesized similarly to compounds 2.5 except for replacing primary or secondary amines with alkoxides to provide final compound 7.1.

Scheme 7: A general method is illustrated for the synthesis of benzimidazole analogs with olefinic linkages:

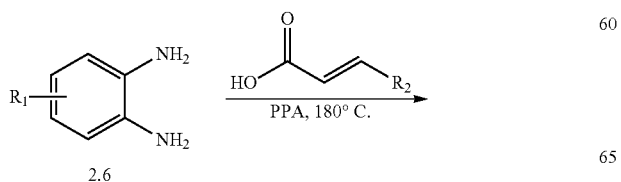

Compounds of general structure 8.2 are synthesized similarly to compounds 2.5 except for replacing glyoxylic acid with substituted cinnamic acids provide final compound 8.2.

Scheme 8 described below (Schering A G U.S. Pat. No. 3,470,194) is an alternative synthesis scheme for making clemizole or clemizole analogs. Scheme 8 starts with commercially available 2-nitroaniline 2.11 followed by reductive alkylation to provide 2.12. Reduction with Raney nickel followed by treatment with chloroacetic acid provides the benzimidazole methyl chloride 2.14. Treatment with pyrrolidine then provides clemizole 2.15. In Synthetic Method 2.2, o-phenylene diamine 2.16 is treated with chloroacetic acid to provide intermediate 2.17. Alkylation with pyrrolidine gives intermediate 2.18. Deprotonation with NaH followed by treatment with p-chlorobenzylchloride provides clemizole 2.15.

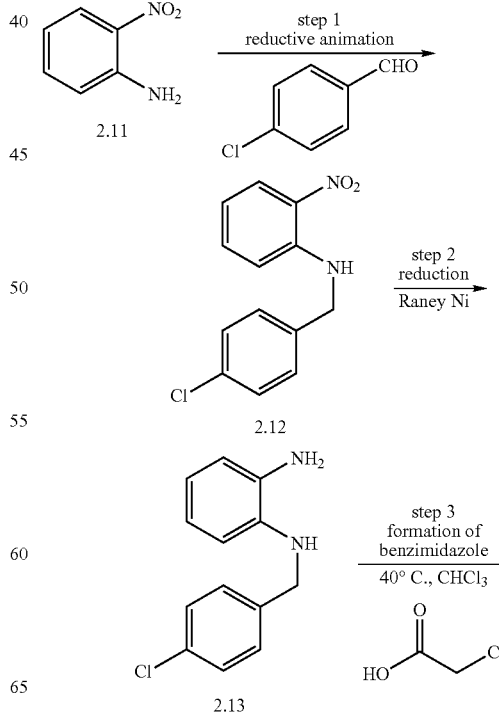

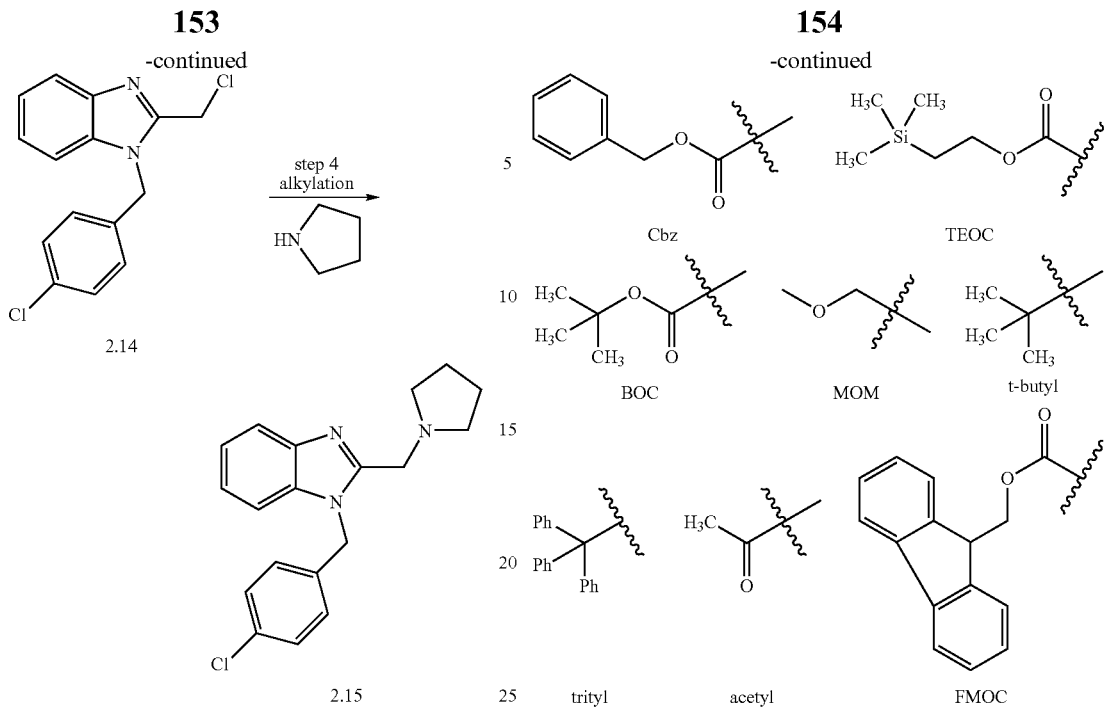

The synthesis of one or more of the inhibiting agents of the present invention may employ protecting groups and blocking groups. Allyl blocking groups are useful in the presence of acid- and base-protecting groups since the former are stable and can be subsequently removed by metal or pi-acid catalysts. For example, an allyl-blocked carboxylic acid can be deprotected with a palladium(0)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups are known in the art and include, but are not limited to, the following moieties.

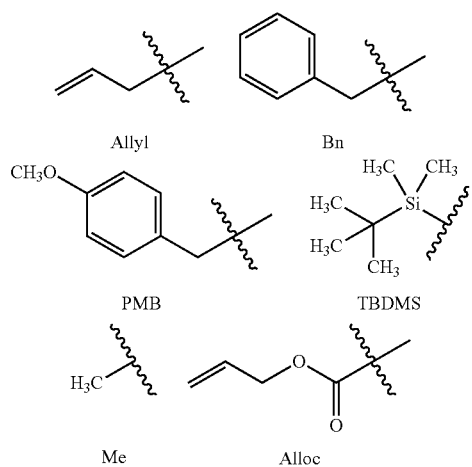

Pharmaceutical Formulations and Routes of Administration

The present invention provides pharmaceutical compositions comprising one or more inhibiting agents disclosed herein with or without pharmaceutically acceptable excipients, diluents, carriers and/or adjuvants. In some embodiment, the clemizole- or clemizole analog-containing pharmaceutical compositions are formulated to be substantially free of excipients. In other embodiments, inhibiting agents can be formulated with one or more pharmaceutically acceptable auxiliary substances.

In an embodiment, the inhibiting agent can be combined with another anti-viral agent to prepare a composition of the invention, and the composition can include one or more pharmaceutically acceptable excipients, diluents, carriers and/or adjuvants.

A wide variety of pharmaceutically acceptable excipients are known in the art. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In an embodiment of the present disclosure, the inhibiting agent is administered to the host using any means capable of resulting in the desired effect (e.g., reduction in viral load, reduction in liver fibrosis, increase in liver function, and the like). Thus, the inhibiting agent can be incorporated into a variety of formulations for therapeutic administration. For example, the inhibiting agent can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the inhibiting agent may be administered in the form of its pharmaceutically acceptable salts, or a subject active agent may be used alone or in appropriate association, as well as in combination, with other pharmaceutically active compounds. The following methods and excipients are merely exemplary and are in no way limiting.

For oral preparations, the inhibiting agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Embodiments of the inhibiting agent can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Embodiments of the inhibiting agent can be utilized in aerosol formulation to be administered via inhalation. Embodiments of the inhibiting agent can be formulated into pressurized acceptable propellants such as dichlorodifluoromethane, propane, nitrogen and the like.

Furthermore, embodiments of the inhibiting agent can be made into suppositories by mixing with a variety of bases such as emulsifying bases or water-soluble bases. Embodiments of the inhibiting agent can be administered rectally via a suppository. The suppository can include vehicles such as cocoa butter, carbowaxes and polyethylene glycols, which melt at body temperature, yet are solidified at room temperature.

Unit dosage forms for oral or rectal administration, such as syrups, elixirs, and suspensions, may be provided wherein each dosage unit, for example, teaspoonful, tablespoonful, tablet or suppository, contains a predetermined amount of the composition containing one or more inhibiting agents. Similarly, unit dosage forms for injection or intravenous administration may comprise the inhibiting agent in a composition as a solution in sterile water, normal saline or another pharmaceutically acceptable carrier.

Embodiments of the inhibiting agent can be formulated in an injectable composition in accordance with the invention. Typically, injectable compositions are prepared as liquid solutions or suspensions; solid forms suitable for solution in, or suspension in, liquid vehicles prior to injection may also be prepared. The preparation may also be emulsified or the active ingredient (inhibiting agent) encapsulated in liposome vehicles in accordance with the invention.

In an embodiment, the inhibiting agent is formulated for delivery by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present disclosure. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of the inhibiting agent can be accomplished using any of a variety of refillable, pump systems. Pumps provide consistent, controlled release over time. In some embodiments, the inhibiting agent is in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to, a subdermal, subcutaneous, intramuscular, or other suitable site within a subject's body. Subcutaneous implantation sites are used in some embodiments because of convenience in implantation and removal of the drug delivery device.

Drug release devices suitable for use in the disclosure may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, and the like.

Drug release devices based upon a mechanical or electromechanical infusion pump can also be suitable for use with the present disclosure. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems are generally preferred due to their generally more consistent, controlled release over time. Osmotic pumps are used in some embodiments due to their more consistent controlled release and relatively small size (see, e.g., PCT published application no. WO 97/27840 and U.S. Pat. Nos. 5,985,305 and 5,728,396). Exemplary osmotically-driven devices suitable for use in the disclosure include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted herein, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, an active agent is delivered using an implantable drug delivery system, e.g., a system that is programmable to provide for administration of the agent. Exemplary programmable, implantable systems include implantable infusion pumps. Exemplary implantable infusion pumps, or devices useful in connection with such pumps, are described in, for example, U.S. Pat. Nos. 4,350,155; 5,443, 450; 5,814,019; 5,976,109; 6,017,328; 6,171,276; 6,241,704; 6,464,687; 6,475,180; and 6,512,954. A further exemplary device that can be adapted for the present disclosure is the Synchromed infusion pump (Medtronic).

Suitable excipient vehicles for the inhibiting agent are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pa., 17th edition, 1985. The composition or formulation to be administered will, in any event, contain a quantity of the inhibiting agent adequate to achieve the desired state in the subject being treated.

Compositions of the present invention include those that comprise a sustained-release or controlled release matrix. In addition, embodiments of the present invention can be used in conjunction with other treatments that use sustained-release formulations. As used herein, a sustained-release matrix is a matrix made of materials, usually polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho) esters, polypeptides, hyaluronic acid, collagen, chondroitin sulfate, carboxcylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix. Similarly, the sustained release formulations of embodiments of the invention can help maintain viral-inhibiting concentrations over a longer time interval.

In another embodiment, the pharmaceutical composition of the present disclosure (as well as combination compositions) is delivered in a controlled release system. For example, the inhibiting agent may be administered using intravenous infusion, an implantable osmotic pump, a transdermal patch, liposomes, or other modes of administration. In one embodiment, a pump may be used (Sefton (1987). *CRC Crit. Ref. Biomed. Eng.* 14:201; Buchwald et al. (1980). *Surgery* 88:507; Saudek et al. (1989). *N. Engl. J. Med.* 321:574). In another embodiment, polymeric materials are used. In yet another embodiment a controlled release system is placed in proximity of the therapeutic target, e.g., the liver, thus requiring a fraction of the systemic dose. Other controlled release systems are discussed in the review by Langer (1990). *Science* 249:1527-1533.

In another embodiment, the compositions of the present invention (as well as combination compositions separately or together) include those formed by impregnation of an inhibiting agent described herein into absorptive materials, such as sutures, bandages, and gauze, or coated onto the surface of solid phase materials, such as surgical staples, zippers and catheters to deliver the compositions. Other delivery systems of this type will be readily apparent to those skilled in the art in view of the instant disclosure.

The inhibiting agents disclosed herein can be formulated in a pharmaceutical composition comprising an effective amount of the inhibiting agent for its intended use. For example, clemizole or clemizole analog of the present invention can be formulated in a unit dose of about 10 mg to about 500 mg for treating viral infections, especially infections by a virus of the Flaviviridae family. In some embodiments, clemizole or clemizole analog of the present invention is formulated in a unit dose of about 25 mg to about 250 mg, of about 25 mg to about 100 mg, or of about 50 mg to about 100 mg. In particular, clemizole can be formulated in 25 mg, 50 mg, 75 mg, 100 mg, 125 mg, 150 mg or 200 mg unit dose form. In one embodiment, the unit dose form is a tablet; in another, the unit dose form is a capsule. The tablet can be formulated as immediate release dose form or as sustained release form. In yet another embodiment, the unit dose form is a liquid.

Uses of the Compounds and Pharmaceutical Compositions of the Present Invention

The subject compounds and pharmaceutical compositions thereof are particularly useful for treating infection by a virus of the Flaviviridae family. The treatment methods typically comprise administering to a subject infected with such virus a therapeutically effective amount of an inhibiting agent in one or more doses. For subjects already infected with a virus of the Flaviviridae family such as Hepatitis Virus C, the method of the present invention is generally effective in reducing the viral load over a period of a few days, a few weeks or a few months.

The present invention also provides methods of prophylactically treating an infection by a virus of the Flaviviridae family of viruses comprising administering an effective amount of an inhibiting agent described herein to a subject in need thereof. Prophylactic treatment of infection by a virus of the Flaviviridae family (including but not limited to HCV) is particularly important for patients who will be undergoing liver transplantation for HCV-associated end stage liver disease (ESLD). It has been reported that the new graft is nearly certain to be infected with HCV if viremia is present at the time of transplantation. Prophylactic treatment with clemizole or clemizole analogs or the isosterers thereof can be performed to reduce or eliminate HCV viral load prior to liver transplantation, and can help prevent the recurrence of HCV after transplantation. The administration of clemizole, clemizole analogs, or isosterers of the present invention may also be used for patients who cannot tolerate full doses of standard of care therapy (pegylated interferon and ribavirin). Where desired, for pre-transplant patients with ESLD, or post-transplant patients with HCV recurrence, either clemizole or clemizole analog monotherapy, or clemizole/clemizole analog in combination with reduced doses of pegylated interferon and ribavirin, can be used to treat these patients. Similarly, clemizole or clemizole analogs in combination with nitazoxanide (or another thiazolide, or sustained formulations of either of these) can be used to treat these patients, as can clemizole plus nitazoxanide (or another thiazolide, or sustained formulations of either of these) plus standard of care medications, at reduced or regular doses, as tolerated.

The inhibiting agent of the present invention and pharmaceutical composition comprising the same can be administered to a subject in one or more doses. In an embodiment, the inhibiting agent can be administered in an amount of about 10 mg to 1000 mg per dose, e.g., about 10 mg to 20 mg, about 20 mg to 25 mg, about 25 mg to 50 mg, about 50 mg to 75 mg, about 75 mg to 100 mg, about 100 mg to 125 mg, about 125 mg to 150 mg, about 150 mg to 175 mg, about 175 mg to 200 mg, about 200 mg to 225 mg, about 225 mg to 250 mg, about 250 mg to 300 mg, about 300 mg to 350 mg, about 350 mg to 400 mg, about 400 mg to 450 mg, about 450 mg to 500 mg, about 500 mg to 750 mg, or about 750 mg to 1000 mg per dose. In one embodiment, the agent is clemizole hydrochloride, the unit dose is 50 mg, and two unit doses are administered orally BID (a 200 mg daily dose). In another embodiment, the agent is clemizole hydrochloride, the unit dose is 100 mg, and one unit dose is administered orally in the morning and another in the evening for a total of 200 mg daily dose.

In an embodiment, the amount of the inhibiting agent per dose is determined on a per body weight basis. For example, in an embodiment, the inhibiting agent can be administered in an amount of about 0.5 mg/kg to 100 mg/kg, e.g., about 0.5 mg/kg to 1 mg/kg, about 1 mg/kg to 2 mg/kg, about 2 mg/kg to 3 mg/kg, about 3 mg/kg to 5 mg/kg, about 5 mg/kg to 7 mg/kg, about 7 mg/kg to about 10 mg/kg, about 10 mg/kg to 15 mg/kg, about 15 mg/kg to 20 mg/kg, about 20 mg/kg to 25 mg/kg, about 25 mg/kg to 30 mg/kg, about 30 mg/kg to 40 mg/kg, about 40 mg/kg to 50 mg/kg per dose, about 50 mg/kg to 60 mg/kg, about 60 mg/kg to 70 mg/kg, about 70 mg/kg to 80 mg/kg, about 80 mg/kg to 90 mg/kg, or about 90 mg/kg to 100 mg/kg, or more than about 100 mg/kg.

Those of skill will readily appreciate that dose levels can vary as a function of the specific inhibiting agent administered, the severity of the symptoms, and the susceptibility of the subject to side effects. Preferred dosages for a given compound are readily determinable by those of skill in the art by a variety of means.

In an embodiment, multiple doses of the inhibiting agent are administered. The frequency of administration of the inhibiting agent can vary depending on any of a variety of factors, e.g., severity of the symptoms, and the like. For example, in an embodiment, the inhibiting agent is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). As discussed above, in one embodiment, the inhibiting agent is administered continuously.

By way of illustration, efficacious dosing of clemizole can include dosing at about 200 mg po BID, 75 mg po BID, or 50 mg po BID. The total daily dose can also be split among multiple doses, which allows for a lower dose at each administration with less potential for sedation while maintaining sufficient efficacy. Alternatively, a more frequent dosing schedule can be applied for sever cases, for example, TID administration or administration every 4, 6, 8, or 12 hours of a 25 mg, 50 mg, 75 mg, 150 mg or higher dose.

Clemizole was marketed in the United States as Allercur®, a product of J. B. Roerig and Company, Div., Chas. Pfizer & Co., Inc. The trade name of J. B. Roerig & Co. Division, Chas. Pfizer & Co., Inc., for clemizole tannate was Allercur oral suspension; for clemizole hydrochloride, Alkrcur parenteral and Allercur tablets. The 1966 PDR touted clemizole's advantage of being exceptionally well tolerated. In some embodiments, a simple and convenient dosing regimen for treating patients with an HCV infection includes any regimen previously shown effective for use of clemizole as an antipruritic. In one embodiment, a BID dosing regimen is employed. In one embodiment, the regimen is 100 mg po BID.

The duration of administration of the inhibiting agent, e.g., the period of time over which the inhibiting agent is administered, can vary, depending on any of a variety of factors, e.g., patient response, and the like. For example, the inhibiting agent can be administered over a period of time of about one day to one week, about two weeks to four weeks, about one month to two months, about two months to four months, about four months to six months, about six months to eight months, about eight months to 1 year, about 1 year to 2 years, or about 2 years to 4 years, or more.

The practice of a method of the present invention typically involves administering an effective amount of an inhibiting agent or a pharmaceutical composition comprising such inhibiting agent. The specific dose will vary depending on the particular compounds chosen, the dosing regimen to be followed, whether it is administered in combination with other compounds, timing of administration, the tissue to which it is administered, and the physical delivery system in which it is carried. In an embodiment, an effective amount of the inhibiting agent is an amount that, when administered in one or more doses to a host (e.g., human) in need thereof, reduces HCV viral load in the individual by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% or more, compared to the viral load in the individual not treated with the inhibiting agent.

Viral load can be measured by measuring the titer or level of virus in serum. These methods include, but are not limited to, a quantitative polymerase chain reaction (PCR) and a branched DNA (bDNA) test. Quantitative assays for measuring the viral load (titer) of HCV RNA have been developed. Many such assays are available commercially, including a quantitative reverse transcription PCR(RT-PCR) (Amplicor HCV Monitor™, Roche Molecular Systems, New Jersey); and a branched DNA (deoxyribonucleic acid) signal amplification assay (Quantiplex™ HCV RNA Assay (bDNA), Chiron Corp., Emeryville, Calif.). See, e.g., Gretch et al. (1995) *Ann. Intern. Med.* 123:321-329. Also of interest is a nucleic acid test (NAT) sold by Chiron Corporation under the trade name Procleix®, which NAT simultaneously tests for the presence of HIV-1 and HCV. See, e.g., Vargo et al. (2002) *Transfusion* 42:876-885.

In some embodiments, an effective amount of the inhibiting agent is an amount that, when administered in one or more doses to a host (e.g., human) in need thereof, increases liver function in the individual by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%, or more, compared to the liver function in the individual not treated with the inhibiting agent.

In some embodiments, an effective amount of the inhibiting agent is an amount that, when administered in one or more doses to a host (e.g., a human) in need thereof, reduces liver fibrosis in the host by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%, or more, compared to the degree of liver fibrosis in the individual not treated with the inhibiting agent.

Liver fibrosis reduction can be determined by analyzing a liver biopsy sample. An analysis of a liver biopsy comprises assessments of two major components: necroinflammation assessed by "grade" as a measure of the severity and ongoing disease activity, and the lesions of fibrosis and parenchymal or vascular remodeling as assessed by "stage" as being reflective of long-term disease progression. See, e.g., Brunt (2000) Hepatol. 31:241-246; and METAVIR (1994) Hepatology 20:15-20. Based on analysis of the liver biopsy, a score is assigned. A number of standardized scoring systems exist which provide a quantitative assessment of the degree and severity of fibrosis. These include the METAVIR, Knodell, Scheuer, Ludwig, and Ishak scoring systems.

The METAVIR scoring system is based on an analysis of various features of a liver biopsy, including fibrosis (portal fibrosis, centrilobular fibrosis, and cirrhosis); necrosis (piecemeal and lobular necrosis, acidophilic retraction, and ballooning degeneration); inflammation (portal tract inflammation, portal lymphoid aggregates, and distribution of portal inflammation); bile duct changes; and the Knodell index (scores of periportal necrosis, lobular necrosis, portal inflammation, fibrosis, and overall disease activity). The definitions of each stage in the METAVIR system are as follows: score: 0, no fibrosis; score: 1, stellate enlargement of portal tract but without septa formation; score: 2, enlargement of portal tract with rare septa formation; score: 3, numerous septa without cirrhosis; and score: 4, cirrhosis.

Knodell's scoring system, also called the Hepatitis Activity Index, classifies specimens based on scores in four categories of histologic features: I. Periportal and/or bridging necrosis; II. Intralobular degeneration and focal necrosis; III. Portal inflammation; and IV. Fibrosis. In the Knodell staging system, scores are as follows: score: 0, no fibrosis; score: 1, mild fibrosis (fibrous portal expansion); score: 2, moderate fibrosis; score: 3, severe fibrosis (bridging fibrosis); and score: 4, cirrhosis. The higher the score, the more severe the liver tissue damage. Knodell (1981) Hepatol. 1:431.

In the Scheuer scoring system scores are as follows: score: 0, no fibrosis; score: 1, enlarged, fibrotic portal tracts; score: 2, periportal or portal-portal septa, but intact architecture; score: 3, fibrosis with architectural distortion, but no obvious cirrhosis; score: 4, probable or definite cirrhosis. Scheuer (1991) J. Hepatol. 13:372.

The Ishak scoring system is described in Ishak (1995) J. Hepatol. 22:696-699. Stage 0, No fibrosis; Stage 1, Fibrous expansion of some portal areas, with or without short fibrous septa; stage 2, Fibrous expansion of most portal areas, with or without short fibrous septa; stage 3, Fibrous expansion of most portal areas with occasional portal to portal (P-P) bridging; stage 4, Fibrous expansion of portal areas with marked bridging (P-P) as well as portal-central (P-C); stage 5, Marked bridging (P-P and/or P-C) with occasional nodules (incomplete cirrhosis); stage 6, Cirrhosis, probable or definite.

The benefit of a therapy provided by the invention can also be measured and assessed by using the Child-Pugh scoring system which comprises a multicomponent point system based upon abnormalities in serum bilirubin level, serum albumin level, prothrombin time, the presence and severity of ascites, and the presence and severity of encephalopathy. Based upon the presence and severity of abnormality of these parameters, patients may be placed in one of three categories of increasing severity of clinical disease: A, B, or C.

The subject inhibiting agents and pharmaceutical compositions containing the agents can be used in combination of one or more other therapeutic agents for treating viral infection and other diseases. For example, the inhibiting agents and pharmaceutical formulations provided herein can be employed in combination with other anti-viral agents to treat viral infection. In an embodiment, in accordance with the methods of the present invention, an inhibiting agent that is used to treat a host infected by a Flaviviridae family viral infection is used in combination with one or more other anti-HCV agents to treat HCV infection. In another embodiment, in accordance with the methods of the present invention, an inhibiting agent that prevents the binding of NS4B to the 3'-UTR of HCV RNA (also referred to herein as an "HCV NS4B antagonist") can be used in combination with one or more other anti-HCV agents to treat HCV infection.

In addition, the inhibiting agents and pharmaceutical compositions containing the agents can be used in combination with another agent (e.g., an anti-viral agent) to prophylactically treat an infection with a virus from the Flaviviridae family of viruses including but not limited to HCV. Embodiments of the method involve administering to an individual in need thereof one or more inhibiting agents that inhibit binding of an NS4B polypeptide to the 3'UTR of HCV negative strand RNA.

In some embodiments, the combination therapies described herein provided a synergistic effect. As used herein, a synergistic effect is achieved when a greater therapeutic effect results with a combination therapy than using either drug or monotherapy alone. In combination therapy with a synergistic effect, lower dosages of one or both of the drugs or therapies may be used so that the therapeutic index is increased and toxic side effects are reduced.

Current medical practice to treat HCV infection typically employs either interferon-alpha monotherapy or combination therapy with ribavirin (such as Rebetol or Copegus) and either an interferon-alpha (such as interferon alpha 2b) or pegylated interferon (such as Pegasys, marketed by Roche, or PEG-Intron, marketed by Schering Plough). In accordance with the methods of the present disclosure, an inhibiting compound can be used in combination with these standard therapies to treat HCV infection.

A number of HCV protease inhibitors are in development for the treatment of HCV infection, and in accordance with the methods of the present disclosure, co-administration of an inhibiting agent that prevents the binding of NS4B to the 3'-UTR of HCV RNA and an HCV protease inhibitor can be efficacious in the treatment of HCV. In one embodiment, an interferon alpha and/or a nucleoside analog such as ribavirin is/are also employed in this combination therapy. Suitable HCV protease inhibitors include, but are not limited to, telaprevir (VX-950, Vertex), BILN 2061 and BI12202 (Boehringer Ingelheim), boceprevir (SCH 503034, Schering Plough), ITMN191 (Roche/InterMune/Array BioPharma), MK-7009 (Merck), TMC435350 (Tibotec/Medivir), ACH-1095 and ACH-806 (Achillion/Gilead), and other inhibitors of NS3/NS4A protease, including, but not limited to, compounds in development by Presidio.

A number of HCV RNA polymerase (NS5B) inhibitors are in development for the treatment of HCV infection, and in accordance with the methods of the present disclosure, co-administration of an inhibiting agent that prevents the binding of NS4B to the 3'-UTR of HCV RNA and an HCV RNA polymerase inhibitor can be efficacious in the treatment of HCV. In one embodiment, an interferon alpha and/or a nucleoside analog such as ribavirin and/or an HCV protease inhibitor is/are also employed in this combination therapy. Suitable HCV RNA polymerase inhibitors include, but are not limited to, valopicitabine (NM283, Idenix/Novartis), HCV-796 (Wyeth/ViroPharma), R1626 (Roche), R7128

(Roche/Pharmasset), GS-9190 (Gilead), MK-0608 (Merck), PSI-6130 (Pharmasset), and PFE-868,554 (PFE).

A number of toll-like receptor (TLR) agonists are in development for the treatment of HCV infection, and in accordance with the methods of the present disclosure, co-administration of an NS4B antagonist that prevents the binding of NS4B to the 3'-UTR of HCV RNA and a TLR agonist can be efficacious in the treatment of HCV. In one embodiment, an interferon alpha and/or a nucleoside analog such as ribavirin and/or an HCV protease inhibitor and/or an HCV RNA polymerase inhibitor is/are also employed in this combination therapy. Suitable TLR agonists include, but are not limited to, TLR7 agonists (i.e., ANA245 and ANA975 (Anadys/Novartis)) and TLR9 agonists (i.e., Actilon (Coley) and IMO-2125 (Idera)).

A number of thiazolide derivatives are in development for the treatment of HCV infection, and in accordance with the methods of the present disclosure, co-administration of an NS4B antagonist that prevents the binding of NS4B to the 3'-UTR of HCV RNA and a thiazolide, including, but not limited to, Nitazoxanide (Alinia, or other sustained release formulations of nitazoxanide or other thiazolides, Romark Laboratories) can be efficacious in the treatment of HCV. In an embodiment, an interferon alpha and/or a nucleoside analog such as ribavirin and/or an HCV protease inhibitor and/or an HCV RNA polymerase inhibitor and/or a TLR agonist is/are also employed in this combination therapy.

In another embodiment of the methods of the present disclosure, co-administration of an inhibiting agent that prevents the binding of NS4B to the 3'-UTR of HCV RNA and a cyclophilin inhibitor (i.e., NIM-811 (Novartis) and DEBIO-025 (Debiopharm)) and/or an alpha-glucosidase inhibitor (i.e., Celgosivir (Migenix)) and/or one or more agents from one or more of the other classes of HCV therapeutic agents discussed herein is used to treat HCV infection. Moreover, there are several targets within NS4B, and compounds that interact with these other targets can, in accordance with the methods of the present disclosure, be used in combination with an NS4B antagonist that prevents the binding of NS4B to the 3'-UTR of HCV RNA and, optionally, one or more of the other classes of inhibiting agents mentioned herein, to treat HCV infection. Such additional NS4B targets include: the N-terminal amphipathic helix (see PCT publication WO 2002/089731, incorporated herein by reference), the NS4B GTPase (see PCT publication WO 2005/032329, incorporated herein by reference), the second amphipathic helix, the PIP2 binding activity of the first amphipathic helix in NS4B (see U.S. provisional patent application Ser. No. 60/057,188, incorporated herein by reference).

Other agents that can be used in combination with inhibiting agents of the present disclosure that prevent the binding of NS4B to the 3'-UTR of HCV RNA include (i) agents targeting NS5A, including, but not limited to, A-831 (Arrow Therapeutics), AZD2836 (Astra Zeneca), and agents in development by XTL/Presidio or BMS (see PCT publications WO 2006/133326 and WO 2008/021928, incorporated herein by reference); (ii) agents targeting TBCID$_2$O and/or NS5A's interaction with TBC1D20 (see PCT publication WO 2007/018692 and U.S. patent application Ser. No. 11/844,993, incorporated herein by reference), (iii) agents targeting NS4B's GTPase activity (see PCT publication WO 2005/032329 and US patent application publication 2006/0199174, incorporated herein by reference); (iv) agents inhibiting membrane association mediated by the HCV amphipathic helices, such as those found in NS5A, NS4B, and NS5B (see PCT publication WO 2002/089731, supra), (v) agents targeting PIP2 or BAAPP domains in HCV proteins, such as those found in NS4B and NS5A (see U.S. provisional patent application 60/057,188, supra); (vi) agents targeting HCV entry, assembly, or release, including antibodies to co-receptors; (vii) agents targeting HCV NS3 helicase; (viii) siRNAs, shRNAs, antisense RNAs, or other RNA-based molecules targeting sequences in HCV; (ix) agents targeting microRNA122 or other microRNAs modulating HCV replication; (x) agents targeting PD-1, PD-L1, or PD-L2 interactions or pathway (see U.S. patent application publications 20080118511, 20070065427, 20070122378, incorporated herein by reference); and (xi) agents targeting HCV amphipathic helix function, such as AH2 inhibitors.

In another embodiment of the present disclosure, an inhibiting agent that prevents the binding of NS4B to the 3'-UTR of HCV RNA is used in combination with one or more drugs capable of treating an HIV infection to treat a patient that is co-infected with HIV and HCV. In another embodiment of the present disclosure, an inhibiting agent that prevents the binding of NS4B to the 3'-UTR of HCV RNA is used in combination with one or more drugs capable of treating an HBV infection to treat a patient that is co-infected with HBV and HCV. In an embodiment, an inhibiting agent that prevents the binding of NS4B to the 3'-UTR of HCV RNA is used in combination with a PD-L1 inhibitor to treat a viral infection.

As mentioned above, embodiments of the present include the administration of an inhibiting agent identified herein (or by using an embodiment of the screen of the invention) in conjunction with at least one additional therapeutic agent to treat a viral infection. Suitable additional therapeutic agents include, but are not limited to, ribavirin; a nucleoside analog (e.g., levovirin, viramidine, and the like.); an NS3 inhibitor; an NS5 inhibitor; an interferon; and a side effect management agent.

In an embodiment, the at least one additional suitable therapeutic agent includes ribavirin. Ribavirin, 1-β-D-ribofuranosyl-1H-1,2,4-triazole-3-carboxamide, available from ICN Pharmaceuticals, Inc., Costa Mesa, Calif., is described in the Merck Index, compound No. 8199, Eleventh Edition. Its manufacture and formulation is described in U.S. Pat. No. 4,211,771. The disclosure also contemplates use of derivatives of ribavirin (see, e.g., U.S. Pat. No. 6,277,830).

In an embodiment, the at least one additional suitable therapeutic agent includes levovirin. Levovirin is the L-enantiomer of ribavirin, and exhibits the property of enhancing a Th1 immune response over a Th2 immune response. Levovirin is manufactured by ICN Pharmaceuticals.

In an embodiment, the at least one additional suitable therapeutic agent includes viramidine. Viramidine is a 3-carboxamidine derivative of ribavirin, and acts as a prodrug of ribavirin. It is efficiently converted to ribavirin by adenosine deaminases.

Nucleoside analogs that are suitable for use in a combination therapy include, but are not limited to, ribavirin, levovirin, viramidine, isatoribine, an L-ribofuranosyl nucleoside as disclosed in U.S. Pat. No. 5,559,101 and encompassed by Formula I of U.S. Pat. No. 5,559,101 (e.g., 1-β-L-ribofuranosyluracil, 1-β-L-ribofuranosyl-5-fluorouracil, 1-β-L-ribofuranosylcytosine, 9-β-L-ribofuranosyladenine, 9-β-L-ribofuranosylhypoxanthine, 9-β-L-ribofuranosylguanine, 9-β-L-ribofuranosyl-6-thioguanine, 2-amino-α-L-ribofuranl[1',2':4,5]oxazoline, O$^2$,O$^2$-anhydro-1-α-L-ribofuranosyluracil, 1-α-L-ribofuranosyluracil, 1-(2,3,5-tri-O-benzoyl-α-ribofuranosyl)-4-thiouracil, 1-α-L-ribofuranosylcytosine, 1-α-L-ribofuranosyl-4-thiouracil, 1-α-L-ribofuranosyl-5-fluorouracil, 2-amino-β-L-arabinofurano[1',2':4,5]oxazoline, O$^2$,O$^2$-anhydro-o-L-arabinofuranosyluracil, 2'-deoxy-β-L-uridine, 3'5'-Di-O-benzoyl-2'deoxy-4-thio β-L-uridine, 2'-deoxy-β-L-cytidine, 2'-deoxy-β-L-4-thiouridine, 2'-deoxy-β-L-thymidine, 2'-deoxy-β-L-5-fluorouridine, 2',3'-dideoxy-β-L-uridine, 2'-deoxy-β-L-5-fluorouridine, and 2'-deoxy-β-L-inosine); a compound as disclosed in U.S. Pat. No. 6,423,695 and encompassed by Formula I of U.S. Pat. No. 6,423,695; a compound as disclosed in U.S. Patent Publication No. 2002/0058635, and encompassed by Formula 1 of U.S. Patent Publication No. 2002/0058635; a nucleoside analog as disclosed in WO 01/90121 A2 (Idenix); a nucleoside analog as disclosed in WO 02/069903 A2 (Biocryst Pharmaceuticals Inc.); a nucleoside analog as disclosed in WO 02/057287 A2 or WO 02/057425 A2 (both Merck/Isis); and the like.

In an embodiment, the at least one additional suitable therapeutic agent can include HCV NS3 inhibitors. Suitable HCV non-structural protein-3 (NS3) inhibitors include, but are not limited to, a tri-peptide as disclosed in U.S. Pat. Nos. 6,642,204, 6,534,523, 6,420,380, 6,410,531, 6,329,417, 6,329,379, and 6,323,180 (Boehringer-Ingelheim); a compound as disclosed in U.S. Pat. No. 6,143,715 (Boehringer-Ingelheim); a macrocyclic compound as disclosed in U.S. Pat. No. 6,608,027 (Boehringer-Ingelheim); an NS3 inhibitor as disclosed in U.S. Pat. Nos. 6,617,309, 6,608,067, and 6,265,380 (Vertex Pharmaceuticals); an azapeptide compound as disclosed in U.S. Pat. No. 6,624,290 (Schering); a compound as disclosed in U.S. Pat. No. 5,990,276 (Schering); a compound as disclosed in Pause et al. (2003) *J. Biol. Chem.* 278:20374-20380; NS3 inhibitor BILN 2061 (Boehringer-Ingelheim; Lamarre et al. (2002) *Hepatology* 36:301A; and Lamarre et al. (Oct. 26, 2003) *Nature* doi: 10.1038/nature02099); NS3 inhibitor VX-950 (Vertex Pharmaceuticals; Kwong et al. (Oct. 24-28, 2003) $54^{th}$ Ann. Meeting AASLD); NS3 inhibitor SCH6 (Abib et al. (Oct. 24-28, 2003) Abstract 137. Program and Abstracts of the $54^{th}$ Annual Meeting of the American Association for the Study of Liver Diseases (AASLD). Oct. 24-28, 2003. Boston, Mass.); any of the NS3 protease inhibitors disclosed in WO 99/07733, WO 99/07734, WO 00/09558, WO 00/09543, WO 00/59929 or WO 02/060926 (e.g., compounds 2, 3, 5, 6, 8, 10, 11, 18, 19, 29, 30, 31, 32, 33, 37, 38, 55, 59, 71, 91, 103, 104, 105, 112, 113, 114, 115, 116, 120, 122, 123, 124, 125, 126 and 127 disclosed in the table of pages 224-226 in WO 02/060926); an NS3 protease inhibitor as disclosed in any one of U.S. Patent Publication Nos. 2003019067, 20030187018, and 20030186895; and the like.

In an embodiment, the NS3 inhibitor used in a combination therapy of the invention is a member of the class of specific NS3 inhibitors, e.g., NS3 inhibitors that inhibit NS3 serine protease activity and that do not show significant inhibitory activity against other serine proteases such as human leukocyte elastase, porcine pancreatic elastase, or bovine pancreatic chymotrypsin, or cysteine proteases such as human liver cathepsin B.

In an embodiment, the at least one additional suitable therapeutic agent includes NS5B inhibitors. Suitable HCV non-structural protein-5 (NS5; RNA-dependent RNA polymerase) inhibitors include, but are not limited to, a compound as disclosed in U.S. Pat. No. 6,479,508 (Boehringer-Ingelheim); a compound as disclosed in any of International Patent Application Nos. PCT/CA02/01127, PCT/CA02/01128, and PCT/CA02/01129, all filed on Jul. 18, 2002 by Boehringer Ingelheim; a compound as disclosed in U.S. Pat. No. 6,440,985 (ViroPharma); a compound as disclosed in WO 01/47883, e.g., JTK-003 (Japan Tobacco); a dinucleotide analog as disclosed in Zhong et al. (2003) *Antimicrob. Agents Chemother.* 47:2674-2681; a benzothiadiazine compound as disclosed in Dhanak et al. (2002) *J. Biol Chem.* 277(41): 38322-7; an NS5B inhibitor as disclosed in WO 02/100846 A1 or WO 02/100851 A2 (both Shire); an NS5B inhibitor as disclosed in WO 01/85172 A1 or WO 02/098424 A1 (both Glaxo SmithKline); an NS5B inhibitor as disclosed in WO 00/06529 or WO 02/06246 A1 (both Merck); an NS5B inhibitor as disclosed in WO 03/000254 (Japan Tobacco); an NS5B inhibitor as disclosed in EP 1 256,628 A2 (Agouron); JTK-002 (Japan Tobacco); JTK-109 (Japan Tobacco); and the like.

In an embodiment, the NS5 inhibitor used in the combination therapies of the invention is a member of the class of specific NS5 inhibitors, e.g., NS5 inhibitors that inhibit NS5 RNA-dependent RNA polymerase and that lack significant inhibitory effects toward other RNA dependent RNA polymerases and toward DNA dependent RNA polymerases.

In an embodiment, the at least one additional therapeutic agent is an interferon, e.g., interferon-alpha (IFN-α). Any known IFN-α can be used in the treatment methods of the invention. The term "interferon-alpha" as used herein refers to a family of related polypeptides that inhibit viral replication and cellular proliferation and modulate immune response. The term "IFN-α" includes naturally occurring IFN-α; synthetic IFN-α; derivatized IFN-α (e.g., PEGylated IFN-α, glycosylated IFN-α, and the like); and analogs of naturally occurring or synthetic IFN-α; essentially any IFN-α that has antiviral properties, as described for naturally occurring IFN-α.

Suitable alpha interferons include, but are not limited to, naturally-occurring IFN-α (including, but not limited to, naturally occurring IFN-α2a, IFN-α2b); recombinant interferon alpha-2b such as Intron-A interferon available from Schering Corporation, Kenilworth, N.J.; recombinant interferon alpha-2a such as Roferon interferon available from Hoffmann-La Roche, Nutley, N.J.; recombinant interferon alpha-2C such as Berofor alpha 2 interferon available from Boehringer Ingelheim Pharmaceutical, Inc., Ridgefield, Conn.; interferon alpha-n1, a purified blend of natural alpha interferons such as Sumiferon available from Sumitomo, Japan or as Wellferon interferon alpha-n1 (INS) available from the Glaxo-Wellcome Ltd., London, Great Britain; and interferon alpha-n3 a mixture of natural alpha interferons made by Interferon Sciences and available from the Purdue Frederick Co., Norwalk, Conn., under the Alferon tradename.

The term "IFN-α" also encompasses consensus IFN-α. Consensus IFN-α (also referred to as "CIFN" and "IFN-con" and "consensus interferon") encompasses, but is not limited to, the amino acid sequences designated IFN-$con_1$, IFN-$con_2$ and IFN-$con_3$ which are disclosed in U.S. Pat. Nos. 4,695,623 and 4,897,471; and consensus interferon as defined by determination of a consensus sequence of naturally occurring interferon alphas (e.g., Infergen®, InterMune, Inc., Brisbane, Calif.). IFN-$con_1$ is the consensus interferon agent in the Infergen® alfacon-1 product. The Infergen® consensus interferon product is referred to herein by its brand name (Infergen®) or by its generic name (interferon alfacon-1). DNA sequences encoding IFN-con may be synthesized as described in the aforementioned patents or other standard methods. In an embodiment, the at least one additional therapeutic agent is CIFN.

In an embodiment, fusion polypeptides comprising an IFN-α and a heterologous polypeptide can also be used in the combination therapies of the invention. Suitable IFN-α fusion polypeptides include, but are not limited to, Albuferon-alpha™ (a fusion product of human albumin and IFN-α; Human Genome Sciences; see, e.g., Osborn et al. (2002) *J. Pharmacol. Exp. Therap.* 303:540-548). Also suitable for use in the present disclosure are gene-shuffled forms of IFN-α. See e.g., Masci et al. (2003) *Curr. Oncol. Rep.* 5:108-113.

Other suitable interferons include), Multiferon (Viragen), Medusa Interferon (Flamel Technology), Locteron (Octopus), and Omega Interferon (Intarcia/Boehringer Ingelheim).

The term "IFN-α" also encompasses derivatives of IFN-α that are derivatized (e.g., are chemically modified relative to the naturally occurring peptide) to alter certain properties such as serum half-life. As such, the term "IFN-α" includes glycosylated IFN-α; IFN-α derivatized with polyethylene glycol ("PEGylated IFN-α"); and the like. PEGylated IFN-α, and methods for making same, is discussed in, e.g., U.S. Pat. Nos. 5,382,657; 5,981,709; and 5,951,974. PEGylated IFN-α encompasses conjugates of PEG and any of the above-described IFN-α molecules, including, but not limited to, PEG conjugated to interferon alpha-2a (Roferon, Hoffman La-Roche, Nutley, N.J.), interferon alpha 2b (Intron, Schering-Plough, Madison, N.J.), interferon alpha-2c (Berofor Alpha, Boehringer Ingelheim, Ingelheim, Germany); and consensus interferon as defined by determination of a consensus sequence of naturally occurring interferon alphas (Infergen®, InterMune, Inc., Brisbane, Calif.).

In an embodiment, the IFN-α polypeptides can be modified with one or more polyethylene glycol moieties, i.e., PEGylated. The PEG molecule of a PEGylated IFN-α polypeptide is conjugated to one or more amino acid side chains of the IFN-α polypeptide. In an embodiment, the PEGylated IFN-α contains a PEG moiety on only one amino acid. In another embodiment, the PEGylated IFN-α contains a PEG moiety on two or more amino acids, e.g., the IFN-α contains a PEG moiety attached to two, three, four, five, six, seven, eight, nine, or ten different amino acid residues. IFN-α may be coupled directly to PEG (i.e., without a linking group) through an amino group, a sulfhydryl group, a hydroxyl group, or a carboxyl group.

To determine the optimum combination of an inhibiting agent, such as clemizole, with other anti-HCV agents, HCV replication assays and/or animal studies can be performed in the presence of various combinations of the various anti-HCV agents. Increased inhibition of replication in the presence of an additional agent (above that observed with monotherapy) is evidence for the potential benefit of the combination therapy.

Figure 1B:
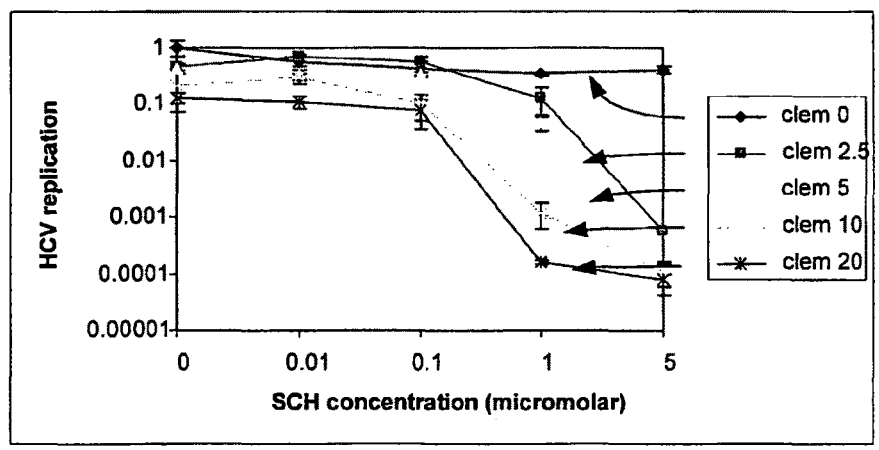

For example, HCV replication assays employing a luciferase reporter-linked HCV genome in the presence of various combinations of clemizole and an NS3 protease inhibitor (SCH503034) are shown in FIGS. 1A and 1B. In such assays, luciferase activity is directly proportional to HCV RNA genome replication. In this method, Huh 7.5 cells were electroporated with a wild-type luciferase reporter-linked HCV genome, and plated replicates were cultured in the presence of the indicated concentrations of clemizole and SCH503034 (SCH) for 72 hours, followed by lysis and determination of luciferase activity, essentially as described (Nature Biotechnology 26, 1019-1027 (2008), which is incorporated herein by reference). The results can be plotted on a linear or log scale as a function of drug concentrations to generate replication inhibition curves. The inhibition curve for the NS3 inhibitor shows significantly more inhibition in the presence of increasing concentrations of clemizole. In particular, at low micromolar concentrations of SCH503034 (such as 1-5 micromolar), addition of clemizole can increase the inhibition of HCV replication in a dose-dependent manner by up to several logs. Similarly increased efficacy of combination therapy (over monotherapy) should occur in accordance with the methods of the invention when an NS4B antagonist is co-administered with other NS3 protease inhibitors, and with other anti-HCV agents that have a mechanism of action distinct from NS4B antagonists that have the same mechanism of action as clemizole. These results not only provide clear evidence for the benefit of combination therapy of clemizole and SCH503034, but also demonstrate that improved efficacy and likely decreased resistance can occur following in vivo therapy with this and similar combination therapies provided by the present disclosure. Moreover, these results demonstrate that one skilled in the art can readily perform assays to determine optimal combination therapies with the NS4B antagonists useful in embodiments of the methods of the present invention and other anti-HCV agents in view of the disclosure herein.

In an embodiment, side effect management agents can be used in the treatment methods of the invention, and these include agents that are effective in pain management; agents that ameliorate gastrointestinal discomfort; analgesics, anti-inflammatories, antipsychotics, antineurotics, anxiolytics, and hematopoietic agents. In addition, embodiments of the invention contemplate the use of any compound for palliative care of patients suffering from pain or any other side effect in the course of treatment with a subject therapy. Exemplary palliative agents include acetaminophen, ibuprofen, other NSAIDs, H2 blockers, and antacids.

The inhibiting agents and pharmaceutical compositions provided herein can be used to treat a variety of patients or hosts infected with a virus of the Flavirivirus family. The subject treatment methods may particularly benefit "treatment failure patients". Such patients include but are not limited to those who have failed to respond to previous therapy for HCV (referred to as "non-responders") or who initially responded to previous therapy, but in whom the therapeutic response was not maintained (referred to as "relapsers"). The previous therapy generally can include treatment with any anti-viral agent other than an inhibiting agent of the present disclosure.

Other patients that may benefit from the subject treatments are individuals who have been clinically diagnosed as infected with HCV. Such individuals include naïve individuals (e.g., individuals not previously treated for HCV). Individuals who are infected with HCV can be identified by detecting HCV RNA in their blood, and/or having an anti-HCV antibody in their serum.

In some embodiments, hosts suitable for treatments of the present invention have an HCV titer of at least about $10^5$, at least about $5 \times 10^5$, or at least about $10^6$, genome copies of HCV per milliliter of serum. The patient may be infected with any HCV genotype (genotype 1, including 1a and 1b, 2, 3, 4, 6, and the like and subtypes (e.g., 2a, 2b, 3a, and the like.)), particularly a difficult to treat genotype such as HCV genotype 1 and particular HCV subtypes and quasispecies.

Also suitable for treatment are HCV-positive hosts (as described above) who exhibit severe fibrosis or early cirrhosis (non-decompensated, Child's-Pugh class A or less), or more advanced cirrhosis (decompensated, Child's-Pugh class B or C) due to chronic HCV infection and who are viremic despite prior anti-viral treatment, or who have a contraindication to therapy with a known anti-viral agent.

In an embodiment, HCV-positive hosts with stage 3 or 4 liver fibrosis according to the METAVIR scoring system are suitable for treatment with the methods of the present disclosure. In another embodiment, hosts suitable for treatment with embodiments of the present disclosure are patients with decompensated cirrhosis with clinical manifestations, including patients with far-advanced liver cirrhosis, including those awaiting liver transplantation. In still another embodiment, hosts suitable for treatment with embodiments of the present disclosure include patients with milder degrees of fibrosis including those with early fibrosis (stages 1 and 2 in the METAVIR, Ludwig, and Scheuer scoring systems; or stages 1, 2, or 3 in the Ishak scoring system).

In an embodiment of the present disclosure, to help optimally select patients most likely to benefit from therapy, as well as to monitor efficacy of therapy—especially in the face of potential drug resistant mutant viruses—the use of appropriate diagnostic tests provided by the present invention can be of great benefit. For example, assessing the sensitivity of the specific virus found in a given patient to the contemplated therapy can help identify the best match between candidate patient and the corresponding appropriate therapy. In the case of clemizole, clemizole analogs, compounds having a clemizole scaffold, or other inhibiting agents identified herein, this can be done by isolating the NS4B sequence from a given patient's HCV isolate and determining the efficacy of the drug's inhibition of RNA binding by the patient's NS4β isoform. This is especially important, because there currently is no efficient way of studying the drug sensitivity of a given patient's virus, because patient-derived inoculums cannot be readily cultured. The value of using such diagnostic assays to guide therapy has been extensively validated in HIV.

Combination therapy with clemizole in accordance with embodiments of the present invention includes, for example and without limitation, (1) treatment with clemizole plus nitazoxanide, (2) treatment with clemizole followed by nitazoxanide, (3) treatment with clemizole plus nitazoxanide and a NS3 protease inhibitor, (4) treatment with clemizole plus nitazoxanide plus a NS3 protease inhibitor plus a NS5B polymerase inhibitor, (5) treatment with clemizole plus a NS3 protease inhibitor plus a NS5B polymerase inhibitor, (6) treatment with clemizole plus nitazoxanide plus a NS3 protease inhibitor plus a NS4B second amphipathic helix inhibitor, (7) treatment with clemizole plus nitazoxanide plus a NS4B second amphipathic helix inhibitor, (8) treatment with clemizole plus a NS3 protease inhibitor plus a NS4B second amphipathic helix inhibitor, (9) treatment with clemizole plus ribavirin, (10) treatment with clemizole followed by nitazoxanide plus ribavirin; and (11) any other combinations of one or more agents listed above (1)-(10). In some embodiments, the one or more additional therapeutica agents are administered prior to, concurrent with, or subsequent to the treatment with clemizole, clemizole analogs or isosterers of the present invention. In various embodiments, the inhibiting agent is clemizole hydrochloride (1-p-chlorobenzyl-2-(1-pyrrolidinyl)methylbenzimidazole hydrochloride), an analog or clemizole, or a derivative thereof.

Nitazoxanide administration in accordance with the combination therapies of the invention can be, for illustration and without limitation, 500 mg po BID. Other doses, other thiazolides, or other formulations of nitazoxanide or another thiazolide, such as sustained release formulations, can also be used in the combination therapies of the invention.

The inhibiting agents and pharmaceutical compositions thereof can be administered to a subject using any available method and route suitable for drug delivery, including in vivo and ex vivo methods, as well as systemic and localized routes of administration.

Routes of administration include intranasal, intramuscular, intratracheal, subcutaneous, intradermal, topical application, intravenous, rectal, nasal, oral, and other enteral and parenteral routes of administration. Routes of administration may be combined, if desired, or adjusted depending upon the agent and/or the desired effect. An active agent can be administered in a single dose or in multiple doses.

Embodiments of the inhibiting agent can be administered to a host using available conventional methods and routes suitable for delivery of conventional drugs, including systemic or localized routes. In general, routes of administration contemplated by the disclosure include, but are not limited to, enteral, parenteral, or inhalational routes.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be conducted to effect systemic or local delivery of the inhibiting agent. Where systemic delivery is desired, administration typically involves invasive or systemically absorbed topical or mucosal administration of pharmaceutical preparations.

The inhibiting agent can also be delivered to the subject by enteral administration. Enteral routes of administration include, but are not limited to, oral and rectal (e.g., using a suppository) delivery.

Methods of administration of the inhibiting agent through the skin or mucosa include, but are not limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more. In some embodiments, clemizole or clemizole analog is administered by oral, intravenous, transdermal, sublingual, intramuscular, or rectal route.

In a separate but related embodiment, the present invention further provides an in vitro cell-free method of identifying agents (inhibiting agents) that modulate RNA binding to an RNA-binding protein. A test agent that inhibits binding of NS4B polypeptide to the 3'UTR of HCV negative strand RNA can be further tested for its ability to inhibit HCV replication in a cell-based assay. For example, a test agent of interest can be contacted with a mammalian cell that harbors all or part of an HCV genome; and the effect of the test agent on HCV replication is determined. Suitable cells include mammalian liver cells that are permissive for HCV replication, e.g., an immortalized human hepatocyte cell line that is permissive for HCV. For example, a suitable mammalian cell is Huh7 hepatocyte or a subclone of Huh7 hepatocyte, e.g., Huh-7.5. Suitable cell lines are described in, e.g., Blight et al. (2002) *J. Virol.* 76:13001; and Zhang et al. (2004) *J. Virol.* 78:1448. In an embodiment, the HCV genome in the cell comprises a reporter, e.g., a nucleotide sequence encoding luciferase, a fluorescent protein, or other protein that provides a detectable signal; and determining the effect, if any, of the test agent on HCV replication is achieved by detection of a signal from the reporter.

In an embodiment, the test agents are organic moieties. In this embodiment, as is generally described for other purposes in WO 94/24314, which is incorporated herein by reference, test agents are synthesized from a series of substrates that can be chemically modified. "Chemically modified" herein includes traditional chemical reactions as well as enzymatic reactions. These substrates generally include, but are not limited to, alkyl groups (including alkanes, alkenes, alkynes and heteroalkyl), aryl groups (including arenes and heteroaryl), alcohols, ethers, amines, aldehydes, ketones, acids, esters, amides, cyclic compounds, heterocyclic compounds (including purines, pyrimidines, benzodiazepines, beta-lactams, tetracyclines, cephalosporins, and carbohydrates), steroids (including estrogens, androgens, cortisone, ecodysone, and the like.), alkaloids (including ergots, vinca, curare, pyrollizdine, and mitomycines), organometallic compounds, hetero-atom bearing compounds, amino acids, and nucleosides. Chemical (including enzymatic) reactions may be done on the moieties to form new substrates or candidate agents which can then be tested using the present methods.

EXAMPLES

The following examples are put forth so as to provide those of ordinary skill in the art with a complete disclosure and description of how to make and use the present disclosure, and are not intended to limit the scope of what the inventors regard as their disclosure nor are they intended to represent that the experiments below are all or the only experiments performed. Efforts have been made to ensure accuracy with respect to numbers used (e.g., amounts, temperature, and the like.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

The 9.6-kb positive single-stranded RNA HCV genome encodes a 3,000-amino-acid polyprotein which is proteolytically processed into structural proteins, which are components of the mature virus, and nonstructural proteins (NS), which are involved in replicating the viral genome. Like other positive strand RNA viruses, HCV appears to replicate in association with intracellular membrane structures. In the case of HCV, the structures are termed the membranous web and are believed to be induced by the NS4B protein. NS4B is also used to assemble the other viral NS proteins within the apparent sites of RNA replication. NS4B and HCV RNA have been shown to colocalize to the membranous web suggesting that NS4B is in intimate contact with viral RNA in the context of authentic viral RNA replication. The hepatitis A and polio picornaviruses have proteins termed 2C which are used for replication, bind RNA, and have an N-terminal amphipathic helix and a nucleotide binding motif. NS4B contains the same structural features, and both of them are used for HCV replication. Like the majority of drug targets, NS4B is a membrane protein (SEQ ID NO 5).

The use of the microfluidic platform for RNA binding was validated by studying two human proteins from the embryonic lethal abnormal visual system (ELAV) family, the RNA binding activity of which has been previously well-characterized. This methodology was then applied to screen a compound library for pharmacologic inhibitors of NS4B RNA binding and HCV replication. These pharmacologic inhibitors have great therapeutic potential for HCV treatment and prevention.

High-Throughput Screening for Inhibitory Compounds.

In accordance with the methods described in priority applications US/2008/076804 and US/2008/076806 (both of which are incorporated herein by reference), a compound library was screened to identify small molecules that could inhibit the RNA-NS4B interaction. As shown in FIG. 5a, 1280 compounds from a small molecular library were spotted on epoxy-coated slides as a microarray. The array was allowed to dry, and was then aligned and bonded to a microfluidic device as described above. The rest of the assay was performed as before, except that the device was loaded with NS4B-GFP followed by Cy5-labeled 3' terminus negative RNA probe. In the primary screen, the compounds were spotted at a concentration of ~1 mM. The entire library was screened in duplicate using only two microfluidic devices. Out of 1280 compounds, 104 were found to have an inhibitory effect (>90% inhibition) on RNA binding by NS4B. In addition, there were 110 compounds for which there was a significant discrepancy between the two tested replicates or to which one or two of the measurements were disrupted due to technical reasons.

The 214 compounds (104+110) identified in the primary screen were subjected to a secondary screen (FIG. 5a). This was done in a similar manner except that a smaller device was used, the spotted compound concentration was 10 fold lower than in the primary screen and 5 replicates were spotted for each compound. Eighteen compounds were confirmed to significantly inhibit RNA binding by NS4B out of the 214 compounds tested (FIG. 5b). Most of the identified compounds did not inhibit binding of HuR protein to its own 4A target RNA sequence (FIG. 7) nor did they inhibit HuR binding to its previously described HCV RNA target: the 3' terminus of the negative viral strand, suggesting that these hits are specific.

Inhibitors of HCV RNA Replication.

Figures 8A, 8B:
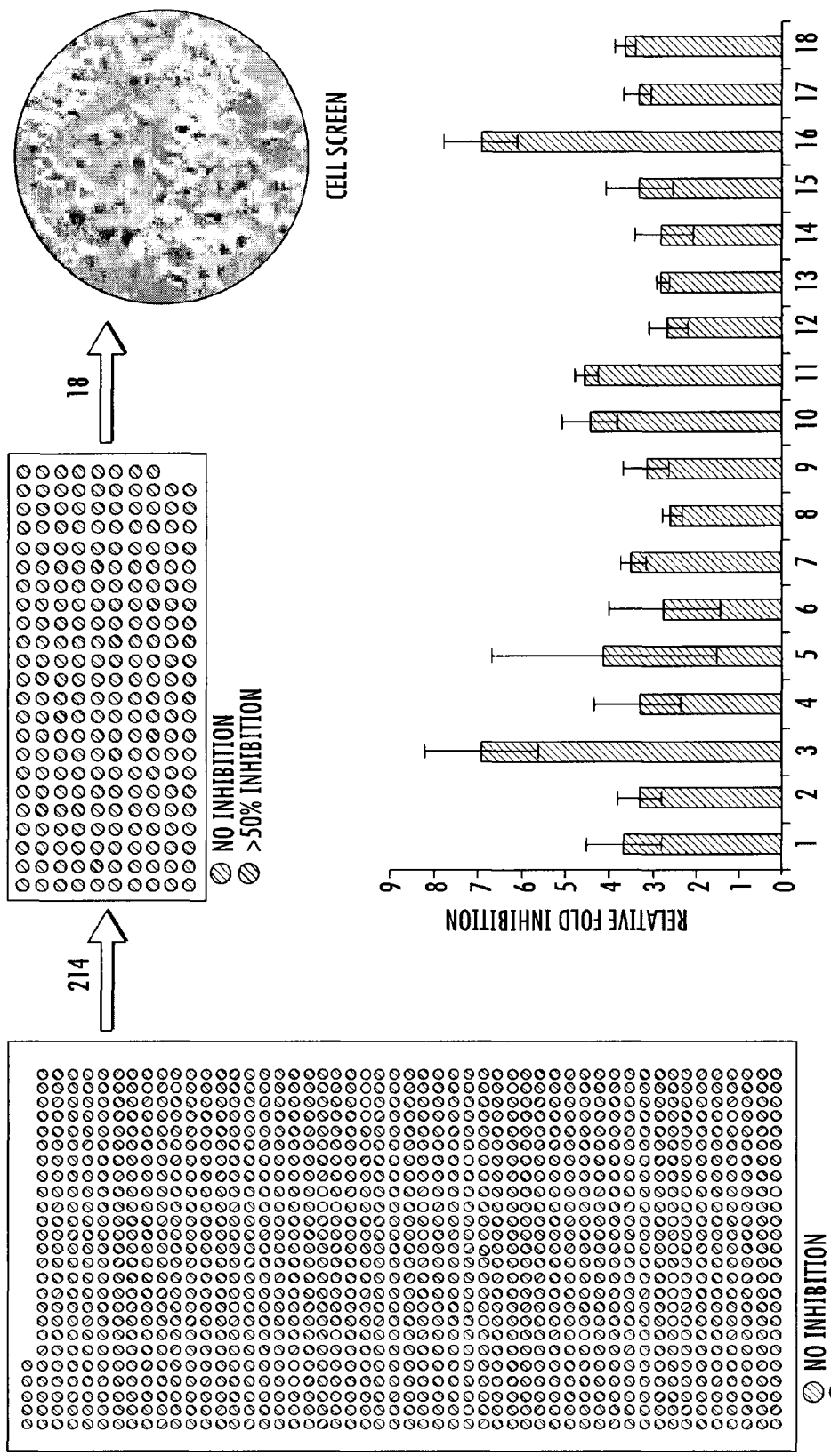
FIG. 8 illustrates results that show that clemizole inhibits HCV replication as evidenced by real-time PCR assays. Real-time PCR assay of HCV replication levels show that clemizole inhibits HCV replication (left axis ♦ (bottom curve)) with no measurable toxicity to the cell (right axis, ■ (top curve)).
Figure 8D:
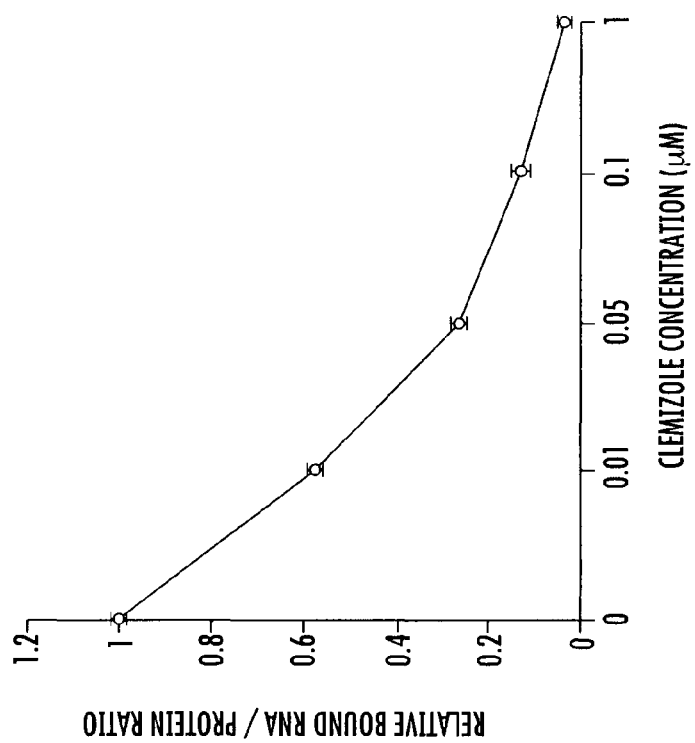
Figure 8C:
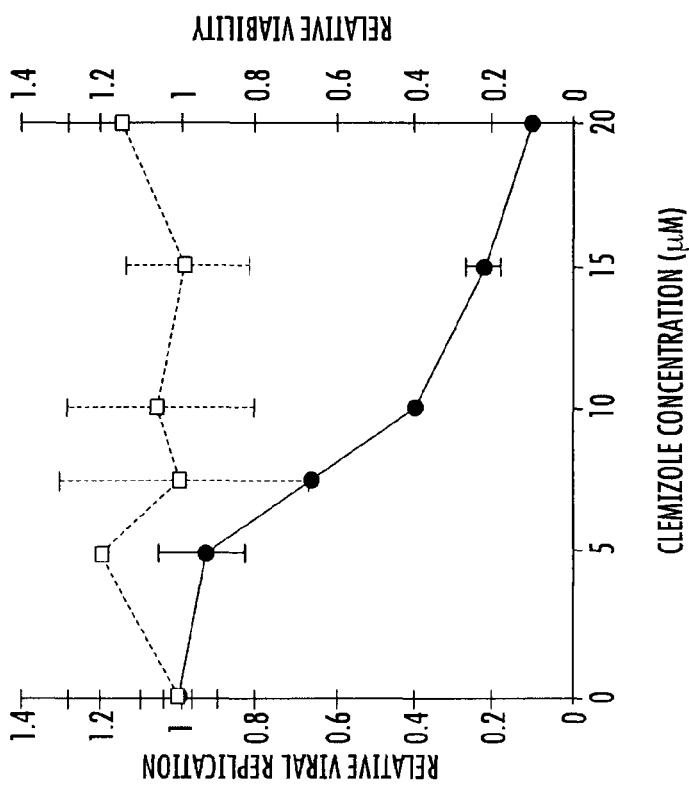

The in vivo antiviral effect on HCV RNA replication of the inhibitory compounds identified in the above screen was measured. Following electroporation with a full-length HCV RNA genome harboring a luciferase reporter gene, Huh7.5 cells were grown in the presence of increasing concentrations of these compounds. Luciferase assays were performed at 72 hr. In parallel, the viability of cells in the presence of the compounds was assessed by an Alamar Blue-based assay. Six of the compounds showed some antiviral effect above that solely attributable to cellular toxicity. Clemizole hydrochloride (1-p-Chlorobenzyl-2-(1-pyrrolidinyl)methylbenzimidazole hydrochloride), an H1 histamine receptor antagonist, was found to significantly inhibit HCV replication. A tenfold decrease in viral replication was measured at 20 µM concentration of the drug, with an EC50 of ~8 µM (FIG. 5c). At these concentrations, there was no measurable cellular toxicity (FIG. 5c). Similar results were obtained by real-time PCR assays performed in clemizole-treated Huh7.5 cells infected with the infectious HCV clone (J6/JFH) (FIG. 8). The in vitro IC50 of clemizole for RNA binding by NS4B is ~24±1 nM (FIG. 5d).

Figure 9A:
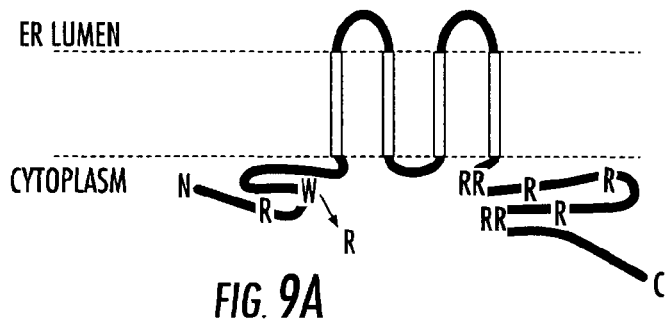
FIG. 9A shows the chemical structure of clemizole hydrochloride.
Figure 9B:
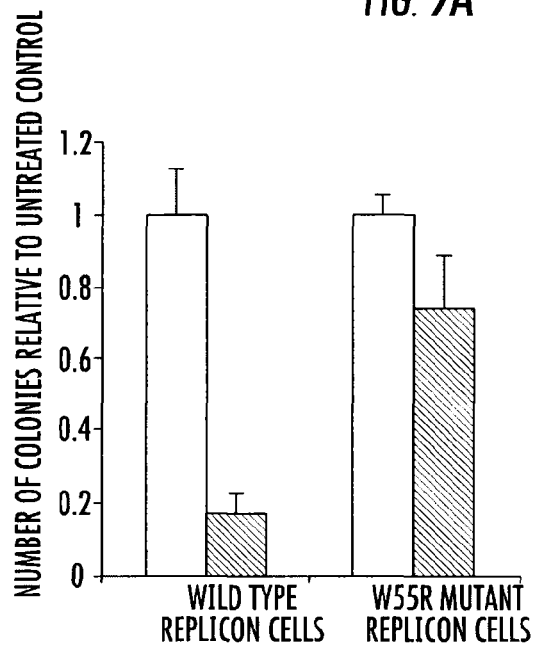
FIG. 9B shows the chemical structure of a clemizole derivative molecule with increased potency and efficacy.
Figure 9C:
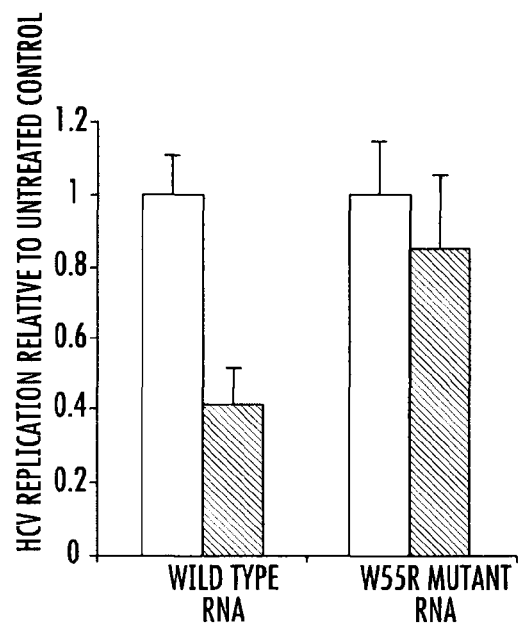
FIG. 9C illustrates a graph that shows the in vitro inhibition curve of a clemizole derivative molecule (•) and the parental clemizole hydrochloride compound (□), as measured by microfluidics (bound RNA/protein ratio vs compound concentration (μM)).
Figure 9D:
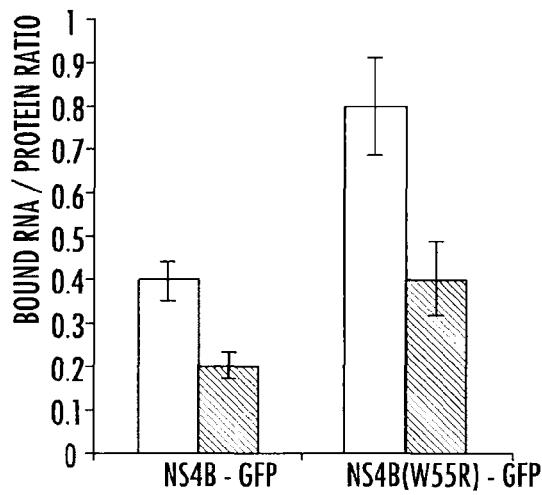
FIG. 9D illustrates a graph that shows a dose response curve of HCV replication in the presence of increasing concentrations of a clemizole derivative molecule (•) and the parental clemizole hydrochloride compound (□), as measured by a real-time PCR assay in HCV-infected cells (relative viral replication vs compound concentration (μM)).
Figure 9E:
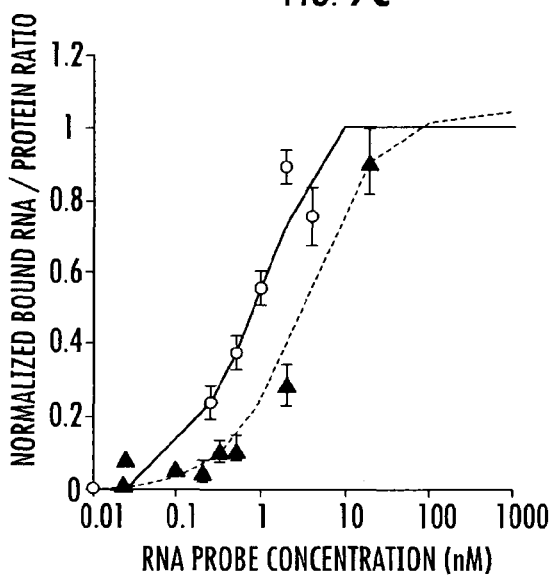

Increased Potency and Efficacy of a Clemizole Hydrochloride Derivative Molecule:

Screening conducted using the methods described herein this application to identify a clemizole analog with increased potency. An example of one such molecule is shown in FIG. 9 which has increased in vitro potency (IC50 of 6 nM vs 24 mM for Clemizole) (FIG. 9C). Importantly, this compound also demonstrated a higher antiviral activity against HCV replication in cells with an EC50 of 1 µM (versus 8 µM for Clemizole) (FIG. 9D).

Taken together, the above data combined with the analysis of resistant mutants provides compelling genetic, biochemical, and pharmacologic evidence for clemizole's mechanism of action. Moreover these data demonstrate that more potent inhibitory molecules can be identified using the methods of the invention.

Clemizole-Resistant Mutants.

The mechanism of action of clemizole's antiviral activity was further substantiated by selecting for clemizole resistant HCV mutants. Established HCV replicon-harboring cells and Huh7 cells electroporated de novo with a genotype 1b subgenomic HCV replicon (Bart 79I) were passaged in the presence of the drug, yielding ~60 colonies that were able to grow in the presence of the compound. 11 individual colonies were successfully expanded, passaged 5-10 times and the HCV RNA replicating in the cells was subjected to sequence analysis. In addition, RNA from a pool of clemizole-resistant colonies was isolated and subjected to a similar analysis. Three colonies were found to harbor replicons with mutations that mapped to the NS4B region, and 6 colonies were found to harbor replicons with mutations that mapped to the negative strand 3' terminus RNA region. (Of note, the location of resistance mutations selected in the presence of the clemizole derivative molecule of FIG. 9B mapped to similar locations within the HCV genome). In addition, there was one colony with mutations that mapped to both NS4B and the negative strand 3' terminus, and one where the location of the mutation conferring resistance to clemizole was not yet identified. No such mutations were identified in 10 replicon colonies that were passaged in parallel in the absence of the drug.

Figure 6A:
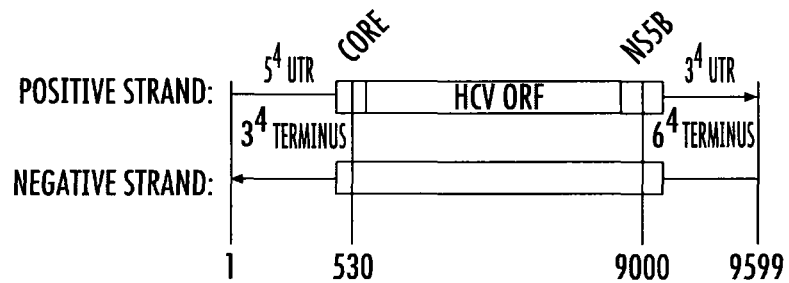
Figure 6B:
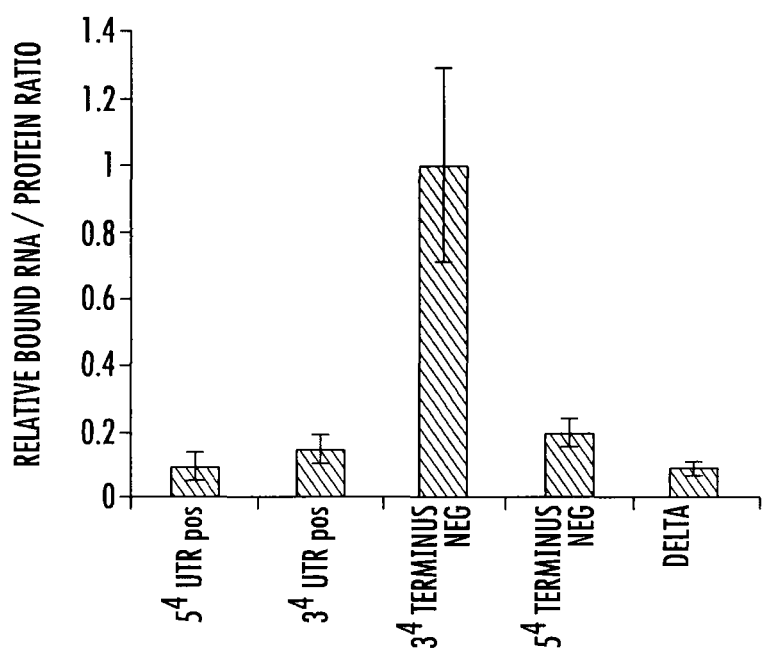

Two of the clemizole-resistant NS4B mutants were characterized in detail. The first, W55R is depicted in FIG. 6a. It involves the substitution of an arginine for the tryptophan at amino acid 55 within a predicted cytoplasmically-oriented segment of NS4B. This mutation is sufficient to confer a clemizole-resistant phenotype in cells: Huh7.5 cells transfected with either whole cell RNA extracted from the W55R mutant cells (FIG. 6b) or with in vitro-transcribed J6/JFH RNA encoding this point mutation and a linked luciferase reporter gene (FIG. 6c) were unaffected by 10 µM clemizole. EC50 of clemizole on the W55R mutant J6/JFH RNA was ~18 µM (2.25 times the EC50 on the wild type RNA). Similar to other HCV mutants resistant to an NS3 protease inhibitor, the absolute level of replication of the W55R mutant was lower than that of the wild type genome, indicating that the drug-resistant mutation comes at the cost of impaired replication fitness.

This mutation was also introduced into the NS4B-GFP vector and the resulting vector tested for its RNA binding activity using the in vitro microfluidic assay of the invention. Although both mutant and wild type NS4B proteins experienced ~a 2 fold reduction of RNA binding in the presence of 10 nM clemizole, because the baseline RNA binding of the mutant is higher, the residual amount of RNA bound by the mutant in the presence of clemizole was comparable to that bound by the wild type in the absence of clemizole (FIG. 6d). Furthermore, as shown in FIG. 6e, this mutant demonstrates greater apparent affinity to the viral RNA with a Kd of 0.75 nM (vs 3.4 nM for wild type NS4B).

The second clemizole-resistant mutation, termed R214Q, was identified in a resistant colony as well as in pooled resistant cells. It involves the substitution of a glutamine for the arginine at amino acid 214 within the cytoplasmic C-terminal segment of NS4B. Similar results to the first mutation were obtained in cellular and in vitro analyses done on this mutation, with an EC50 of 40.3 µM (~5 times higher than the EC50 on the wild type RNA) in the luciferase reporter linked replication assay and a Kd of 0.6 nM in the in vitro binding assay. Presumably, both of these mutations alter the conformation of NS4B so as to increase its affinity for the viral RNA. Indeed the Kd's measured by the in vitro RNA binding assay reflect this. Taken together, the above data provides compelling genetic and biochemical evidence for clemizole's mechanism of action. Clemizole hydrochloride was found to have a significant in vivo antiviral effect on HCV RNA replication mediated by its inhibition of NS4B's RNA binding, with little toxicity for the host cell.

The in vitro IC50 of clemizole for RNA binding by NS4B is ~24±1 nM, whereas its EC50 for viral replication is ~8 µM. It is possible that the low cellular permeability accounts for the ~400 fold difference between the IC50 measured for in vitro RNA binding by NS4B and the EC50 measured for the antiviral effect in cells. Improved drug delivery and optimization of the compound following structure-activity relationship (SAR) analysis can provide more potent antiviral agents and the microfluidic system and screening methods disclosed herein can facilitate this process. More potent inhibitors than clemizole hydrochloride can be identified through the methods disclosed herein. However, because clemizole hydrochloride has already been extensively used in humans (albeit for a different indication), it can find immediate use as an anti-HCV therapeutic and serve as a critical component of next generation anti-HCV strategies in accordance with the present invention.

Not being bound by any particular theory, the binding of NS4B to HCV RNA offers a mechanism to incorporate the viral genome into the HCV replication compartment. This may facilitate the initiation of synthesis of nascent positive strand from the membrane anchored negative strand. NS4B may also act by recruiting the polymerase complex to the HCV RNA, via its interaction with the NS5B polymerase or other components of the replication complex. An arginine rich-like motif in NS4B appears mediate RNA binding and HCV replication.

Methods and Materials

Plasmids:

Standard recombinant DNA technology was used to construct and purify all plasmids. All regions that were amplified by PCR were analyzed by automated DNA sequencing. Plasmid DNAs were prepared from large-scale bacterial cultures and purified by a Maxiprep kit (Marligen Biosciences). Restriction enzymes were purchased from New England Biolabs.

The open reading frames (ORF) of HuR and HuD were obtained from the ORFeome library of cDNA clones (Open biosystems). These ORFs were inserted into the expression vector pcDNA-Dest 40 vector (Invitrogen) by the use of gateway technology (Invitrogen) allowing addition of a C-terminal V5-his tag.

The plasmid pcDNA-NS4B-GFP encoding NS4B of genotype 1a fused in frame with a C-terminal GFP was previously described. The mutations RRa, RRb and W55R were introduced into this plasmid by site-directed mutagenesis (using the QuikChange kit (Stratagene)). The plasmid NS5A(AH) GFP was constructed as previously reported. Gus-his vector was obtained from Roche.

The plasmids pcDNA3.1-5' UTR pos which encodes the 5' UTR of the positive viral strand, was generated by amplification of the 5' UTR positive sequence from the Bart79I plasmid with primers containing EcoRV restriction sites, digestion with EcoRV and ligation into the corresponding site in pcDNA3.1 (Invitrogen). The plasmid pcDNA3.1-3' negative terminus which encodes the 3' terminal region of the negative RNA strand was generated the same way except that the EcoRV-flanked insert was ligated in an inverse orientation.

The plasmids pcDNA3.1-3' UTR pos and 5' negative terminus were similarly generated except that the inserted gene was flanked by HindIII and XhoI restriction sites.

The vector encoding the delta virus genomic RNA sequence was cloned by inserting NheI flanked HDV sequence into a pSPT19 vector (Roche Diagnostics) cut with XbaI.

The plasmid FL-J6/JFH-5'C19Rluc2AUbi that consists of the full-length HCV genome and expresses *Renilla* luciferase was a gift from Dr. Charles M. Rice. The W55R mutation was introduced into this plasmid by site-directed mutagenesis (using the QuikChange kit (Stratagene)).

In Vitro RNA Transcription and Fluorescent and Radioactive Labeling.

Plasmid DNA of the 5' and 3' terminal regions of the negative and positive viral strands were linearized with XbaI. The plasmid DNA of the delta genomic sequence was linearized with XbaI. Linearized plasmids were then treated with proteinase K, followed by phenol-chloroform extraction and precipitation with ethanol. The DNA was resuspended in RNase free water to a final concentration of 1 μg/μl. 4 μgs of DNA were used as a template for transcription with the T7 MEGAscript (Ambion) according to the manufacturer's protocol. The template DNA was digested by the addition of 5 U of RQ1 DNase (Ambion) and a 15-min incubation at 37° C. The unincorporated ribonucleotides were removed by size exclusion with a Micro Bio-Spin P-30 column (Bio-Rad), and the transcribed RNA was extracted with phenol-chloroform, followed by precipitation in ethanol. The RNA pellet was washed with 70% ethanol and resuspended in $H_2O$. Determination of the RNA concentration was performed by measurement of the optical density at 260 nm. The integrity of the RNA and its concentration were confirmed by 1% agarose gel electrophoresis and ethidium bromide staining.

The RNA sequences were labeled with Cy5 by using Label IT kit (Mirus) according to the manufacturer protocol followed by purification on a microspin column (Mirus) and ethanol precipitation. The number of fluorescent labels per RNA molecule was determined by measuring the spectrophotometric absorbance of the nucleic-dye conjugate at 260 nm and the $\lambda_{MAX}$ for Cy5 (650 nm). This was proportional to the probe's length and was used to adjust binding experiments results.

Cy3-labeled RNA probes used to study RNA binding by HuR and HuD were purchased from IDT.

Radioactive labeling of RNA probes with 32P was done as previously described.

Device Design:

The microfluidic device used for screening anti-viral compounds was fabricated according to methods described in the priority patent application US/2008/076804 and US/2008/076806, both of which are incorporated herein by reference.

The performance of RNA binding assay with the fluidic device as well as imaging and data analyses were carried out in accordance with the methods disclosed in the above-referenced priority applications.

Screening of Inhibitory Compound Library.

The 1280 compounds of the Lopac library (Sigma) solubilized in Dimethyl sulfoxide (DMSO) were spotted onto epoxy coated glass substrates slide (CEL Associates) using an OmniGrid Micro (GeneMachines) microarrayer and a CMP3B pin (TeleChem International, Inc.) as a microarray. For the primary screen, compounds were spotted at a high concentration (~1 mM) in duplicates. The array was allowed to dry, and was then aligned and bonded to a microfluidic device. Two large devices (2400 unit cells per device) were used for the primary screen. The rest of the procedure was done similarly to the procedure described above (RNA binding assay). In brief, the device was subjected to surface patterning that resulted in a circular area coated with biotinylated anti-GFP antibodies within each unit cell. Next, NS4B-GFP expressed prepared "off chip" using coupled transcription/translation rabbit reticulocyte system (Promega) in the presence of microsomal membranes (Promega) was loaded into the chip and bound to the surface biotinylated anti-GFP antibodies. Cy5-labeled 3' neg terminus RNA probe was then loaded at a concentration of 1.5 nM. Each unit cell was then isolated followed by a 30 min incubation to allow binding of the protein to surface biotinylated anti-GFP antibodies, salvation of library compounds, and equilibration of proteins and target RNA. Next, MITOMI was performed trapping surface-bound complexes while expelling any solution phase molecules. After a brief wash to remove untrapped unbound material, the device was scanned and results analyzed. The ratio of bound RNA to expressed protein was calculated for each data point by measuring the median signal of Cy3 to median signal of bodipy. Results were normalized to signal measured in unit cells containing no inhibitory compound. Greater than 90% inhibition was defined as the cutoff for inhibition in the primary screen. 104 compounds which were above this cutoff and additional 110 yielding ambiguous results were subjected to a secondary screen. This was performed similarly, except that two smaller devices (640 unit cells per each) were used, the spotted compound concentration was 10 fold lower than in the primary screen, and 5 replicates were spotted for each compound. Inhibition greater than 2.5 fold was considered significant. 18 compounds identified in this screen were further analyzed for their antiviral effect on HCV RNA replication.

Determination of IC50 for In Vitro RNA Binding.

For an accurate measurement of IC50s, serial dilutions of the inhibitory compound were loaded onto the microfluidic device by continuous flow while maintaining a steady concentration of the compound in the flow channel. This helped to avoid losses of the spotted compounds from incomplete solubilization and/or binding of the compound to PDMS. The experiment was performed essentially as described for the RNA binding assay for transmembrane proteins except that the expressed protein and the Cy5-labeled HCV RNA probes were incubated in the device in the presence of the inhibitory compounds or their absence. IC50s were measured as described in the Statistical Analysis section below.

Expression and Purification of Recombinant NS4B.

GST-NS4B and GST were expressed in *E. coli* BL21 and purified as described elsewhere. NS4B was fused in frame with an N-terminal 6his-MISTIC protein (membrane-integrating sequence for translation of IM protein constructs). Overnight cultures of *E. coli* transformed with mistic-NS4B plasmid were diluted 1:100 in 400 ml of fresh medium and grown at 37° C. to an OD of 0.8. Isopropyl-β-D-thiogalactopyranoside (IPTG) (Invitrogen) was then added to a final concentration of 0.1 mM. After 3 hours growth at 37° C., cells were pelleted and resuspended in 30 ml lysis buffer (50 mM NaCl, 50 mM Tris HCL (pH8), 100 mM Imidazole, 10 mM Decylmaltoside, Complete EDTA free protease inhibitors (Roche Applied Science)). Cells were lysed by one cycle in a French Press at a pressure of 10,000 psi for 1 minute, followed by centrifugation at 12,000 g for 5 minutes at 4° C. The supernatant was loaded on nickel column (Amersham). Following washes, protein was eluted in a buffer containing 400 mM Imidazole. Glycerol was added at a final concentration of 20% and samples were stored at −20° C. Purification was monitored by SDS-PAGE. Total protein concentration was measured using the RC-DC assay (Bio-Rad). NS4B-mistic was identified by Western blot analyses using monoclonal antibodies against 6-his (Santa Cruz Biotechnology) and NS4B (Virostat). 6his-mistic was expressed and purified in a similar manner.

GST Pull Down Assay.

Similar to a previously described strategy, 1 μg of purified GST-NS4B or GST was incubated for an hour at 37° C. in a 50

µl reaction mixture containing $^{32}$P-labeled in vitro transcribed HCV RNA (corresponding to the 3' terminus of the negative viral strand) and binding buffer (10 mM DTT, 10 mM Na HEPES (pH 7.4), 33 mM NaCl, 0.1 mM EDTA, 10 mM MgCl2). 50 µl of tRNA pre-coated glutathione-agarose beads (Sigma) were then added, followed by 1 hour incubation at 4° C. to allow binding of GST to the beads. The beads were then washed three times in binding buffer and bound RNA was measured by liquid scintillation counting of sample aliquots. Control incubations with an RNA probe prepared in the absence of T7 RNA polymerase were used for background subtraction.

RNA Filter Binding Assay.

Assays were performed essentially as described. Briefly, various concentrations of mistic-NS4B protein or mistic control were incubated for 1 hour at 30° C. with 3.3 nM $^{32}$P-labeled in vitro transcribed HCV RNA probe in binding buffer (50 mM HEPES pH 7.0, 50 mM NaCl, 1 mM MgCl2, 10 ng/µl tRNA, and 0.2 mM Decylmaltoside) in a final volume of 40 µl. Membranes were pre-soaked in the binding buffer and assembled in a dot blot apparatus (Schleicher & Schull) from top to bottom as follows: nitrocellulose (Biorad), Hybond N+ (Amersham Biosciences), Whatman 3 mm filter paper. The binding reactions were loaded onto the dot-plot apparatus and filtered through the membranes. After washing, the membranes were air-dried and visualized by Phospho-imaging. Results represent percentage of bound RNA calculated by dividing the signal detected in the nitrocellulose membrane by the sum of the signals detected in the nitrocellulose and the Hybond membranes.

Cell Cultures and Electroporation.

Huh-7.5 cells were maintained in Dulbecco's modified minimal essential medium (Gibco) supplemented with 1% L-glutamine (Gibco), 1% penicillin, 1% streptomycin (Gibco), 1× nonessential amino acids (Gibco) and 10% fetal bovine serum (Omega Scientific). Cell lines were passaged twice weekly after treatment with 0.05% trypsin-0.02% EDTA and seeding at a dilution of 1:5. Subconfluent Huh-7.5 cells were trypsinized and collected by centrifugation at 700 g for 5 min. The cells were then washed three times in ice-cold RNase-free PBS (BioWhittaker) and resuspended at 1.5*10$^7$ cells/ml in PBS. Wild type or mutant FL-J6/JFH-5'C19Rluc2AUbi RNA for electroporation was generated by in vitro transcription of XbaI-linearized DNA templates using the T7 MEGAscript kit (Ambion), followed by purification, essentially as described above (In vitro RNA transcription and fluorescent labeling). 5 µg of RNA was mixed with 400 µl of washed Huh-7.5 cells in a 2 mm-gap cuvette (BTX) and immediately pulsed (0.82 kV, five 99 µs pulses) with a BTX-830 electroporator. After a 10 min recovery at 25° C., pulsed cells were diluted into 10 ml of prewarmed growth medium. Cells from several electroporations were pooled to a common a stock and seeded in 6 well plates (5*10$^5$ cells per well). After 24 hr, medium was replaced and cells were grown in the presence of serial dilutions of the various inhibitory compounds (Sigma) identified in the screen. 17 commercially available compounds, out of the 18 identified, were analyzed. Untreated cells were used as a negative control for water soluble compounds. For compounds solubilized in DMSO, untreated cells were grown in the presence of corresponding concentrations of the solvent as a negative control. Medium was changed daily. After 72 hr of treatment, cells were subjected to an alamar blue based viability assay and luciferase assay.

Viability Assay.

Following 72 hrs of treatment, cells were incubated for 3 hrs at 37° C. in the presence of 10% Alamar Blue reagent (TREK Diagnostic Systems). Plates were then scanned and fluorescence was detected by using FLEXstation II 384 (Molecular Devices, Inc.). Depending on the inhibitory compound's solvent, water (other compounds not in DMSO) or DMSO (D042, (allylnorapomorphine), R-108, Tropicamide, Thalidomide, Glyburide, LFM-A13), signal was normalized relatively to untreated samples or samples grown in the presence of DMSO, respectively.

Luciferase Assay.

Viral RNA replication was determined using Renilla luciferase assay (Promega). The same samples subjected to the viability assay described above were analyzed in this assay. According to the manufacturer's protocol, cells were washed with ice cold PBS and scraped off the plate into 250 oil of ice-cold Renilla lysis buffer. 20 µl of the cell lysates were then loaded onto 96 well plates. 100 µl of the Renilla luciferase assay buffer containing the assay substrate were injected and luciferase activity was measured using a Berthold LB 96 V luminometer. As above, signal was normalized relative to untreated samples or samples grown in the presence of the corresponding concentration of DMSO.

Luciferase activity detected in samples treated with 100 u/ml Interferon alpha B2 (PBL biomedical labs) was used as a positive control, demonstrating three log reduction at 72 hr treatment. The experiment was repeated four times, each time with triplicates. IC50s were measured by fitting data to a three parameter logistic curve using the formula $Y=a+(b-a)/(1+10^{(X-c)})$ (BioDataFit, Chang Bioscience, Inc).

Real-Time PCR.

$5\times10^4$ Huh7.5 ells were infected with cell culture-grown HCV titered at $1.4\times10^4$ TCID50/ml, as described. 2 hours after infection, cells were washed three times in culture medium. Cells were then treated daily with various concentrations of clemizole. After 72 hours, samples were subjected to the viability assay described above, following which TRIzol Reagent (Invitrogen) was added and total cell RNA was extracted in triplicates according to the manufacturer's instructions. Reverse transcription was then performed using random hexamers and Superscript II reverse transcriptase (Invitrogen, Carlsbad, Calif.). Real-time PCR was performed on the resulting cDNA to quantify the amounts of HCV and actin RNA (in separate reactions) in each sample. Standards were made using an in vitro-transcribed HCV RNA and human actin standard (Applied Biosystems, Foster City, Calif.). HCV was quantified using primers AGAGCCAT-AGTGGTCT (SEQ ID NO 8) and CCAAATCTCCAG-GCATTGAGC (SEQ ID NO 9) and probe 6-carboxyfluorescein-CACCGGAATTGCCAGGACGACCGG-6 (SEQ ID NO 10) carboxytetramethylrhodamine. Actin was quantified using beta-actin control reagents (Applied Biosystems) according to the manufacturer's instructions. HCV RNA level was adjusted to actin level and normalized relative to untreated samples.

Selection of Resistant Mutants.

Established HCV replicons-harboring cells and Huh7 cells electroporated de novo with a genotype 1b subgenomic HCV replicon (Bart 79I) were passaged in the presence of neomycin and increasing concentrations of clemizole (1-16 µM). Colonies that were able to grow in the presence of the compound were isolated and propagated for 5-10 passages. Eleven colonies (out of ~60) survived the passages and were subjected to sequence analysis, as previously described.

Whole Cell RNA Electroporation.

Whole cell RNA was extracted from clemizole-resistant replicon clones and from untreated replicon cells using TRIzol reagent (Invitrogen). Equal amounts of whole cell RNA (50 µg) were electroporated into Huh7.5 cells as described above. Cells were grown under G418 selection in the presence or absence of clemizole for 3 weeks. The number of colonies was determined using Image J (NIH) following fixation and staining with Crystal violet.

Statistical Analysis.

Dissociation equilibrium constants were determined by fitting data to the equation describing equilibrium binding; Y=a*X/(b+X) (a and b represent maximum binding and Kd, respectively) by nonlinear least squares regression fitting (BioDataFit, Chang Bioscience). IC50s were measured by fitting data to a three parameter logistic curve using the formula Y=a+(b−a)/(1+10^(X−c)) (a, b and c represent minimum binding, maximum binding and logEC50, respectively) (BioDataFit, Chang Bioscience, Inc).

Specificity of hits identified in the small molecule screen: To determine the specificity of the hits identified in the small molecule screen, the HuR protein (one of the human RNA binding protein used to validate our RNA binding assay) was selected. Interestingly, other than binding to its target RNA sequence, 4A (FIG. 7), this protein has been previously shown by others (*Virology* 274, 378-390 (2000), which is incorporated herein by reference) to bind the 3' terminus of the negative HCV strand. Binding of HuR to the consensus 4A RNA sequence was tested in the presence of the inhibitory molecules shown to inhibit RNA binding by NS4B. No inhibitory effect on RNA binding was detected with the majority of the hits, including clemizole, at a concentration of 0.1 mM. Similarly, 0.1 mM of the identified compounds didn't have an inhibitory effect on binding of HuR to the 3' terminus of the negative HCV RNA strand. In contrast to the other hits, ATA, known as a non-specific inhibitor of protein-nucleic acids interactions, significantly inhibited HuR binding to both 4A and 3' terminus of the negative HCV strand. These results support the conclusion that the identified hits including clemizole are indeed specific to RNA binding by NS4B.

Example 2

To demonstrate the in vivo efficacy of clemizole in treating patients infected with HCV, 3 patients chronically-infected with HCV (genotype 4) were treated with clemizole 100 milligrams, p.o. BID for 8 weeks. After the first four weeks of clemizole monotherapy, pegylated interferon (180 micrograms Pegasus (Roche) s.q. per week) was added. Thereafter the patients are continued on the pegylated interferon and nitazoxanide (500 mg. (Romark) p.o. BID. The baseline characteristics and serial HCV viral loads in the serum are presented in FIG. 2. HCV viral loads decreased significantly on treatment with clemizole alone, becoming completely, or nearly, undetectable after 4 weeks of treatment. These results demonstrate that clemizole is effective in treating patients infected with HCV.

Example 3

Chemical Synthesis

Figure 4A:
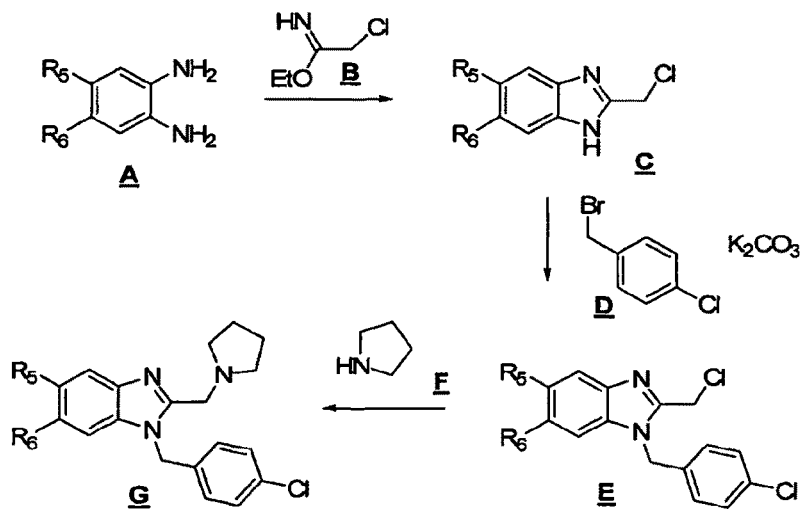
FIG. 4A illustrates an embodiment of a general method of synthesizing 5,6-disubstituted clemizole compounds.
Figure 4B:
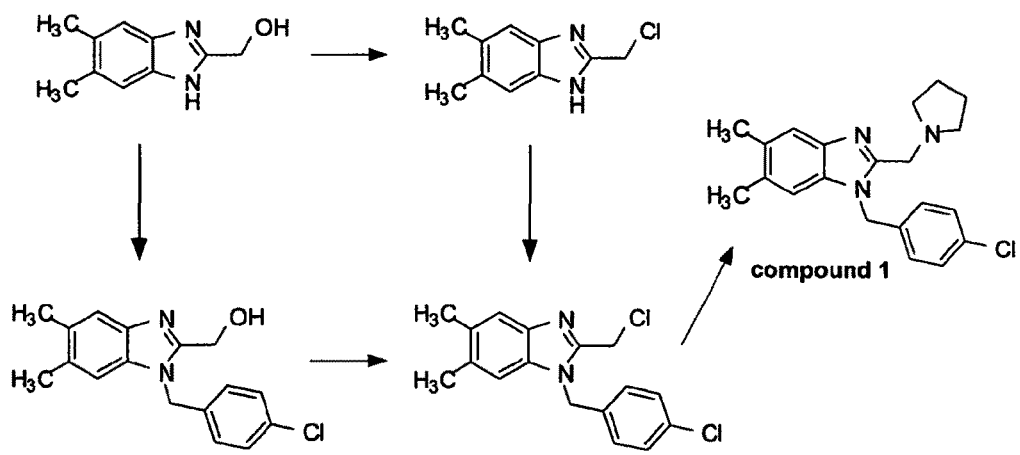

FIG. 4A illustrates a method that can be used to produce 5-6-disubstituted chemizole compounds. In particular, the methods can produce Compound 1 (disubstituted with methyl groups at the 5 and 6 positions (FIG. 4B)) and Compound 2 (disubstituted with Cl groups at the 5 and 6 positions (FIG. 4C)).

The disubstituted clemizole can be synthesized by: condensation of 4,5-disubstituted-benzene-1,2-diamine (A) and 2-chloro-acetimidic acid ethyl ester (B) yields 2-chloromethyl-5,6-disubstituted-1H-benzoimidazole (C); followed by alkylation with 1-bromomethyl-4-chloro-benzene (D) affords 1-(4-chloro-benzyl)-2-chloromethyl-5,6-disubstituted-1H-benzoimidazole (E); and the final alkylation of 1-(4-chloro-benzyl)-2-chloromethyl-5,6-disubstituted-1H-benzoimidazole (E) with pyrrolidine yields the 5,6-disubstituted Clemizole (1-(4-Chloro-benzyl)-5,6-disubstituted-2-pyrrolidin-1-ylmethyl-1H-benzoimidazole) (G).

Synthetic Method 1

{1-[1-(4-Chloro-benzyl)-1H-benzoimidazol-2-ylmethyl]-pyrrolidin-2-yl}-(S)-methanol

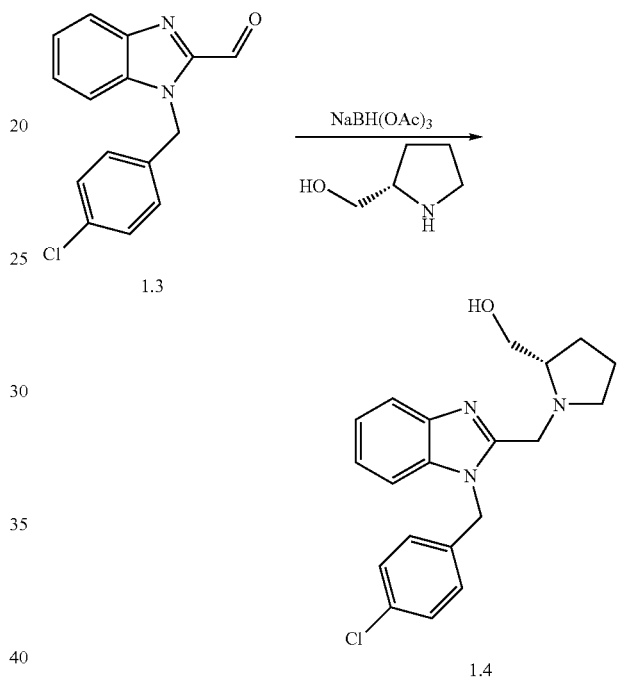

To a solution of 1-(4-chlorobenzyl)-1H-benzimidazole-2-carbaldehyde 1.3 (0.050 g, 0.18 mmol) and (S)-(+)-2-pyrrolidine-methanol (0.22 g, 0.20 mmol) in CH$_2$Cl$_2$ (10 mL) was added 1 drop AcOH and NaBH(OAc)$_3$ (0.50 g, 0.24 mmol). After stirring for 30 min, the reaction solution was diluted with CH$_2$Cl$_2$ (5 mL) and washed with aqueous saturated NaHCO$_3$ (2×5 mL). The organic layer was dried with Na$_2$SO$_4$ and concentrated in vacuo. The crude residue was purified by reverse phase preparative HPLC to provide the title compound.

Synthetic Method 2

{1-[1-(4-Chloro-benzyl)-5,6-dimethyl-1H-benzoimidazol-2-ylmethyl]-pyrrolidin-2-yl}-methanol

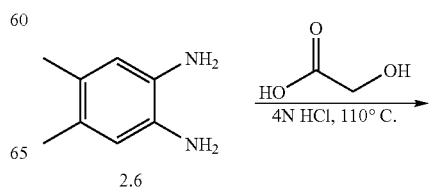

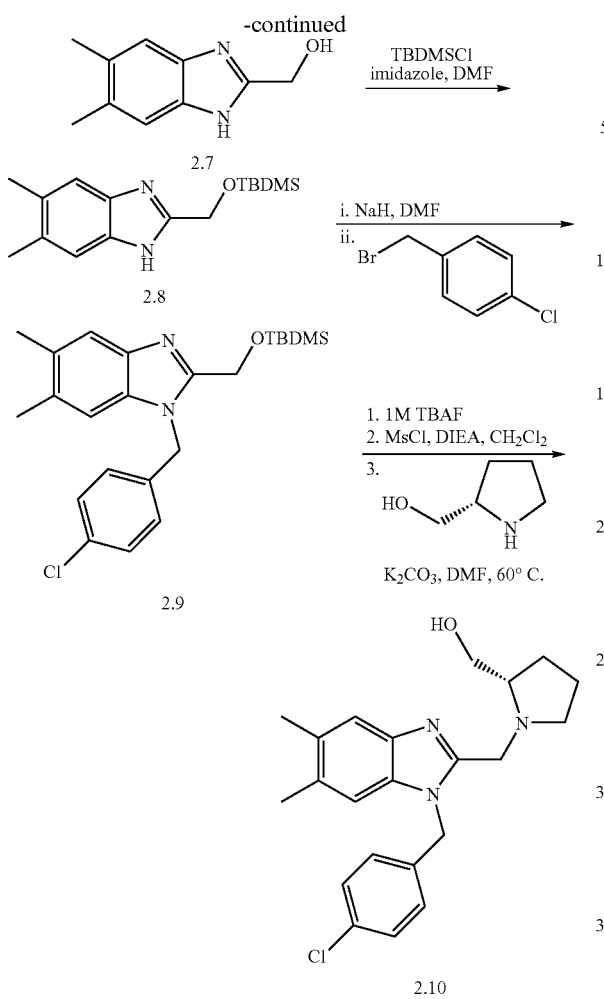

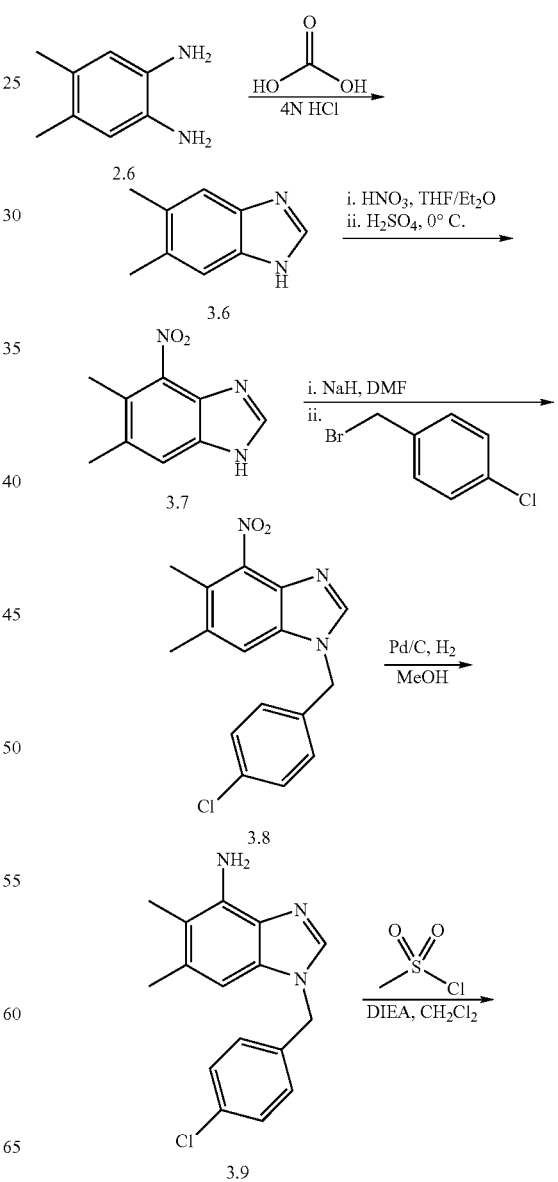

diluted with EtOAc (20 mL) and washed with water (2×10 mL). The organic layer was dried with Na₂SO₄ and concentrated in vacuo to provide the crude alcohol. To a solution of the crude alcohol (0.54 g, 1.8 mmol) in CH₂Cl₂ (10 mL) was added methanesulfonyl chloride (0.152 mL, 2.0 mmol) and DIEA (0.345 mL, 2.0 mmol). After stirring for 15 min, the solvent was removed in vacuo to provide crude mesylate. To a solution of the crude mesylate (0.10 g, 0.30 mmol) in DMF (5 mL) was added (S)-(+)-2-pyrrolidine-methanol (0.061 g, 0.60 mmol) and K₂CO₃ (0.124 g, 0.90 mmol). After heating at 60° C. for 2 h, the reaction mixture was cooled to rt, diluted with MeOH (1 mL), filtered, and purified by reverse phase preparative HPLC to provide the title compound 2.10.

Synthetic Method 3

N-[1-(4-Chloro-benzyl)-5,6-dimethyl-1H-benzoimidazol-4-yl]-methanesulfonamide

To a solution of 4,5-dimethyl-1,2-phenylenediamine 2.6 (1.5 g, 11 mmol) in 4 N HCl (60 mL) was added glycolic acid (2.5 g, 33 mmol). After heating at 110° C. for 3 h, the solution was cooled to room temperature and basified with solid NaOH until basic by pH paper. The resulting precipitate was filtered and washed with water to provide 2.7 which was used without further purification.

To a solution of 2.7 (6.7 g, 38 mmol) in DMF (125 mL) was added TBDMSCl (6.3 g, 42 mmol) and imidazole (2.9 g, 42 mmol). After stirring for 6 h, the reaction solution was diluted with EtOAc (100 mL) and washed with water (2×50 mL). The aqueous layers were back-extracted with EtOAc (3×50 mL). The combined organic layers were dried with Na₂SO₄ and concentrated in vacuo to provide crude silylated alcohol which was purified via silica gel chromatography (20% EtOAc in hexanes) to provide 2.8.

To a solution of 2.8 (1.59 g, 5.5 mmol) in DMF (20 mL) was added 60% NaH (0.204 g, 6.1 mmol). After stirring for 30 min, 4-chloro-benzylbromide (1.25 g, 6.1 mmol) was added and the solution was heated to 60° C. for 2 h. The reaction solution was diluted with EtOAc (100 mL) and washed with water (2×50 mL). The combined organic layers were dried with Na₂SO₄ and concentrated in vacuo to provide crude alkylated intermediate which was purified via silica gel chromatography (20% EtOAc in hexanes) to provide 2.9.

To a solution of 2.9 (0.750 g, 1.8 mmol) in THF (5 mL) was added 1 M THF (2 mL, 2 mmol). After stirring for 1 h, the solvent was removed in vacuo, and the crude residue was

Synthetic Method 4

1-(4-Chloro-benzyl)-5,6-dimethyl-2-(2-pyridin-4-yl-vinyl)-1H-benzoimidazole

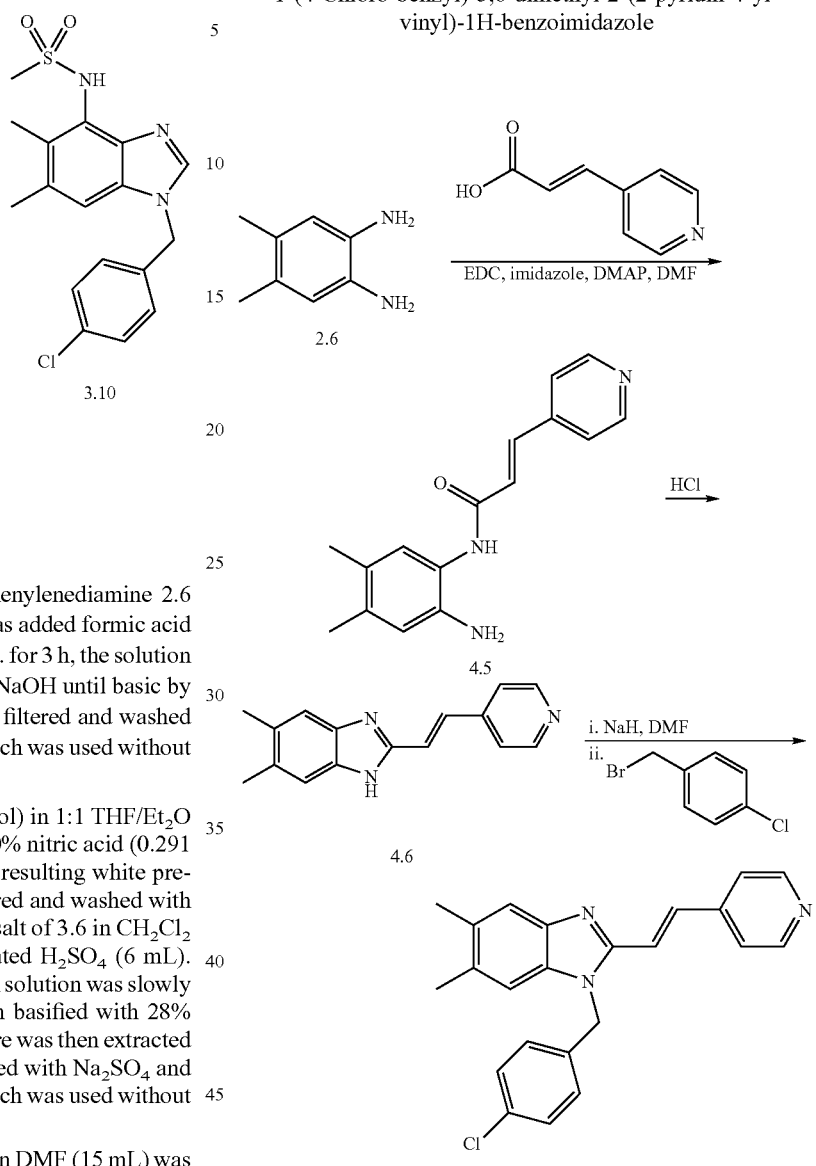

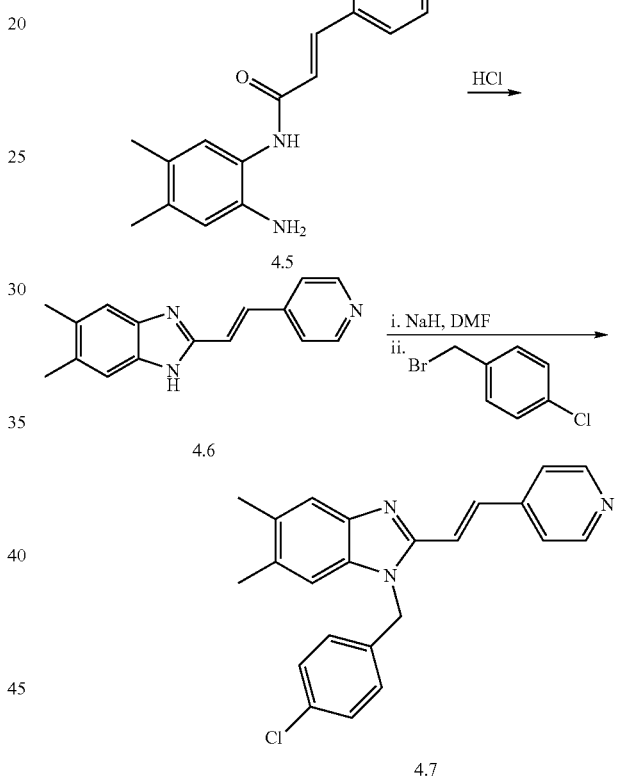

To a solution of 4,5-dimethyl-1,2-phenylenediamine 2.6 (3.0 g, 22 mmol) in 4 N HCl (30 mL) was added formic acid (3.0 g, 66 mmol). After heating at 110° C. for 3 h, the solution was cooled to rt and basified with solid NaOH until basic by pH paper. The resulting precipitate was filtered and washed with water (3×50 mL) to provide 3.6 which was used without further purification.

To a solution of 3.6 (0.474 g, 7.1 mmol) in 1:1 THF/Et$_2$O (20 mL) at 0° C. was dropwise added 70% nitric acid (0.291 g, 7.1 mmol). After stirring for 1 h, the resulting white precipitate (nitric acid salt of 3.6) was filtered and washed with Et$_2$O. To a suspension of the nitric acid salt of 3.6 in CH$_2$Cl$_2$ at 0° C. was dropwise added concentrated H$_2$SO$_4$ (6 mL). After stirring for 1 h at 0° C., the reaction solution was slowly added to 10 mL of cold water and then basified with 28% NH$_4$OH solution until pH 10. The mixture was then extracted with CH$_2$Cl$_2$. The organic layer was dried with Na$_2$SO$_4$ and concentrated in vacuo to provide 3.7 which was used without further purification.

To a solution of 3.7 (0.8 g, 4.2 mmol) in DMF (15 mL) was added 60% NaH (0.218 g, 5.5 mmol). After stirring for 30 min, 4-chlorobenzylbromide (0.946 g, 4.6 mmol) was added and the solution was heated to 60° C. for 2 h. The solution was then cooled to rt, diluted with EtOAc (20 mL) and washed with water (3×10 mL). The organic layer was dried with Na$_2$SO$_4$ and concentrated in vacuo to provide 3.8.

To a solution of 3.8 (4.2 mmol) in MeOH (20 mL) was added 50% w/w palladium on carbon (0.200 g) in water. A balloon of hydrogen was then placed on the reaction flask and the reaction was stirred for 2 h. The reaction mixture was then filtered and washed with MeOH over a pad of Celite. The filtrate was concentrated in vacuo to provide 3.9.

To a solution of 3.9 (0.100 g, 0.3 mmol) in CH$_2$Cl$_2$ (10 mL) was added MsCl (0.086 mL, 0.4 mmol) and DIEA (0.069 mL, 0.4 mmol). After stirring for 15 min, the reaction solution was concentrated in vacuo to provide crude 3.10 which was purified by reverse-phase preparative HPLC to provide the title compound.

To a solution of 2.6 (0.5 g, 3.7 mmol) in DMF (20 mL) was added substituted cinnamic acid (0.548 g, 3.7 mmol, EDC (1.0 g, 5.6 mmol), imidazole (0.12 g, 0.185 mmol), and DMAP (0.022 g, 0.185 mmol). After stirring for 48 h, the reaction solution was diluted with EtOAc and washed with saturated NaHCO$_3$. The organic layer was dried and the solvent was removed under reduced pressure to provide the crude product which was purified by silica gel chromatography to give 4.5.

Intermediate 4.5 can then be treated with 4 N HCl to provide cyclized product 4.6. Deprotonation with NaH, followed by treatment with alkylators will provide examples of structure 4.7.

Synthetic Method 5

1-(4-Chloro-benzyl)-6-methoxy-2-pyrrolidin-1-ylm-ethyl-1H-benzoimidazole

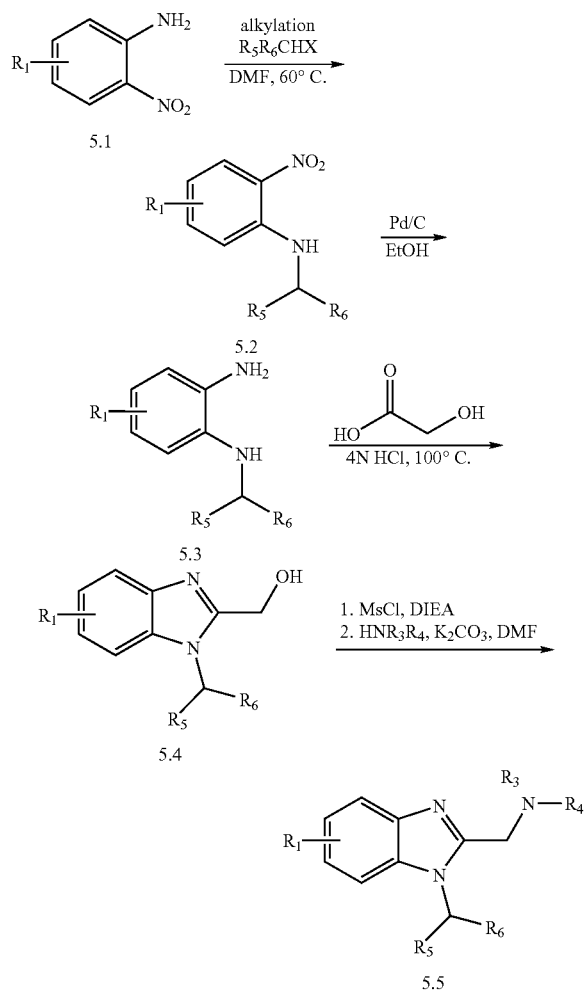

To a solution of nitroaniline 5.1 (1 eq) in DMF was added alkylator (1.1 eq), K₂CO₃ (3 eq). After stirring at 60° C. for 2 h, the reaction was diluted with EtOAc and washed with H₂O. The organic layer was dried and the solvent removed under reduced pressure to provide 5.2 which was purified by silica gel chromatography (30% EtOAc in hexanes).

To a solution of 5.2 (1 eq) in EtOH was added Pd/C (0.2 eq). The reaction was purged of O₂ and the reaction was stirred under a balloon of H₂ for 6 h. The reaction was filtered over a pad of Celite, and the filtrate was concentrated in vacuo to provide 5.3.

To a solution of 5.3 (1 eq) in 4 N HCl was added glycolic acid (3 eq). After stirring at 100° C. for 2 h, the reaction was basified with solid NaOH until pH 10. The resulting precipitate was filtered and washed with water to provide 5.4.

To a solution of 5.4 (1 eq) was added MsCl (1.5 eq) and DIEA (2 eq) in CH₂Cl₂. After 15 min, the solvent was removed in vacuo to provide the mesylate. To a solution of mesylate (1 eq) in DMF was added K₂CO₃ (3 eq) and heated to 60° C. for 3 h. The crude reaction was diluted with 1 mL MeOH and then directly purified by reverse-phase HPLC to provide 5.5.

Synthetic Method 6

1-(4-Chloro-benzyl)-1H-benzoimidazole-5,6-diol

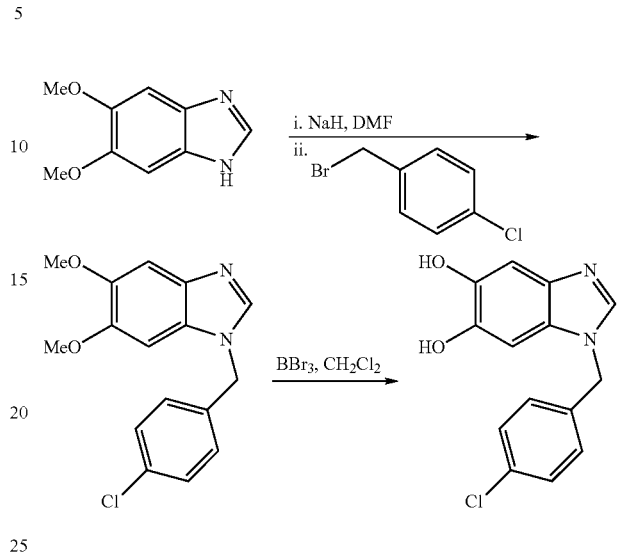

To a solution of 5,6-dimethoxybenzimidazole (0.100 g, 0.8 mmol) was added 60% NaH (0.021 g, 0.88 mmol). After stirring for 30 min, the 4-chlorobenzylbromide (0.171 g, 0.8 mmol) was added and the solution was heated to 60° C. for 2 h. The reaction solution was diluted with EtOAc (10 mL) and washed with aqueous saturated NaHCO₃ (2×10 mL). The organic layer was dried with Na₂SO₄ and concentrated in vacuo. To a solution of the crude alkylated intermediate (0.8 mmol) in CH₂Cl₂ (10 mL) was added 1 M BBr₃ in CH₂Cl₂ (1 mL, 1 mmol). After stirring for 16 h, the solvent was removed in vacuo and the crude product was purified by reverse-phase preparative HPLC to provide 1-(4-chloro-benzyl)-1H-benzoimidazole-5,6-diol.

Synthetic Method 7

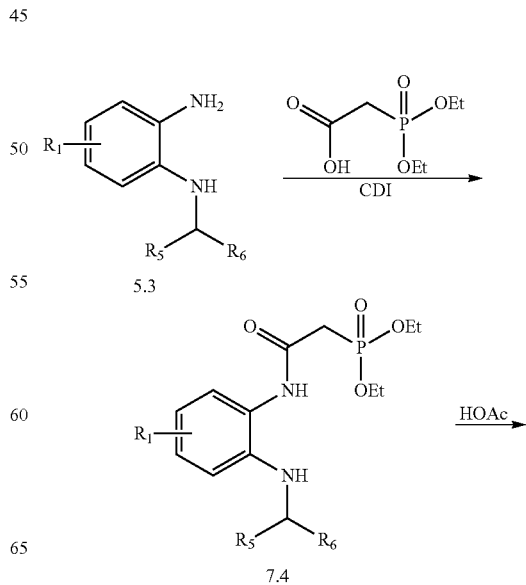

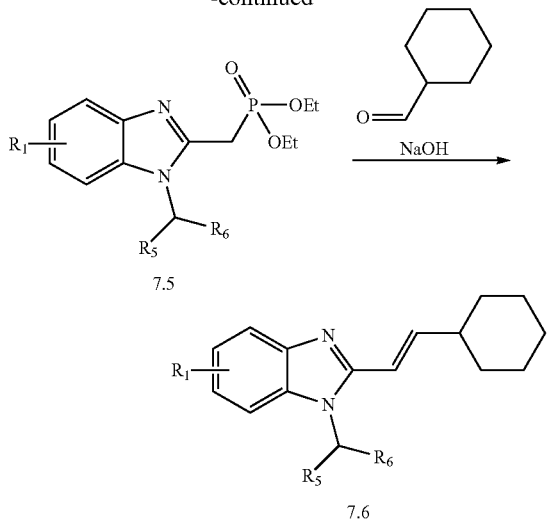

To a solution of 5.3 is added 2-(diethoxyphosphoryl)acetic acid and CDI to provide 7.4. Heating 7.4 in acetic acid gives 7.5. Treatment of 7.5 with an aldehyde and NaOH gives compounds of general structure 7.6.

Example 4

Invitro Assay Results

Table 4 shown below illustrates the effects of clemizole analogs on HCV RNA replication (AV) and cell viability (Viab) using the Luciferase and Alamar Blue assays described herein. Compound activities were measured at two concentrations to determine whether the effects were dose-dependent. Numerical values represent the percent of normal activity (either viral replication or cell viability) remaining after compound treatment; these values have also been binned to provide a rough measure of relative activity.

The amount of residual luciferase activity (indicating HCV replication) in the treated cells relative to the no drug control for each compound was determined at two concentrations of compound, 5 micromolar and 10 micromolar, and recorded in Table 4. In addition, these percentages were converted to a scoring system as follows: "+"=>80% residual activity; "++"=<80% residual activity; "+++"=<55% residual activity; "++++"=<20% residual activity. Thus a compound scored as +++ in the replication assay has greater antiviral activity (AV) than a compound scored as +.

The results demonstrate that H1 antagonism can be separated from antiviral activity, and that compounds lacking the tertiary amine group required for H1 activity can show enhanced antiviral effects relative to clemizole; numerous compounds show a strong separation between antiviral activity and impact on cell viability, supporting the conclusion that the former activity results from specific inhibition of NS4B/RNA binding; and many compounds demonstrate dose-dependent activity, as inhibition of HCV RNA replication is more pronounced at the higher (10 uM) concentration. Taken together, these structure-activity relationships demonstrate that the known and novel analogs of clemizole described herein can prevent HCV replication, and that analogs that lack H1 antagonism (and attendant CNS effects) maintain an acceptable therapeutic ratio.

Table 4

TABLE 4

| | In-vitro activity of the compounds of the invention in the RNA replication inhibition assay described herein. | | | |
|---|---|---|---|---|
| Residual Luciferase activity[1] | 20% or less ++++ (Compound No.) | 55% or less +++ (Compound No.) | 80% or less ++ (Compound No.) | >80% + (Compound No.) |
| 5 micromolar | 13, 50, 51, 60, 62, 99, 117, 135, 140 | 8, 49, 53, 59, 78, 80, 87, 88, 89, 92, 97, 98, 104, 106, 108, 111, 116, 118, 122, 124, 127, 128, 130, 134, 136, 141, 142, 144, 148, 155 | 5, 10, 12, 14, 18, 25, 27, 31, 32, 36, 37, 38, 39, 40, 41, 43, 44, 47, 52, 54, 55, 56, 57, 58, 63, 64, 65, 66, 67, 73, 79, 83, 84, 90, 93, 94, 96, 102, 106, 107, 108, 115, 119, 120, 125, 126, 131, 136, 137, 138, 139, 142, 145, 146, 147, 148, 150, 151, 152, 154, 156, 157, 158, 159, 160 | 1, 2, 3, 4, 6, 7, 9, 11, 15, 16, 17, 19, 20, 21, 22, 23, 24, 26, 28, 29, 33, 34, 35, 42, 45, 46, 48, 61, 68, 69, 70, 71, 72, 74, 75, 76, 77, 81, 82, 85, 86, 91, 95, 100, 101, 103, 105, 109, 110, 112, 113, 114, 121, 123, 125, 129, 132, 133, 143, 149, 153, 161 |
| 10 micromolar | 13, 50, 51, 53, 60, 62, 78, 88, 92, 97, 98, 99, 106, 108, 111, 116, 117, 121, 125, 130, 134, 135, 141, 145, 148, 155, 160 | 5, 8, 25, 27, 28, 29, 31, 43, 49, 54, 56, 57, 59, 65, 66, 73, 87, 89, 90, 93, 94, 96, 103, 104, 106, 107, 108, 118, 119, 120, 122, 124, 126, 127, 128, 131, 133, 136, 139, 140, 142, 144, 148, 150, 151, 152, 154, 156, 157, 159 | 1, 2, 6, 10, 11, 12, 14, 18, 22, 32, 39, 40, 41, 42, 46, 47, 48, 52, 55, 58, 61, 64, 67, 69, 75, 76, 77, 80, 81, 83, 85, 86, 95, 100, 101, 102, 112, 123, 125, 137, 143, 146, 147, 153, 158 | 3, 4, 7, 9, 15, 16, 17, 19, 20, 21, 23, 24, 26, 33, 34, 35, 36, 37, 38, 44, 45, 63, 68, 70, 71, 72, 74, 79, 82, 84, 91, 105, 109, 110, 113, 114, 115, 129, 132, 138, 149, 161 |

[1]Luciferase reporter activity is stated as a percentage of the luciferase reporter activity in a treated cell population compared to the luciferase activity in an untreated control population of same cell type.

TABLE 5

In-vitro activity of the compounds of the invention in the cell viability assay described herein.

| Cell Viability[2] | 90% or greater ++++ (Compound No.) | 75% or greater +++ Compound No.) | 50% or greater ++ (Compound No.) | <50% + (Compound No.) |
|---|---|---|---|---|
| 5 micromolar | 1, 2, 3, 4, 5, 6, 7, 9, 10, 11, 12, 14, 15, 16, 17, 19, 20, 21, 22, 23, 24, 25, 26, 27, 28, 29, 31, 32, 33, 34, 35, 36, 37, 38, 39, 40, 41, 42, 43, 44, 45, 47, 48, 49, 54, 55, 56, 57, 58, 61, 63, 64, 65, 67, 68, 70, 71, 72, 73, 74, 75, 76, 77, 78, 79, 81, 82, 83, 84, 85, 86, 90, 91, 94, 95, 96, 97, 98, 100, 101, 102, 103, 105, 106, 107, 108, 109, 110, 112, 113, 114, 115, 120, 121, 123, 129, 131, 132, 133, 136, 139, 144, 145, 146, 147, 148, 149, 150, 151, 152, 153, 154, 156, 157, 158, 159, 160, 161 | 18, 53, 59, 60, 66, 80, 87, 89, 92, 93, 104, 108, 111, 116, 118, 119, 122, 126, 128, 130, 134, 136, 138, 139, 141, 142, 143, 144, 155 | 8, 62, 88, 99, 117, 124, 127, 135, 137, 140 | 13 |
| 10 micromolar | 1, 2, 3, 4, 5, 6, 7, 9, 10, 11, 12, 14, 15, 16, 17, 18, 19, 20, 21, 22, 23, 24, 25, 26, 27, 28, 29, 31, 32, 33, 34, 35, 36, 37, 38, 39, 40, 41, 43, 44, 45, 55, 57, 58, 63, 64, 67, 68, 70, 71, 72, 73, 74, 75, 76, 77, 79, 81, 82, 83, 84, 85, 91, 95, 96, 102, 105, 106, 107, 109, 110, 113, 114, 115, 129, 132, 136, 139, 145, 146, 147, 149, 150, 151, 152, 153, 154, 156, 157, 158, 161 | 42, 47, 48, 49, 54, 56, 60, 61, 65, 66, 78, 86, 87, 90, 94, 98, 100, 101, 103, 108, 112, 118, 119, 122, 123, 131, 133, 134, 137, 138, 139, 141, 142, 143, 144, 148, 159 | 8, 53, 59, 80, 88, 89, 92, 93, 97, 99, 104, 108, 111, 117, 120, 121, 124, 126, 127, 128, 130, 135, 136, 140, 141, 142, 155, 160 | 13, 62, 116, 135 |

[2]Cell viability is stated as a percentage of viable cells in a treated population of cells in comparison to an untreated population of same cell type.

TABLE 6

Structures of the compounds listed in Tables 4 and 5.

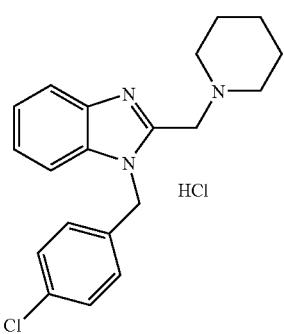

Compound 1

TABLE 6-continued

Structures of the compounds listed in Tables 4 and 5.

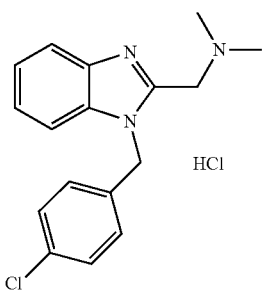

Compound 2

TABLE 6-continued
Structures of the compounds listed in Tables 4 and 5.
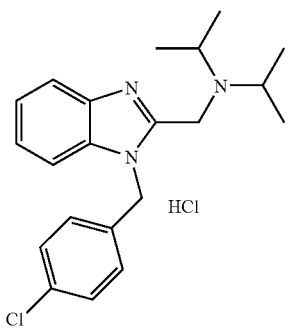
Compound 3
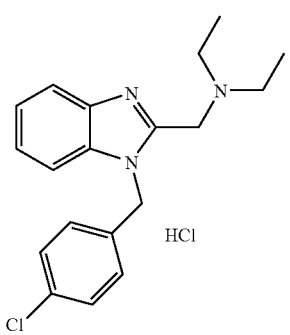
Compound 4
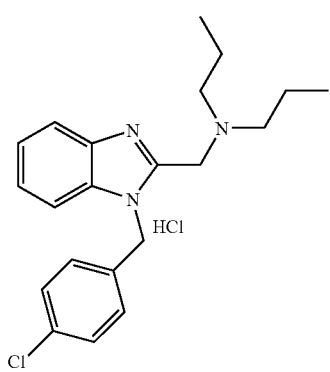
Compound 5
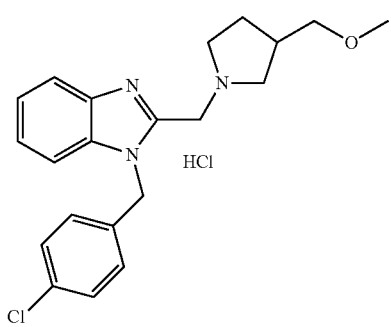
Compound 6
TABLE 6-continued
Structures of the compounds listed in Tables 4 and 5.
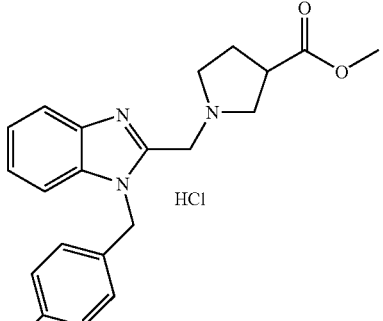
Compound 7
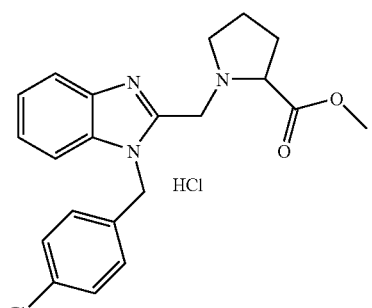
Compound 8
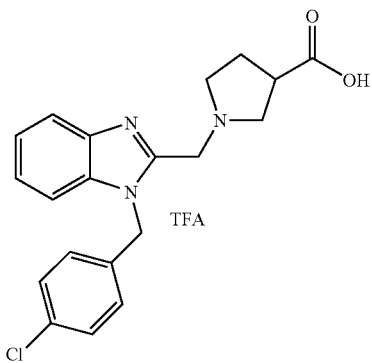
Compound 9
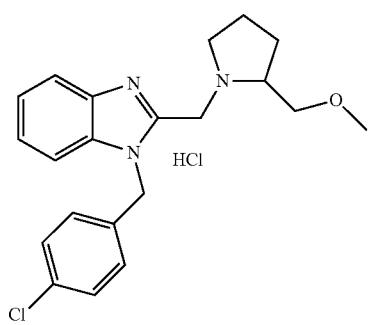
Compound 10

TABLE 6-continued
Structures of the compounds listed in Tables 4 and 5.
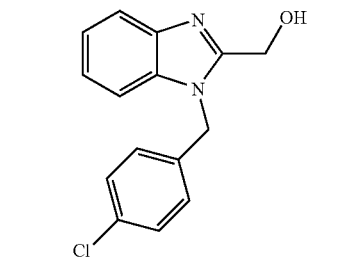
Compound 11
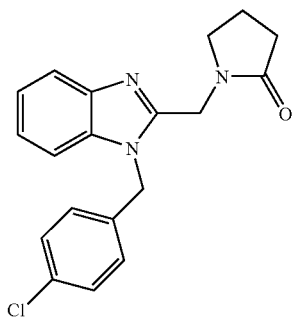
Compound 12
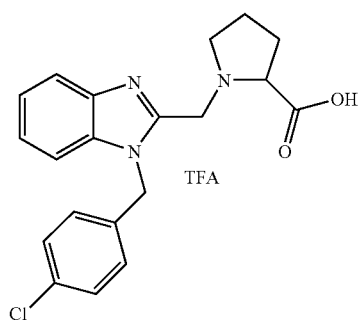
Compound 13
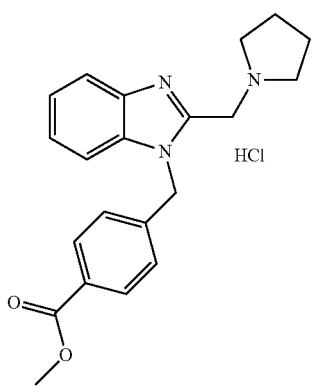
Compound 14
TABLE 6-continued
Structures of the compounds listed in Tables 4 and 5.
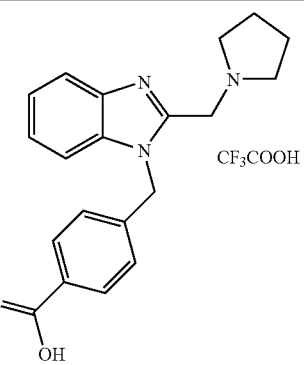
Compound 15
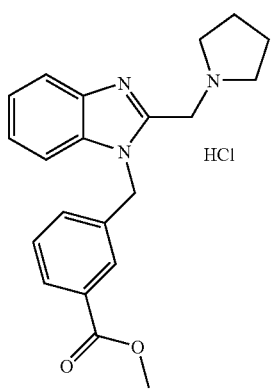
Compound 16
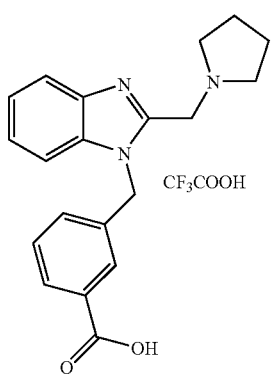
Compound 17

TABLE 6-continued
Structures of the compounds listed in Tables 4 and 5.
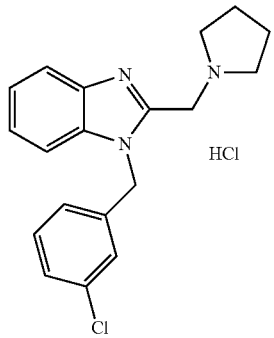
Compound 18
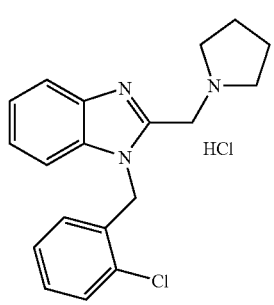
Compound 19
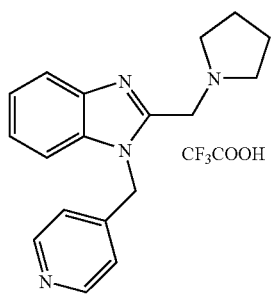
Compound 20
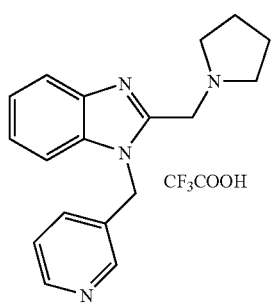
Compound 21
TABLE 6-continued
Structures of the compounds listed in Tables 4 and 5.
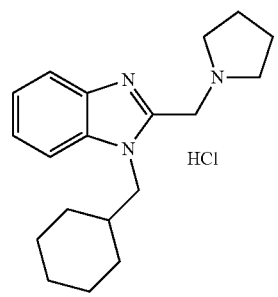
Compound 22
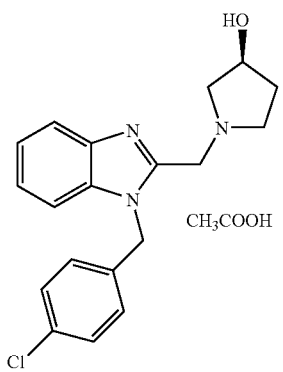
Compound 23
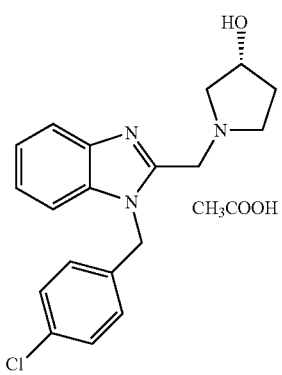
Compound 24
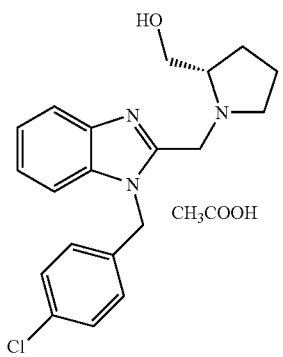
Compound 25

TABLE 6-continued
Structures of the compounds listed in Tables 4 and 5.
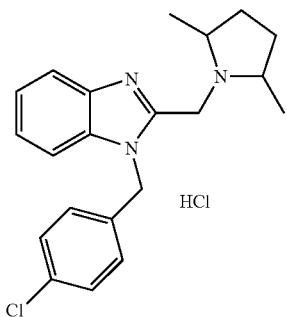
Compound 26
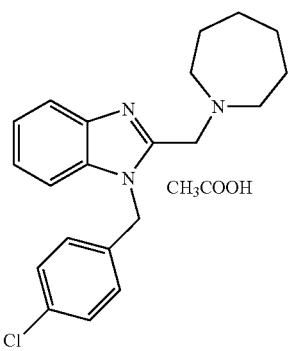
Compound 27
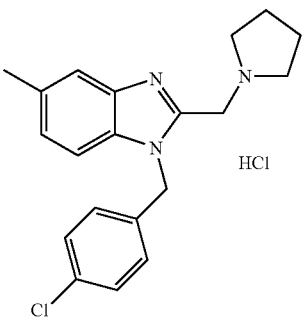
Compound 28
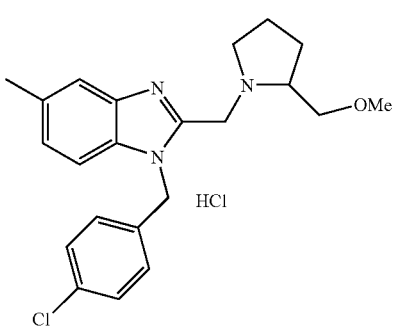
Compound 29
TABLE 6-continued
Structures of the compounds listed in Tables 4 and 5.
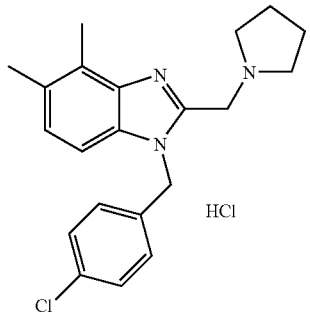
Compound 30
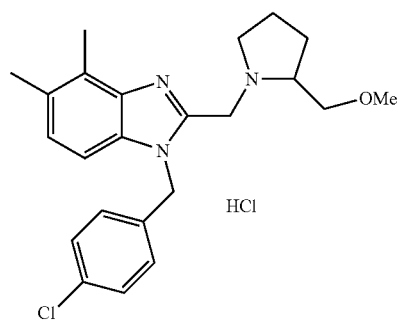
Compound 31
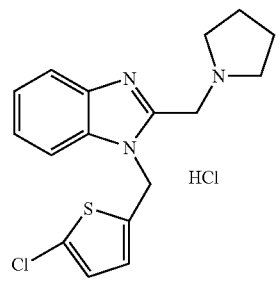
Compound 32
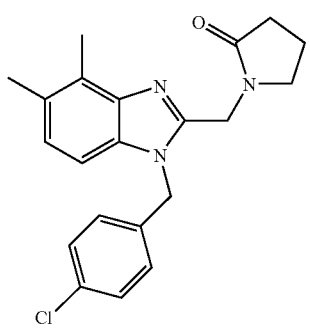
Compound 33

TABLE 6-continued
Structures of the compounds listed in Tables 4 and 5.
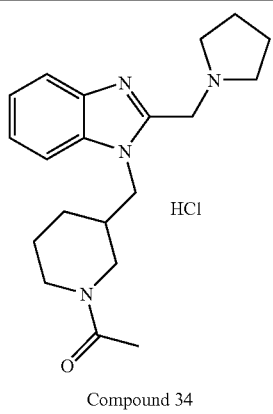
HCl
Compound 34
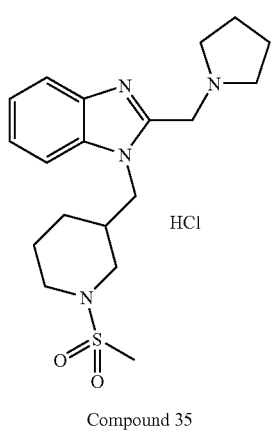 [SMILES: CS(=O)(=O)N1CCCC(Cn2c(CN3CCCC3)nc3ccccc32)C1 ; Cl]
HCl
Compound 35
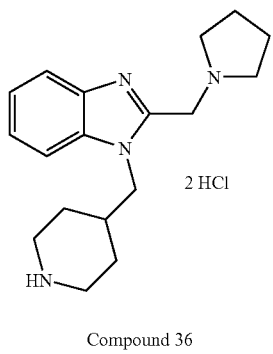 [SMILES: c1ccc2c(c1)nc(CN1CCCC1)n2CC1CCNCC1 ; "2 HCl"]
2 HCl
Compound 36
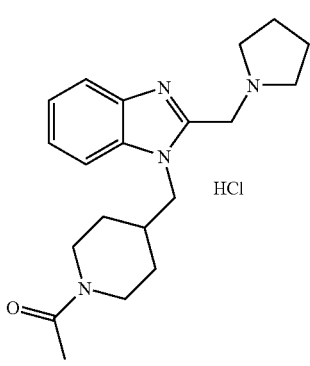
HCl
Compound 37
TABLE 6-continued
Structures of the compounds listed in Tables 4 and 5.
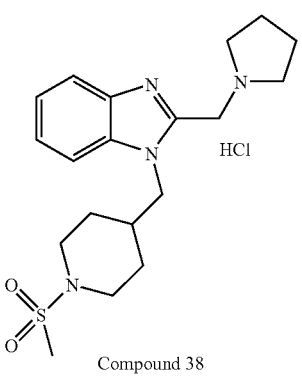 [SMILES: CS(=O)(=O)N1CCC(Cn2c(CN3CCCC3)nc3ccccc32)CC1 ; Cl]
HCl
Compound 38
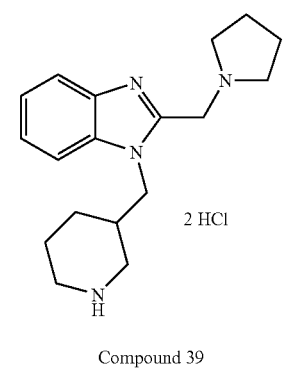 [SMILES: c1ccc2c(c1)nc(CN1CCCC1)n2CC1CCCNC1 ; "2 HCl"]
2 HCl
Compound 39
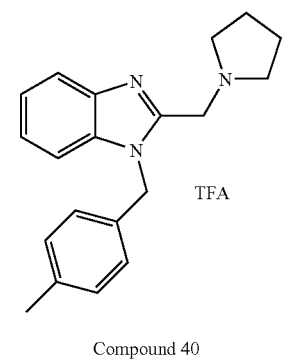 [SMILES: "TFA" ; Cc1ccc(Cn2c(CN3CCCC3)nc3ccccc32)cc1]
TFA
Compound 40
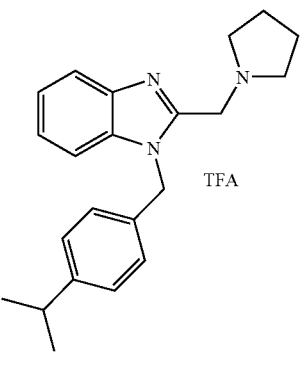
TFA
Compound 41

TABLE 6-continued

Structures of the compounds listed in Tables 4 and 5.

Compound 42

Compound 43

Compound 44

Compound 45

Compound 46

Compound 47

Compound 48

Compound 49

TABLE 6-continued
Structures of the compounds listed in Tables 4 and 5.
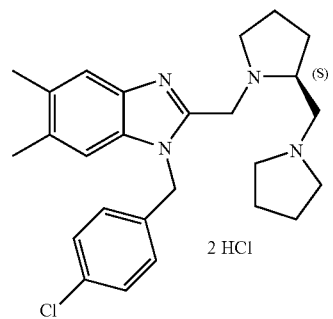
Compound 50
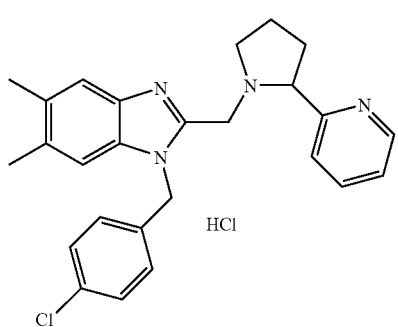
Compound 51
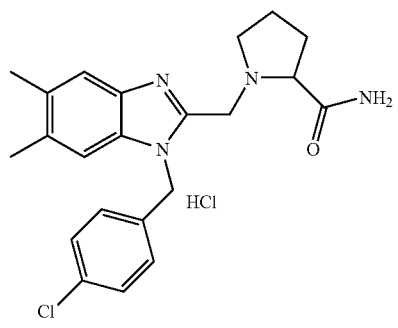
Compound 52
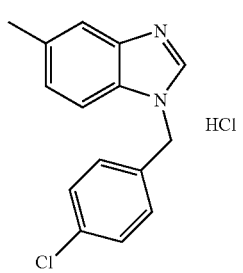
Compound 53
TABLE 6-continued
Structures of the compounds listed in Tables 4 and 5.
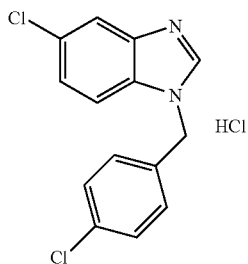
Compound 54
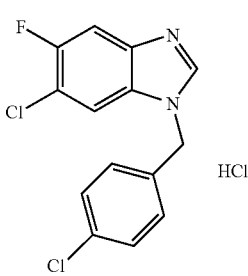
Compound 55
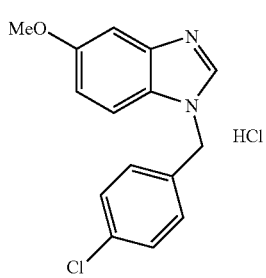
Compound 56
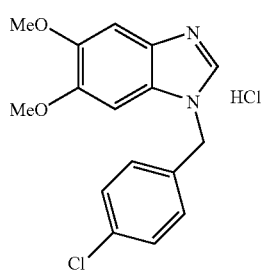
Compound 57
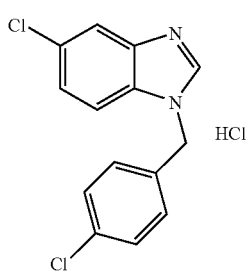
Compound 58

TABLE 6-continued
Structures of the compounds listed in Tables 4 and 5.
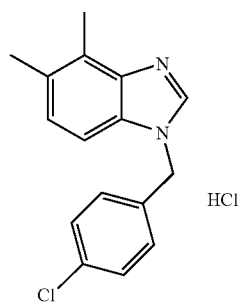
Compound 59
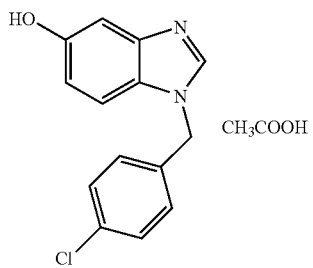
Compound 60
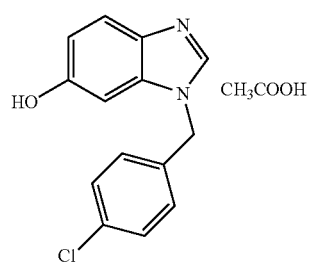
Compound 61
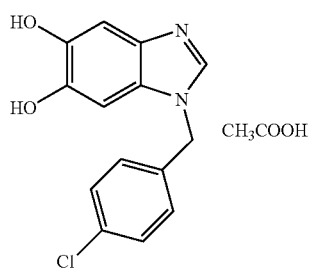
Compound 62
TABLE 6-continued
Structures of the compounds listed in Tables 4 and 5.
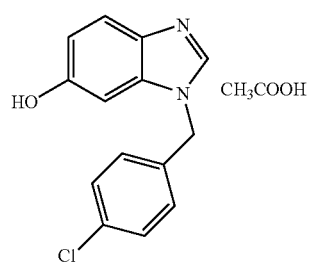
Compound 63
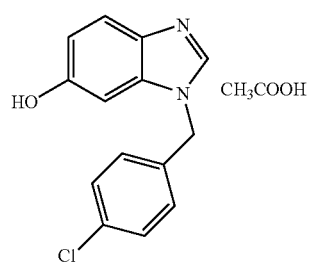
Compound 64
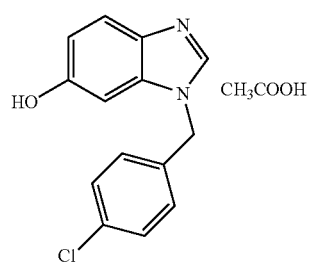
Compound 65
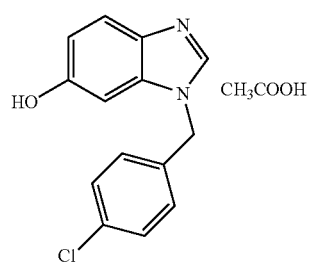
Compound 66

TABLE 6-continued
Structures of the compounds listed in Tables 4 and 5.
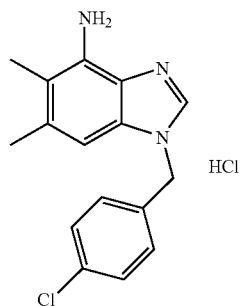
Compound 67
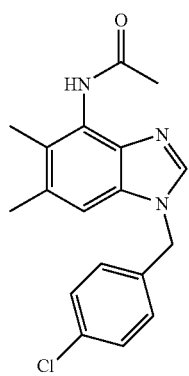
Compound 68
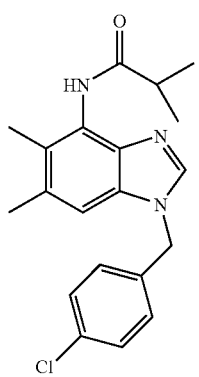
Compound 69
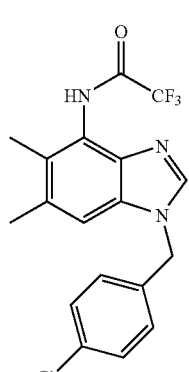
Compound 70
TABLE 6-continued
Structures of the compounds listed in Tables 4 and 5.
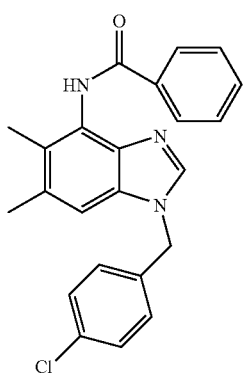
Compound 71
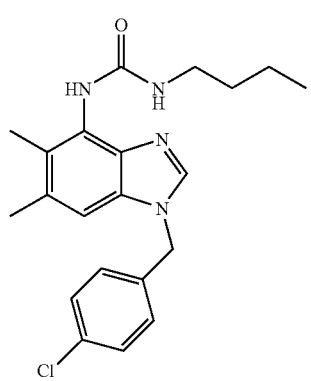
Compound 72
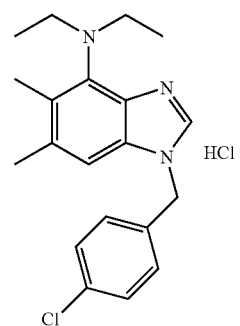
Compound 73
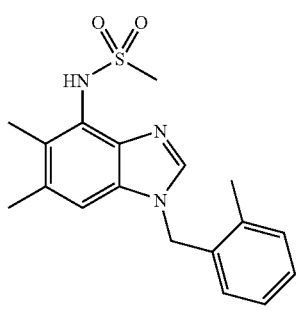
Compound 74

TABLE 6-continued
Structures of the compounds listed in Tables 4 and 5.
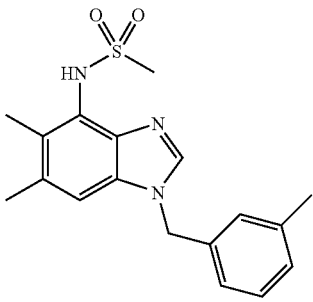
Compound 75
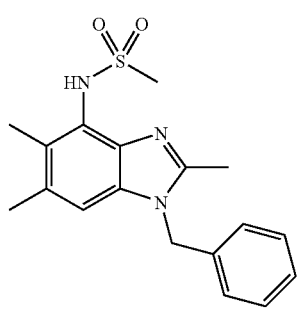
Compound 76
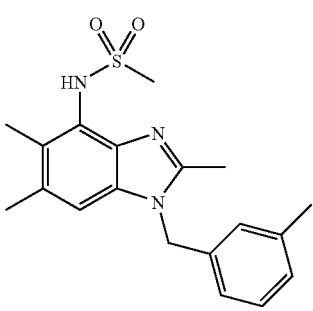
Compound 77
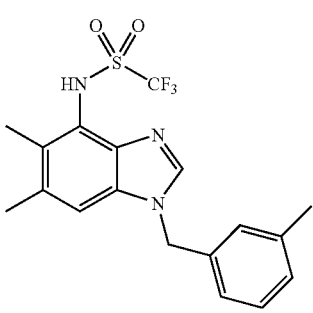
Compound 78
TABLE 6-continued
Structures of the compounds listed in Tables 4 and 5.
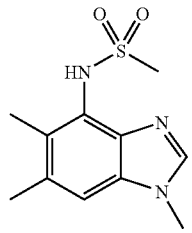
Compound 79
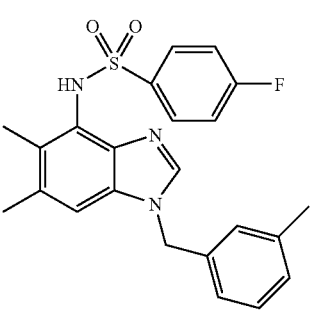
Compound 80
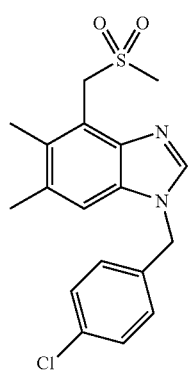
Compound 81
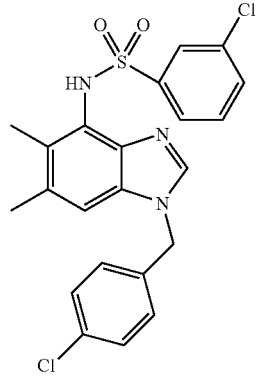
Compound 82

TABLE 6-continued
Structures of the compounds listed in Tables 4 and 5.
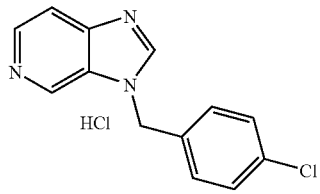
Compound 83
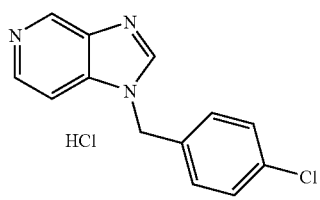
Compound 84
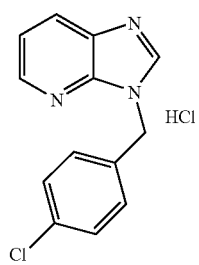
Compound 85
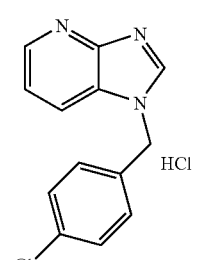
Compound 86
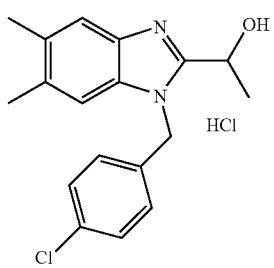
Compound 87
TABLE 6-continued
Structures of the compounds listed in Tables 4 and 5.
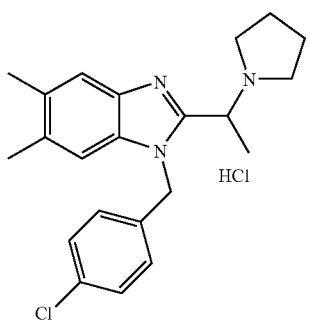
Compound 88
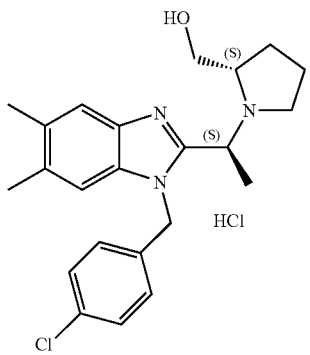
Compound 89
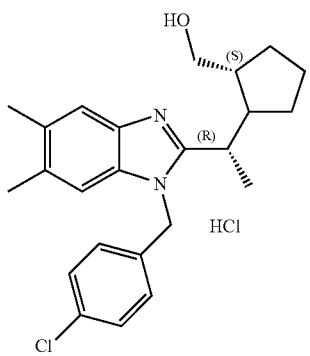
Compound 90
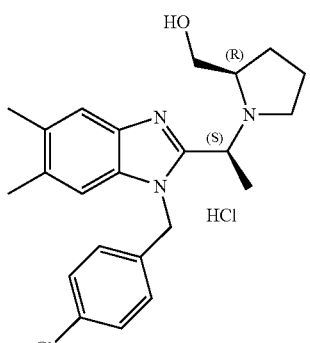
Compound 91

TABLE 6-continued
Structures of the compounds listed in Tables 4 and 5.
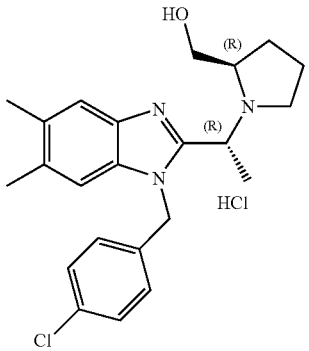
Compound 92
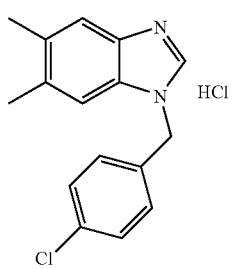
Compound 93
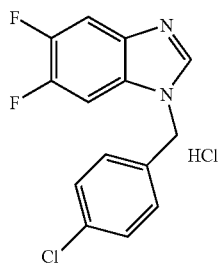
Compound 94
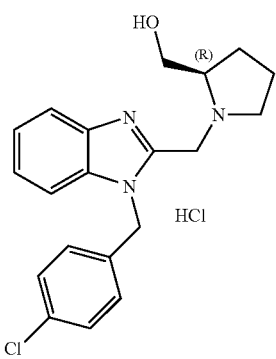
Compound 95
TABLE 6-continued
Structures of the compounds listed in Tables 4 and 5.
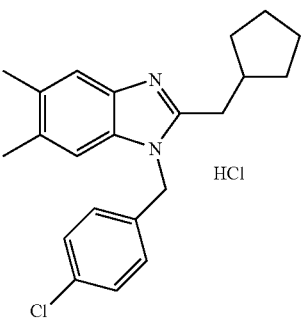
Compound 96
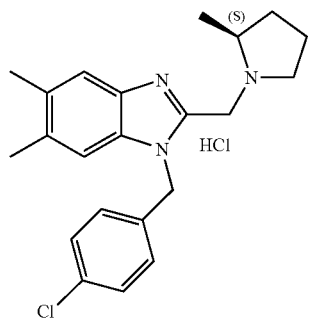
Compound 97
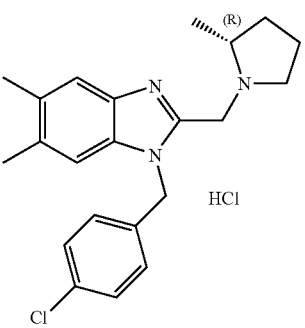
Compound 98
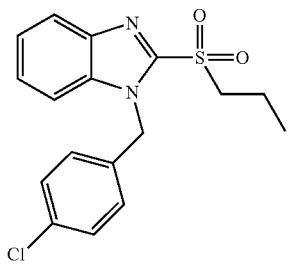
Compound 99

TABLE 6-continued
Structures of the compounds listed in Tables 4 and 5.
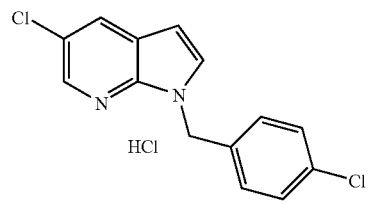
Compound 100
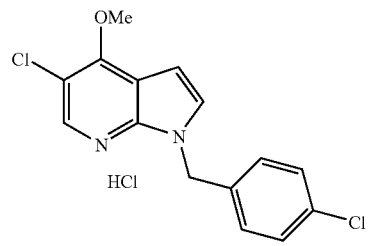
Compound 101
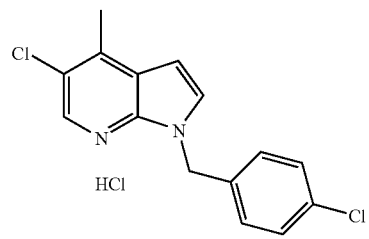
Compound 102
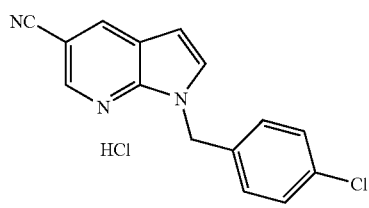
Compound 103
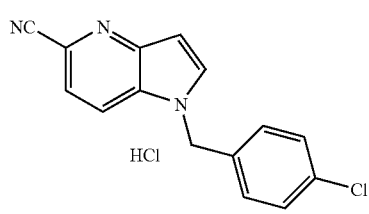
Compound 104
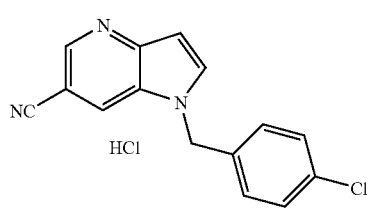
Compound 105
TABLE 6-continued
Structures of the compounds listed in Tables 4 and 5.
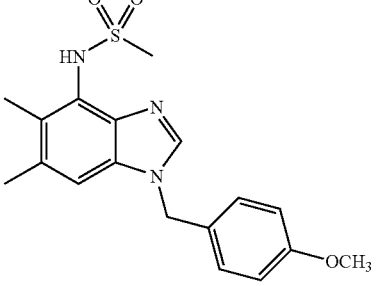
Compound 106
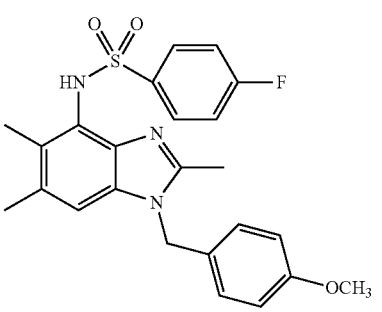
Compound 107
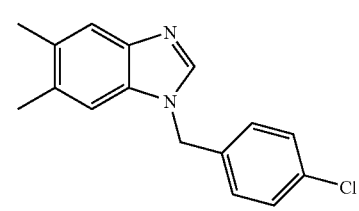
Compound 108
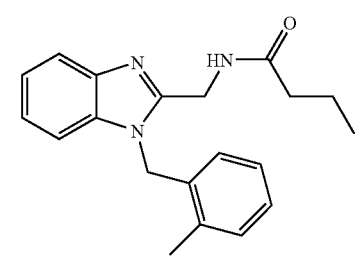
Compound 109
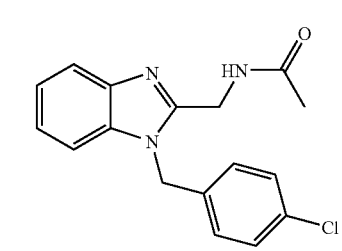
Compound 110

TABLE 6-continued
Structures of the compounds listed in Tables 4 and 5.
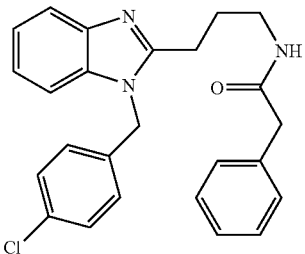
Compound 111
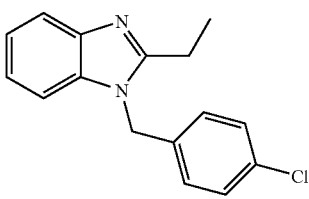
Compound 112
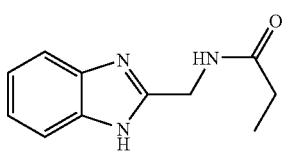
Compound 113
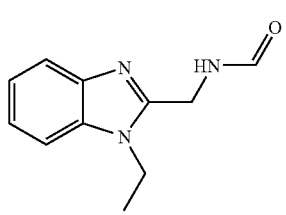
Compound 114
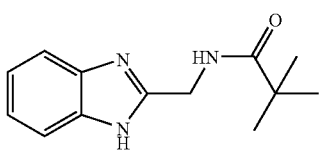
Compound 115
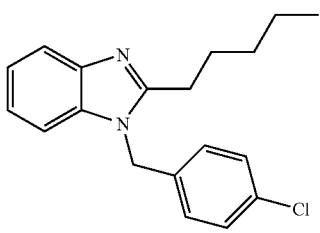
Compound 116
TABLE 6-continued
Structures of the compounds listed in Tables 4 and 5.
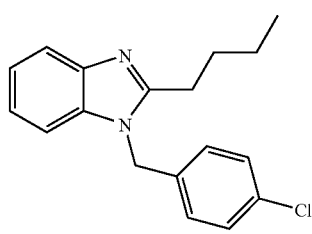
Compound 117
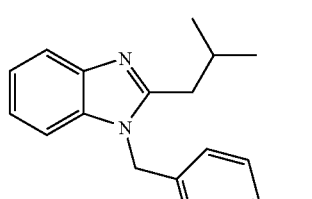
Compound 118
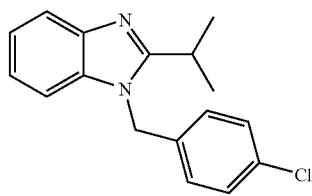
Compound 119
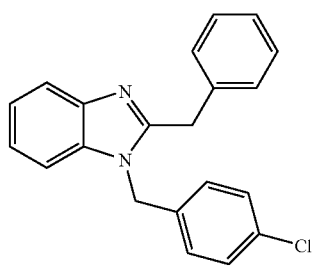
Compound 120
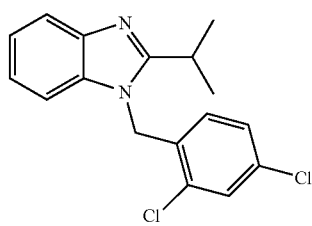
Compound 121

TABLE 6-continued
Structures of the compounds listed in Tables 4 and 5.
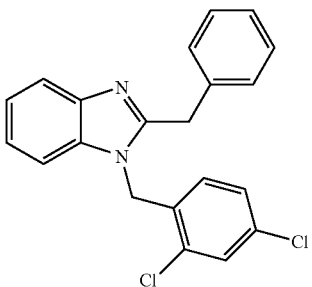
Compound 122
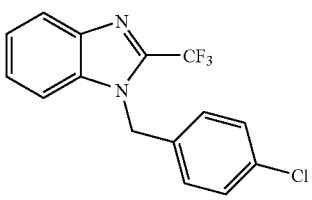
Compound 123
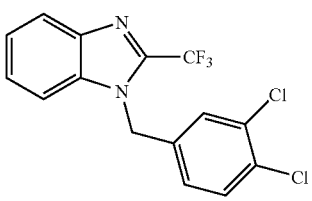
Compound 124
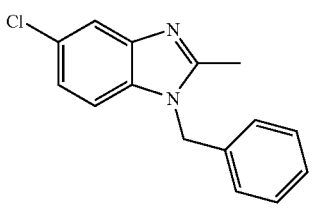
Compound 125
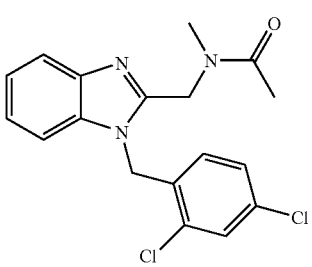
Compound 126
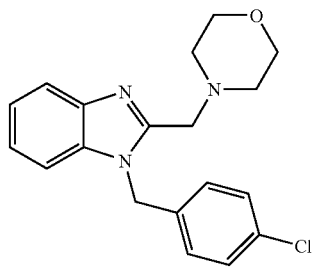
Compound 127
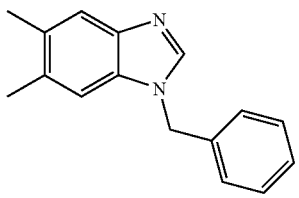
Compound 128
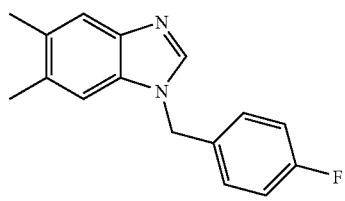
Compound 129
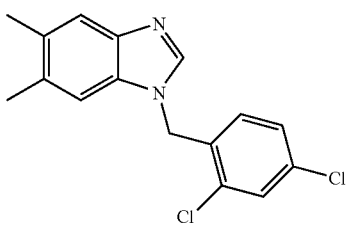
Compound 130
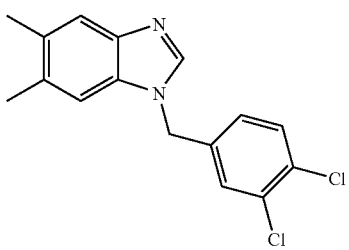
Compound 131
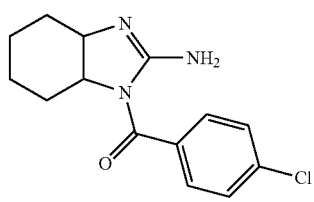
Compound 132

TABLE 6-continued
Structures of the compounds listed in Tables 4 and 5.
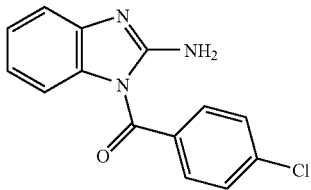
Compound 133
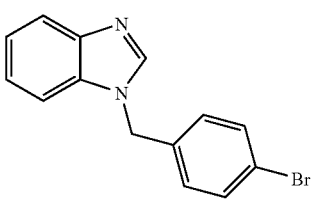
Compound 134
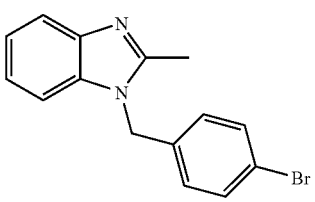
Compound 135
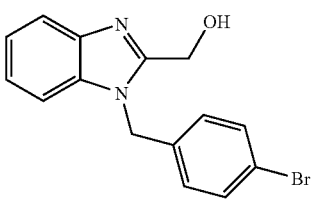
Compound 136
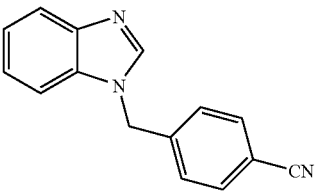
Compound 137
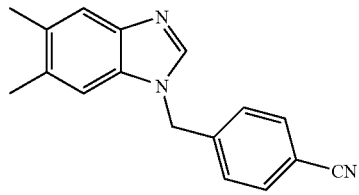
Compound 138
TABLE 6-continued
Structures of the compounds listed in Tables 4 and 5.
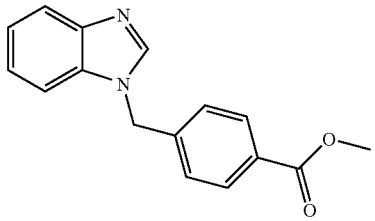
Compound 139
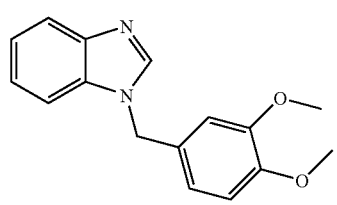
Compound 140
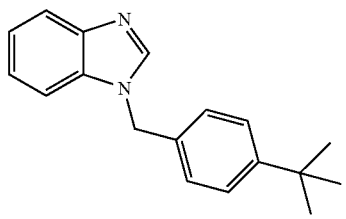
Compound 141
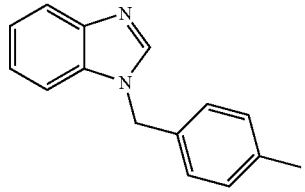
Compound 142
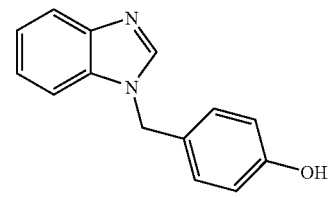
Compound 143
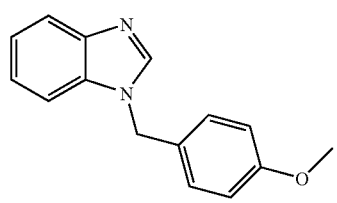
Compound 144

TABLE 6-continued
Structures of the compounds listed in Tables 4 and 5.
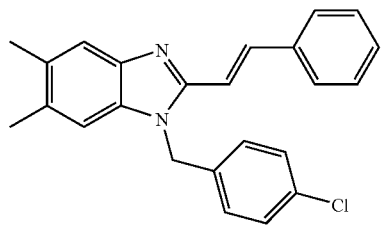
Compound 145
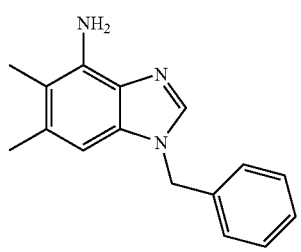
Compound 146
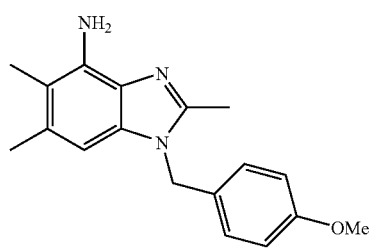
Compound 147
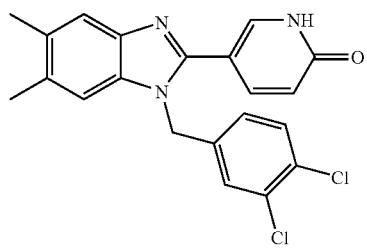
Compound 148
Compound 149
TABLE 6-continued
Structures of the compounds listed in Tables 4 and 5.
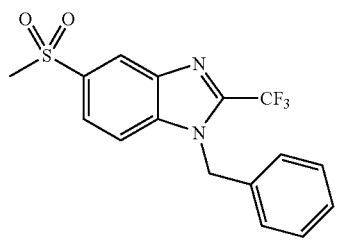
Compound 150
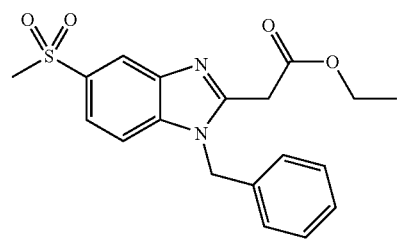
Compound 151
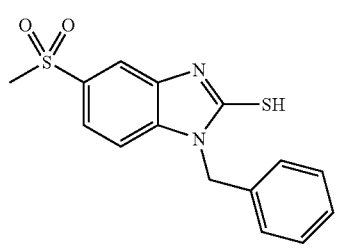
Compound 152
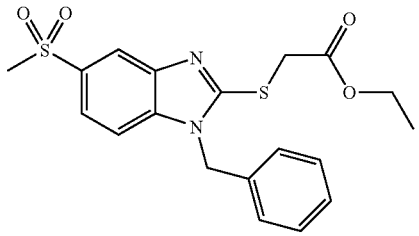
Compound 153
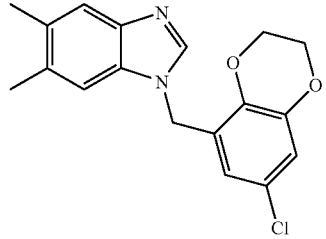
Compound 154

TABLE 6-continued
Structures of the compounds listed in Tables 4 and 5.
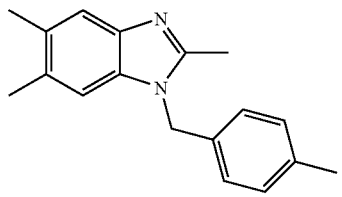
Compound 155
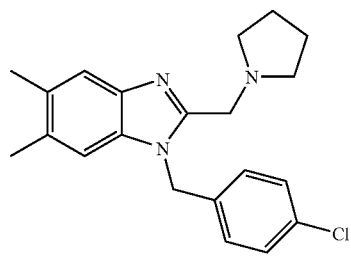
Compound 156
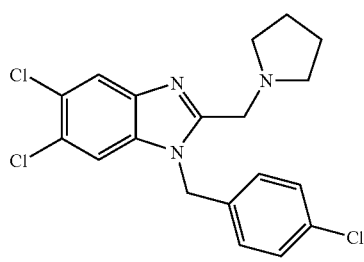
Compound 157
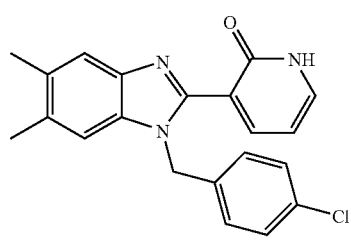
Compound 158
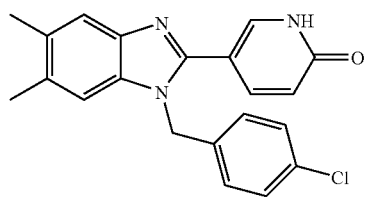
Compound 159
TABLE 6-continued
Structures of the compounds listed in Tables 4 and 5.
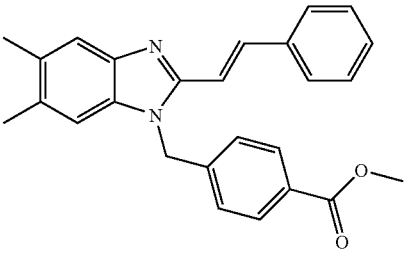
Compound 160
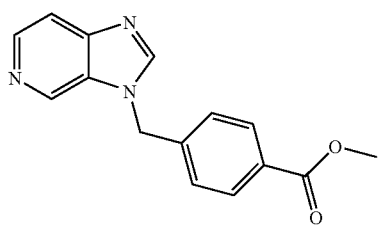
Compound 161
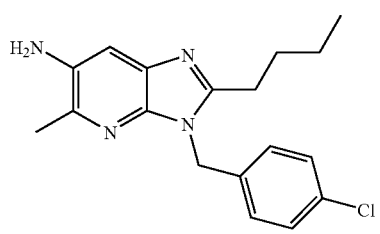
Compound 162
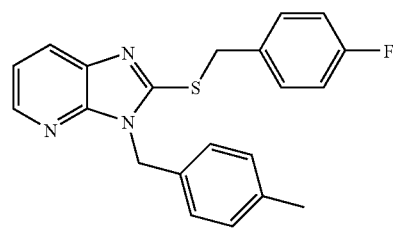
Compound 163
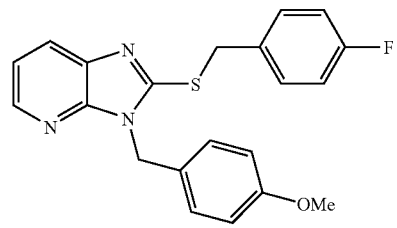
Compound 164

TABLE 6-continued
Structures of the compounds listed in Tables 4 and 5.
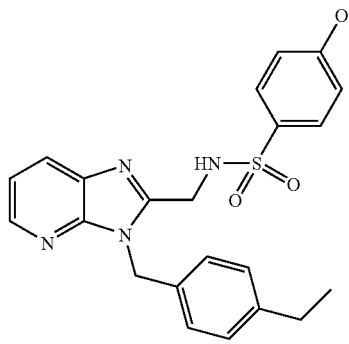
Compound 165
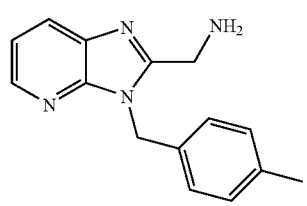
Compound 166
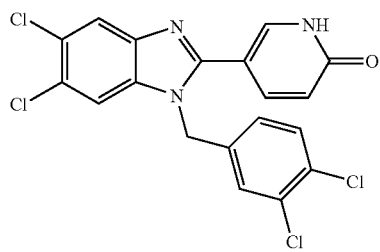
Compound 167
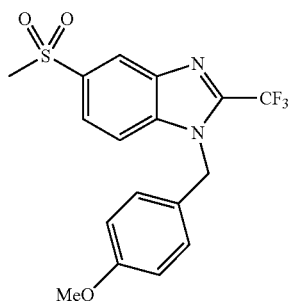
Compound 168
TABLE 6-continued
Structures of the compounds listed in Tables 4 and 5.
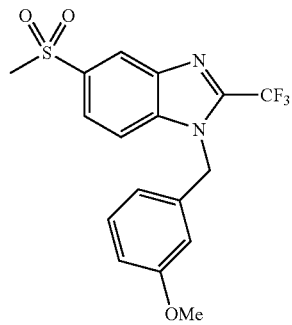
Compound 169
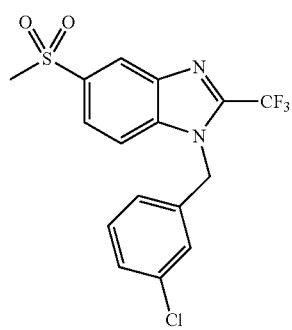
Compound 170
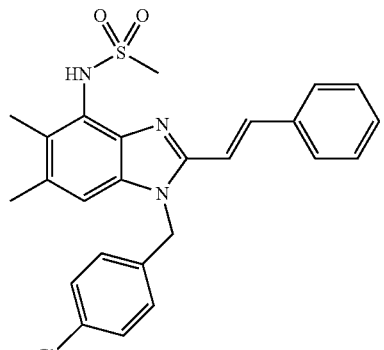
Compound 171
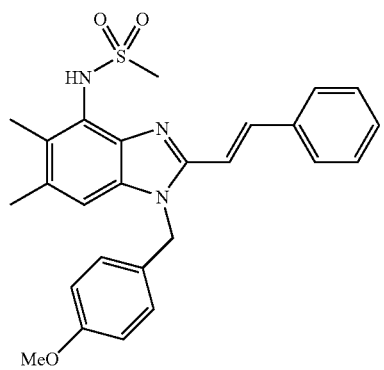
Compound 172

TABLE 6-continued
Structures of the compounds listed in Tables 4 and 5.
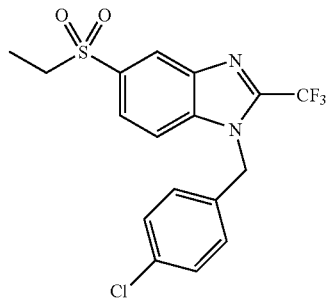
Compound 173
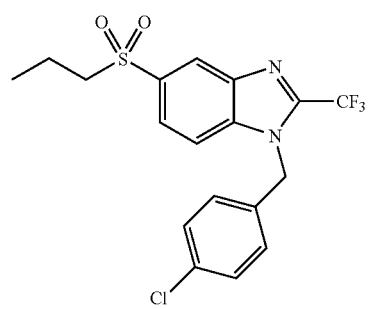
Compound 174
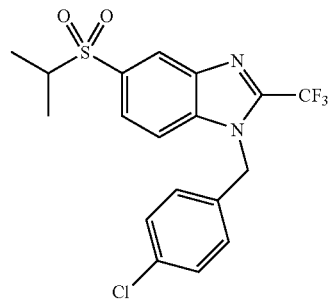
Compound 175
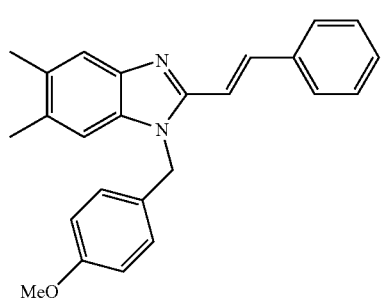
Compound 176
TABLE 6-continued
Structures of the compounds listed in Tables 4 and 5.
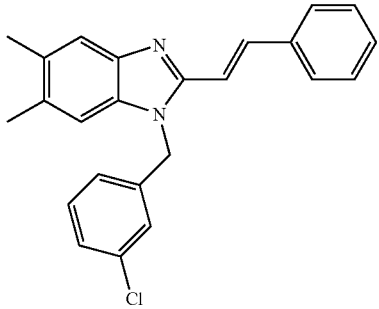
Compound 177
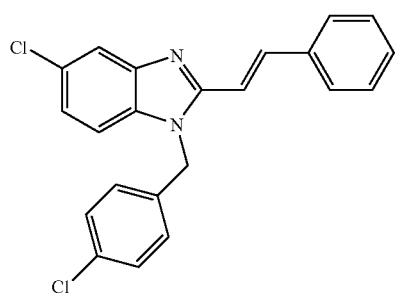
Compound 178
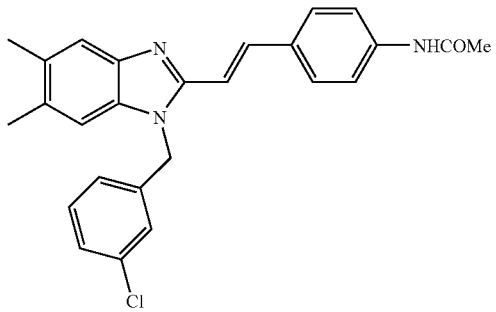
Compound 179
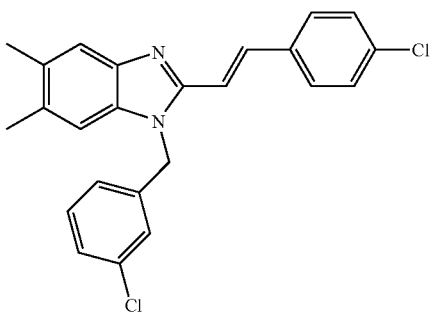
Compound 180

TABLE 6-continued
Structures of the compounds listed in Tables 4 and 5.
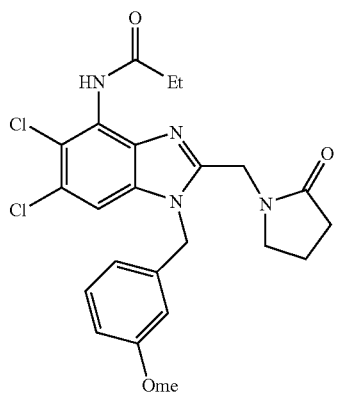
Compound 181
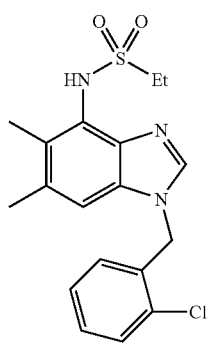
Compound 182
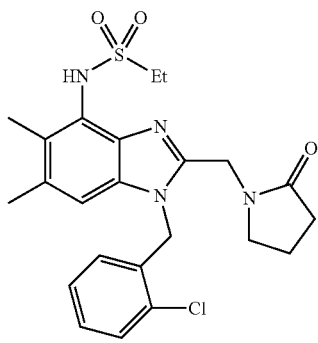
Compound 183
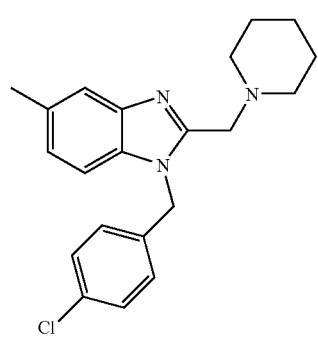
Compound 184
TABLE 6-continued
Structures of the compounds listed in Tables 4 and 5.
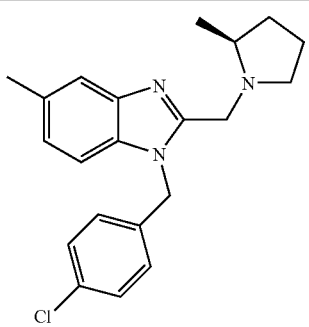
Compound 185
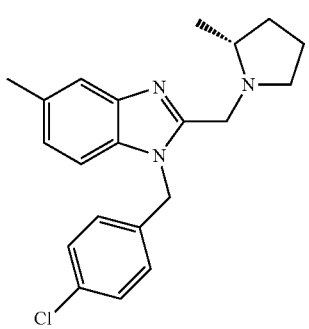
Compound 186
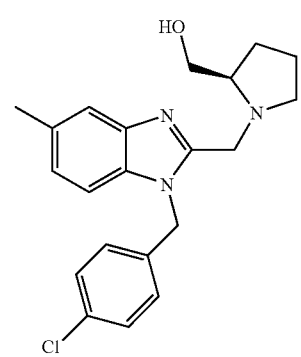
Compound 187
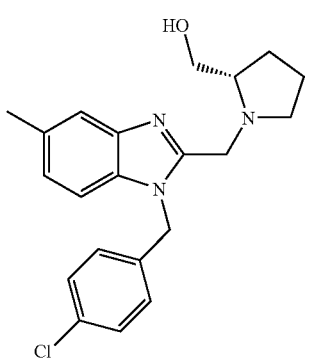
Compound 188

TABLE 6-continued
Structures of the compounds listed in Tables 4 and 5.
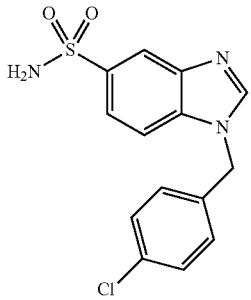
Compound 189
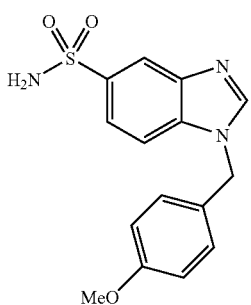
Compound 190
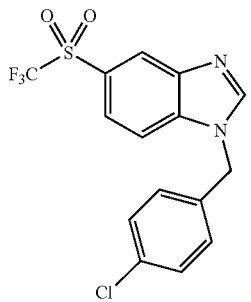
Compound 191
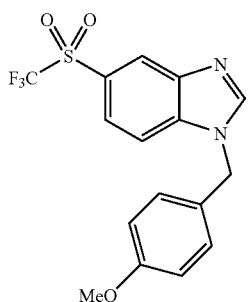
Compound 192
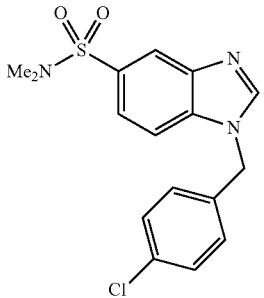
Compound 193
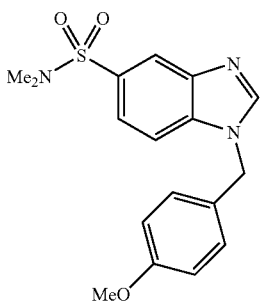
Compound 194
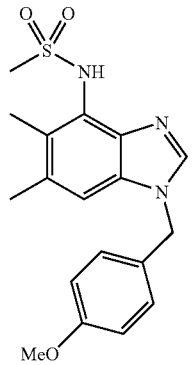
Compound 195
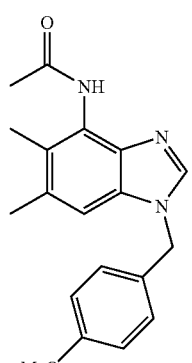
Compound 196

TABLE 6-continued
Structures of the compounds listed in Tables 4 and 5.
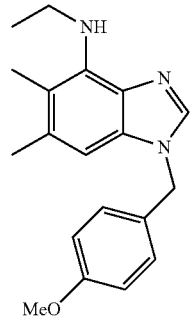
Compound 197
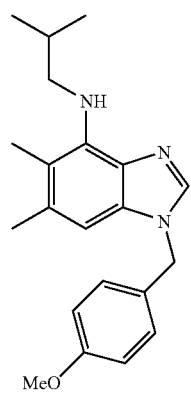
Compound 198
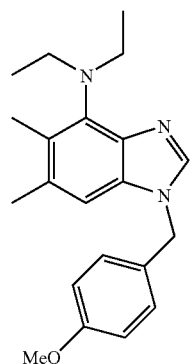
Compound 199
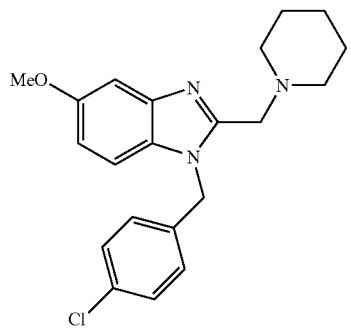
Compound 200
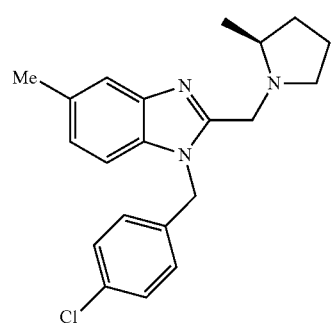
Compound 201
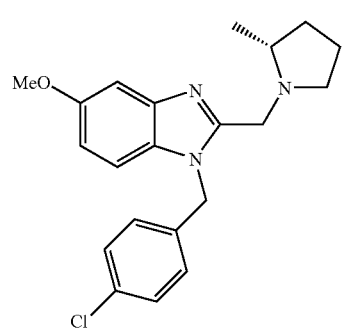
Compound 202
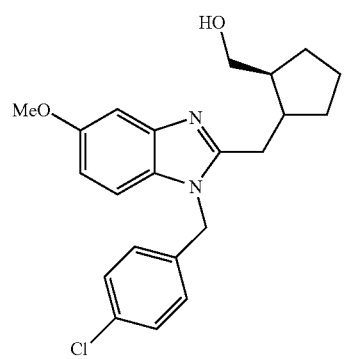
Compound 203
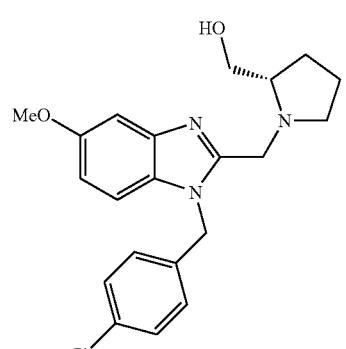
Compound 204

TABLE 6-continued

Structures of the compounds listed in Tables 4 and 5.

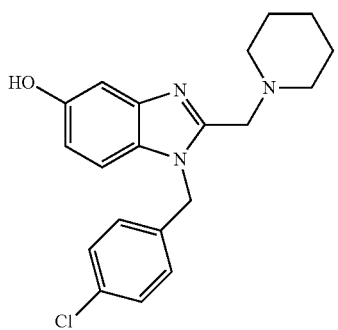

Compound 205

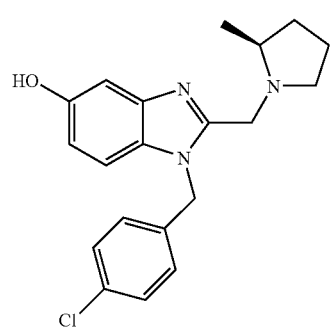

Compound 206

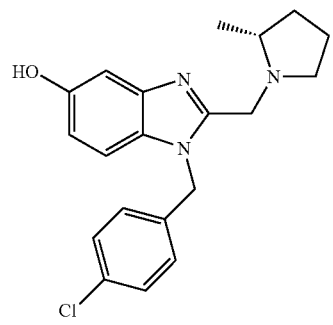

Compound 207

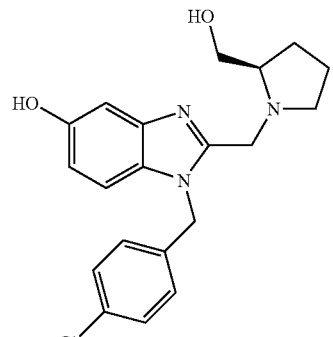

Compound 208

TABLE 6-continued

Structures of the compounds listed in Tables 4 and 5.

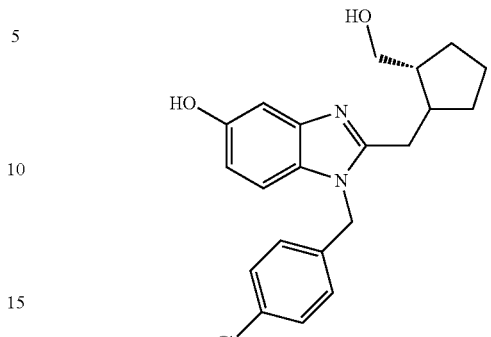

Compound 208

Example 5

Replication Assay Protocol

In an embodiment, the replication assay protocol can include the following stages. It should be noted that the following replication assay protocol is non-limiting, and presented as an illustrative embodiment of a replication assay protocol.

Stage 1: RNA Transcription

1) Linearize the FL-J6/JFH-5'C19Rluc2AUbi plasmid with XbaI at 37° C. for 2 hrs, and run on 1% agarose gel to check completeness of digestion.

2) Digest the 5' overhangs by treatment with mung bean nuclease at 30° C. for 30 min.

3) For linearization of the Bart79I-luc plasmid (similar to Bart79I plasmid as described in Elazar et al. J. Virol. 2003, 77(10):6055-61 except that the neomycinphosphotransferase gene has been replaced with the gene encoding firefly luciferase) use ScaI restriction endonuclease, then examine the linearized template DNA on a gel to confirm that cleavage is complete, follow this with proteinase k digestion.

4) Purify templates by digestion with proteinase K for 30 min, phenol-chloroform extraction, ethanol precipitation, and then resuspend at 1 μg/μl.

5) For the transcription reaction, use 1 μg of purified template by using the T7 Megascript kit for FL-J6/JFH-5C19Rluc2AUbi (Ambion, Austin, Tex.) or the RiboMax™ kit for Bart79I-luc (Promega, Madison, Wis.). Incubate reactions at 37° C. for 4 h.

6) Add DNAse for 15 min.

7) Extract with an equal volume of phenol/chloroform and then with an equal volume of chloroform. Recover aqueous phase and transfer to new tube.

8) Precipitate the RNA by adding 1 volume of isopropanol and mixing well.

9) Chill the mixture for at least 15 min at −20° C. Centrifuge at 4° C. for 15 min at maximum speed to pellet the RNA.

10) Carefully remove the supernatant solution and resuspend the RNA in RNase/DNase-free Water at 1 μg/μl.

11) Run on a gel and check RNA concentration.

12) Make aliquots and store in −80° C.

Stage 2: Electroporating Huh7.5 Cells

1) Wash cells once with PBS, trypsinize.

2) Resuspend cells in a total volume of 5 ml per 10 cm plate of complete medium (pull all together) in 50 ml tubes.

3) Pellet cells at 1000×RPM for 5 min at 4° C. Aspirate sup and resuspend in 10 ml ice cold RNAse free filtered 1×PBS (BioWhitaker)—pipette up and down ~5 times gently to get rid of cell clumps.

4) Pellet cells again at 1000×RPM as before and again resuspend in 10 ml ice cold PBS (BioWhitaker).

5) Remove a 10 µl aliquot to determine cell concentration.

6) Pellet cells again and resuspend in a final concentration of $1.5×10^7$ cells/ml in ice cold RNAse free-PBS.

Need: $6×10^6$ cells in 0.4 ml per each electroporation (ep) and 5 µg of FL-J6/JFH-5'C19Rluc2AUbi RNA or Bart79I-luc RNA 7) Place 5 µg RNA aliquot in an eppendorf tube (1 tube per ep)

8) Remove 0.4 ml of the cell suspension and add to the RNA. Mix twice by pipetting.

9) Immediately transfer 0.4 ml to a 2 mm gap ep cuvette

10) Pulse the cells: 820 v, 5 pulses, 99 µsec, 220 ms interval, unipolar.

11) Allow cells to rest for 15 min.

12) Transfer cells using the Pasteur pipette in the cuvette package to medium. Make a common stock from all tubes.

13) Plate 10,000 cells/well in 96 well plates.

14) Rotate plate a little for even cell plating.

15) Incubate for 24 hr before treatment.

Stage 3: Treating Plates

1) About 24 hr following electroporation prepare medium with the desired concentration of the drug.

2) Aspirate the medium and add 100 µl of fresh medium and drug. Leave untreated wells at the beginning and again at the end.

3) Repeat daily for 2 more days.

Stage 4: Harvesting (Day 5 from Electroporation)

1) Alamar blue assay— a) Include medium for background subtraction (and also for seeing change in color easily).

b) Aspirate medium.

c) Make a stock of medium plus 10% Alamar blue. Total volume per well is 100 µl.

d) Incubate for 2-2.5 hrs at 37° C. (or until there is a color change).

c) Read plates at flex station.

2) *Renilla* Luciferase assay— a) Aspirate medium with Alamar blue.

b) Wash with 1×PBS.

c) Aspirate completely (aspirate, then tilt and aspirate remainders of buffer again).

d) Make sure which lysis buffer is needed: firefly or *renilla*.

e) Add 30 µl of 1× lysis buffer (add 1 volume of 5× lysis buffer to 4 volumes of sterile water).

f) Shake the plate for 15 min.

g) Freeze at −80° C. At this point, one can stop or continue to the next phase.

Stage 5: Reading by Luminometer a) Thaw the plate.

b) Leave plate on ice until ready to read.

c) Prepare substrate reagent you need; for the *renilla*: thaw *renilla* buffer, make 1 volume 100× *Renilla* luc substrate plus 100 vol luc assay buffer+2 ml for priming luminometer. (e.g., for 4 ml *Renilla* lucsubstrate, add 40 ul assay buffer). For the firefly; thaw 10 ml firefly buffer and add to the luciferase reagent.

d) Read plates using a standard luminometer according to the manufacturer's directions.

Example 6

HERG Channel Assay

Drugs belonging to different classes have been shown to be associated with QT prolongation and in some cases serious ventricular arrhythmias. The most common mechanism for these adverse events is the inhibition of one or more cardiac potassium channels, in particular hERG. This current is important for cardiac myocyte repolarization and is a common target for drugs that prolong the QT interval. Test articles in this study were therefore characterized to determine their ability to inhibit the hERG channel. Ion channel activity was measured using a stably transfected Chinese Hamster Ovary (CHO) cell line expressing the hERG mRNA. The pharmacology of this cloned channel expressed in the CHO cell line is very similar to that observed in native tissue.

Experimental Methods

Cells:

AVIVA's CHO cell line, which stably expresses hERG channels, was used for the study. Cells were cultured in DMEM/F12 containing 10% FBS, 1% penicillin/streptomycin and 500 µg/ml G418. Before testing, cells were harvested using Accumax (Innovative Cell Technologies).

Solutions:

For electrophysiological recordings, the following solutions were used:

External Solution: 2 mM CaCl2; 2 mM MgCl2; 4 mM KCl; 150 mM NaCl; 10 mM Glucose; 10 mM HEPES; 310-320 mOsm; pH 7.4 (adjusted with 1M NaOH.)

Internal Solution: 140 mM KCl; 10 mM MgCl2; 6 mM EGTA; 5 mM HEPESNa; mM ATP-Mg; 300-320 mOsm; pH 7.25 (adjusted with 1M KOH).

Electrophysiology:

Whole cell recordings were-performed using PX 7000A (Axon Instruments) with VIVA's SealChip™ technology. Cells were voltage clamped at a holding potential of −80 mV. The hERG current was then activated by a depolarizing step to −50 mV for 300 ms. This first step at −50 mV was used as a baseline for measuring peak amplitude of the tail current. Next, a voltage step to +20 mV was applied for 5 s to activate the channels. Finally a step back to −50 mV for 5 seconds removed activation and the deactivating tail current was recorded.

Compound Handling and Dilutions:

All compounds were prepared from either 10 or 30 mM DMSO stock solutions. Solutions were mixed by sonication for 20 min, followed by vigorous vortexing. Prior to testing, compounds were diluted to test concentrations in glass vials using External Solution. Dilutions were prepared no longer than 20 min prior to use. Equal amounts of DMSO (0.1%) were present in all final dilutions.

Electrophysiology Procedures

After achieving whole cell configuration, cells were monitored for 90 s to assess stability and then washed with External Solution for 66 s. The voltage protocol described above was then applied to the cells every 12 s throughout the procedure. Only stable cells with recording parameters above threshold (see Quality Control section) were allowed to enter the drug addition procedure. External solution containing 0.1% DMSO (vehicle) was applied to the cells to establish a baseline. After allowing the current to stabilize for 3 to 5 min, test articles were applied. Test article solutions were added to cells in 4 separate additions. Cells were kept in test solution until effect of the test article reached steady state, to a maximum of 12 min. Next, 1 µM cisapride (positive control) was added. Finally, washout with External Solution was performed until the recovery current reached a steady state.

Data Analysis

Data analysis was performed using DataXpress (Axon Instruments), Clampfit (Axon Instruments) and Origin (Originlab Corporation) software.

Quality Control

Data included in the report originated from experiments that satisfied all of the following criteria:

a) Recording Parameters: membrane resistance (Rm): >200 MΩ; access resistance (Ra): <15MΩ; tail current amplitude: >150 pA Following these procedures, several compounds provided by the present invention are found to lack substantial cross reactivity with hERG channel.

b) Pharmacological Parameters: 1 µM cisapride: >95% inhibition

| Compound | HERG IC$_{50}$ (µM) |
|---|---|
| 150 | +++ |
| 184 | ++ |
| 145 | ++ |
| 106 | +++ |
| 167 | ++ |
| 11 | +++ |
| 12 | ++ |

"+++" indicates that HERG IC50 value is greater than 10 uM.
"++" indicates that HERG IC50 value is greater than 1 uM.

Experiment 7

Clemizole's Antiviral Effect is Highly Synergistic with HCV Protease Inhibitor

Figure 10A:
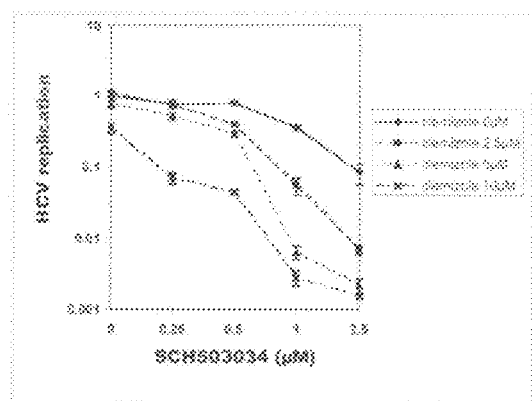
FIGS. 10a-10d illustrate the synergy between clemizole and compound SCH503034 in inhibiting HCV genotype 2a replication as evidenced by a luciferase reporter gene assay.

The synergistic antiviral activity of clemizole in combination with one of the protease inhibitors currently studied in phase 2 trials, SCH503034 (Boceprevir) was tested. Following electroporation with a full-length J6/JFH (genotype 2a) HCV RNA genome harboring a luciferase reporter gene, Huh7.5 cells were grown in the presence of various concentrations of the individual compounds and their combinations. Luciferase assays were performed at 72 hr. In parallel, the viability of cells in the presence of the compounds was assessed by an Alamar Blue-based assay. Cells harboring the above HCV replicon with the luciferase reporter gene were treated with four different concentrations of SCH503034 in the absence or presence of three different concentrations of clemizole. As shown in FIG. 10A, the combination of the two compounds resulted in a greater inhibition than either compound alone at all tested concentrations. For example, while SCH503034 alone at a concentration of 2.5 µM decreased viral replication by a ~1 log(0.08 relative to 1, untreated), when combined with 2.5 µM clemizole viral replication was inhibited by ~2 logs (0.007 vs. 1). Combining 2.5 µM SCH503034 with higher concentrations of clemizole at 5 uM and 10 uM further increased the antiviral effect for a total of ~3 log reduction in viral replication. Furthermore, no significant cytotoxicity was measured by an Alamar Blue-based assay with either compound alone or with any of the above combinations. These results suggest that addition of even low concentrations of clemizole has a dramatic effect on viral replication when added to SCH503034 and that this combination appeared to be synergistic.

Treatment with either compound alone for 72 h resulted in a concentration-dependent inhibition of HCV replication, as indicated by the reduction of luciferase reporter activity. When used alone, the average EC50 of clemizole from multiple experiments was 8 µM, with a CC50 of 35±0.5 µM (measured by both an Alamar Blue-based assay and a Cell-Titer-Blue assay). While EC50s between ~0.2 µM to 0.574 µM have been previously reported for SCH503034 for genotype 1b, the average EC50 from 3 experiments using 2a genotype luciferase reporter gene assays was 0.8 µM with a CC50>100 µM (see Table 7, as shown in FIG. 15)).

Figure 10B:
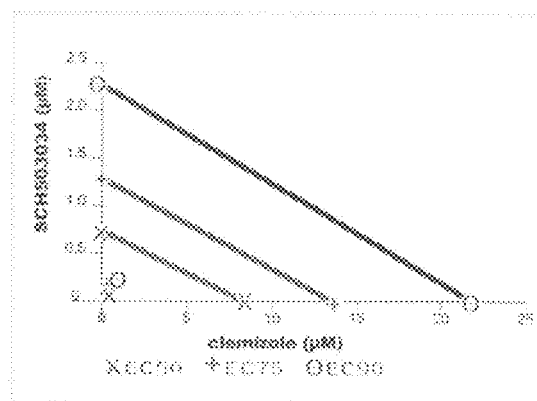
Figure 10C:
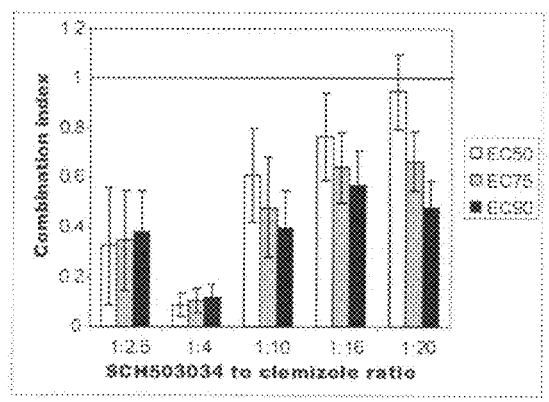

To more formally characterize the enhanced antiviral effect observed for the SCH503034-clemizole combination, a subset of the generated combination data was analyzed using CalcuSyn™ (Biosoft, Inc., Cambridge, UK). As determined by this software, the data points analyzed were those where the drugs were mixed at a fixed molar ratio matching their equipotent concentrations (SCH503034 to clemizole ratio of 1:10, derived from their measured EC50s). This molar ratio was maintained during serial dilutions, as previously described (Korba, 1996). As shown in the resulting isobologram (FIG. 10b), the calculated EC50, EC75, and EC90 values for the SCH503034-clemizole combinations all plotted far to the left of the corresponding lines of theoretical additivity. These results suggest that the tested combination is indeed synergistic. The combination indices (CIs) at the EC50, EC70, and EC90 levels were also determined using Calcusyn™ software (Biosoft, Inc., Cambridge, UK). As shown in FIG. 10C, at a ratio of 1:10, matching their equipotent concentration, the combination indices at the EC50, EC70, and EC90 were 0.61, 0.479 and 0.397, respectively. Being below 0.9, these indices confirm that the interaction is synergistic. Of note, these combination indices are similar in magnitude to the most potent synergistic interaction measured by others between a HCV protease inhibitor and a HCV polymerase inhibitor. Changing the ratio of the 2 drugs in the combination affected the calculated combination indices (FIG. 10C). While the interaction was found to be synergistic at any tested ratio, lowest combination indices at 0.087, 0.102 and 0.119 for the EC50, EC70, and EC90 respectively were measured at SCH503034 to clemizole ratio of 1:4.

Figure 10D:
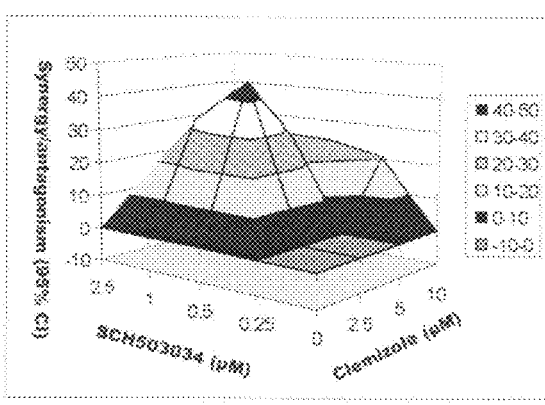

We further analyzed the data by the MacSynergy mathematic model to better quantify the degree of the observed synergy. In this model, the effect of the combination is determined by subtracting the actual experimental values from theoretical additive values, calculated from the dose-response curves for single compound treatments based on Bliss Independence theory. When presented as a three-dimensional differential surface plot, synergy is demonstrated by peaks above a theoretical additive plane and antagonism as depressions below it. Only statistically significant effects based on the 95% confidence interval were considered at any given concentrations of the two compounds. As shown in FIG. 10D, the combination of clemizole with SCH503034 had antiviral effects that were significantly more potent than the theoretical additive effects, supporting that this combination was indeed synergistic. No evidence of antiviral antagonism was seen with any of the tested doses. The synergism observed was reproducible in three independent experiments. The calculated synergy (volume under the curve) and log volume at 95% confidence interval (CI) were 210 µM$^2$% and 19, respectively, and 200 µM$^2$% and 18 at 99.9% CI. Data sets assessed at the 95% confidence level should be interpreted as follows: volumes of synergy or antagonism at values of <25 µM$^2$ are considered insignificant, those at values of >25 but <50 µM$^2$ are considered minor but significant, those at values of >50 but <100 µM$^2$ are considered moderate and probably important in vivo, and those at values of >100 µM$^2$ are considered strong and likely to be important in vivo. According to these criteria, the combination of clemizole with SCH503034 is considered synergistic. Importantly, since there was no cellular toxicity with either drug alone at the studied concentrations and no increase in cytotoxicity when used in combinations, suggesting that the measured synergy is indeed specific and does not reflect synergistic toxicity.

Experiment 8

The Synergy of Clemizole-SCH503034 Combination is not Genotype-Specific

Figure 11A:
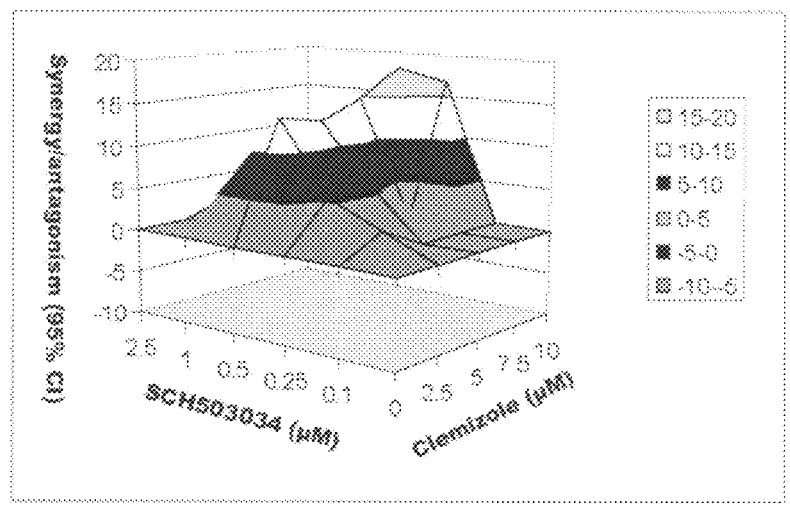
FIG. 11A illustrates a synergistic relationship between SCH503034 and clemizole in inhibiting genotype 1b replication.

In order to determine whether the observed synergy of the clemizole-SCH503034 combination is genotype-specific, the experiments outlined above were repeated using genotype 1b luciferase reporter gene assays. Huh7.5 cells were electroporated with a subgenomic Bart 79I HCV RNA replicon harboring a luciferase reporter gene, and grown in the presence of increasing concentrations of the individual compounds or their combinations. As described above, luciferase assays and Alamar Blue-based viability assays were performed at 72 hr. The average EC50 of SCH503034 in three independent experiments was ~0.21±0.034 µM ($p<0.002$) with a CC50>100 µM ($P<0.05$), similar to measurements previously reported by others (Table 7). In contrast to its effect in genotype 2a, very mild concentration-dependent inhibition of HCV replication was measured following 72 hr treatment with clemizole alone, with an average EC50 of 23±7 µM ($p<0.05$) and an average CC50 of 40±5 µM ($p<0.05$). It is possible that the lower sensitivity of this assay compared with the 2a luciferase reporter gene assay (resulting from lower level of genotype 1b replication compared with the genotype 2a clone) accounts for the difference in the measured EC50s of clemizole. Alternatively, differential antiviral activity of clemizole against the two genotypes may explain it. Selection of clemizole resistant mutants in replicon cells expressing the 1b genotype HCV genome (NBT), suggests that clemizole does have an antiviral effect against genotype 1b in the context of authentic viral replication. We thus favor the former possibility. Nevertheless, even low concentrations of clemizole surprisingly had a significant effect on genotype 1b viral replication when added to escalating concentrations of SCH503034. As shown in FIG. 11a, MacSynergy analysis revealed a large cluster of data points peaking above the surface of additivity with a synergy volume of 100.04 µM$^2$ (95% confidence interval). Importantly, no cellular toxicity was measured at the concentrations used. Similar to its effect on replication of HCV 2a genotype, the combination of clemizole with SCH503034 is thus highly synergistic in inhibiting genotype 1b HCV replication. These results suggest that even though clemizole's antiviral effect on viral replication as measured by the genotype 1b luciferase reporter gene assay is not as high as for genotype 2a, its combination with SCH503034 is highly synergistic and achieves significant antiviral effects. These results suggest that the highly synergistic antiviral effect of combined clemizole-SCH503034 treatment is not genotype-specific.

Experiment 9

The Clemizole-SCH503034 Combination is Synergistic in HCV-Infected Cells

Figure 11B:
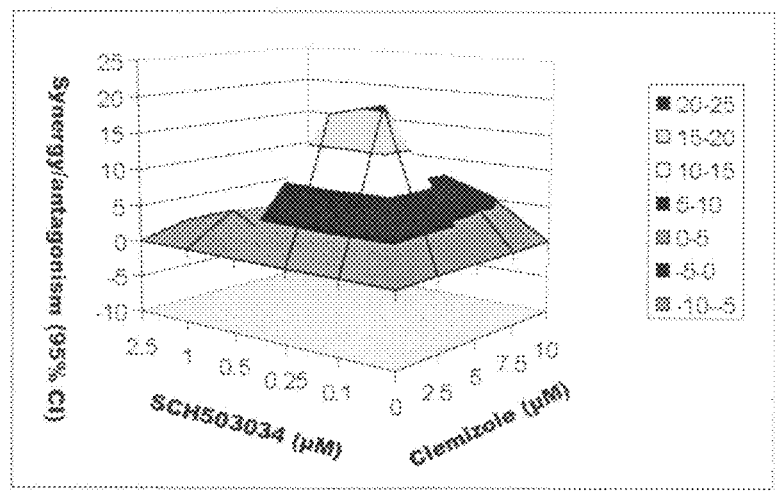
FIG. 11B illustrates an analysis of a focus formation assay of HCV genotype 2a replication using Bliss Independence Theory as implemented in MacSynergy II.

The synergistic effect of the clemizole and SCH503034 combination in inhibiting direct viral replication (versus activity of a luciferase gene) was determined by focus formation assays. Huh7.5 cells were infected in triplicates with cell culture-grown HCV titered at $1.2\times10^4$ TCID50/ml, as described. 2 hours after infection, cells were washed three times with culture medium. Cells were then treated daily with five different concentrations of clemizole in the absence or presence of five different concentrations of SCH503034. After 72 hours samples were subjected to an Alamar Blue-based viability assay, followed by fixation and immunofluorescence staining with anti-core antibody. Foci were counted under inverted microscope using the 20× magnification. While the average number of foci in untreated wells was 46, lower numbers of foci were counted with each drug alone in a dose dependent manner. When combined, the two drugs resulted in substantially more potent antiviral effects than the single agent in all concentrations tested. Importantly, neither drug alone nor the combinations showed cytotoxicity at the concentrations tested (data not shown). As shown in FIG. 11b, when analyzed by the MacSynergy model, similar to the luciferase reporter-linked replication assays, a large cluster of data points was plotted above the theoretical plane of additivity with a synergy volume of 113 µM$^2$ (95% CI). These results suggest that the highly synergistic antiviral effect of combined clemizole-SCH503034 treatment is also achieved in the context of authentic viral infection.

Experiment 10

Figures 12A, 12B:
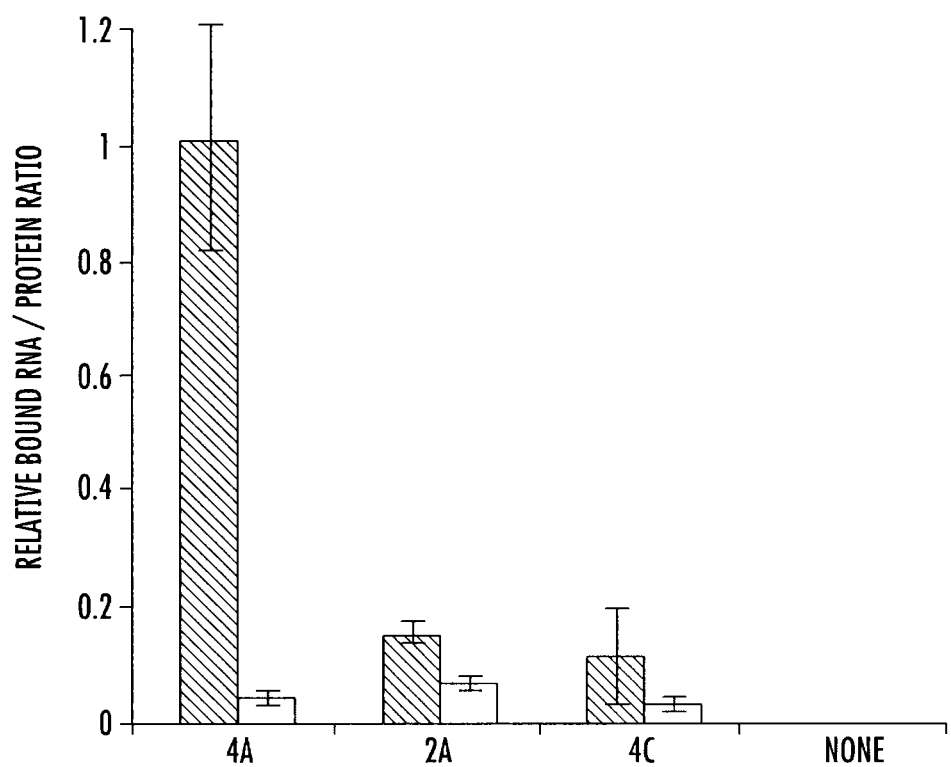
FIG. 12 illustrates a synergistic relationship between treatment with clemizole and treatment with the protease inhibitor VX-950 for inhibiting HCV replication using a luciferase reporter gene assay.
Figure 12C:
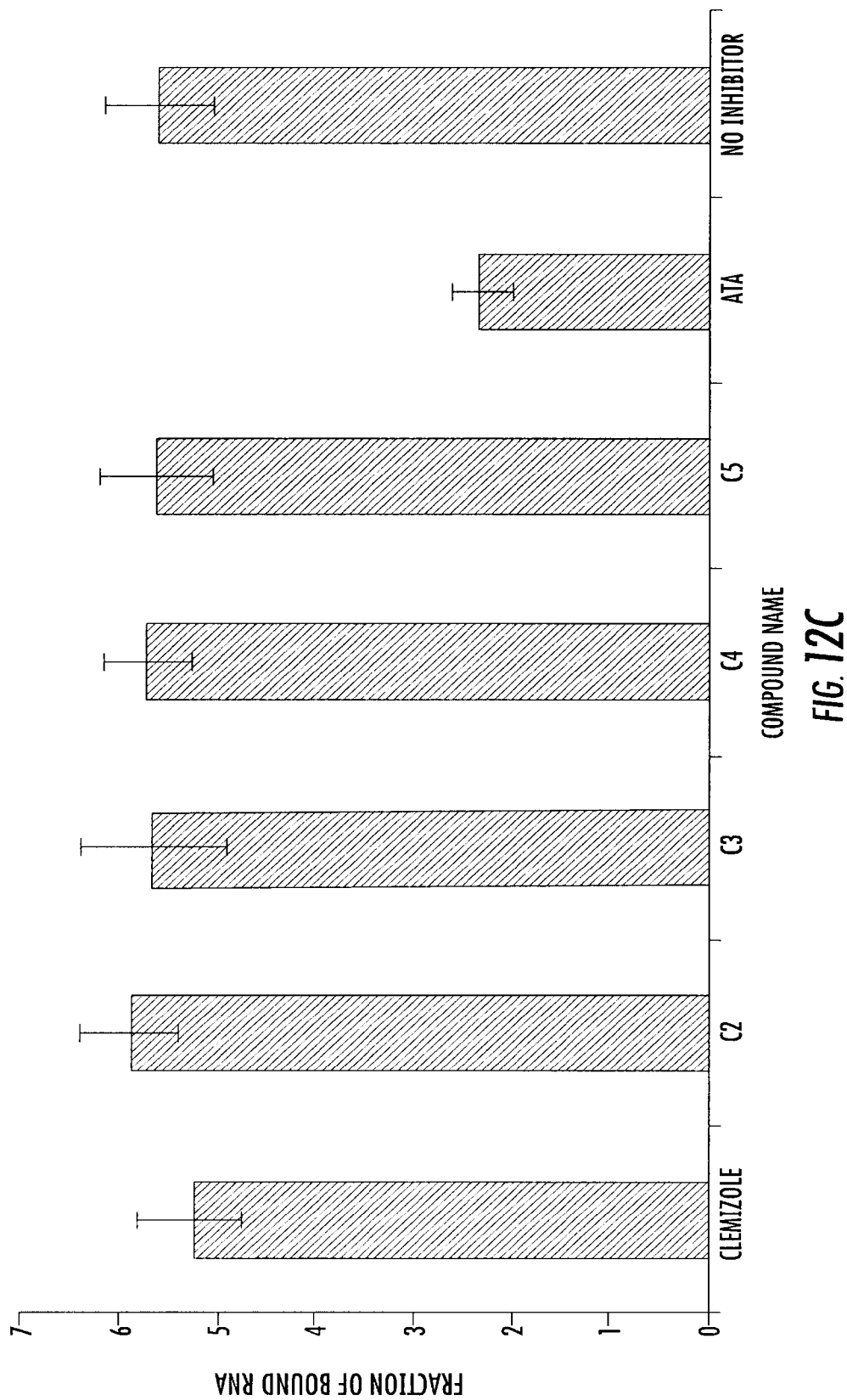

The Synergistic Effect of NS4B RNA Binding Inhibitors and Protease Inhibitors Combinations Applies to Different Types of Protease Inhibitors The observed synergistic antiviral effect is not specific to clemizole-SCH503034 combinations but is also achieved when combining other NS4B RNA binding inhibitors with different protease inhibitors. The antiviral effect of clemizole in combination with VX-950 (Telaprevir), another protease inhibitor, was thus determined. Luciferase reporter gene assays and viability assays were performed as described above and data was analyzed using the MacSynegy software. The EC50 of VX-950 alone was measured at ~300 nM (comparable to an EC50 of 354-560 nM reported by others using a different assay and 1b genotype) (Perni RB AAC 2006, Matthew F. McCown AAC 2008) (Table 7). As shown in FIG. 12, in most concentrations tested, the combined two drugs resulted in substantially more potent antiviral effects than the corresponding single agents. The synergy volume for the 95% CI synergy plot was 97.51 µM$^2$ with antagonism volume of −2.83 µM$^2$. This minimal antagonistic effect (appearing in a single combination mixture) was insignificant and was not reflected in the 99% CI analysis, which yielded synergy volume of 87.77 µM$^2$ and antagonism volume of 0 µM$^2$. Importantly, neither drug alone nor the combinations showed cytotoxicity at the concentrations tested (data not shown). Furthermore, we have recently embarked on a clemizole derivitization program and identified a variety of such derivative molecules that have potency similar or greater than clemizole. When combined with SCH503034, one such clemizole derivatives demonstrated significant synergistic effects similar to the parental compound (data not shown). Taken together, these results suggest that the synergistic antiviral effect of the clemizole-SCH503034 combination is generalizable and may reflect a broad synergism potential between the protease inhibitor and NS4B RNA binding inhibitor classes of drugs. The synergistic effects comtemplated herein include but are not limited to (1) synergistic antiviral activity; and/or (2) reduction in frequency of phenotypic resistance.

Experiment 11

Figure 13A:
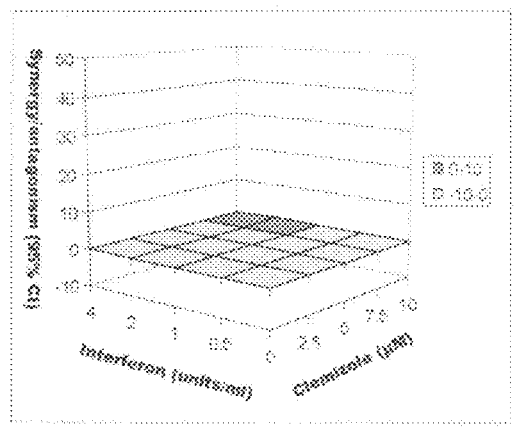
FIGS. 13A-13C illustrate the lack of a synergistic relationship between clemizole treatment and other non-protease inhibitor based inhibitors of HCV replication.

Combinations of Clemizole with Either Interferon, a Nucleoside Analog or a Non-Nucleoside Analog Polymerase Inhibitors are not Synergistic but Additive We then studied the antiviral activity of clemizole in combination with interferon using the 2a luciferase reporter gene assays, as described above. Escalating doses of clemizole were added to a standard dose response study of interferon to generate a 4 by 4 matrix of concentrations. The calculated EC50 of interferon alone was 2.8±0.4 units/ml compared with an EC50 of 1.8 units/ml previously determined by others in genotype 2a (Takanobu Kato, JCM, 2005) (Table 7). As shown in FIG. 13a, the combination of clemizole with interferon resulted in antiviral effects that were not significantly different from the theoretical additive effects at the various assayed concentrations. The synergy volume for the 95% CI synergy plot was 0.4 $\mu M^2$, suggesting that the effect of this combination is additive. Similarly, 2 dimensional analysis using CalcuSyn revealed no statistically significant deviation of the isobole from the line of additivity, as well as combination indices that were close to 1.

Figure 13B:
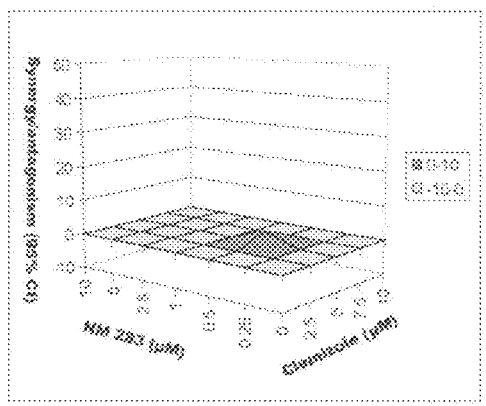
Figure 13C:
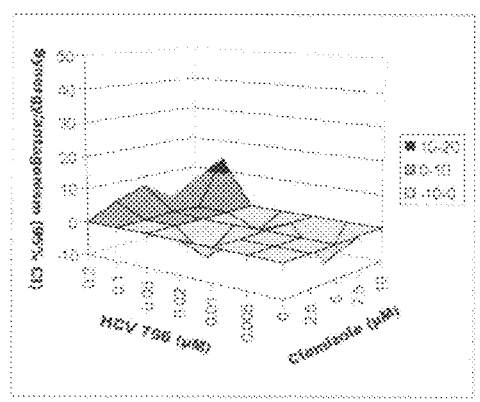

Next, the effect of combination treatment of clemizole with HCV polymerase inhibitors was assayed. Two polymerase inhibitors were chosen: NM283 (valopicitabine) a nucleoside analog, and HCV796, a non-nucleoside analogue, both shown to have an antiviral effect in HCV patients. As shown in Table 7, the calculated EC50 of NM283 was as previously measured by others in genotype 1b 1.16±0.2 $\mu M$ (P<0.02), whereas the EC50 of HCV 796 was a little above the reported value: 68±8 nM (P<0.0005) vs. 17 nM. As described above, 4 by 6 matrix was generated by adding increasing doses of clemizole to 5 different concentrations of each polymerase inhibitor. Luciferase reporter gene assays were performed as above and data was analyzed using MacSynergy. The combination of clemizole with NM 283 was additive with a synergy volume of 3.57 and antagonistic volume of −0.14 for the 95% CI synergy plot (FIG. 13b). As shown in FIG. 13c, while there were combination mixtures of clemizole and HCV 796 that yielded an antiviral effect that was above the additive effect, there were only few of these and their peaks were relatively low (synergy volume of 31.35 $\mu M^2$ in the 95% CI synergy plot). Furthermore, a similar volume was measured under the additive plain (antagonistic volume of −33.26 $\mu M^2$ in the 95% CI synergy plot), suggesting that overall this combination is also additive.

Experiment 12

Figure 14:
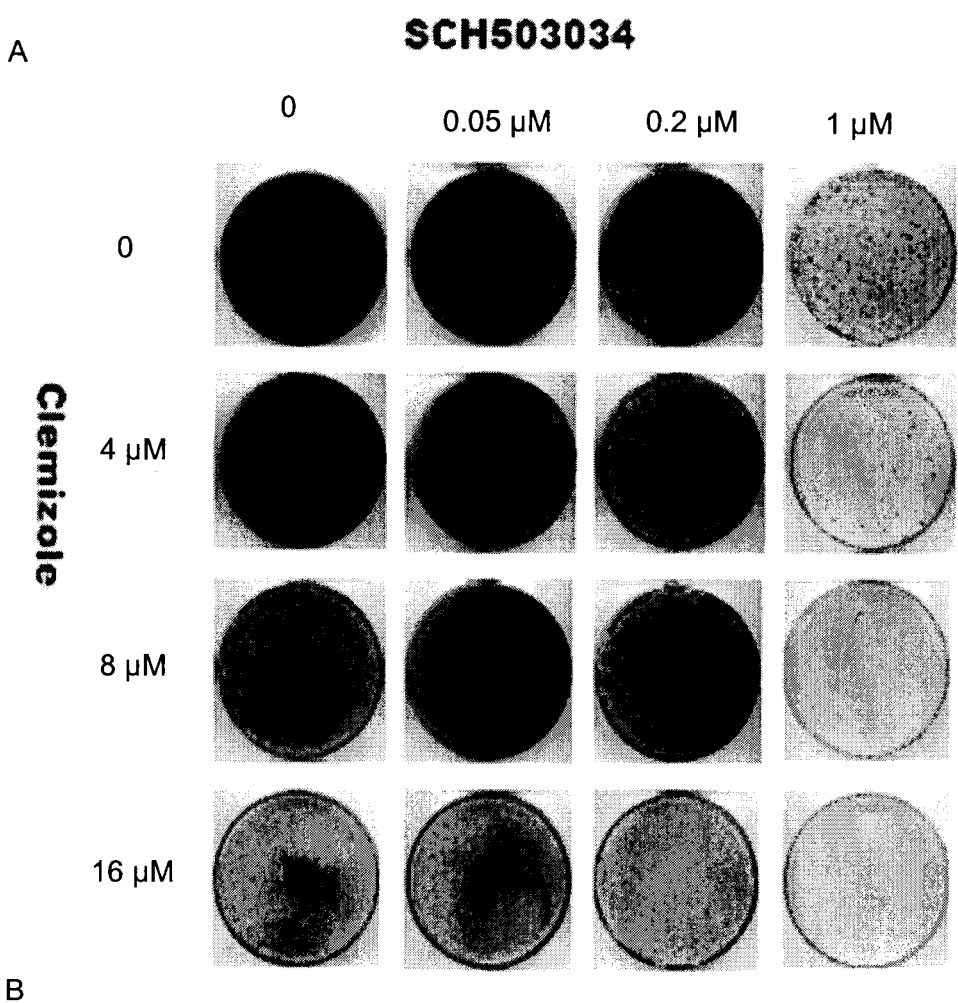
FIG. 14 illustrates the inverse correlation between the number of colonies and the concentration of clemizole and SCH503034 in a colony formation assay to detect the emergence of phenotypic resistance to the drugs. The use of combination treatment results in a decreased frequency of drug resistant colonies.

Combinations of Clemizole with SCH503034 Significantly Reduce the Frequency of Phenotypic Resistance One of the major goals in using combination antiviral drugs is to delay and/or decrease the emergence of viral resistance. The clemizole-SCH503034 combination can be effective in decreasing the emergence of phenotypic resistance as shown below. Huh7 cells electroporated de novo with a genotype 1b subgenomic HCV replicon (Bart 79I) were treated in duplicates with various concentrations of clemizole and SCH503034, either alone or in combination. G418 was included to provide the selective pressure on HCV replicon cells such that cells bearing wild type replicons are desired to die while cells bearing resistant replicons are desired to grow and form visible colonies after about 3 weeks of treatment. Plates were stained with crystal violet and the number of colonies was used to calculate the frequency of resistance (number of colonies/number of input cells). As shown in FIG. 14A, there was an inverse correlation between the number of colonies and the concentration of the compounds, i.e., the higher the inhibitor concentration the lower the resistance frequency. The addition of clemizole even at a low concentration to SCH503034 significantly decreased the frequency of resistant colonies compared with SCH503034 alone. For example, although at 4 uM clemizole by itself was not able to sufficiently suppress viral replication and sensitize cells to G418-mediated death, when combined with SCH503034 it efficiently reduced the frequency of resistant colonies compared with SCH503034 alone (FIG. 14A). As shown in FIGS. 14a and 14b, 4 $\mu M$ and 8 $\mu M$ of clemizole decreased the frequency of resistant colonies selected with 1 $\mu M$ of SCH503034 by 6 and 18 folds respectively. A concentration of 16 $\mu M$ of clemizole further augmented this effect resulting in a single resistant colony on a single plate when used with 1 $\mu M$ SCH503034.

To confirm that the emerged colonies were indeed resistant to the respective inhibitor, HCV RNA replicating in cells from pools of drug-resistant colonies was isolated and subjected to sequence analysis. Replicons selected under 1 $\mu M$ SCH503034 pressure harbored mutations within the NS3 coding region, such as the A156T and A156V mutations previously shown to confer resistance to SCH503034. Similarly, previously described clemizole resistant mutations were again selected within the NS4B coding region and the 3' terminus of the negative viral genome in replicons extracted from cells treated with 16 $\mu M$ clemizole (NBT). The effect of clemizole on the frequency of HCV resistance provides further rationale for its use in combination therapy with protease inhibitors.

Experiment 13

There is No Cross-Resistance Between Clemizole and SCH503034

The reduced frequency of drug-resistant colonies during combination treatment with clemizole and SCH503034 suggests a lack of cross-resistance among these two different classes of inhibitors. To confirm this, established HCV replicon-harboring cells were passaged in the presence of either drug in 5 replicates yielding colonies that were able to grow in the presence of 2-5× the EC50 of the respective compound. Colonies were pooled, expanded, passaged 15-20 times and the HCV RNA replicating in the cells was subjected to sequence analysis. None of the 5 independent SCH503034 treated pooled clones harbored replicons with mutations that mapped to the NS4B or the 3' negative terminus. Similarly, we did not identify replicons that harbored mutations that mapped to the NS3 coding region in 5 parallel pooled clones treated with clemizole.

Lastly, Huh7.5 cells transfected with whole cell RNA extracted from a clemizole resistant clone harboring the W55R mutation (NBT) were unaffected by 10 $\mu M$ clemizole, but remained sensitive to 2.5 $\mu M$ SCH503034. Reciprocally, decreased sensitivity to SCH503034 but not to clemizole was demonstrated in Huh7.5 cells transfected with whole cell RNA extracted from a SCH503034 resistant clone harboring the A156T mutation. Cells transfected with whole cell RNA extracted from wild type replicon cells were sensitive to both drugs.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

SEQUENCE LISTING

```
<160> NUMBER OF SEQ ID NOS: 10

<210> SEQ ID NO 1
<211> LENGTH: 341
<212> TYPE: DNA
<213> ORGANISM: Hepatitis C Virus

<400> SEQUENCE: 1
gccagccccc tgatggggc gacactccac catgaatcac tccctgtga ggaactactg    60 tcttcacgca gaaagcgtct agccatggcg ttagtatgag tgtcgtgcag cctccaggac   120 cccctccc gggagagcca tagtggtctg cggaaccggt gagtacaccg gaattgccag   180
gacgaccggg tcctttcttg gataaacccg ctcaatgcct ggagatttgg gcgtgccccc   240
gcaagactgc tagccgagta gtgttgggtc gcgaaaggcc ttgtggtact gcctgatagg   300
gtgcttgcga gtgccccggg aggtctcgta gaccgtgcac c                      341

<210> SEQ ID NO 2
<211> LENGTH: 341
<212> TYPE: RNA
<213> ORGANISM: Hepatitis C Virus

<400> SEQUENCE: 2
cggucggggg acuaccccg cugugaggug guacuuagug aggggacacu ccuugaugac    60
agaagugcgu cuuucgcaga ucgguaccgc aaucauacuc acagcacguc ggagguccug   120
gggggagggg cccucucggu aucaccagac gccuuggcca cucaugugg cuuaacgguc   180 cugcuggccc aggaaagaac cuauuugggc gaguuacgga ccucuaaacc cgcacggggg   240
cguucugacg aucggcucau cacaacccag cgcuuuccgg aacaccauga cggacuaucc   300
cacgaacgcu cacggggccc uccagagcau cuggcacgug g                      341

<210> SEQ ID NO 3
<211> LENGTH: 526
<212> TYPE: DNA
<213> ORGANISM: Hepatitis C Virus

<400> SEQUENCE: 3
agacccaagc tggctagcgt ttaaacttaa gcttggtacc gagctcggat ccactagtcc    60
agtgtggtgg aattctgcag atatcataat acgactcact atagccagcc ccgattggg   120 ggcgacactc caccatagat cactccctg tgaggaacta ctgtcttcac gcagaaagcg   180
tctagccatg gcgttagtat gagtgtcgtg cagcctccag gacccccct cccgggagag   240 ccatagtggt ctgcggaacc ggtgagtaca ccggaattgc caggacgacc gggtcctttc   300
ttggatcaac ccgctcaatg cctggagatt tgggcgtgcc ccgcgagac tgctagccga   360
```

```
gtagtgttgg gtcgcgaaag gccttgtggt actgcctgat agggtgcttg cgagtgcccc     420
gggaggtctc gtagaccgtg caccatgagc acgaatccta aacctcaaag aaaaaccaaa     480
gggcgcgcca tggatcgata tccagcacag tggcggccgc tcgagt                   526
```

<210> SEQ ID NO 4
<211> LENGTH: 526
<212> TYPE: RNA
<213> ORGANISM: Hepatitis C Virus

<400> SEQUENCE: 4

```
acucgagcgg ccgccacugu gcuggauauc gauccauggc gcgcccuuug guuuuucuuu      60
gagguuuagg auucgugcuc auggugcacg gucuacgaga ccucccgggg cacucgcaag     120 caccuauca ggcaguacca caaggccuuu cgcgacccaa cacuacucgg cuagcagucu      180 cgcggggca cgcccaaauc uccaggcauu gagcgguug auccaagaaa ggacccgguc      240
guccuggcaa uuccgugua cucaccgguu ccgcagacca cuauggcucu cccgggaggg     300 ggguccugg aggcugcacg acacucauac uaacgccaug gcuagacgcu uucugcguga      360
agacaguagu uccucacagg ggagugaucu auggugagu gucgcccca aucggggcu       420 ggcuauagug agucguauua ugauaucgc agaauuccac cacacuggac uaguggaucc     480
gagcucggua ccaagcuuaa guuuaaacgc uagccagcuu ggucu                    526
```

<210> SEQ ID NO 5
<211> LENGTH: 261
<212> TYPE: PRT
<213> ORGANISM: Artificial Sequence
<220> FEATURE:
<223> OTHER INFORMATION: Membrane Protein Sequence

<400> SEQUENCE: 5

```
Ala Ser His Leu Pro Tyr Ile Glu Gln Gly Met Met Leu Ala Glu Gln
1               5                   10                  15

Phe Lys Gln Lys Ala Leu Gly Leu Leu Gln Thr Ala Ser Arg His Ala
            20                  25                  30

Glu Val Ile Thr Pro Ala Val Gln Thr Asn Trp Gln Lys Leu Glu Val
        35                  40                  45

Phe Trp Ala Lys His Met Trp Asn Phe Ile Ser Gly Ile Gln Tyr Leu
    50                  55                  60

Ala Gly Leu Ser Thr Leu Pro Gly Asn Pro Ala Ile Ala Ser Leu Met
65                  70                  75                  80

Ala Phe Thr Ala Ala Val Thr Ser Pro Leu Thr Thr Gly Gln Thr Leu
                85                  90                  95

Leu Phe Asn Ile Leu Gly Gly Trp Val Ala Ala Gln Leu Ala Ala Pro
            100                 105                 110

Gly Ala Ala Thr Ala Phe Val Gly Ala Gly Leu Ala Gly Ala Ala Ile
        115                 120                 125

Gly Ser Val Gly Leu Gly Lys Val Leu Val Asp Ile Leu Ala Gly Tyr
    130                 135                 140

Gly Ala Gly Val Ala Gly Ala Leu Val Ala Phe Lys Ile Met Ser Gly
145                 150                 155                 160

Glu Val Pro Ser Thr Glu Asp Leu Val Asn Leu Leu Pro Ala Ile Leu
                165                 170                 175

Ser Pro Gly Ala Leu Val Val Gly Val Val Ser Ala Ala Ile Leu Arg
            180                 185                 190
```

```
Arg His Val Gly Pro Gly Glu Gly Ala Val Gln Trp Met Asn Arg Leu
        195                 200                 205

Ile Ala Phe Ala Ser Arg Gly Asn His Val Ser Pro Thr His Tyr Val
    210                 215                 220

Pro Glu Ser Asp Ala Ala Arg Val Thr Ala Ile Leu Ser Ser Leu
225                 230                 235                 240

Thr Val Thr Gln Leu Leu Arg Arg Leu His Gln Trp Ile Ser Ser Glu
                245                 250                 255

Cys Thr Thr Pro Cys
            260
```

<210> SEQ ID NO 6
<211> LENGTH: 17
<212> TYPE: RNA
<213> ORGANISM: Artificial Sequence
<220> FEATURE:
<223> OTHER INFORMATION: RNA Probe Sequence

<400> SEQUENCE: 6
auuuauuuau uuauuua                                                17

<210> SEQ ID NO 7
<211> LENGTH: 17
<212> TYPE: RNA
<213> ORGANISM: Artificial Sequence
<220> FEATURE:
<223> OTHER INFORMATION: RNA Probe Sequence

<400> SEQUENCE: 7 cuucuuucu uucuuuc                                                 17

<210> SEQ ID NO 8
<211> LENGTH: 16
<212> TYPE: PRT
<213> ORGANISM: Artificial Sequence
<220> FEATURE:
<223> OTHER INFORMATION: Chemically synthesized primer sequence

<400> SEQUENCE: 8

```
Ala Gly Ala Gly Cys Cys Ala Thr Ala Gly Thr Gly Gly Thr Cys Thr
1               5                   10                  15
```

<210> SEQ ID NO 9
<211> LENGTH: 21
<212> TYPE: PRT
<213> ORGANISM: Artificial Sequence
<220> FEATURE:
<223> OTHER INFORMATION: Chemically synthesized primer sequence

<400> SEQUENCE: 9

```
Cys Cys Ala Ala Ala Thr Cys Thr Cys Cys Ala Gly Gly Cys Ala Thr
1               5                   10                  15

Thr Gly Ala Gly Cys
            20
```

<210> SEQ ID NO 10
<211> LENGTH: 24
<212> TYPE: PRT
<213> ORGANISM: Artificial Sequence
<220> FEATURE:
<223> OTHER INFORMATION: Chemically synthesized primer sequence -continued

```
<400> SEQUENCE: 10

Cys Ala Cys Cys Gly Gly Ala Ala Thr Thr Gly Cys Cys Ala Gly Gly
1               5                   10                  15

Ala Cys Gly Ala Cys Cys Gly Gly
                20
```

The invention claimed is:

1. A method of treating a subject infected with a Hepatitis C virus, the method comprising administering to said subject clemizole, or a pharmaceutically acceptable salt, an isomer, or a tautomer, in combination with an HCV NS3 protease inhibitor selected from the group consisting of boceprevir and telaprevir, in an amount that is effective in reducing viral load of said virus in said subject.

2. The method of claim 1, wherein the HCV NS3 protease inhibitor is boceprevir.

3. The method of claim 1, wherein the HCV NS3 protease inhibitor is telaprevir.

* * * * *